(12) United States Patent
Borriello et al.

(10) Patent No.: US 8,828,987 B2
(45) Date of Patent: Sep. 9, 2014

(54) PYRIDINE AMIDE DERIVATIVES AS EP4 RECEPTOR ANTAGONISTS

(75) Inventors: Manuela Borriello, Monza (IT); Lucio Rovati, Monza (IT); Luigi Piero Stasi, Monza (IT); Benedetta Buzzi, Meda (IT); Fabrizio Colace, Monza (IT)

(73) Assignee: Rottapharm Biotech S.R.L., Monza (IT)

( * ) Notice: Subject to any disclaimer, the term of this patent is extended or adjusted under 35 U.S.C. 154(b) by 0 days.

(21) Appl. No.: 13/992,258

(22) PCT Filed: Dec. 10, 2010

(86) PCT No.: PCT/EP2010/069355
§ 371 (c)(1),
(2), (4) Date: Jun. 7, 2013

(87) PCT Pub. No.: WO2012/076063
PCT Pub. Date: Jun. 14, 2012

(65) Prior Publication Data
US 2013/0261100 A1    Oct. 3, 2013

(51) Int. Cl.
*A61K 31/00* (2006.01)
*C07D 401/04* (2006.01)
*C07D 401/14* (2006.01)
*C07D 413/14* (2006.01)

(52) U.S. Cl.
CPC ........... *C07D 413/14* (2013.01); *C07D 401/04* (2013.01); *C07D 401/14* (2013.01)
USPC ..................................................... 514/210.2

(58) Field of Classification Search
CPC ........... A61K 31/4427; A61K 31/4439; A61K 31/4444; C07D 213/72
USPC ..................................................... 514/210.2
See application file for complete search history.

(56) References Cited

FOREIGN PATENT DOCUMENTS

WO    00/20371 A1    4/2000
WO    2005/105733 A1    11/2005

OTHER PUBLICATIONS

International Search Report and Written Opinion dated Aug. 9, 2011 from corresponding PCT/EP2010/069355, pp. 10.

*Primary Examiner* — Wu-Cheng Winston Shen
*Assistant Examiner* — Christopher R Stone
(74) *Attorney, Agent, or Firm* — Ohlandt, Greeley, Ruggiero & Perle, L.L.P.

(57) ABSTRACT

The invention relates pyridine amide derivative of Formula (I) or a pharmaceutically acceptable salt thereof, wherein $R_1$ and $R_2$ are independently hydrogen, linear o branched (C1-C3) alkyl or joined together they form a cyclopropyl ring; R is independently selected from the group consisting of halogens and trifluoromethyl and p is 1, 2 or 3; A is C or N; E is a group of formula (B) or (C), wherein B is C(O)OH, C(O)O(C1-C3) alkyl, and C is selected from the group consisting of formula (I) m is 1,2 or 3, n is 0 or 1, W is —O—, —O(C1-C3 alkyl)-; —(C1-C3 alkyl)O—; —C(O)—; —C(=N—O(C1-C3 alkyl))-; —NH— or —NH(C1-C3alkyl)-; Ar is phenyl, optionally substituted with one or more substituents selected from the group consisting of halogen, trifluoromethyl, trifluoromethoxy, methyl, —NH(C1-C3alkyl)-; —N(C1-C3alkyl)(C1-C3alkyl)-, a from 5 to 7 membered heterocyclic ring containing one nitrogen atom which is covalently bonded to Ar and optionally containing one or two heteroatoms selected from N, O and S; and a 5- or 6-membered heteroaromatic ring containing 1 to 3 heteroatoms selected from S, O e N, such heteroaromatic ring being substituted with one or two substituents selected from the group consisting of (C1-C3) alkyl, (C3-C5)cycloalkyloxy, (C1-C3)alkylcarbonyl. The compounds of the invention could be used for manufacturing a medicament for the treatment of pathologies which require the use of an antagonist of the EP4 receptor, such as the treatment of acute and chronic pain, inflammatory pain, osteoarthritis, inflammation-associated disorder as arthritis, rheumatoid arthritis, cancer, endometriosis and migraine.

(I)

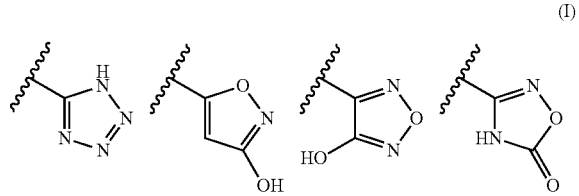

27 Claims, No Drawings

PYRIDINE AMIDE DERIVATIVES AS EP4 RECEPTOR ANTAGONISTS

FIELD OF THE INVENTION

The present invention relates to novel pyridine amide derivative compounds, processes for their preparation, pharmaceutical compositions containing them and their use as medicaments, inter alia for the treatment or alleviation of Prostaglandin E mediated diseases such as acute and chronic pain, osteoarthritis, inflammation-associated disorder as arthritis, rheumatoid arthritis, cancer, migraine and endometriosis.

BACKGROUND OF THE INVENTION

A number of review articles describe the characterization and therapeutic relevance of the prostanoid receptors as well as the most commonly used selective agonists and antagonists; *Eicosanoids: From Biotechnology to therapeutic Applications*, Folco, Samuelson, Maclouf and Velo eds, Plenum Press, New York, 1996, chap. 14, 137-154; "*Molecular aspects of the structures and functions of the prostaglandin E receptors*", Journal of Lipid Mediators and Cell Signalling, 1996, 14, 83-87; "*Function of prostanoid receptors: studies on knockout mice*", Prostaglandins & other Lipid Mediators, 2002, 68-69, 557-573 and "*Prostanoid receptor antagonists: development strategies and therapeutic applications*", British Journal of Pharmacology (2009), 158, 104-145. Prostaglandin E2 (PGE2) is a member of the prostanoid family with a variety of physiological effects, including mucosal protection, induction of gastris acid secretion in stomach, generation of fever, hyperalgesia, inflammation and immunity. These actions of PGE2 are mediated by four G-protein-coupled PGE2 receptors, EP1, EP2, EP3 and EP4.

The EP4 receptor is a 7-transmembrane receptor whose activation is normally associated with elevation of intracellular cyclic adenosine monophosphate (cAMP) levels. PGE2-activated EP4 receptor signalling may be involved in various pathologic states, such as pain, inflammation, cancer, dermatitis, bone disease and immune system disfunction.

In The Journal of Immunology (2008, 181, 5082-5088) studies suggest that PGE2 inhibits proteoglycan synthesis and stimulates matrix degradation in osteoarthritic chondrocytes via the EP4 receptor. Targeting EP4, rather than cyclooxygenase 2, could represent a future strategy for osteoarthritis disease modification.

In European Journal of Pharmacology (2008, 580, 116-121) studies suggest that that a pharmacological blockade of the prostanoid EP4 receptor may represent a new therapeutic strategy in signs and symptomatic relief of osteoarthritis and/or rheumatoid arthritis.

Certain nicotinamide compounds are generally disclosed in US20022111495A, said compounds being described as inhibitors of phosphodiesterases 4 isoenzymes. Patent application publications WO2005021508, WO2005105732, WO2005105733, WO2007121578 and WO2009139373 disclose compounds as being useful in the treatment of prostaglandin mediated disease.

SUMMARY OF THE INVENTION

The present invention is directed to novel compounds that are selective antagonists of the EP4 subtype of PGE2 receptors, specifically with analgesic and antiinflammatory activity.

Therefore, the invention concerns pyridine compound of Formula (I):

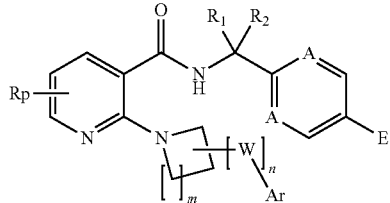

(I)

or a pharmaceutically acceptable salt thereof,
wherein:
$R_1$ and $R_2$ are independently hydrogen, linear o branched (C1-C3)alkyl or joined together they form a cyclopropyl ring;
R is independently selected from the group consisting of halogens and trifluoromethyl and p is 1, 2 or 3;
A is C or N;
E is a group of formula (B) or (C), wherein
B is C(O)OH, C(O)O(C1-C3)alkyl, and
C is selected from the group consisting of:

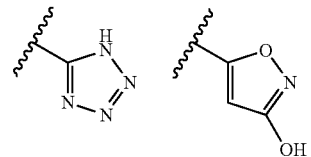

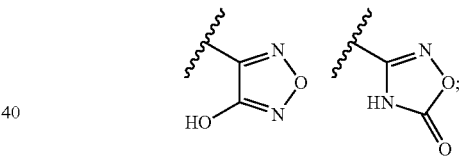

m is 1, 2 or 3,
n is 0 or 1,
W is —O—, —O(C1-C3 alkyl)-; —(C1-C3 alkyl)O—; —C(O)—; —C(=N—O(C1-C3 alkyl))-; —NH— or —NH(C1-C3alkyl)-;
Ar is phenyl, optionally substituted with one or more substituents selected from the group consisting of halogen, trifluoromethyl, trifluoromethoxy, methyl, —NH(C1-C3alkyl)-; —N(C1-C3alkyl)(C1-C3alkyl)-, a from 5 to 7 membered heterocyclic ring containing one nitrogen atom which is covalently bonded to Ar and optionally containing one or two heteroatoms selected from N, O and S; and a 5- or 6-membered heteroaromatic ring containing 1 to 3 heteroatoms selected from S, O e N, such heteroaromatic ring being substituted with one or two substituents selected from the group consisting of (C1-C3)alkyl, (C3-C5)cycloalkyloxy, (C1-C3)alkylcarbonyl.

In this invention compounds of Formula (I) may exist as R and S enantiomers and as racemic mixture. This invention includes in its scope of protection all the possible isomers and racemic mixtures. Wherever should be present further symmetry centres, this invention includes all the possible diastereoisomers and relative mixtures as well.

In another aspect the invention concerns a compound of Formula (I) as medicament, in particular it concerns its use for the treatment of pathologies where an antagonist of the EP4 receptor is needed, such as the treatment of acute and chronic pain, inflammatory pain, osteoarthritis, inflammation-associated disorder as arthritis, rheumatoid arthritis, cancer endometriosis and migraine.

DETAILED DESCRIPTION OF THE INVENTION

The invention thus concerns pyridine amide derivative of Formula (I):

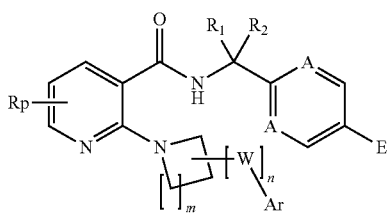

(I)

or a pharmaceutically acceptable salt thereof,
wherein:
$R_1$ and $R_2$ are independently hydrogen, linear o branched (C1-C3)alkyl or joined together they form a cyclopropyl ring;
R is independently selected from the group consisting of halogens and trifluoromethyl and p is 1, 2 or 3;
A is C or N;
E is a group of formula (B) or (C), wherein
B is C(O)OH, C(O)O(C1-C3)alkyl, and
C is selected from the group consisting of:

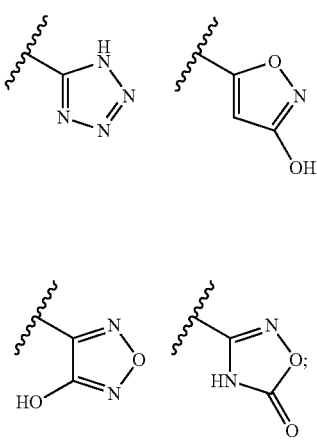

m is 1, 2 or 3,
n is 0 or 1,
W is —O—, —O(C1-C3 alkyl)-; —(C1-C3 alkyl)O—; —C(O)—; —C(=N—O(C1-C3 alkyl))-; —NH— or —NH(C1-C3alkyl)-;
Ar is phenyl, optionally substituted with one or more substituents selected from the group consisting of halogen, trifluoromethyl, trifluoromethoxy, methyl, —NH(C1-C3alkyl)-;
—N(C1-C3alkyl)(C1-C3alkyl)-, a from 5 to 7 membered heterocyclic ring containing one nitrogen atom which is covalently bonded to Ar and optionally containing one or two heteroatoms selected from N, O and S; and a 5- or 6-membered heteroaromatic ring containing 1 to 3 heteroatoms selected from S, O e N, such heteroaromatic ring being substituted with one or two substituents selected from the group consisting of (C1-C3)alkyl, (C3-C5)cycloalkyloxy, (C1-C3)alkylcarbonyl.

Preferably p is 1 and R is selected from alogen and trifluoromethyl, more preferably p is 1 and R is alogen, still more preferably R is chloro.

R1 and R2 are independently preferably selected from hydrogen, methyl or they form together a cyclopropane ring, and more preferably R1 and R2 form together a cyclopropane ring.

In a first aspect of the invention embodiment, pyridine amide derivative of Formula (I) contains E which is COOH.

This is a compound of Formula (Ia):

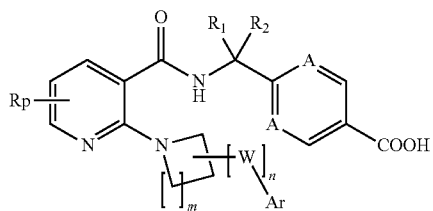

(Ia)

In this embodiment, preferably m is 1 and 2 and when n is 0, W is bond.

A preferred embodiment of the first aspect of the invention concerns compounds with W is selected from the group consisting of O, NH and N(C1-C3)alkyl.

In a first embodiment, Ar is phenyl, optionally substituted with one or more substituents selected from the group consisting of halogen, trifluoromethyl, trifluoromethoxy, methyl, —NH(C1-C3alkyl)-; —N(C1-C3alkyl)(C1-C3alkyl)-, a from 5 to 7 membered heterocyclic ring containing one nitrogen atom, which is covalently bonded to Ar, and optionally containing one or two heteroatoms selected from N, O and S.

Examples of heterocyclic ring include piperazinyl, piperidinyl, morpholinyl and the like. More preferably Ar is phenyl substituted by alogen, still more preferably said halogen is F.

In a second embodiment Ar is preferably a 5- or 6-membered heteroaromatic ring containing 1 to 3 heteroatoms selected from S, O e N, such ring being substituted with one or two substituents selected from the group consisting of (C1-C3)alkyl, (C3-C5)cycloalkyloxy, (C1-C3)alkylcarbonyl.

Examples of 5- or 6-membered heteroaromatic ring are pyridine, pyrimidine, oxazole, isoxazole, oxadiazole. Preferably in the second embodiment Ar is pyridine In a second aspect of the invention, pyridine amide derivative of Formula (I) contains E which is B.

This is a compound of Formula (Ib):

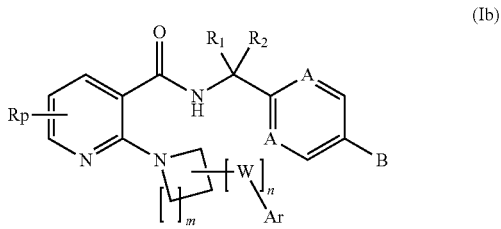

In this embodiment, preferably m is 1 and 2 and when n is 0, W is bond.

A preferred embodiment of the first embodiment of the invention concerns compounds with W is selected from the group consisting of O, NH and N(C1-C3)alkyl.

In a first embodiment, Ar is preferably phenyl optionally substituted with one or more halogen atoms, trifluoromethyl, trifluoromethoxy, methyl, —NH(C1-C3alkyl)-; —N(C1-C3alkyl)(C1-C3alkyl)-, a from 5 to 7 membered heterocyclic ring containing one nitrogen atom, which is covalently bonded to Ar, and optionally containing one or two heteroatoms selected from N, O and S.

Examples of heterocyclic include piperazinyl, piperidinyl, morpholinyl and the like. More preferably Ar is phenyl substituted by alogen, still more preferably F. In a second embodiment Ar is preferably a 5- or 6-membered heteroaromatic ring containing 1 to 3 heteroatoms selected from S, O e N, such ring being substituted with one or two substituents selected from the group consisting of (C1-C3)alkyl, (C3-C5)cycloalkyloxy, (C1-C3)alkylcarbonyl.

Examples of 5- or 6-membered heteroaromatic ring are pyridine, pyrimidine, oxazole, isoxazole, oxadiazole. Advantageously, Ar is pyridine The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methyl-glucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids. It will be understood that, as used herein, references to the compounds of Formula (I), (Ia) and (Ib) are meant to also include the pharmaceutically acceptable salts.

The preferred compounds of the invention are selected from the group consisting of:

4-(1-(5-chloro-2-(2-phenylpyrrolidin-1-yl)nicotinamido)cyclopropyl)benzoic acid (racemic mixture)

4-(1-(5-chloro-2-(2-phenylpyrrolidin-1-yl)nicotinamido)cyclopropyl)benzoic acid (enantiomer 1)

4-(1-(5-chloro-2-(2-phenylpyrrolidin-1-yl)nicotinamido)cyclopropyl)benzoic acid (enantiomer 2)

4-(1-(5-chloro-2-(3-phenylpyrrolidin-1-yl)nicotinamido)cyclopropyl)benzoic acid 4-(1-(5-chloro-2-(3-phenylpyrrolidin-1-yl)nicotinamido)cyclopropyl)benzoic acid (enantiomer 1)

4-(1-(5-chloro-2-(3-phenylpyrrolidin-1-yl)nicotinamido)cyclopropyl)benzoic acid (enantiomer 2)

4-(1-(2-(2-benzylpyrrolidin-1-yl)-5-chloronicotinamido)cyclopropyl)benzoic acid (racemic mixture)

4-(1-(2-(2-benzylpyrrolidin-1-yl)-5-chloronicotinamido)cyclopropyl)benzoic acid (enantiomer 1)

4-(1-(2-(2-benzylpyrrolidin-1-yl)-5-chloronicotinamido)cyclopropyl)benzoic acid (enantiomer 2)

4-(1-(5-chloro-2-(3-phenoxyazetidin-1-yl)nicotinamido)cyclopropyl)benzoic acid (S)-4-(1-(5-chloro-2-(3-(4-fluorophenoxy)azetidin-1-yl)nicotinamido)ethyl)benzoic acid (S)-4-(1-(5-chloro-2-(3-(3-fluorophenoxy)azetidin-1-yl)nicotinamido)ethyl)benzoic acid 4-(1-(5-chloro-2-(3-(4-(trifluoromethyl)phenoxy)azetidin-1-yl)nicotinamido)cyclo-propyl)benzoic acid 4-(1-(5-chloro-2-(3-(3-(trifluoromethyl)phenoxy)azetidin-1-yl)nicotinamido)cyclo-propyl)benzoic acid 4-(1-(5-chloro-2-(3-(4-fluorophenoxy)azetidin-1-yl)nicotinamido)cyclopropyl)-benzoic acid 4-(1-(5-chloro-2-(3-(3-fluorophenoxy)azetidin-1-yl)nicotinamido)cyclopropyl)-benzoic acid 4-(1-(5-chloro-2-(3-(4-fluoro-3-(trifluoromethyl)phenoxy)azetidin-1-yl)nicotinamido)cyclopropyl)-benzoic acid 4-(1-(5-chloro-2-(3-(3-(trifluoromethoxy)phenoxy)azetidin-1-yl)nicotinamido)cyclopropyl)-benzoic acid 4-(1-(5-chloro-2-(3-(2,4-difluorophenoxy)azetidin-1-yl)nicotinamido)cyclopropyl)-benzoic acid 4-(1-(5-chloro-2-(3-(3,4-difluorophenoxy)azetidin-1-yl)nicotinamido)cyclopropyl)-benzoic acid 4-(1-(5-chloro-2-(3-(3-(piperazin-1-yl)phenoxy)azetidin-1-yl)nicotinamido)cyclo-propyl)benzoic acid 4-((5-chloro-2-(3-(3-fluorophenoxy)azetidin-1-yl) nicotinamido) methyl)benzoic acid 6-((5-chloro-2-(3-(3-fluorophenoxy)azetidin-1-yl)nicotinamido)methyl)nicotinic acid 6-((5-chloro-2-(3-(3-fluorophenoxy)azetidin-1-yl)nicotinamido)methyl)nicotinic acid 4-(1-(5-chloro-2-(3-(3-fluorobenzoyl)azetidin-1-yl)nicotinamido)cyclopropyl)benzoic acid 4-(1-(5-chloro-2-(3-((3-fluorophenyl)(methoxyimino)methyl)azetidin-1-yl)-nicotinamido)cyclopropyl)benzoic acid (isomeric mixture)

4-(1-(5-chloro-2-(3-(3-fluorophenyl)-3-hydroxyazetidin-1-yl)nicotinamido)cyclo-propyl)benzoic acid 4-(1-(5-chloro-2-(3-(4-fluorophenyl)-3-hydroxyazetidin-1-yl)nicotinamido)cyclo-propyl)benzoic acid 4-(1-(5-chloro-2-(3-((4-fluorophenoxy)methyl)azetidin-1-yl)nicotinamido)cyclo-propyl)benzoic acid
4-(1-(5-chloro-2-(3-((4-fluorophenoxy)methyl)azetidin-1-yl)nicotinamido)cyclo-propyl)benzoic acid
4-(1-(5-chloro-2-(3-((3-(trifluoromethyl)phenyl)amino)azetidin-1-yl)nicotinamido)-cyclopropyl)benzoic acid
4-(1-(5-chloro-2-(3-((3-fluorophenyl)amino)azetidin-1-yl)nicotinamido)-cyclopropyl)benzoic acid
4-(1-(5-chloro-2-(3-((4-fluorophenyl)amino)azetidin-1-yl)nicotinamido)cyclopropyl)-benzoic acid
4-(1-(5-chloro-2-(3-((4-fluoro-2-methylphenyl)amino)azetidin-1-yl)nicotinamido)-cyclopropyl)benzoic acid
4-(1-(5-chloro-2-(3-((2,4-difluorophenyl)amino)azetidin-1-yl)nicotinamido)-cyclopropyl)benzoic acid
4-(1-(5-chloro-2-(3-((2-methyl-4-(trifluoromethyl)phenyl)amino)azetidin-1-yl)-nicotinamido)cyclopropyl)benzoic acid
4-(1-(5-chloro-2-(3-((4-fluoro-2-methylphenyl)(methyl)amino)azetidin-1-yl)-nicotinamido)cyclopropyl)benzoic acid
4-(1-(2-(3-(3-fluorophenoxy)azetidin-1-yl)-5-(trifluoromethyl)nicotinamido)-cyclopropyl)benzoic acid
4-(1-(2-(3-(4-fluorophenoxy)azetidin-1-yl)-5-(trifluoromethyl)nicotinamido)-cyclopropyl)benzoic acid
4-(1-(2-(3-(4-chlorophenoxy)azetidin-1-yl)-5-(trifluoromethyl)nicotinamido)-cyclopropyl)benzoic acid
4-(1-(2-(3-(3-chlorophenoxy)azetidin-1-yl)-5-(trifluoromethyl)nicotinamido)-cyclopropyl)benzoic acid
4-(1-(2-(3-(4-fluoro-3-(trifluoromethyl)phenoxy)azetidin-1-yl)-5-(trifluoromethyl)-nicotinamido)cyclopropyl)benzoic acid
4-(1-(2-(3-(3-(trifluoromethoxy)phenoxy)azetidin-1-yl)-5-(trifluoromethyl)-nicotinamido)cyclopropyl)benzoic acid
4-(1-(2-(3-(2,4-difluorophenoxy)azetidin-1-yl)-5-(trifluoromethyl)nicotinamido)-cyclopropyl)benzoic acid
4-(1-(2-(3-(3,4-difluorophenoxy)azetidin-1-yl)-5-(trifluoromethyl)nicotinamido)-cyclopropyl)benzoic acid
4-(1-(2-(3-((5-methylisoxazol-3-yl)oxy)azetidin-1-yl)-5-(trifluoromethyl)-nicotinamido)cyclopropyl)benzoic acid
4-(1-(5-(trifluoromethyl)-2-(3-((6-(trifluoromethyl)pyridin-2-yl)oxy)azetidin-1-yl)nicotinamido)cyclopropyl)benzoic acid
4-(1-(2-(3-((5-fluoropyrimidin-2-yl)oxy)azetidin-1-yl)-5-(trifluoromethyl)-nicotinamido)cyclopropyl)benzoic acid
4-(1-(2-(3-((3-fluorophenyl)amino)azetidin-1-yl)-5-(trifluoromethyl)-nicotinamido)cyclopropyl)benzoic acid
4-(1-(2-(3-((4-fluorophenyl)amino)azetidin-1-yl)-5-(trifluoromethyl)nicotinamido)-cyclopropyl)benzoic acid
4-(1-(2-(3-((4-fluoro-2-methylphenyl)amino)azetidin-1-yl)-5-(trifluoromethyl)-nicotinamido)cyclopropyl)benzoic acid
4-(1-(2-(3-((2,4-difluorophenyl)amino)azetidin-1-yl)-5-(trifluoromethyl)-nicotinamido)cyclopropyl)benzoic acid
4-(1-(5-fluoro-2-(3-(3-fluorophenoxy)azetidin-1-yl)nicotinamido)cyclopropyl)benzoic acid
4-(1-(5-fluoro-2-(3-(3-chlorophenoxy)azetidin-1-yl)nicotinamido)cyclopropyl)-benzoic acid
4-(1-(5-fluoro-2-(3-(3-(trifluoromethoxy)phenoxy)azetidin-1-yl)nicotinamido)-cyclopropyl)benzoic acid
4-(1-(5-fluoro-2-(3-((4-fluoro-2-methylphenyl)amino)azetidin-1-yl)nicotinamido)-cyclopropyl)benzoic acid
4-((1S)-1-(5-chloro-2-(3-(4-(trifluoromethyl)phenoxy)pyrrolidin-1-yl)nicotinamido)-ethyl)benzoic acid
4-((1S)-1-(5-chloro-2-(3-(3-(trifluoromethyl)phenoxy)pyrrolidin-1-yl)nicotinamido)-ethyl)benzoic acid
4-((1S)-1-(5-chloro-2-(3-(4-fluorophenoxy)pyrrolidin-1-yl)nicotinamido)-ethyl)benzoic acid
4-(1-(5-chloro-2-(3-phenoxy)pyrrolidin-1-yl)nicotinamido)cyclopropyl)benzoic acid (racemic mixture)
4-(1-(5-chloro-2-(3-phenoxy)pyrrolidin-1-yl)nicotinamido)cyclopropyl)benzoic acid (enantiomer 1)
4-(1-(5-chloro-2-(3-phenoxy)pyrrolidin-1-yl)nicotinamido)cyclopropyl)benzoic acid (enantiomer 2)
4-(1-(5-chloro-2-(3-3-(trifluoromethyl)phenoxy)pyrrolidin-1-yl)nicotinamido)-cyclopropyl)benzoic acid (racemic mixture)
4-(1-(5-chloro-2-(3-3-(trifluoromethyl)phenoxy)pyrrolidin-1-yl)nicotinamido)-cyclopropyl)benzoic acid (enantiomer 1)
4-(1-(5-chloro-2-(3-3-(trifluoromethyl)phenoxy)pyrrolidin-1-yl)nicotinamido)-cyclopropyl)benzoic acid (enantiomer 2)
4-(1-(5-chloro-2-(3-(4-fluorophenoxy)pyrrolidin-1-yl)nicotinamido)cyclopropyl)-benzoic acid (racemic mixture)
4-(1-(5-chloro-2-(3-(4-fluorophenoxy)pyrrolidin-1-yl)nicotinamido)cyclopropyl)-benzoic acid (enantiomer 1)
4-(1-(5-chloro-2-(3-(4-fluorophenoxy)pyrrolidin-1-yl)nicotinamido)cyclopropyl)-benzoic acid (enantiomer 2)
4-(1-(5-chloro-2-(3-(3-fluorophenoxy)pyrrolidin-1-yl)nicotinamido)-cyclopropyl)benzoic acid (racemic mixture)
4-(1-(5-chloro-2-(3-(3-fluorophenoxy)pyrrolidin-1-yl)nicotinamido)cyclopropyl)-benzoic acid (enantiomer 1)
4-(1-(5-chloro-2-(3-(3-fluorophenoxy)pyrrolidin-1-yl)nicotinamido)cyclopropyl)-benzoic acid (enantiomer 2)
4-(1-(5-chloro-2-(3-(m-tolyloxy)pyrrolidin-1-yl)nicotinamido)cyclopropyl)benzoic acid
4-(1-(5-chloro-2-(3-(4-(trifluoromethyl)phenoxy)pyrrolidin-1-yl)nicotinamido)-cyclopropyl)benzoic acid (racemic mixture)
4-(1-(5-chloro-2-(3-(4-(trifluoromethyl)phenoxy)pyrrolidin-1-yl)nicotinamido)cyclo-propyl)benzoic acid (enantiomer 1)
4-(1-(5-chloro-2-(3-(4-(trifluoromethyl)phenoxy)pyrrolidin-1-yl)nicotinamido)cyclo-propyl)benzoic acid (enantiomer 2)
4-(1-(5-chloro-2-(3-((3-fluorophenoxy)methyl)pyrrolidin-1-yl)nicotinamido)cyclo-propyl)benzoic acid
4(R)-4-(1-(5-chloro-2-(2-((3-fluorophenoxy)methyl)pyrrolidin-1-yl)nicotinamido)cyclopropyl)benzoic acid
4(S)-4-(1-(5-chloro-2-(2-((3-fluorophenoxy)methyl)pyrrolidin-1-yl)nicotinamido)-cyclopropyl)benzoic acid
4-(1-(5-chloro-2-(3-((3-fluorophenoxy)methyl)piperidin-1-yl)nicotinamido)cyclo-propyl)benzoic acid
(R)-4-(1-(5-chloro-2-(3-(3-fluorophenoxy)pyrrolidin-1-yl)nicotinamido)cyclo-propyl)benzoic acid
(S)-4-(1-(5-chloro-2-(3-(3-fluorophenoxy)pyrrolidin-1-yl)nicotinamido)cyclo-propyl)benzoic acid
N-(1-(4-(1H-tetrazol-5-yl)phenyl)cyclopropyl)-5-chloro-2-(3-(3-fluorophenoxy)-azetidin-1-yl)nicotinamide More preferred compounds of the invention are selected from the group consisting of:
4-(1-(5-chloro-2-(2-phenylpyrrolidin-1-yl)nicotinamido)cyclopropyl)benzoic acid (racemic mixture)
4-(1-(5-chloro-2-(2-phenylpyrrolidin-1-yl)nicotinamido)cyclopropyl)benzoic acid (enantiomer 2)
4-(1-(5-chloro-2-(3-phenylpyrrolidin-1-yl)nicotinamido)cyclopropyl)benzoic acid
4-(1-(5-chloro-2-(3-phenoxyazetidin-1-yl)nicotinamido)cyclopropyl)benzoic acid
(S)-4-(1-(5-chloro-2-(3-(4-fluorophenoxy)azetidin-1-yl)nicotinamido)ethyl)benzoic acid
(S)-4-(1-(5-chloro-2-(3-(3-fluorophenoxy)azetidin-1-yl)nicotinamido)ethyl)benzoic acid 4-(1-(5-chloro-2-(3-(4-(trifluoromethyl)phenoxy)azetidin-1-yl)nicotinamido)cyclo-propyl)benzoic acid
4-(1-(5-chloro-2-(3-(3-(trifluoromethyl)phenoxy)azetidin-1-yl)nicotinamido)-cyclopropyl)benzoic acid
4-(1-(5-chloro-2-(3-(4-fluorophenoxy)azetidin-1-yl)nicotinamido)cyclopropyl)-benzoic acid
4-(1-(5-chloro-2-(3-(3-fluorophenoxy)azetidin-1-yl)nicotinamido)cyclopropyl)-benzoic acid
4-(1-(5-chloro-2-(3-(4-fluoro-3-(trifluoromethyl)phenoxy)azetidin-1-yl)nicotinamido)-cyclopropyl)benzoic acid
4-(1-(5-chloro-2-(3-(3-(trifluoromethoxy)phenoxy)azetidin-1-yl)nicotinamido)cyclo-propyl)benzoic acid
4-(1-(5-chloro-2-(3-(2,4-difluorophenoxy)azetidin-1-yl)nicotinamido)cyclopropyl)-benzoic acid
4-(1-(5-chloro-2-(3-(3,4-difluorophenoxy)azetidin-1-yl)nicotinamido)cyclopropyl)-benzoic acid
4-(1-(5-chloro-2-(3-(3-(piperazin-1-yl)phenoxy)azetidin-1-yl)nicotinamido)cyclo-propyl)benzoic acid
4-((5-chloro-2-(3-(3-fluorophenoxy)azetidin-1-yl) nicotinamido) methyl)benzoic acid
6-((5-chloro-2-(3-(3-fluorophenoxy)azetidin-1-yl)nicotinamido)methyl)nicotinic acid
4-(1-(5-chloro-2-(3-(3-fluorobenzoyl)azetidin-1-yl)nicotinamido)cyclopropyl)benzoic acid
4-(1-(5-chloro-2-(3-(4-fluorophenyl)-3-hydroxyazetidin-1-yl)nicotinamido)cyclo-propyl)benzoic acid
4-(1-(5-chloro-2-(3-((4-fluorophenoxy)methyl)azetidin-1-yl)nicotinamido)cyclo-propyl)benzoic acid
4-(1-(5-chloro-2-(3-((4-fluorophenoxy)methyl)azetidin-1-yl)nicotinamido)cyclo-propyl)benzoic acid
4-(1-(5-chloro-2-(3-((3-(trifluoromethyl)phenyl)amino)azetidin-1-yl)nicotinamido)-cyclopropyl)benzoic acid
4-(1-(5-chloro-2-(3-((3-fluorophenyl)amino)azetidin-1-yl)nicotinamido)cyclopropyl)-benzoic acid
4-(1-(5-chloro-2-(3-((4-fluorophenyl)amino)azetidin-1-yl)nicotinamido)cyclopropyl)-benzoic acid
4-(1-(5-chloro-2-(3-((4-fluoro-2-methylphenyl)amino)azetidin-1-yl)nicotinamido)-cyclopropyl)benzoic acid
4-(1-(5-chloro-2-(3-((2,4-difluorophenyl)amino)azetidin-1-yl)nicotinamido)-cyclopropyl)benzoic acid
4-(1-(5-chloro-2-(3-((2-methyl-4-(trifluoromethyl)phenyl)amino)azetidin-1-yl)-nicotinamido)cyclopropyl)benzoic acid
4-(1-(5-chloro-2-(3-((4-fluoro-2-methylphenyl)(methyl)amino)azetidin-1-yl)-nicotinamido)cyclopropyl)benzoic acid
4-(1-(2-(3-(3-fluorophenoxy)azetidin-1-yl)-5-(trifluoromethyl)nicotinamido)-cyclopropyl)benzoic acid
4-(1-(2-(3-(4-fluorophenoxy)azetidin-1-yl)-5-(trifluoromethyl)nicotinamido)-cyclopropyl)benzoic acid
4-(1-(2-(3-(4-chlorophenoxy)azetidin-1-yl)-5-(trifluoromethyl)nicotinamido)-cyclopropyl)benzoic acid
4-(1-(2-(3-(3-chlorophenoxy)azetidin-1-yl)-5-(trifluoromethyl)nicotinamido)-cyclopropyl)benzoic acid
4-(1-(2-(3-(4-fluoro-3-(trifluoromethyl)phenoxy)azetidin-1-yl)-5-(trifluoromethyl)-nicotinamido)cyclopropyl)benzoic acid
4-(1-(2-(3-(3-(trifluoromethoxy)phenoxy)azetidin-1-yl)-5-(trifluoromethyl)-nicotinamido)cyclopropyl)benzoic acid
4-(1-(2-(3-(2,4-difluorophenoxy)azetidin-1-yl)-5-(trifluoromethyl)-nicotinamido)cyclopropyl)benzoic acid
4-(1-(2-(3-(3,4-difluorophenoxy)azetidin-1-yl)-5-(trifluoromethyl)-nicotinamido)-cyclopropyl)benzoic acid
4-(1-(5-(trifluoromethyl)-2-(3-((6-(trifluoromethyl)pyridin-2-yl)oxy)azetidin-1-yl)-nicotinamido)cyclopropyl)benzoic acid
4-(1-(2-(3-((3-fluorophenyl)amino)azetidin-1-yl)-5-(trifluoromethyl)nicotinamido)-cyclopropyl)benzoic acid
4-(1-(2-(3-((4-fluorophenyl)amino)azetidin-1-yl)-5-(trifluoromethyl)nicotinamido)-cyclopropyl)benzoic acid
4-(1-(2-(3-((4-fluoro-2-methylphenyl)amino)azetidin-1-yl)-5-(trifluoromethyl)-nicotinamido)cyclopropyl)benzoic acid
4-(1-(2-(3-((2,4-difluorophenyl)amino)azetidin-1-yl)-5-(trifluoromethyl)-nicotinamido)cyclopropyl)benzoic acid
4-(1-(5-fluoro-2-(3-(3-fluorophenoxy)azetidin-1-yl)nicotinamido)cyclopropyl)benzoic acid
4-(1-(5-fluoro-2-(3-(3-chlorophenoxy)azetidin-1-yl)nicotinamido)cyclopropyl)-benzoic acid
4-(1-(5-fluoro-2-(3-(3-(trifluoromethoxy)phenoxy)azetidin-1-yl)nicotinamido)cyclo-propyl)benzoic acid
4-(1-(5-fluoro-2-(3-((4-fluoro-2-methylphenyl)amino)azetidin-1-yl)nicotinamido)-cyclopropyl)benzoic acid
4-(1-(5-chloro-2-(3-phenoxy)pyrrolidin-1-yl)nicotinamido)cyclopropyl)benzoic acid (racemic mixture)
4-(1-(5-chloro-2-(3-phenoxy)pyrrolidin-1-yl)nicotinamido)cyclopropyl)benzoic acid (enantiomer 2)
4-(1-(5-chloro-2-(3-(3-(trifluoromethyl)phenoxy)pyrrolidin-1-yl)nicotinamido)cyclo-propyl)benzoic acid (racemic mixture)
4-(1-(5-chloro-2-(3-(3-(trifluoromethyl)phenoxy)pyrrolidin-1-yl)nicotinamido)-cyclopropyl)benzoic acid (enantiomer 1)
4-(1-(5-chloro-2-(3-(3-(trifluoromethyl)phenoxy)pyrrolidin-1-yl)nicotinamido)-cyclopropyl)benzoic acid (enantiomer 2)
4-(1-(5-chloro-2-(3-(4-fluorophenoxy)pyrrolidin-1-yl)nicotinamido)cyclopropyl)-benzoic acid (racemic mixture)
4-(1-(5-chloro-2-(3-(4-fluorophenoxy)pyrrolidin-1-yl)nicotinamido)cyclopropyl)-benzoic acid (enantiomer 2)
4-(1-(5-chloro-2-(3-(3-fluorophenoxy)pyrrolidin-1-yl)nicotinamido)cyclopropyl)-benzoic acid (racemic mixture)
4-(1-(5-chloro-2-(3-(3-fluorophenoxy)pyrrolidin-1-yl)nicotinamido)cyclopropyl)-benzoic acid (enantiomer 2)
4-(1-(5-chloro-2-(3-((3-fluorophenoxy)methyl)pyrrolidin-1-yl)nicotinamido)cyclo-propyl)benzoic acid
(R)-4-(1-(5-chloro-2-(2-((3-fluorophenoxy)methyl)pyrrolidin-1-yl)nicotinamido)cyclopropyl)benzoic acid
(S)-4-(1-(5-chloro-2-(3-(3-fluorophenoxy)pyrrolidin-1-yl)nicotinamido)cyclopropyl)benzoic acid
N-(1-(4-(1H-tetrazol-5-yl)phenyl)cyclopropyl)-5-chloro-2-(3-(3-fluorophenoxy)-azetidin-1-yl)nicotinamide Still more preferred compounds of the invention are selected from the group consisting of:
4-(1-(5-chloro-2-(3-phenoxyazetidin-1-yl)nicotinamido)cyclopropyl)benzoic acid
4-(1-(5-chloro-2-(3-(3-fluorophenoxy)azetidin-1-yl)nicotinamido)cyclopropyl)-benzoic acid
6-((5-chloro-2-(3-(3-fluorophenoxy)azetidin-1-yl)nicotinamido)methyl)nicotinic acid
4-(1-(5-chloro-2-(3-((4-fluoro-2-methylphenyl)amino)azetidin-1-yl)nicotinamido)-cyclopropyl)benzoic acid
4-(1-(2-(3-(3-fluorophenoxy)azetidin-1-yl)-5-(trifluoromethyl)nicotinamido)cyclo-propyl)benzoic acid
4-(1-(2-(3-((4-fluoro-2-methylphenyl)amino)azetidin-1-yl)-5-(trifluoromethyl)-nicotinamido)cyclopropyl)benzoic acid A further aspect of this invention concerns a process for the preparation of a compound of Formula (I) comprising the following steps represented in the general scheme below:

GENERAL SCHEME

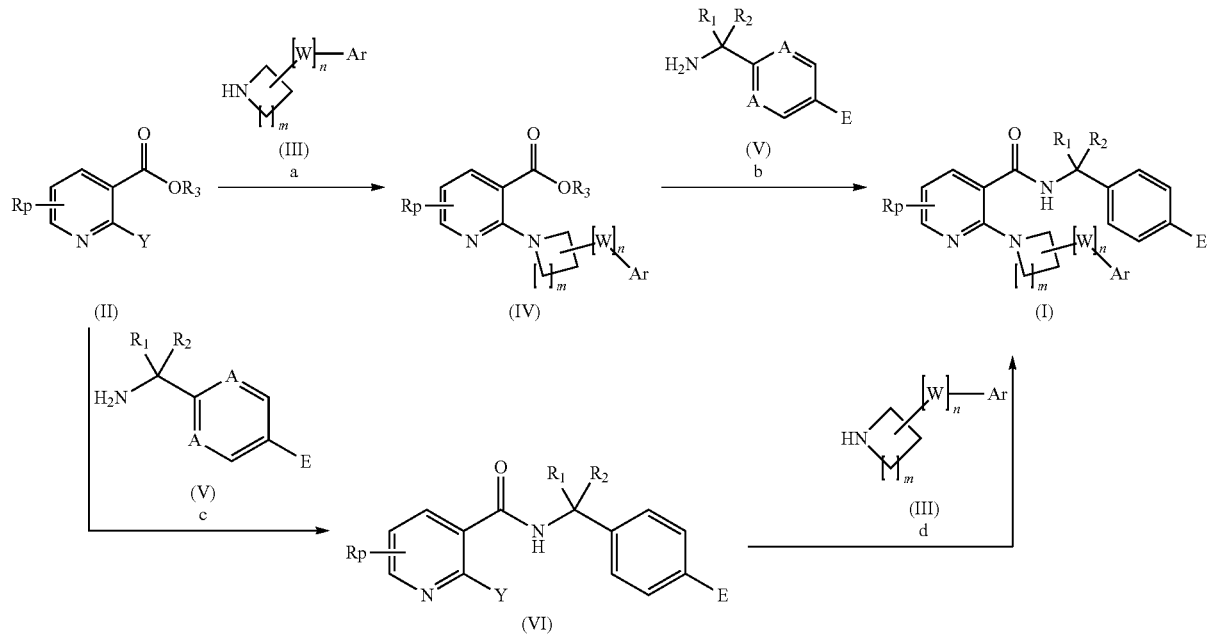

a) reacting a compound (II) with compound of (III) with suitable base thus obtaining a compound of Formula (IV);

b) reacting a compound of Formula (IV) or the corresponding acyl chlorides RCOCl with a compound of formula (V) in the presence of coupling reagents in the presence of a base thus obtaining a compound of Formula (I);

c) reacting a compound of formula (II) with a compound of formula (V) in the presence of coupling reagents and in the presence of a base thus obtaining a compound of Formula (VI);

d) reacting a compound of formula (VI) with compound of (III) with suitable base thus obtaining a compound of Formula (I)

In the above general scheme, Y represents a leaving group selected from the group of halogen atoms, such as chlorine, bromine and iodine.

A further aspect of this invention concerns a process for the preparation of a compound of Formula (Ia), when E is COOH, W is selected from the group consisting of O, NH and N(C1-C3)alkyl and n is 1, comprising the following steps represented in the scheme below (Scheme 1):

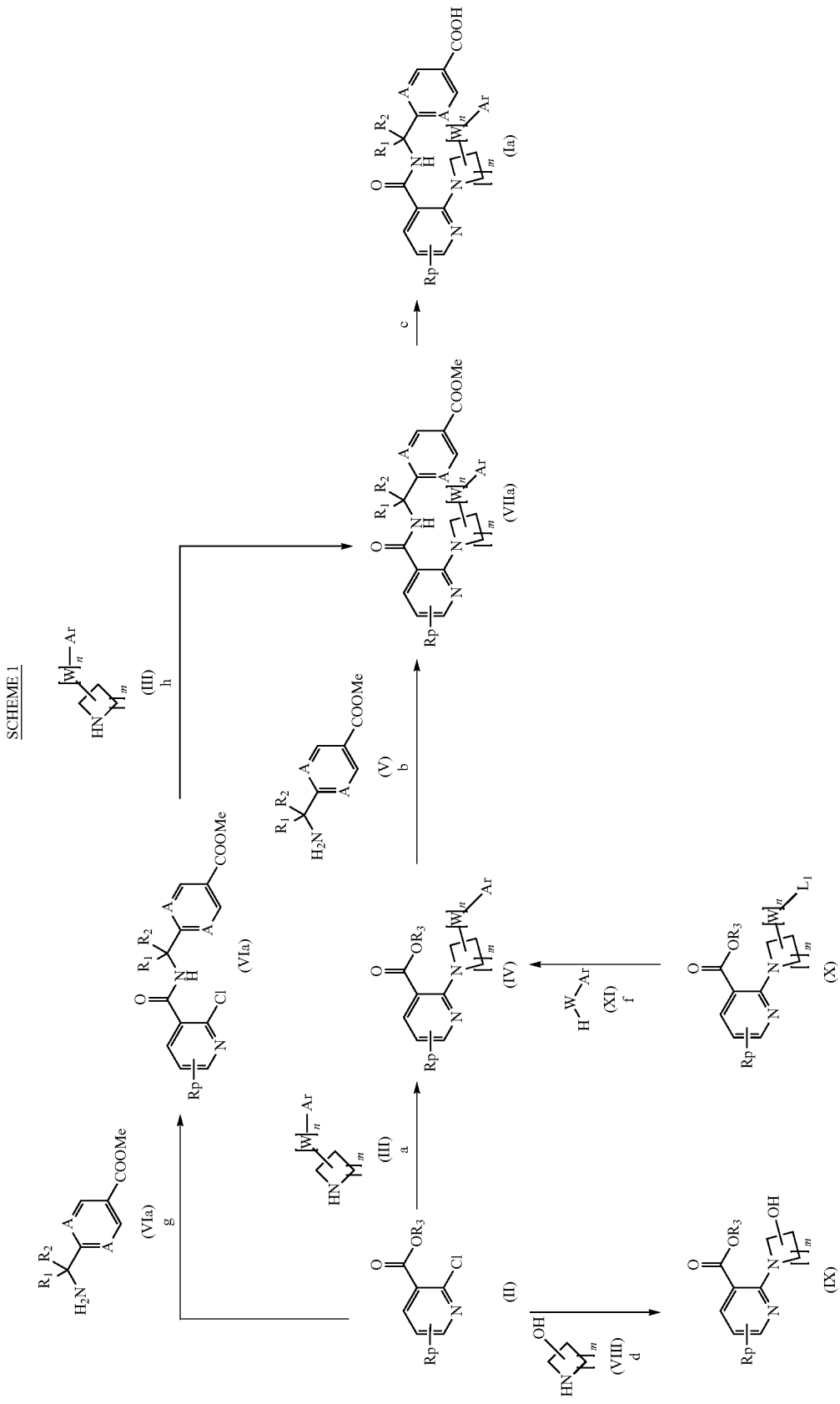
SCHEME 1 a') reacting a compound (II) with compound of (III) with suitable base thus obtaining a compound of Formula (IV);
b') reacting a compound of Formula (IV) or the corresponding acyl chlorides RCOCl with a compound of formula (V) in the presence of coupling reagents in the presence of a base thus obtaining a compound of Formula (VII);
c') hydrolising an ester compound (Via) with strong bases in 1,4-dioxane/H2O, thus obtaining a compound of Formula (Ia);
d') reacting a compound (II) with compound of (VIII) with suitable base thus obtaining a compound of Formula (VIII);
e') converting a free hydroxy group of compound (IX), in presence of a suitable base, into a suitable leaving group L1, thus obtaining compound (X);
f') reacting a compound of formula (X) with a compound of formula (XI) in presence of a base, thus obtaining a compound of formula (IV);
g') reacting a compound of formula (II) with a compound of formula (Va) in the presence of coupling reagents in the presence of a base thus obtaining a compound of Formula (VIa); and
h') reacting a compound of formula (VIa) with compound of (III) with suitable base thus obtaining a compound of Formula (Ia).

A further aspect of this invention concerns a process for the preparation of a compound of Formula (Ib), when E is the group B, W is selected from the group consisting of O, NH and N(C1-C3)alkyl and n is 1, comprising the following steps represented in the scheme below (Scheme 2):

in the presence of coupling reagents in the presence of a base thus obtaining a compound of Formula (VIIa);
c") converting a compound (VIIa) in a compound of Formula (Ib).

It will be appreciated that compounds of formula (I), (Ia), and (IV), may be converted into other compounds of formula (I), (Ia), and (IV), by synthetic methods known to the skilled person in the art.

Examples of such conversion reactions are:
i) compounds of formula (IV), when R3 is H, may be prepared by hydrolysis of the corresponding compounds, wherein R3 is (C1-C3) alkyl. The hydrolysis is carried out in the presence of a base (e.g lithium hydroxide) in aqueous 1,4-dioxane at a high temperature and/or by application of microwaves.
ii) compounds of formula (I) when E is COOH may be prepared by hydrolysis of the corresponding compounds wherein E is COO(C1-C3)alkyl. The hydrolysis is carried out in the presence of a base (e.g lithium hydroxide) in aqueous 1,4-dioxane at a high temperature and/or by application of microwaves.
iii) compounds of formula (I) when E is CONH2 may be prepared by amide formation reaction from the corresponding compounds wherein E is COOH by reacting the corresponding acyl chloride with ammonia in the presence of a base (triethylamine) in tetrahydrofuran at room temperature.

The invention concerns a compound of Formula (I) as medicament, in particular it concerns its use f for the treatment of pathologies where an antagonist of the EP4 receptor is needed, such as the treatment of acute and chronic pain,

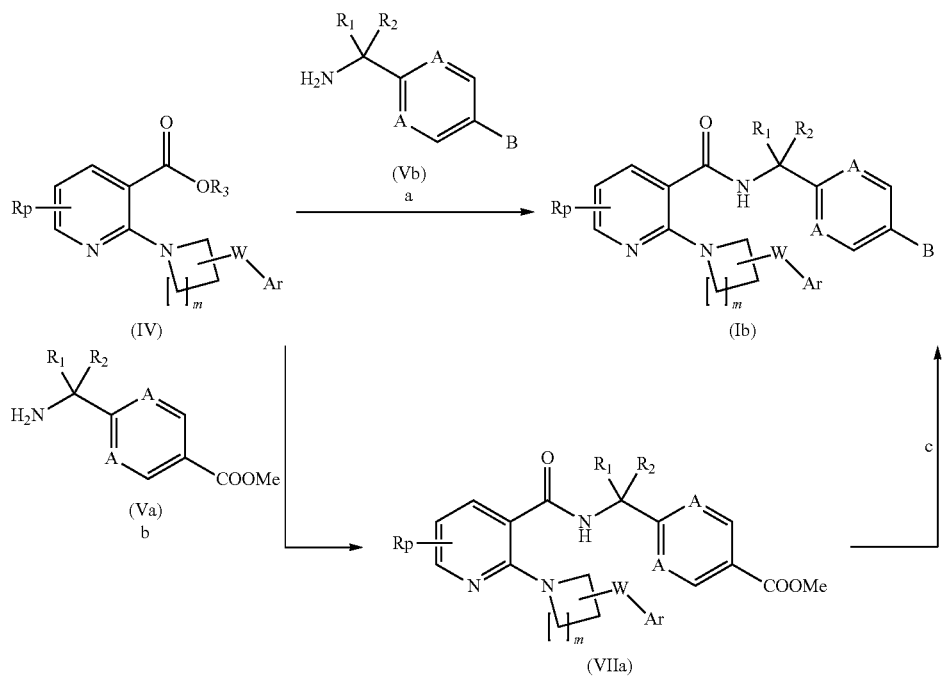

a") reacting a compound of Formula (IV) or the corresponding acyl chlorides RCOCl with a compound of formula (Vb) in the presence of coupling reagents and in the presence of a base thus obtaining a compound of Formula (Ib);
b") reacting a compound of Formula (IV) or the corresponding acyl chlorides RCOCl with a compound of formula (Va)

inflammatory pain, osteoarthritis, inflammation-associated disorder as arthritis, rheumatoid arthritis, cancer endometriosis and migraine.

In another aspect the invention concerns a compound of Formula (I) as medicament, in particular it concerns its use for the treatment of pathologies where an antagonist of the EP4 receptor is needed, such as the treatment of acute and chronic pain, inflammatory pain, osteoarthritis, inflammation-associated disorder as arthritis, rheumatoid arthritis, cancer endometriosis and migraine.

Compounds of the invention are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention are useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

Compounds of the invention are also useful in the treatment of immunological diseases such as autoimmune diseases, immunological deficiency diseases or organ transplantation. The compounds of the invention are also effective in increasing the latency of HIV infection.

Compounds of the invention are also useful in the treatment of diseases of abnormal platelet function (e.g. occlusive vascular diseases).

Compounds of the invention are also useful for the preparation of a drug with diuretic action.

Compounds of the invention are also useful in the treatment of impotence or erectile dysfunction.

Compounds of the invention are also useful in the treatment of bone disease characterized by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis. In a further aspect compounds of the invention may be useful in inhibiting bone resorption and/or promoting bone generation.

Compounds of the invention are also useful for attenuating the hemodynamic side effects of NSAIDs and COX-2 inhibitors.

Compounds of the invention are also useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

Compounds of the invention are also useful in the treatment of neurodegenerative diseases and neurodegeneration such as dementia, particularly degenerative dementia (including senile dementia, Alzheimer's disease, Pick's disease, Huntingdon's chores, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of Formula (I), (Ia) and (Ib) are also useful in the treatment of neuroprotection and in the treatment of neurodegeneration following stroke, cardiac arrest, pulmonary bypass, traumatic brain injury, spinal cord injury or the like. Compounds of the invention are also useful for the treatment of stroke and multiple sclerosis.

Compounds of the invention are also useful in the treatment of tinnitus.

Compounds of the invention are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

Compounds of the invention are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

Compounds of the invention are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

Compounds of the invention are also useful for treating or preventing a neoplasia in a subject in need of such treatment or prevention. The term "treatment" includes partial or total inhibition of the neoplasia growth, spreading or metastasis, as well as partial or total destruction of the neoplastic cells and/or symptoms associated with neoplasia including pain, anorexia or weight loss. The term also includes the use of compounds as sensitizing agents for other chemotherapies. The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia. The term "subject" for purposes of treatment includes any human or mammal subject who has any one of the known neoplasias, and preferably is a human subject. For methods of prevention, the subject is any human or animal subject, and preferably is a human subject who is at risk for obtaining a neoplasia. The subject may be at risk due to exposure to carcinogenic agents, being genetically predisposed to have the neoplasia, and the like. The term "neoplasia" includes both benign and cancerous tumors, growths and polyps. Thus, the compounds of the invention are useful for treating or preventing benign tumors, growths and polyps including squamous cell papilloma, basal cell tumor, transitional cell papilloma, adenoma, gastrinoma, cholangiocellular adenoma, hepatocellular adenoma, renal tubular adenoma, oncocytoma, glomus tumor, melanocyte nevus, fibroma, myxoma, lipoma, leiomyoma, rhabdomyoma, benign teratoma, hemangioma, osteoma, chondroma and meningioma. The compounds of the invention are also useful for treating or preventing cancerous tumors, growths and polyps including squamous cell carcinoma, basal cell carcinoma, transitional cell carcinoma, adenocarcinoma, malignant gastrinoma, cholangiocelleular carcinoma, hepatocellular carcinoma, renal cell carcinoma, malignant melanoma, fibrosarcoma, myxosarcoma, liposarcoma, leimyosarcoma, rhabdomyosarcoma, malignant teratoma, hemangiosarcoma, Kaposi sarcoma, lymphangiosarcoma, ostreosarcoma, chondrosarcoma, malignant meningioma, non-Hodgkin lymphoma, Hodgkin lymphoma and leukemia. For purposes of this specification, "neoplasia" includes brain cancer, bone cancer, epithelial cell-derived neoplasia (epithelial carcinoma), basal cell carcinoma, adenocarcinoma, gastrointestinal cancer such as lip cancer, mouth cancer, esophogeal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that affect epithelial, mesenchymal or blood cells throughout the body. The compounds of the invention are useful for treating or preventing any of the aforementioned cancers. The compounds of the invention are useful for treating or preventing benign and cancerous tumors, growths and polyps of the following cell types: squamous epithelium, basal cells, transitional epithelium, glandular epithelium, G cells, bile ducts epithelium, hepatocytes, tubules epithelium, melanocytes, fibrous connective tissue, cardiac skeleton, adipose tissue, smooth muscle, skeletal muscle, germ cells, blood vessels, lymphatic vessels, bone, cartilage, meninges, lymphoid cells and hematopoietic cells. The compounds can be used to treat subjects having adenomatous polyps, including those with familial adenomatous polyposis (FAP). Additionally, the compounds can be used to prevent polyps from forming in patients at risk of FAP. Preferably, the compounds of the invention are useful for treating or preventing the following cancers: colorectal, esophagus stomach, breast, head and neck, skin, lung, liver, gall bladder, pancreas, bladder, endometrium cervix, prostate, thyroid and brain.

It is to be understood that reference to treatment includes both treatment of established symptoms and prophylactic treatment, unless explicitly stated otherwise.

In another aspect the invention concerns pharmaceutical compositions comprising a compound of Formula (I) and a pharmaceutically acceptable carrier.

They could be used in combination with a pharmaceutically acceptable carrier and, optionally, with suitable excipients, to obtain pharmaceutical compositions. The term "pharmaceutically acceptable carrier" means solvents, carrier agents, diluting agents and the like which are used in the administration of compounds of the invention. Such pharmaceutical compositions can be administered by parenteral, oral, buccal, sublingual, nasal, rectal, topical or transdermal administration. Compositions of this invention suitable for the oral administration will be conveniently discrete units such as tablets, capsules, cachet, powders or pellets, or as liquid suspension.

The tablets can contain also suitable excipients routinely used in pharmaceutical field such as pre-gelatinised starch, microcrystalline cellulose, sodium glycolate starch, talc, lactose, magnesium stearate, sucrose, stearic acid, mannitol.

Compositions for parenteral administration conveniently include sterile preparations.

Compositions for topical administration may conveniently be formulated as creams, pastes, oils, ointments, emulsions, foams, gels, drops, spray solutions and transdermal patches.

The compounds of the invention could be used for manufacturing a medicament for the treatment of pathologies which require the use of an antagonist of the EP4 receptor, such as the treatment of inflammatory pain, osteoarthritis, arthritis.

Method of Synthesis

As above shown, according to a further aspect of this invention there is provided a process for the preparation of compound of formula (I), and (Ia) and (Ib). In a more detailed way, the compounds of the present invention may be prepared according to the following schemes. Unless otherwise indicated R1, R2, R3, Rp, W, and Ar in the reaction schemes and discussion that follow are defined above. The term "protecting group", as used hereinafter, means a hydroxyl or amino protecting group which is selected from typical Hydroxy or amino protecting groups as described in Protective Groups in Organic Synthesis edited by T. W. Greene et al. (John Wiley & Sons, 1999);

Compounds of formula (Ia) may be prepared by hydrolysis reaction of ester compounds of formula (VIIa) according to the reaction scheme 3.

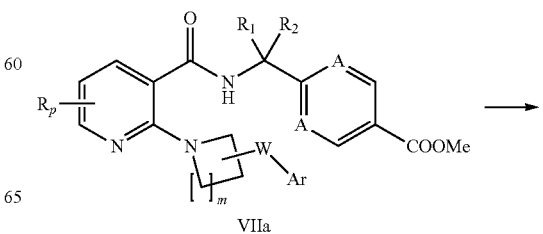

SCHEME 3

VIIa

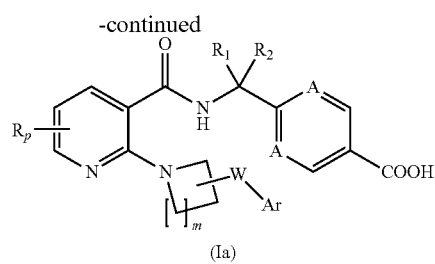

Hydrolysis can be carried out in presence of a base (e.g lithium hydroxide) in aqueous 1,4-dioxane as solvents. This reaction may be carried out at room temperature or at high temperature and/or by application of microwaves.

Compounds of formula (VIIa) may be prepared according to reaction scheme 4.

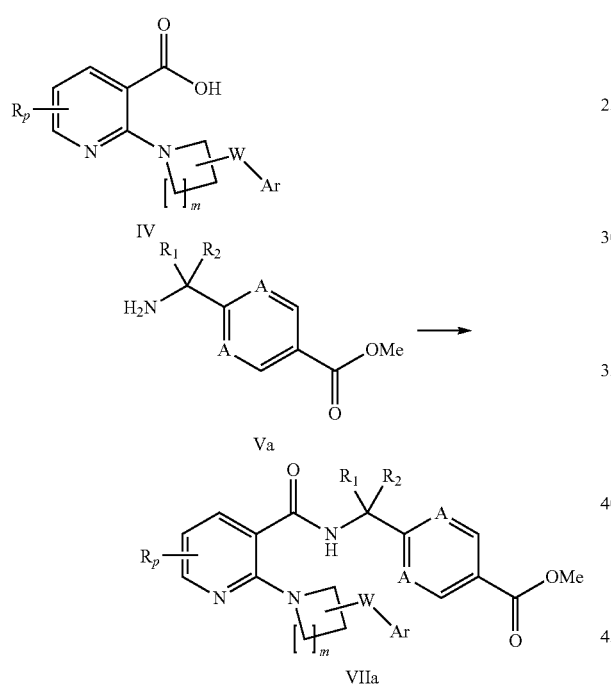

Compounds of formula (IV) are reacted with compounds of formula (Va) in the presence of a suitable coupling reagent, such as (Benzotriazol-1-yloxy)tripyrrolidinophosphonium hexafluorophosphate (PyBOP), (1-Ethyl-3-(3-dimethylaminopropyl)carbodiimide hydrochloride) and 1-Hydroxybenzotriazole.

The reaction is carried out in an aprotic solvent (such as a halohydrocarbon, e.g. dichloromethane, N,N-dimethylformamide, or acetonitrile) at room temperature, or mixture thereof) in presence of a suitable base (such as triethylamine).

Compounds of formula (Va) wherein A is C are either commercially available or known (See published International Patent application WO 2005/105733 and WO2008/104055) or may be prepared in a similar procedure to those described in WO 2005/105733 WO2008017164 and WO2008/104055.

Compounds of formula (Va) wherein at least one A is N may be prepared according to reaction scheme 5

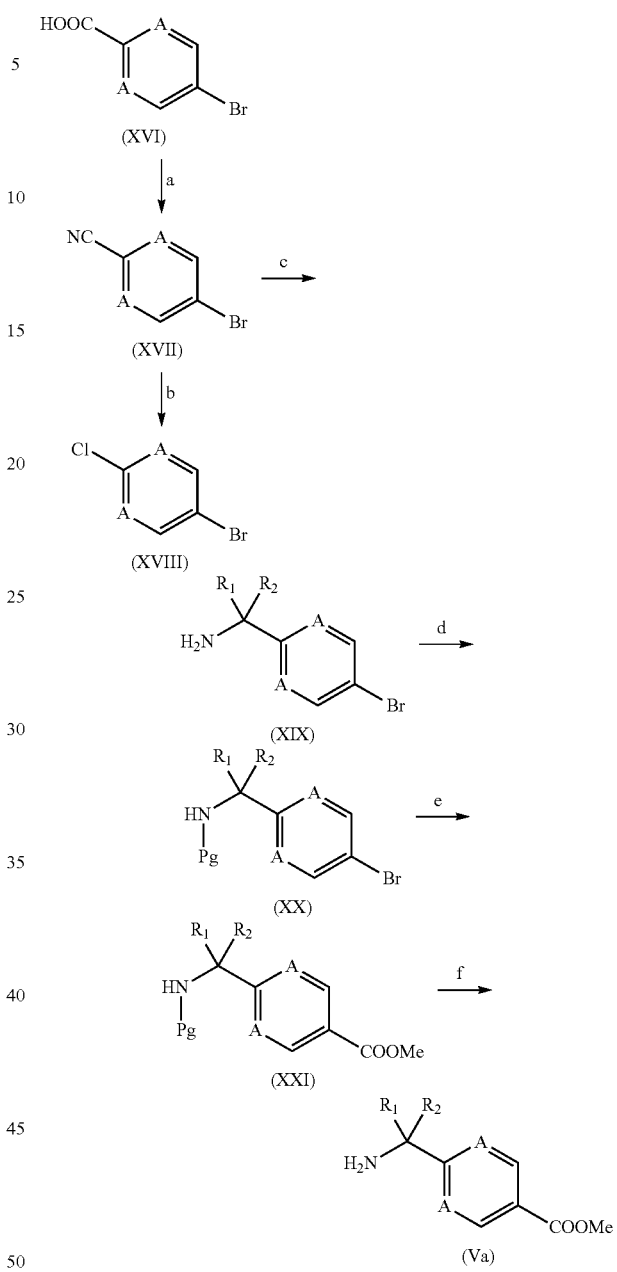

compounds of formula (XVII) when only one A is N may be prepared by transformation of carboxylic acid group in compound (XVI) into a cyano group of compound (XVII) through the preparation of the corresponding amide derivative and subsequent reduction to cyano derivative as reported in step a of scheme 5.

compounds of formula (XVII) when both A are N may be prepared by substitution of the chloro group with cyano group of compound (XVII) 5.

compounds of formula (XIX) are prepared starting from compound (XVII) via Kulinkovich-SzymoniaK reaction using appropriate Grignard reagent in presence of titanium isopropoxide followed by exposure to Lewis acid in a subsequent step.

In the above scheme 5, Pg represents an appropriate protecting group such as Boc. Compound of formula (XX) are prepared by reacting compound of formula (XIX) with an appropriate protecting agent such as di-tert-butyl dicarbonate in presence of a base.

compounds of formula (XXI) may be prepared by carbonylation of the corresponding bromo derivatives (XX) and subsequent ester formation.
having protected the amine with the appropriate protecting group (Pg) as in compound of formula (XX).

compounds of formula (Va) may be prepared by deprotection of amine group of compound of formula (XXI) in presence of hydrochloric acid in ethylylacetate as solvent Alternatively compound of formula (VIIa) may be prepared according to reaction scheme 6 with a reaction sequence starting from compound of formula (II).

SCHEME 6

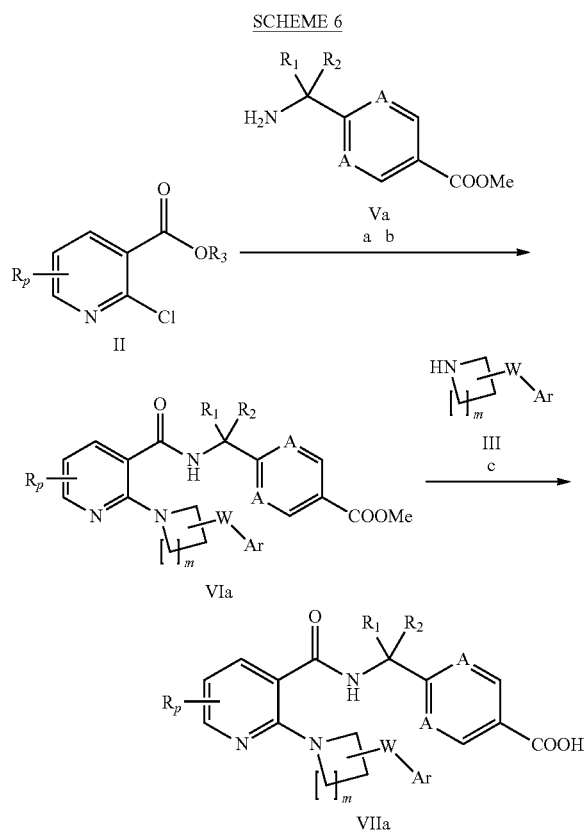

Reaction conditions for the first step of the sequence are hydrolysis reaction of compounds of formula (II) carried out in presence of a base (e.g lithium hydroxide) in a mixture of organic solvents such as dioxane/water. This reaction may be carried out at room temperature or, preferably, at high temperature and/or by application of microwaves.

Reaction for the second step is the reaction of compounds of formula (II) wherein R3 is H with compounds of formula (Va) in the presence of a suitable coupling reagent, such as (Benzotriazol-1-yloxy)tripyrrolidinophosphonium hexafluorophosphate (PyBOP), (1-Ethyl-3-(3-dimethylaminopropyl)carbodiimide hydrochloride) and 1-Hydroxybenzotriazole.

The reaction is carried out in an aprotic solvent (such as a halohydrocarbon, e.g. dichloromethane, N,N-dimethylformamide, or acetonitrile) at room temperature, or mixture thereof) in presence of a suitable base (such as triethylamine).

Reaction for the third is the reaction of compounds of formula (VIa) with compound of formula (III) in presence of a suitable base (such as triethylamine), in a suitable solvent (tetrahydrofuran/methanol mixture) heating at reflux.

Compounds of formula (IV) wherein R3 is H, may be prepared by hydrolysis reaction of related ester compounds of formula (IV) wherein R3 is (C1-C3)alkyl, according to the reaction scheme 7.

SCHEME 7

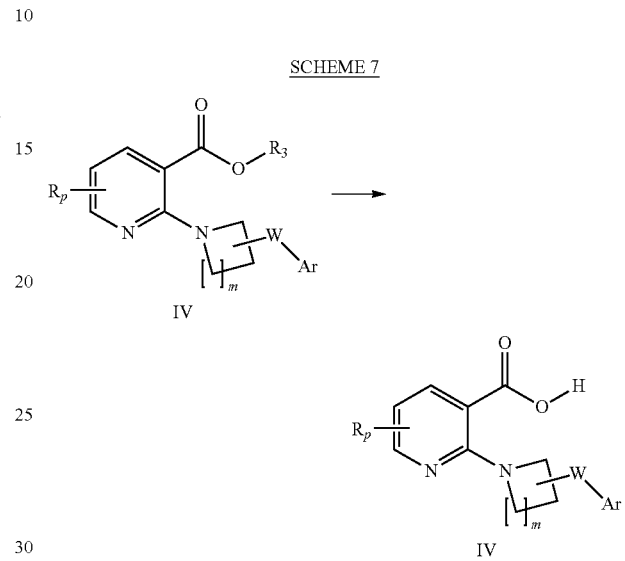

Hydrolysis is carried out in presence of a base (e.g lithium hydroxide) in aqueous 1,4-dioxane as solvents at high temperature and/or by application of microwaves.

Compound of formula (IV) wherein R3 is (C1-C3)alkyl, may be prepared according to scheme 8.

SCHEME 8

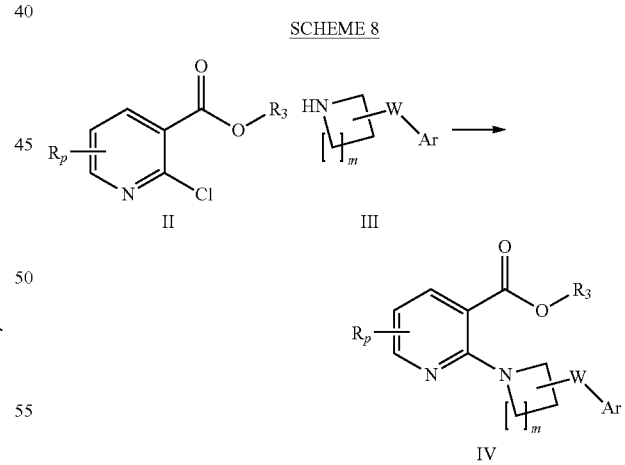

Compounds of formula (II), are reacted with compound of formula (III) in presence of a suitable base (such as triethylamine, diisopropylethylamine). The reaction is preferably carried out in alcohols as solvent (such as methanol, ethanol) heating at high temperature by application of microwaves.

Alternatively compound of formula (IV) may be prepared according to reaction scheme 9 with a reaction sequence starting from compound of formula (II).

SCHEME 9

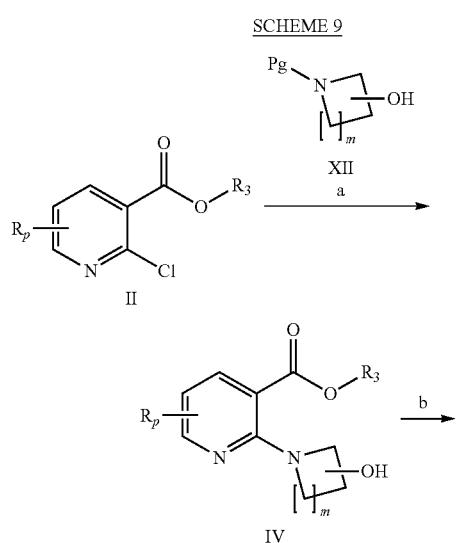

Preferred reaction condition for the first step of the sequence are reactions of compound of formula (II) with commercially available amino alcohols of formula (XII) in presence of a suitable base (such as triethylamine), heating at high temperature by application of microwaves, in suitable solvents (such as methanol), thus obtaining compounds of formula (IX).

Preferred reaction for the second step include the use of methanesulfonyl chloride, more preferably at 0° C., in presence of a suitable base (such as triethylamine) in a suitable organic solvent (such as dimethylformamide) to convert the free hydroxy group of compounds of formula (IX) into a leaving group L1 (described as above) of compounds of formula (X). Compounds (IV) are obtained in the third step by reaction of compound of formula (X) with compound of formula H—W—Ar in presence of a suitable base (such as potassium carbonate), heating at high temperature by application of microwaves, in a suitable solvent (such as acetonitrile).

Compounds of formula (III) may be prepared according to scheme 10.

SCHEME 10

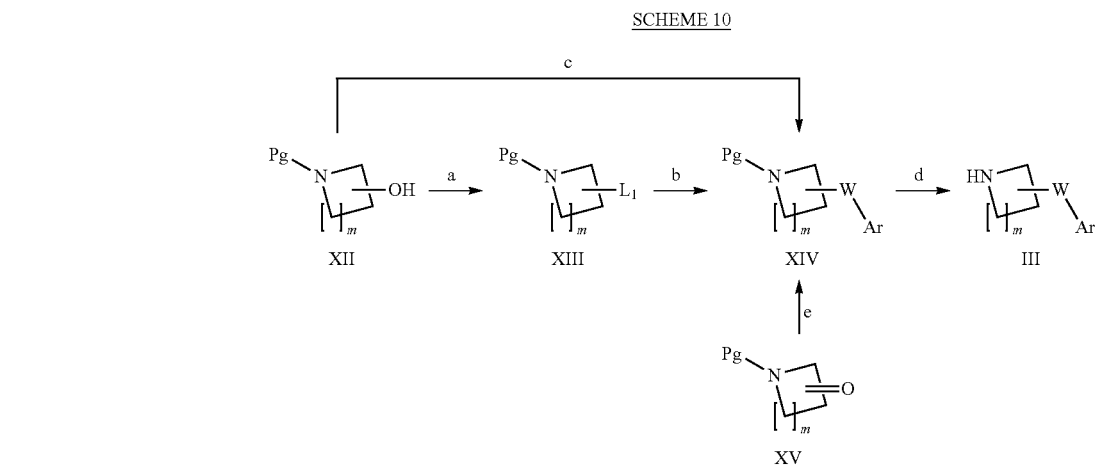

Step (a) is the conversion of free hydroxy group of compound of formula (XII) into an appropriate leaving group L1 of compounds of formula (XIII). Examples of suitable leaving group L1 include sulfonic esters such as TfO (triflates), MsO (mesilates) and TsO (tosylates). The reaction preferably include the use of appropriate sulfonyl chloride, more preferably at 0° C., in presence of a suitable base (such as triethylamine) and in a suitable organic solvent (such as toluene).

When W is O, preferred reaction for step (b), include the reaction of compounds of formula (XIII) with appropriate substituted phenols, in presence of a suitable base (such as potassium carbonate) and in a suitable organic solvent (such as acetonitrile) thus obtaining compounds of formula (XIV) when W is NH.

When m is 2 and W is O, compounds of formula (XIV) may be prepared by direct conversion of compounds of formula (XII) into compounds of formula (XIV) as reported in step (c) (scheme 9).

Reaction in step (c) is the reaction of compounds of formula (XII) with a substituted phenol in presence of diisopropyl azodicarboxylate and triphenylphosphine in a suitable solvent, (such as tetrahydrofuran), preferably at room temperature.

When m is 1 and W is NH, a number of compounds of formula (XIV) may be prepared by conversion of compound of formula (XV) into compounds of formula (XIV) as reported in step (e) (scheme 10). Step (e) is the reaction of compounds of formula (XV) with a substituted amine in presence of a suitable reducing agent, such as sodium cyanoborohydride in presence of acetic acid and in a suitable solvent, (such as dichloroethane), preferably at room temperature.

Step (d) is the deprotection of aminic group of compounds of formula (XIV) according to suitable standard techniques well known to those skilled in the art, thus obtaining deprotected amin compounds of formula (IIIa).

According to the invention, the compounds are obtained using a simple process, easy to scale-up and avoiding lengthy and expensive preparation steps, obtaining high yield of a stable pharmaceutical grade compound.

The various methods described above may be useful for the introduction of the desired group at any stage in the stepwise formation of the required compound, and it will appreciated that these general methods can be combined in different way in such multi-stage processes. The sequence of the reactions in multi-stage processes should of course chosen so that the reaction conditions used do not affect groups in the molecule which are in the final product.

The invention will be now detailed by means of the following examples relating to the preparation of some invention compounds and to the evaluation of their activity against EP4 receptor.

The following Descriptions relating to intermediate products and Examples illustrating the preparation of certain compounds of formula (Ia) and (Ib) or salts thereof follow below. The descriptions illustrate the preparation of intermediates used to make compounds of formula (Ia) and (Ib) or salts thereof.

In the procedures that follow, after each starting material, reference to a description is provided. This is provided merely for assistance to the skilled chemist. The starting material may not necessarily have been prepared from the Description referred to. The stereochemistry of Descriptions and Examples has been assigned on the assumption that the absolute configuration centers are retained.

The yields are calculated assuming that products were 100% pure if not stated otherwise.

Compound are named using ChemBioDraw Ultra 12.0 (CambridgeSoft Corp., 100 CambridgePark Drive, Cambridge, Mass. 02140)

Reagents used in the following examples were commercially available from various suppliers (for example Sigma-Aldrich, Acros, Matrix scientific, Manchester or Apollo) and used without further purifications.

Reactions in anhydrous environment were run under a positive pressure of dry N2 and solvents were used in dry form.

For reaction involving microwave irradiation, an Initiator 2.5 System was used.

Purification was performed using Biotage automatic flash chromatography systems (Sp1 and Isolera systems), Companion CombiFlash (ISCO) automatic flash chromatography, Flash Master or Vac Master systems.

Flash chromatography was carried out on silica gel 230-400 mesh (supplied by Merck AG Darmstadt, Germany), Varian Mega Be-Si pre-packed cartridges, pre-packed Biotage silica cartridges (e.g. Biotage SNAP-Si cartridges), Waters PoraPak RXN RP cartridges, Biotage SNAP-C18.

SPE-Si cartridges are silica solid phase extraction columns.

PoraPakRXN RP cartridges are polimer based reverse phase resin.

Biotage SNAP C18 Gold cartridges are silica based reverse phase column.

SPE-SCX cartridges are ion exchange solid phase extraction columns supplied by Varian. The eluent used with SPE-SCX cartridges is dichloromethane and methanol or only methanol followed by 2N ammonia solution in methanol. The collected fractions are those eluted with ammonia solution in methanol.

Thin layer chromatography was carried out using Merck TLC plates Kieselgel 60F-254, visualized with UV light, aqueous permanganate solution, iodine vapours.

Proton Nuclear Magnetic Resonance (1H NMR) spectra were recorded on Bruker Avance 400 MHz instrument and on Bruker Avance III plus 400 MHz. TMS was used as internal standard. Chemical shifts are reported in ppm ($\delta$) using the residual solvent line as internal standard. Splitting patterns are designated as: s, singlet; d, doublet; t, triplet; q, quartet; m, multiplet; b, broad signal. The NMR spectra were recorded at temperature ranging from 25° C. to 90° C. When more than one conformer was detected the chemical shifts of the most abundant one is usually reported.

In the analytical characterisation of the described compounds "MS" refers to Mass Spectra taken by Direct infusion Mass or to a mass Spectra associated with peaks taken by UPLC/MS or HPLC/MS analysis, where the Mass Spectrometer used is as mentioned below.

Direct infusion Mass Spectra (MS) were run on a Ion Trap Thermo LCQ classic spectrometer, operating in positive ES (+) and negative ES (−) ionization mode using different columns and operating procedures listed below:

Phenomenex Gemini-NX C18 column (100×2 mm, 3 µm particle size), column T=35° C. Mobile phase: A (water+0.1% formic acid)/B (acetonitrile+0.1% formic acid), Gradient: 10% B at t=0 min up to 90% B at t=12 min using different gradient curves, flow rate: 0.3 ml/min;

Acquity™ UPLC-BEH C18 column (50×21 mm, 1.7 µM particle size), column T=35° C. Mobile phase: A (water+0.1% formic acid)/B (acetonitrile+0.1% formic acid), Gradient: 5% B at t=0 min up to 100% B at t=4.5 min, using different gradient curves, flow rate: 0.5 ml/min;

Zorbax SB C18 column (2.1×50 mm, 3.5 µm particle size) column T=35° C. Mobile phase: A (water+0.1% formic acid)/B (acetonitrile+0.1% formic acid), Gradient: 10% B at t=0 min up to 90% B at t=12 min using different gradient curves, flow rate: 0.4 ml/min.

HPLC spectra were performed on a Waters Alliance 2965 instrument equipped with a Waters 2996 UV-Vis detector using a Phenomenex Luna C18 column (150×4.6 mm, 5 µm particle size). [Mobile phase: different mixtures of acetonitrile/methanol/KH2PO4 (20 mM pH 2.5); Elution time: 35 min; column T=30° C.; flow rate=0.6 ml/min. UV detection wavelength range from 220 up to 300 nm]

Total ion current (TIC) and DAD UV chromatografic traces together with MS and UV spectra were taken on a UPLC/MS Acquity™ system equipped with 2996 PDA detector and coupled to a Waters Micromass ZQ™ Mass Spectrometer operating in positive or negative electrospray ionisation mode. UPLC analysis were performed using an Acquity™ UPLC-BEH C18 column (50×21 mm, 1.7 µM particle size), column T=35° C. Mobile phase: A (water+0.1% formic acid)/B (acetonitrile+0.1% formic acid), Gradient: 5% B at t=0 min, up to 100% B at t=2 min or 4.5 min using different gradient curves, flow rate: 0.5 ml/min.

LCMS were taken on a quadrupole Mass spectrometer on Agilent LC/MSD 1200 Series using Column: Welchrom XB- C18 (50×4.6 mm, 5 μm) operating in ES (+) or (−) ionization mode at T=30° C. and with a flow rate=1.5 ml/min.

HPLC spectra for chiral purity determinations were performed on Agilent 1200 instrument and UV detector DAD G1315D using a Daicel Chiralpack IC column (250×4.6 mm, 5 μm particle size) or a Daicel Chiralpack AD-H column (250×4.6 mm, 5 μm particle size). [Mobile phases: isocratic mixtures A (70% n-heptane 30% ethanol+0.1% trifluoroacetic acid) or B (80% n-hexane 20% isopropanol+0.2% trifluoroacetic acid), up to 60 min of elution at 30° C., flow rate of 0.5 ml/min].

Purifications by means of preparative chiral HPLC were performed on Shimadzu Preparative Liquid Chromatograph LC-8A apparatus and UV detector SPD-20A using a Daicel Chiralpack IC column (2×25 cm, 5 μm particle size) or a Daicel Chiralpack AD-H column (2×25 cm, 5 μm particle size).

[Mobile phases: isocratic premixed mixtures A (70% n-heptane 30% ethanol+0.1% trifluoroacetic acid) or B (80% n-hexane 20% isopropanol+0.2% trifluoroacetic acid).

Specific Mobile phase and operating conditions will be specified each time.

DESCRIPTIONS

Description 1: (S)-tert-butyl (1-(4-bromophenyl)ethyl)carbamate (D1)

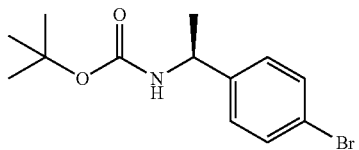 [SMILES: C[C@H](NC(=O)OC(C)(C)C)c1ccc(Br)cc1]

A mixture of (S)-(−)-1-(4-Bromophenyl)ethylamine hydrochloride (9 g, 38.0 mmol, available from Bepharm Ltd #B157615), di-tert-butyl dicarbonate (8.72 g, 1.05 mmol), and triethylamine (16 ml, 114 mmol) in dichloromethane (120 ml) was stirred at room temperature overnight. The mixture was diluted with dichloromethane (200 ml) and washed with water (100 ml). The organic solution was dried over $Na_2SO_4$ and solvents were evaporated in vacuo to afford the title compound (D1) (12.7 g) as a white solid.

$^1$H NMR (400 MHz, CHLOROFORM-d) δ (ppm): 7.47-7.42 (2H, m), 7.18 (2H, d, J=8.4 Hz), 5.30 (2H, br s), 1.41 (12H, br s).

Description 2: (S)-methyl 4-(1-((tert-butoxycarbonyl)amino)ethyl)benzoate (D2)

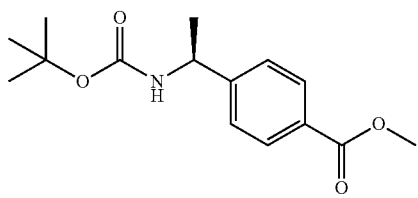 [SMILES: COC(=O)c1ccc([C@H](C)NC(=O)OC(C)(C)C)cc1]

A mixture of (S)-tert-butyl (1-(4-bromophenyl)ethyl)carbamate (D1) (9.20 g, 27.3 mmol), 1,3-bis(diphenylphosphino)-propane (2.25 g, 5.46 mmol), palladium (II) acetate (1.22 g, 5.46 mmol), and triethylamine (11.5 ml, 81.9 mmol) in N,N-dimethylformamide/methanol (60 ml/60 ml) was stirred at 80° C. overnight under carbon monoxide atmosphere. After cooling to room temperature, the mixture was diluted with ether (300 ml) and washed with water (3×100 ml). The organic layer was dried over $Na_2SO_4$ and evaporated in vacuo. The residue was purified by flash chromatography on silica gel eluting with a mixture petroleum ether/ethyl acetate 5:1 to afford the title compound (D2) (6.72 g) as white solid.

$^1$H NMR (400 MHz, CHLOROFORM-d) δ (ppm): 8.00 (2H, d, J=8.4 Hz), 7.36 (2H, d, J=8.4 Hz), 4.83 (2H, br s), 3.91 (3H, s), 1.46-1.42 (12H, m).

Description 3: (S)-methyl 4-(1-aminoethyl)benzoate hydrochloride (D3)

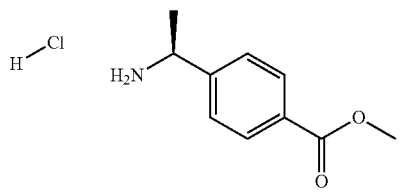

To a cooled solution of (S)-methyl 4-(1-((tert-butoxycarbonyl)amino)ethyl)benzoate (D2) (8.20 g, 29.4 mmol) in ethyl acetate (10 ml) HCl (g)/ethyl acetate (4N, 50 ml) was added and the resulting mixture was stirred at room temperature overnight. Solvents were evaporated in vacuo and the resulting residue was washed with petroleum ether to afford the title compound (D3) (5.7 g) as a white solid.

LCMS: (ES/+) m/z: 180 [MH$^+$] C10H13NO2 requires 179.09

$^1$HNMR (400 MHz, DMSO-d$_6$) δ (ppm): 8.86 (3H, br s), 7.99 (2H, d, J=8.4 Hz), 7.72 (2H, d, J=8.4 Hz), 4.48 (1H, br s), 3.86 (3H, s), 1.54 (3H, d, J=6.8 Hz).

Description 4: tert-butyl (1-(4-bromophenyl)cyclopropyl)carbamate (D4)

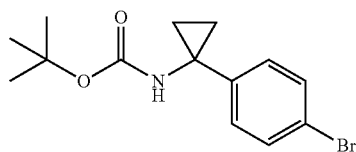

To the solution of 1-(4-bromophenyl)cyclopropanecarboxylic acid (40 g, 165 mmol, available from Amatek Chemical #AC-0350) in toluene (800 ml), in the presence of activated molecular sieves (15 g), N,N-diisopropylethylamine (27.5 g, 497 mmol), Diphenylphosphoryl azide (54.7 g, 215 mmol) and tert-Butanol (380 ml) were added. The resulting mixture was refluxed 5 hours. The mixture was cooled to room temperature and the solvents evaporated in vacuo. The residue was dissolved in ethyl acetate (200 ml) and washed with 5% citric acid (200 ml), aqueous NaHCO$_3$ (200 ml) and brine (200 ml). Collected organics after drying over $Na_2SO_4$ and solvent evaporation afforded a crude residue which was purified by flash chromatography on silica gel eluting with a mixture petroleum ether/ethyl acetate 4:1. Collected fractions after solvent evaporation afforded the title compound (D4) (23.0 g) as a solid.

¹H NMR (400 MHz, CHLOROFORM-d) δ (ppm): 7.39 (2H, d, J=8.0 Hz), 7.09 (2H, d, J=8.0 Hz), 5.27 (1H, s), 1.43-1.37 (9H, s), 1.19-1.28 (4H, m).

Description 5: methyl 4-(1-((tert-butoxycarbonyl)amino)cyclopropyl)benzoate (D5)

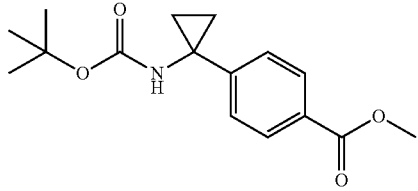

A mixture of tert-butyl (1-(4-bromophenyl)cyclopropyl) carbamate (D4) (2.6 g, 8.33 mmol), 1,3-bis(diphenylphosphine)-propane (680 mg, 0.83 mmol), Palladium(II) acetate (370 mg, 0.83 mmol) and triethylamine (2.52 g, 24.9 mmol) in dimethylformamide (40 ml) and methanol (60 ml) was stirred at 80° C. for 2 days under 4.0 Mpa CO atmosphere. The resulting mixture was cooled to room temperature and water was added. The mixture was extracted with diethylether (3×200 ml) and the collected organics were washed with water (500 ml) and brine (500 ml), dried (Na₂SO₄) and evaporated in vacuo. The residue was purified by flash chromatography on silca gel eluting with a mixture petroleum ether/ethyl acetate from 40:1 to 10:1. Collected fractions after solvent evaporation afforded the title compound (D5) (1 g).

¹H NMR (400 MHz, CHLOROFORM-d) δ (ppm): 7.95 (2H, d, J=8.8 Hz), 7.22 (2H, d, J=8.8 Hz), 3.90 (3H, s), 5.32 (1H, s), 1.45 (9H, s), 1.35-1.30 (4H, m).

Description 6: methyl 4-(1-aminocyclopropyl)benzoate (D6)

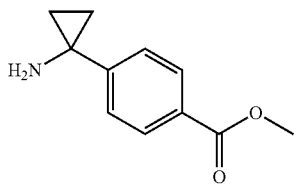

To the solution of methyl 4-cyanobenzoate (100 g, 620 mmol) in diethyl ether (3 L) was added titanium (IV) isopropoxide (194 g, 682 mmol), followed by dropwise addition of ethylmagnesium bromide 3M solution in diethylether (450 ml, 1.36 mol) at −70° C. The mixture was stirred for 1 h, and then boron trifluoride etherate (157 ml, 1.24 mol) was added at once. After 2 hours, aqueous HCl (5%) was added until the pH showed acidy, then the mixture was filtered. The solid was washed with ethylacetate. The aqueous phase was separated and the organic layer was washed with water. All aqueous layers were collected together, basified with 1M NaOH and extracted with ethylacetate. The organic layer was dried (Na₂SO₄) and concentrated to afford the title compound (D6) (32.0 g).

¹H NMR (400 MHz, CHLOROFORM-d) δ (ppm): 7.97-7.98 (2H, m), 7.31-7.34 (2H, m), 3.90 (3H, s,), 1.15-1.18 (2H, m), 1.04-1.07 (2H, m).

Description 7: methyl 4-(1-aminocyclopropyl)benzoate hydrochloride (D7)

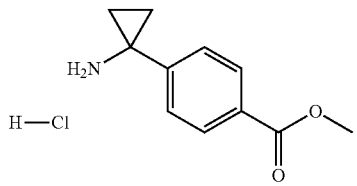

methyl 4-(1-aminocyclopropyl)benzoate hydrochloride (D7) was prepared according to two different procedures reported below:

Procedure A:

To a cooled solution of methyl 4-(1-((tert-butoxycarbonyl)amino)cyclopropyl)benzoate (D5) (7.4 g, 25.4 mmol) in ethyl acetate (10 ml) HCl (g)/ethyl acetate (4N, 50 ml) was added the mixture was stirred at room temperature overnight. Evaporated the solvent, the residue was washed with petroleum ether to afford the title compound (D7) (5.3 g) as a white solid.

Procedure B

To a cooled solution of methyl 4-(1-aminocyclopropyl)benzoate (D6) (100 g, 524 mmol) in ethyl acetate (500 ml) 4N HCl (g)/ethyl acetate solution (300 ml) was added and the resulting mixture was stirred at room temperature for 2 hours. Evaporated the solvent, the residue was recrystallized with petroleum ether/EtOAc to afford the title compound (D7) (68.7 g) as a white solid.

LCMS: (ES/+) m/z: 192 [MH⁺] C11H13NO2 requires 191.09

¹H NMR (400 MHz, CHLOROFORM-d) δ (ppm): 9.14 (3H, brs), 7.97 (2H, d, J=8.4 Hz), 7.53 (2H, d, J=8.4 Hz), 3.87 (3H, s), 1.53-1.49 (2H, m), 1.28-1.31 (2H, m).

Description 8: 5-bromopicolinamide (D8)

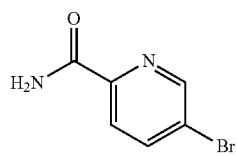

5-bromopicolinic acid (50 g, 0.247 mol) was added to thionyl chloride (100 ml) and the reaction mixture was heated to reflux for 3 hours. The resulting solution was cooled to room temperature and then concentrated in vacuo to afford a white solid. The white solid was dissolved in THF (200 ml) and the solution was added dropwise into a mixture of ice/ammonia/water (500 ml). The solid was filtered, washed with water and dried in vacuo. The crude was purified by recrystallization in ethyl acetate to afford the title compound (D8) (43.0 g) as a white solid.

¹HNMR (400 MHz, DMSO-d6) δ (ppm): 7.73 (s, 1H), 7.97 (d, J=8.0 Hz, 1H), 8.14 (s, 1H), 8.24 (dd, J=6.0, 2.4 Hz, 1H), 8.76 (d, J=2.0 Hz, 1H).

Description 9: 5-bromopicolinonitrile (D9)

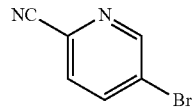

Phosphorus oxychloride (111 g, 0.720 mol) was added to a mixture of 5-bromopicolinamide (D8) (58 g, 0.288 mol) in dry toluene (300 ml) The mixture was heated to reflux for 2 hours. The mixture was poured into ice/water, and basified to pH=12 with 2N NaOH. The resulting mixture was extracted with ethyl acetate and the organic phase was washed with brine, dried over $Na_2SO_4$, and concentrated in vacuo. The residue was purified by column chromatography on silica gel eluting with a mixture petroleum ether/ethyl acetate 10:1. Collected fractions, after solvent evaporation afforded the title compound (D9) (43.6 g) as a yellow solid.

¹HNMR (400 MHz, CHLOROFORM-d) δ (ppm): 7.60 (d, J=8.4 Hz, 1H), 8.00 (dd, J=6.0, 2.0 Hz, 1H), 8.79 (d, J=2.0 Hz, 1H).

Description 10:1-(5-bromopyridin-2-yl)cyclopropanamine (D10)

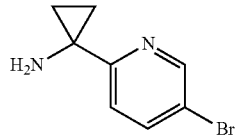 [SMILES: NC1(c2ccc(Br)cn2)CC1]

5-bromopicolinonitrile (D9) (43.6 g, 0.238 mol) was suspended in diethyl ether (1.3 L) and the resulting mixture was cooled to −78° C. Titanium (IV) isopropoxide (74.4 g, 0.262 mol) was added dropwise and the reaction mixture was stirred for 5 min. Ethylmagnesium bromide 1M in diethyl ether (525 ml, 0.525 mol) was added dropwise and the resulting reaction mixture was stirred for 30 mins at −78° C. The reaction mixture was allowed to warm to room temperature for 1 hour then boron trifluoride etherate (107 ml) was added dropwise. After stirred at room temperature for 2 hours, the reaction was quenched with 1M HCl (1.5 L). The aqueous layer was washed with diethyl ether (1 L) and then basified (pH=9) with 2N NaOH (1.25 L). The resulting mixture was extracted with ethyl acetate. The organic layer was dried over $Na_2SO_4$ and evaporated in vacuo. The residue was purified by column chromatography eluting with a mixture petroleum ether/ethyl acetate 1:1. Collected fractions after solvent evaporation afforded the title compound (D10) (15.7 g) as a grey solid.

¹HNMR (400 MHz, CHLOROFORM-d) δ (ppm): 1.13-1.20 (m, 2H), 1.26-1.29 (m, 2H), 7.30 (d, J=8.0 Hz, 1H), 7.71 (dd, J=6.0, 2.4 Hz, 1H), 8.51 (d, J=2.4 Hz, 1H).

Description 11: tert-butyl (1-(5-bromopyridin-2-yl) cyclopropyl)carbamate (D11)

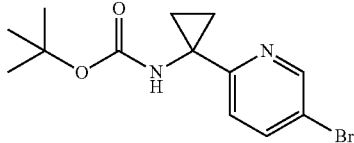 [SMILES: CC(C)(C)OC(=O)NC1(c2ccc(Br)cn2)CC1]

To a solution of 1-(5-bromopyridin-2-yl)cyclopropanamine (D10) (15.7 g, 66.6 mmol) in methanol (350 ml) and water (110 ml) $NaHCO_3$ (16.8 g, 200 mmol) was added followed by addition of and di-tert-buthyl dicarbonate (17.5 g, 79.9 mmol). The reaction mixture was stirred at room temperature overnight. The mixture was concentrated in vacuo and the residue was poured into water (200 ml). The aqueous layer was extracted with ethyl acetate; the organic layer was washed with brine, dried over $Na_2SO_4$, and concentrated in vacuo. The residue was purified by column chromatography eluting with a mixture petroleum ether/ethyl acetate (10:1). Collected fractions after solvent evaporation afforded the title compound (D11) (18 g) as a yellow solid.

¹HNMR (400 MHz, CHLOROFORM-d) δ (ppm): 1.22-1.26 (m, 2H), 1.37-1.46 (m, 9H), 1.57-1.60 (m, 2H), 7.28 (s, 1H), 7.70 (dd, J=6.0, 2.4 Hz, 1H), 8.47 (d, J=2.0 Hz, 1H).

Description 12: methyl 641-((tert-butoxycarbonyl) amino)cyclopropyl)nicotinate (D12)

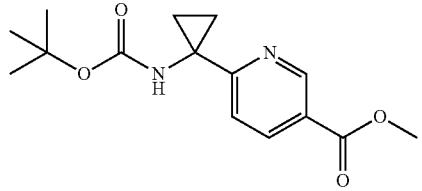 [SMILES: COC(=O)c1ccc(C2(NC(=O)OC(C)(C)C)CC2)nc1]

To a solution of tert-butyl (1-(5-bromopyridin-2-yl)cyclopropyl)carbamate (D11) (18.0 g, 57.5 mmol) in N,N-dimethylformamide (80 ml) and methanol (90 ml) 1,3-bis(diphenylphosphino)-propane (7.1 g, 17.2 mmol), palladium (II) acetate (3 g, 13.4 mmol) and triethylamine (40 ml, 285 mmol) were added. The resulting mixture was stirred at 100° C. for 3 days under carbon monoxide atmosphere (5.0 MPa). After cooling to room temperature, the mixture was diluted with ethyl acetate and washed with brine. The organic layer was dried over $Na_2SO_4$ and concentrated in vacuo. The residue was purified by column chromatography eluting with a mixture petroleum ether/ethyl acetate (4:1). Collected fractions after solvent evaporation afforded the title compound (D12) (15.3 g) as a white solid.

¹HNMR (400 MHz, CHLOROFORM-d) δ (ppm): 1.26-1.48 (m, 13H), 3.92 (s, 3H), 7.44 (d, J=8.0 Hz, 1H), 8.20 (dd, J=6.4, 2.0 Hz, 1H), 9.03 (d, J=1.2 Hz, 1H).

Description 13: methyl 6-(1-aminocyclopropyl)nicotinate hydrochloride (D13)

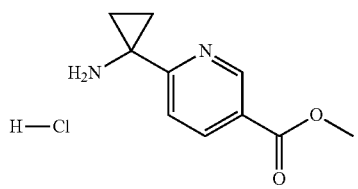

To the cooled solution of methyl 6-(1-((tert-butoxycarbonyl)amino)cyclopropyl)nicotinate (D12) (1 g, 3.42 mmol) in ethyl acetate (10 ml) 4N HCl/ethyl acetate solution (20 ml) was added and the resulting mixture was stirred at room temperature for 1 hour. The mixture was filtered and washed with ethyl acetate to afford the title compound (D13) (800 mg) as a white solid.

$^1$HNMR (400 MHz, DMSO-$d_6$) δ (ppm): 1.48-1.52 (t, 2H), 1.65-1.68 (t, 2H), 3.89 (s, 3H), 7.52 (d, J=8.4 Hz, 1H), 8.31 (dd, J=6.4, 2.0 Hz, 1H), 9.02 (d, J=1.2 Hz, 1H), 9.29 (s, 3H).

LCMS: (ES/+) m/z: 193 [MH$^+$] C10H12N2O2 requires 192.09

Description 14: 4-(1-aminocyclopropyl)benzonitrile (D14)

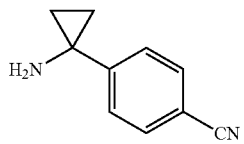 [SMILES: N#Cc1ccc(C2(N)CC2)cc1]

To a solution of terephthalonitrile (3.30 g, 25.8 mmol.) in dichloromethane (130 ml), Titanium (IV) isopropoxide (7.6 ml, 25.8 mmol) was added at room temperature followed by dropwise addition of ethyl magnesium bromide 1M in diethyl ether (47.0 ml). The mixture was stirred at room temperature for 45 min, then boron trifluoride etherate (5 ml) was added at once. After 2 hours, HCl aqueous solution (5%) was added to quench the reaction. The aqueous phase was separated, basified with aqueous 1M NaOH and extracted with ethylacetate. The organic phase was dried over Na$_2$SO$_4$ and concentrated under vacuo. The residue was purified by column chromatography eluting with a mixture petroleum ether/ethyl acetate (5:1). Collected fractions after solvent evaporation afforded the title compound (D14) (500 mg) as a white solid.

$^1$H NMR (400 MHz, DMSO-$d_6$) δ (ppm): 1.01-1.10 (4H, m), 1.23 (2H, bs), 7.47 (2H, d, J=8.4 Hz), 7.72 (2H, d, J=8.4 Hz).

Description 15: tert-butyl (1-(4-cyanophenyl)cyclopropyl)carbamate (D15)

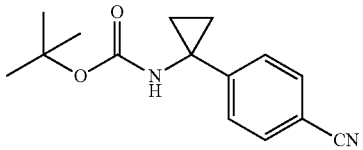 [SMILES: CC(C)(C)OC(=O)NC1(c2ccc(C#N)cc2)CC1]

To a solution of 4-(1-aminocyclopropyl)benzonitrile (D14) (2 g, 12.6 mmol.) in MeOH (30 ml) NaHCO$_3$ (30 ml, 10% aq) was added followed by di-tert-butyl dicarbonate (4.3 g, 19.7 mmol). The mixture was stirred at room temperature overnight. Water was added into the mixture and the mixture was extracted with ethylacetate (200 ml). The organic layer was separated, dried over Na$_2$SO$_4$, filtered and concentrated to give a residue which was purified by column chromatography eluting with a mixture petroleum ether/ethyl acetate (10:1). Collected fractions after solvent evaporation afforded the title compound (D15) (1.8 g).

$^1$H NMR (400 MHz, CHLOROFORM-d) δ (ppm): 1.17-1.38 (13H, m), 5.21 (2H, bs), 7.18 (2H, d, J=8.0 Hz), 7.50 (2H, d, J=8.0 Hz).

Description 16: tert-butyl (1-(4-(1H-tetrazol-5-yl)phenyl)cyclopropyl)carbamate (D16)

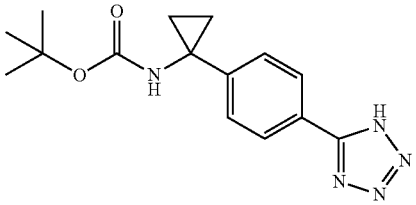 [SMILES: CC(C)(C)OC(=O)NC1(c2ccc(-c3nnn[nH]3)cc2)CC1]

To a solution of tert-butyl (1-(4-cyanophenyl)cyclopropyl)carbamate (D15) (1.5 g, 5.81 mmol) in dimethylformamide (15 ml), NH$_4$Cl (530 mg, 9.90 mmol) was added under nitrogen atmosphere, followed by addition of sodium azide (650 mg, 9.9 mmol). The reaction mixture was heated to 100° C. overnight, then cooled to room temperature with ice-water bath. Water and ethylacetate (100 ml) was added. The organic layer was separated and the solvent was removed. The residue was purified by column chromatography eluting with a mixture petroleum ether/ethyl acetate (1:1). Collected fractions after solvent evaporation afforded the title compound (D16) (830 mg) as a yellow solid.

$^1$H NMR (400 MHz, DMSO-$d_6$) δ (ppm): 1.21-1.40 (13H, m), 7.18 (2H, d, J=8.0 Hz), 7.77 (2H, bs), 7.95 (2H, d, J=8.0 Hz).

Description 17: 1-(4-(1H-tetrazol-5-yl)phenyl)cyclopropanamine hydrochloride (D17)

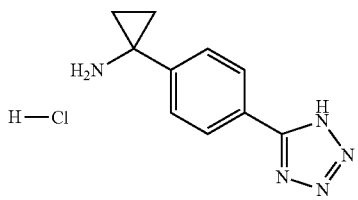 [SMILES: Cl ; NC1(c2ccc(-c3nnn[nH]3)cc2)CC1]

To the solution of tert-butyl (1-(4-(1H-tetrazol-5-yl)phenyl)cyclopropyl)carbamate (D16) (800 mg, 2.65 mmol) in ethylacetate (10 ml), 4N HCl/ethyl acetate solution (20 ml) was added and the mixture was stirred at room temperature for 1 hour, then cooled to 0° C. The solid was filtered and washed with ethylacetate to afford the title compound (D17) (510 mg) as a yellow solid.

$^1$H NMR (400 MHz, DMSO-$d_6$) δ (ppm): 1.23-1.42 (4H, m), 7.62 (2H, d, J=7.2 Hz), 8.10 (2H, d, J=8.0 Hz), 8.99 (3H, bs).

LCMS: (ES/+) m/z: 202 [MH$^+$] C10H11N5 requires 201.10

Description 18: tert-butyl 4-(3-hydroxyphenyl)piperazine-1-carboxylate (D18)

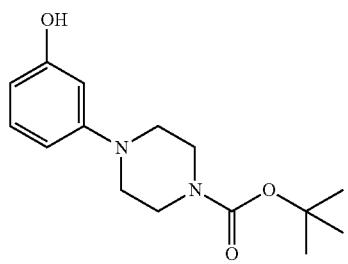 [SMILES: CC(C)(C)OC(=O)N1CCN(c2cccc(O)c2)CC1]

To a cooled (0° C.) solution of 1-(3-Hydroxyphenyl) piperazine (300 mg, 1.683 mmol, available from Aldrich #651672) and triethylamine (0.47 ml, 3.36 mmol) in tetrahydrofuran/water (3 ml/3 ml) Di-tert-butyl dicarbonate (440.6 mg, 2.019 mmol) was added and the reaction mixture was stirred 1 h at room temperature. The solution was diluted with ethylacetate (5 ml) and acidified to pH 5 by addition of 6N HCl. The phases were separated and the aqueous layer was extracted with ethylacetate (2×10 ml). Collected organics after solvent evaporation afforded a residue that was purified by SPE-Si cartridge (10 g) eluting with cycloexane/ethylacetate from 100 to 60/40. Collected fractions after solvent evaporation afforded the title compound (D18) (400 mg)

MS: (ES/+) m/z: 279.3 [MH$^+$] C15H22N2O3 requires 278.16

$^1$H NMR (400 MHz, CHLOROFORM-d) δ=7.14 (t, J=8.1 Hz, 1H), 6.52 (d, J=8.3 Hz, 1H), 6.43 (t, J=2.4 Hz, 1H), 6.37 (dd, J=2.4, 7.8 Hz, 1H), 5.05-4.98 (m, 1H), 3.65-3.54 (m, 4H), 3.19-3.09 (m, 4H), 1.51 (s, 9H)

Description 19: 1-benzhydrylazetidin-3-yl methanesulfonate (D19)

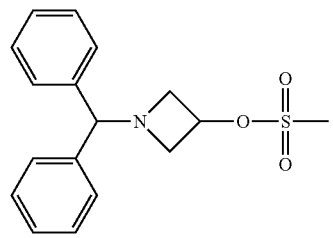 [SMILES: CS(=O)(=O)OC1CN(C(c2ccccc2)c2ccccc2)C1]

To a cooled solution of 1-Benzhhydrylazetidin-3-ol (3.5 g, 14.624 mmol, available from Manchester #A10473) and triethylamine (4.07 ml, 29.25 mmol) in toluene (21 ml) Methanesulfonyl chloride (1.13 ml, 14.62 mmol) was added dropwise keeping the temperature at 0° C. The reaction mixture was stirred 1 h at 0° C. then the solid was filtered off and washed with toluene (2×5 ml). The yellow filtrate was evaporated in vacuo to afford the title compound (D19) (5 g).

$^1$H NMR (400 MHz, CHLOROFORM-d) δ (ppm): 7.42 (d, J=7.3 Hz, 4H), 7.34-7.28 (m, 4H), 7.24-7.17 (m, 2H), 5.13 (quin, J=5.9 Hz, 1H), 4.43 (s, 1H), 3.71-3.58 (m, 2H), 3.27-3.19 (m, 2H), 3.00 (s, 3H)

Description 20: 1-benzhydryl-3-phenoxyazetidine (D20)

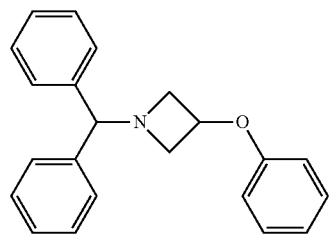 [SMILES: c1ccc(OC2CN(C(c3ccccc3)c3ccccc3)C2)cc1]

Phenol (2.2 g, 23.4 mmol) was added to a suspension of sodium hydride (60% dispersion in mineral oil, 937 mg, 23.4 mmol) in toluene (40 ml) and the mixture was heated at 60° C. for 2 hours. The temperature was then increased to 80° C. and a solution of 1-benzhydrylazetidin-3-yl methanesulfonate (D19) (4.78 g, 14.6 mmol) in toluene (80 ml) was added dropwise. After stirred at 80° C. for 2 hours, the resulting mixture was cooled to room temperature, then washed with water (100 ml) and brine (100 ml), dried over Na$_2$SO4, filtered and evaporated in vacuo. The crude residue was purified by flash chromatography on silica gel eluting with a mixture petroleum ether/ethyl acetate from 30:1 to 20:1. Collected fractions after solvent evaporation were further purified by preparative HPLC to afford the title compound (D20) (1.84 g) as a white solid.

$^1$H NMR (400 MHz, CHLOROFORM-d) δ (ppm): 7.42 (4H, d, J=7.6 Hz), 7.30-7.28 (3H, m), 7.23-7.18 (5H, m), 6.93

(1H, t, J=7.6 Hz), 6.75 (2H, d, J=8.4 Hz), 4.84-4.78 (1H, m), 4.44 (1H, s), 3.75-3.71 (2H, m), 3.14-3.11 (2H, m).

Description 21:
1-benzhydryl-3-(4-fluorophenoxy)azetidine (D21)

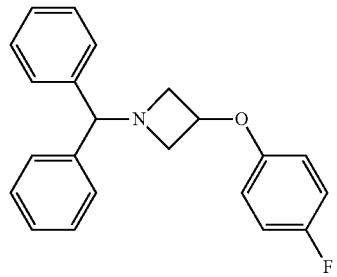 [SMILES: Fc1ccc(OC2CN(C(c3ccccc3)c3ccccc3)C2)cc1]

To a stirred solution of 4-fluorophenol (0.80 g, 7.16 mmol) in acetonitrile (15 ml) potassium carbonate (1.3 g, 9.30 mmol) was added followed by the addition of 1-benzhydry-lazetidin-3-yl methanesulfonate (D19) (2.5 g, 7.87 mmol) and the mixture was stirred under microwave irradiation at 100° C. for 5 mins. The reaction mixture was evaporated in vacuo and the residue was taken up in a mixture diethylether/water (10 ml/10 ml). The aqueous layer was extracted with diethylether (2×10 ml). The organics after solvent evaporation were loaded on SPE-Si (25 g) cartridge eluting with a mixture cyclohexane/ethylacetate (from 100/0 to 85/15. Collected fractions gave, after evaporation, the title compound (D21) (1.8 g).

MS: (ES/+) m/z: 334 [MH⁺] C22H20FNO requires 333.15

¹H NMR (400 MHz, CHLOROFORM-d) δ ppm: 7.44 (d, J=7.3 Hz, 4H), 7.34-7.27 (m, 4H), 7.26-7.15 (m, 2H), 6.88 (t, J=8.8 Hz, 2H), 6.48 (dd, J=4.4, 8.8 Hz, 2H), 4.41 (br. s., 1H), 4.09 (d, J=4.9 Hz, 1H), 3.86 (br. s., 1H), 3.68 (t, J=6.4 Hz, 2H), 2.90 (br. s., 2H)

Description 22:
1-benzhydryl-3-(3-fluorophenoxy)azetidine (D22)

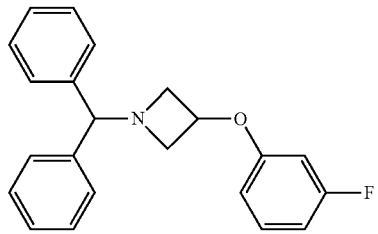 [SMILES: Fc1cccc(OC2CN(C(c3ccccc3)c3ccccc3)C2)c1]

The title compound (D22) (1.93 g) was prepared according to the experimental procedure described in Description 21 starting from 1-benzhydrylazetidin-3-yl methanesulfonate (D19) (2.5 g, 7.87 mmol) and 3-fluorophenol (0.642 ml, 7.16 mmol).

MS: (ES/+) m/z: 334.2 [MH⁺] C22H20FNO requires 333.40

¹H NMR (400 MHz, CHLOROFORM-d) δ (ppm): 7.45 (d, J=7.3 Hz, 4H), 7.40-7.16 (m, 8H), 6.67 (dt, J=2.2, 8.2 Hz, 1H), 6.56 (dd, J=2.0, 8.3 Hz, 1H), 6.53-6.46 (m, 1H), 4.81 (t, J=5.9 Hz, 1H), 4.46 (s, 1H), 3.80-3.70 (m, 2H), 3.22-3.10 (m, 2H)

Description 23: 2-((1-benzhydrylazetidin-3-yl)oxy)-5-fluoropyrimidine (D23)

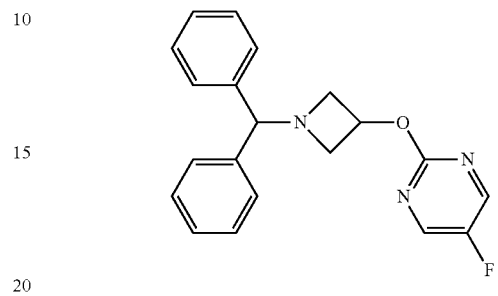

To an ice cooled suspension of 1-Benzhdrylazetidin-3-ol (1.2 g, 5.01 mmol) in dry tetrahydrofuran (40 ml) potassium tert-butoxide (562 mg, 5.01 mmol) was added and the reaction mixture was is stirred for 10 min, then 2-chloro-5-fluoropyrimidine (0.619 ml, 5.01 mmol) is added and the reaction is left to warm to room temperature and stirred for 3.5 h. Solvents were evaporated in vacuo and the crude was taken in dichloromethane (40 ml) and water (50 ml). The aqueous layer was extracted with dichloromethane (2×30 ml). The organics after solvent evaporation were purified by Biotage SNAP-Si cartridge (25 g) eluting with a mixture cycloexane/ethylacetate from 95/5 to 60/40. Collected fractions after solvent evaporation afforded the title compound (D23) (1.10 g)

MS: (ES/+) m/z: 202.2 [MH⁺] C20H18FN3O requires 335.14

¹H NMR (400 MHz, CHLOROFORM-d) δ (ppm): 8.34 (s, 2H), 7.44 (d, J=7.8 Hz, 4H), 7.36-7.25 (m, 4H, under chloroform peak), 7.25-7.15 (m, 2H), 5.24 (t, J=5.9 Hz, 1H), 4.45 (s, 1H), 3.81-3.70 (m, 2H), 3.22-3.11 (m, 2H).

Description 24:
1-benzhydryl-N-(4-fluorophenyl)azetidin-3-amine (D24)

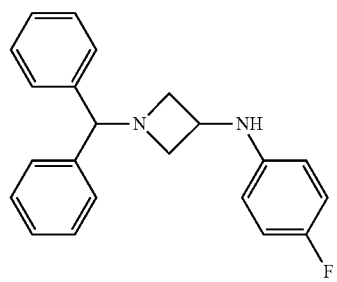

To a solution of 4-fluoro aniline (0.412 ml, 4.296 mmol) in acetonitrile (10 ml) potassium carbonate (771 mg, 5.584 mmol) was added followed by addition of 1-benzhydrylazetidin-3-yl methanesulfonate (D19) (1.5 g, 4.72 mmol). The reaction mixture was stirred at 100° C. for 5 minutes under microwave irradiation. Solvents were evaporated under vacuo and the residue was taken in with diethylether (50 ml)

then water (50 ml) was added. The aqueous layer was extracted with diethylether (2×30 ml). The organics after solvent evaporation were purified by Biotage SNAP-Si cartridge (25 g) eluting with cyclohexane/ethylacetate from 100-0 to 85/15. Collected fractions, after solvent evaporation afforded the title (D24) (0.5 g)

MS: (ES/+) m/z: 333.2 [MH$^+$] C22H21FN2 requires 332.17

$^1$H NMR (400 MHz, CHLOROFORM-d) δ (ppm): 7.44 (d, J=7.34 Hz, 4H) 7.27-7.34 (m, 4H, under chloroform peak) 7.15-7.26 (m, 2H) 6.88 (t, J=8.80 Hz, 2H) 6.48 (dd, J=8.80, 4.40 Hz, 2H) 4.41 (br. s., 1H) 4.09 (d, J=4.89 Hz, 1H) 3.86 (br. s., 1H) 3.68 (t, J=6.36 Hz, 2H) 2.90 (br. s., 2H)

Description 25: 1-(tert-butoxycarbonyl)azetidine-3-carboxylic acid (D25)

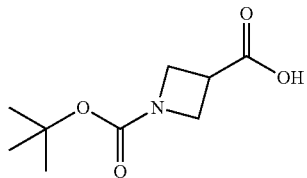

The title compound (D25) (9.9 g) was prepared according to the experimental procedure described in Description 18 starting from 3-azetidine carboxylic acid (5 g, 49.45 mmol, available from Aldrich #391131) (1.5 g, 4.72 mmol). Reaction time: 17 h MS: (ES/+) m/z: 202.2 [MH$^+$] C9H15NO4 requires 201.10

$^1$H NMR (400 MHz, CHLOROFORM-d) δ ppm: 4.15 (d, J=7.3 Hz, 4H), 3.41 (t, J=7.3 Hz, 1H), 1.49-1.44 (m, 9H)

Description 26: tert-butyl 3-(methoxy(methyl)carbamoyl)azetidine-1-carboxylate (D26)

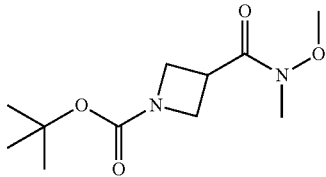 [SMILES: CON(C)C(=O)C1CN(C(=O)OC(C)(C)C)C1]

A mixture of 1-(tert-butoxycarbonyl)azetidine-3-carboxylic acid (D25) (5 g, 24.85 mmol), 1-(3-Dimethylaminopropyl)-3-ethylcarbodiimide hydrochloride (14.39 g, 75.55 mmol), 1-hydroxybenzotriazole hydrate (0.38 g, 2.48 mmol) and N,N-diisopropylethylamine (34.6 ml, 198 mmol) in dimethylformamide (80 ml) was stirred overnight at room temperature. The reaction mixture was then concentrated to half volume in vacuo, poured into water (60 ml) and extracted with ethylacetate (3×60 ml). The combined organic phases were washed with saturated aqueous NH$_4$Cl (100 ml), saturated aqueous NaHCO$_3$ (100 ml), water and brine (100 ml), dried with Na$_2$SO$_4$ anhydrous (50 g) and concentrated under reduced atmosphere. Collected organics after solvent evaporation afforded the title compound (D26) (5.33 g)

MS: (ES/+) m/z: 245 [MH$^+$] C11H20N2O4 requires 244.14

$^1$H NMR (400 MHz, CHLOROFORM-d) δ=4.25-4.11 (m, 2H), 4.11-4.01 (m, 2H), 3.68 (s, 3H), 3.67-3.58 (m, 1H), 3.22 (s, 3H), 1.46 (s, 9H)

Description 27: tert-butyl 3-(3-fluorobenzoyl)azetidine-1-carboxylate (D27)

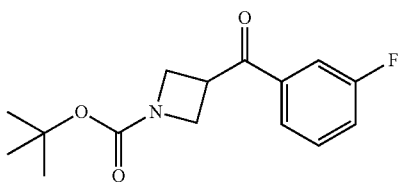 [SMILES: CC(C)(C)OC(=O)N1CC(C(=O)c2cccc(F)c2)C1]

To an ice cooled solution of tert-butyl 3-(methoxy(methyl)carbamoyl)azetidine-1-carboxylate (D26) (61.8 mg, 0.25 mmol) in dry tetrahydrofuran (2 ml), 3-Fluorophenylmagnesiumbromide (1M in tetrahyfrofuran) (0.506 ml, 0.506 mmol) was added dropwise the under stirring under N$_2$ atmosphere. The reaction mixture was stirred at room temperature for 1 h then NH$_4$Cl sat. sol. (10 ml) was added and the mixture was extracted with ethylacetate (3×20 ml). The organic layers were collected, dried with Na$_2$SO$_4$ and filtrated. The solvent was evaporated in vacuo to afford the title compound (D27) (69 mg).

MS: (ES/+) m/z: 280 [MH$^+$] C15H18FNO3 requires 279.13

$^1$H NMR (400 MHz, CHLOROFORM-d) δ=7.63-7.54 (m, 2H), 7.49 (dt, J=5.6, 7.9 Hz, 1H), 7.35-7.29 (m, 1H), 4.31-4.18 (m, 4H), 4.13 (q, J=7.7 Hz, 1H), 1.49-1.44 (m, 9H).

Description 28: tert-butyl 3-(3-fluorophenyl)-3-hydroxyazetidine-1-carboxylate (D28)

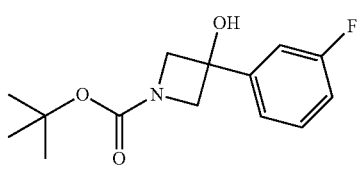 [SMILES: CC(C)(C)OC(=O)N1CC(O)(c2cccc(F)c2)C1]

1-Boc-3-azetidinone (500 mg, 2.77 mmol, available from Aldrich #696315) was dissolved in dry tetrahydrofuran (20 ml) under N$_2$ atmosphere. The solution obtained was cooled at 0° C. and 3-Fluorophenylmagnesiumbromide (1M in THF) (3.33 ml, 3.33 mmol) was added dropwise under stirring. The reaction was warmed to room temperature and stirred overnight. The reaction mixture was diluted with NH$_4$Cl sat. sol. (50 ml) and the organics were extracted with ethylacetate (3×50 ml). Collected organics after solvent evaporation afforded the title compound (D28) (783 mg)

MS: (ES/+) m/z: 268 [MH$^+$] C14H18FNO3 requires 267.13

¹H NMR (400 MHz, CHLOROFORM-d) δ=7.43-7.36 (m, 1H), 7.34-7.29 (m, 1H), 7.26 (td, J=2.3, 10.0 Hz, 1H), 7.04 (ddt, J=1.0, 2.4, 8.3 Hz, 1H), 4.25 (d, J=9.8 Hz, 2H), 4.19 (d, J=9.3 Hz, 2H), 1.49 (s, 9H)

Description 29: tert-butyl 3-(4-fluorophenyl)-3-hydroxyazetidine-1-carboxylate (D29)

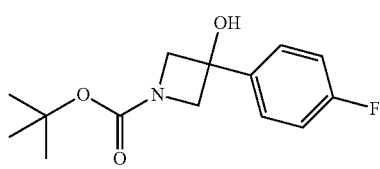 [SMILES: CC(C)(C)OC(=O)N1CC(O)(c2ccc(F)cc2)C1]

The title compound (D29) (819.5 mg) was prepared according to the experimental procedure described in Description 28 starting from 1-Boc-3-azetidinone (500 mg, 2.77 mmol) and 4-Fluorophenylmagnesiumbromide (2M in diethylether) (1.67 ml, 3.33 mmol)).

MS: (ES/+) m/z: 268 [MH⁺] C14H18FNO3 requires 267.13

¹H NMR (400 MHz, CHLOROFORM-d) δ ppm: 7.53-7.47 (m, 2H), 7.14-7.07 (m, 2H), 4.26 (d, J=9.3 Hz, 2H), 4.18 (d, J=9.3 Hz, 2H), 1.49 (s, 9H)

Description 30: tert-butyl 3-((4-fluoro-2-methylphenyl)amino)azetidine-1-carboxylate (D30)

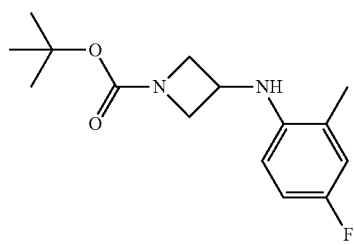 [SMILES: Cc1cc(F)ccc1NC1CN(C(=O)OC(C)(C)C)C1]

A solution of 1-Boc-3-azetidinone (800 mg, 4.67 mmol), 4-fluoro aniline (0.519 ml, 4.67 mmol), acetic acid (0.535 ml, 9.34 mmol) and sodium(triacetoxy)borohydride (1.98 g, 9.34 mmol) in 1,2-dichloroethane (20 ml) was stirred under N2 atmosphere at room temperature for 1 day. Sat. solution of NaHCO₃ (25 ml) was added. After phase separation, the aqueous layer was extracted with dichloromethane (2×35 ml). The collected organics after solvent evaporation were purified by Biotage SNAP-Si cartridge (25 g) eluting with cyclohexane/ethylacetate from 90/10 to 80/20. Collected fractions after solvent evaporation afforded the title compound (D30) (880 mg)

MS: (ES/+) m/z: 225.2 [MH-56⁺] C15H21FN2O2 requires 280.16

¹H NMR (400 MHz, CHLOROFORM-d) δ=6.90-6.77 (m, 2H), 6.30 (br. s., 1H), 4.36-4.30 (m, 2H), 4.24-4.16 (m, 1H), 3.79 (br. s., 2H), 2.20 (s, 3H), 1.47 (s, 9H)

Description 31: tert-butyl 3-((2,4-difluorophenyl)amino)azetidine-1-carboxylate (D31)

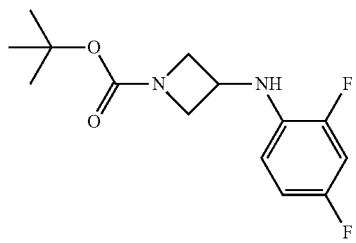

The title compound (D31) (90 mg) was prepared according to the experimental procedure described in Description 30 starting from 1-Boc-3-azetidinone (300 mg, 1.75 mmol) and 2,4-difluoroaniline (0.178 ml, 1.75 mmol). Reaction time: 1 week.

MS: (ES/+) m/z: 229.1 [MH-56⁺] C14H18F2N2O2 requires 284.13

¹H NMR (400 MHz, CHLOROFORM-d) δ ppm: 7.53-7.47 (m, 2H), 7.14-7.07 (m, 2H), 4.26 (d, J=9.3 Hz, 2H), 4.18 (d, J=9.3 Hz, 2H), 1.49 (s, 9H)

Description 32: tert-butyl 3-((2-methyl-4-(trifluoromethyl)phenyl)amino)azetidine-1-carboxylate (D32)

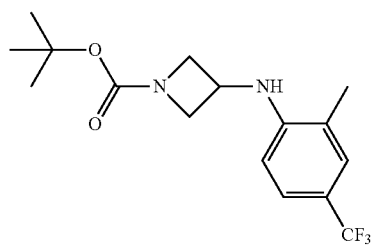 [SMILES: Cc1cc(C(F)(F)F)ccc1NC1CN(C(=O)OC(C)(C)C)C1]

The title compound (D32) (330 mg) was prepared according to the experimental procedure described in Description 30 starting from 1-Boc-3-azetidinone (800 mg, 4.67 mmol) and 4-Amino-3-methylbenzotrifluoride (818.4 mg, 4.67 mmol).

MS: (ES/+) m/z: 275.2 [MH-56⁺] C16H21F3N2O2 requires 330.13

¹H NMR (400 MHz, CHLOROFORM-d) δ ppm: 7.41-7.31 (m, 2H), 6.36 (d, J=8.3 Hz, 1H), 4.41-4.33 (m, 2H), 4.32-4.23 (m, 1H), 3.79 (dd, J=4.4, 8.8 Hz, 2H), 2.22 (s, 3H), 1.50-1.42 (m, 9H)

Description 33: tert-butyl 3-((4-fluoro-2-methylphenyl)(methyl)amino)azetidine-1-carboxylate (D33)

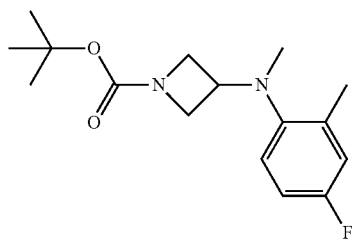

A solution of tert-butyl 3-((4-fluoro-2-methylphenyl)amino)azetidine-1-carboxylate (D30) (240 mg, 0.856 mmol), acetic acid (0.49 ml, 8.56 mmol), Formaldehyde 36% wt. in water (0.066 ml, 0.856 mmol) and sodium(triacetoxy)borohydride (725 mg, 3.424 mmol) in 1,2-dichloroethane (7 ml) was stirred under N2 atmosphere at room temperature for 1 day. NaHCO₃ sat. solution (25 ml) was added. After phase separation, the aqueous layer was extracted with dichloromethane (2×35 ml). The organics after solvent evaporation were purified by Biotage SNAP-Si cartridge (10 g) eluting with cyclohexane/ethylacetate from 90/10 up to 80/20. Collected fractions after solvent evaporation afforded the title compound (D33) (170 mg)

MS: (ES/+) m/z: 295.2 [MH-56$^+$] C16H23FN2O2 requires 294.17

1H NMR (400 MHz, CHLOROFORM-d) δ ppm: 6.94 (d, J=9.3 Hz, 1H), 6.89-6.80 (m, 2H), 4.04-3.89 (m, 3H), 3.78 (d, J=3.9 Hz, 2H), 2.58 (s, 3H), 2.39 (s, 3H), 1.48-1.41 (m, 9H)

Description 34: tert-butyl 3-(4-(trifluoromethyl)phenoxy)pyrrolidine-1-carboxylate (D34)

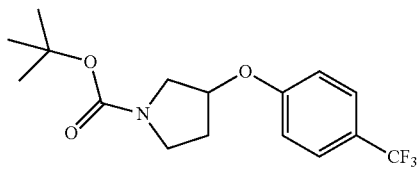 [SMILES: CC(C)(C)OC(=O)N1CCC(Oc2ccc(C(F)(F)F)cc2)C1]

To a stirred solution of 1-Boc-3-pyrrolidinol (1 g, 5.34 mmol; available from Sigma-Aldrich #706620) and 4-(Trifluoromethyl)phenol (0.86 g, 5.34 mmol) in dry tetrahydrofuran (10 ml), Triphenylphosphine (1.54 g, 5.87 mmol) and diisopropyl azodicarboxylate (1.15 ml, 5.87 mmol) were added. The reaction mixture was stirred at room temperature for 2 days. Solvents were evaporated in vacuo and the residue was loaded on SPE-Si (25 g) cartridge and purified eluting with a mixture petroleum ether/ethylacetate (from 100/0 to 80/20). Collected fractions gave, after evaporation, the title compound (D34) (1.8 g).

MS: (ES/+) m/z: 332.1 [MH$^+$] C16H20F3NO3 requires 331.14

Description 35: tert-butyl 3-(3-(trifluoromethyl)phenoxy)pyrrolidine-1-carboxylate (D35)

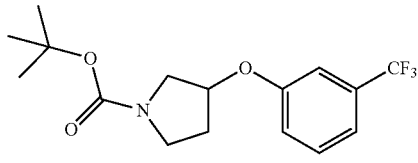 [SMILES: CC(C)(C)OC(=O)N1CCC(Oc2cccc(C(F)(F)F)c2)C1]

The title compound (D35) (1.5 g) was prepared according to the experimental procedure described in Description 34 starting from 1-Boc-3-pyrrolidinol (1 g, 5.34 mmol) and 3-(Trifluoromethyl)phenol (0.640 ml, 5.34 mmol)

MS: (ES/+) m/z: 332.1 [MH$^+$] C16H20F3NO3 requires 331.14

Description 36: tert-butyl 3-(4-fluorophenoxy)pyrrolidine-1-carboxylate (D36)

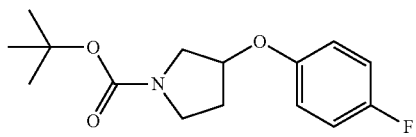 [SMILES: CC(C)(C)OC(=O)N1CCC(Oc2ccc(F)cc2)C1]

The title compound (D36) (1.43 g) was prepared according to the experimental procedure described in Description 34 starting from 1-Boc-3-pyrrolidinol (1 g, 5.34 mmol) and 4-Fluorophenol (598 mg, 5.34 mmol).

MS: (ES/+) m/z: 282.2 [MH$^+$] C15H20FNO3 requires 281.14

Description 37: tert-butyl 3-(3-fluorophenoxy)pyrrolidine-1-carboxylate (D37)

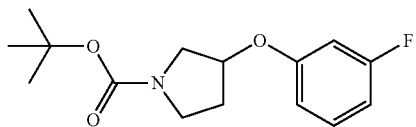

The title compound (D37) (1.26 g) was prepared according to the experimental procedure described in Description 34 starting from 1-Boc-3-pyrrolidinol (1 g, 5.34 mmol) and 3-Fluorophenol (0.478 ml, 5.34 mmol).

MS: (ES/+) m/z: 282.2 [MH$^+$] C15H20FNO3 requires 281.14

Description 38: tert-butyl 3-(m-tolyloxy)pyrrolidine-1-carboxylate (D38)

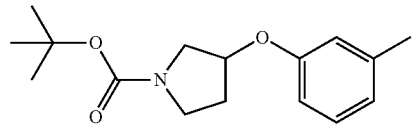 [SMILES: Cc1cccc(OC2CCN(C(=O)OC(C)(C)C)C2)c1]

The title compound (D38) (1.59 g) was prepared according to the experimental procedure described in Description 34 starting from 1-Boc-3-pyrrolidinol (1 g, 5.34 mmol) and 3-Methylphenol (0.558 ml, 5.34 mmol).

MS: (ES/+) m/z: 278.2 [MH$^+$] C16H23NO3 requires 277.36

Description 39: tert-butyl 3-(hydroxymethyl)pyrrolidine-1-carboxylate (D39)

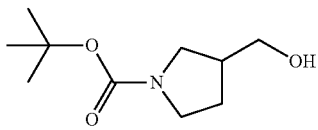

To an ice cooled solution of 1-Boc-pyrrolidine-3-carboxylic acid (1 g, 4.64 mmol) in dry tetrahydrofuran (6 ml) Borane-methyl sulfide complex (2M in tetrahydrofuran) (3.48 ml, 6.96 mmol) was added dropwise the under $N_2$ atmosphere The reaction mixture was stirred overnight at room temperature. $NaHCO_3$ sat. sol. (20 ml) was added and the resulting mixture was stirred for 30 min. The mixture was extracted with ethylacetate (3×20 ml). Collected organics after solvent evaporation afforded the title compound (D39) (1.02 g)

MS: (ES/+) m/z: 146.1 [M-56H$^+$] C10H19NO3 requires 201.14

$^1$H NMR (400 MHz, CHLOROFORM-d) δ ppm: 3.64 (br. s., 2H), 3.57-3.27 (m, 3H), 3.20-3.06 (m, 1H), 2.43 (br. s., 1H), 1.99 (br. s., 1H), 1.69 (br. s., 1H), 1.48 (s, 9H).

Description 40: tert-butyl 3-((3-fluorophenoxy)methyl)pyrrolidine-1-carboxylate (D40)

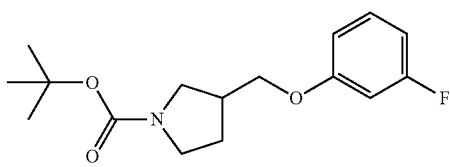 [SMILES: CC(C)(C)OC(=O)N1CCC(COc2cccc(F)c2)C1]

To a solution of tert-butyl 3-(hydroxymethyl)pyrrolidine-1-carboxylate (D39) (200 mg, 0.993 mmol) in dry tetrahydrofuran (4 ml) 3-Fluorophenol (0.089 ml, 0.993 mmol) was added under $N_2$ atmosphere followed by addition of Diisopropyl azodicarboxylate (0.215 ml, 1.093 mmol) and Triphenylphosphine (286.7 mg, 1.093 mmol). The solution was stirred overnight at room temperature. The solvent was evaporated under vacuo and the resulting residue was purified by ISOLUTE SPE-Si cartridge (10 g) eluting with cyclohexane/ethylacetate from 95:5 to 80:20. Collected fractions, after solvent evaporation afforded the title compound (D40) (218.5 mg)

MS: (ES/+) m/z: 240.2 [M-56H$^+$] C16H22FNO3 requires 295.16

$^1$H NMR (400 MHz, CHLOROFORM-d) δ ppm: 7.26-7.16 (m, 1H), 6.73-6.60 (m, 3H), 4.02-3.83 (m, 2H), 3.62 (dd, J=7.6, 11.0 Hz, 1H), 3.57-3.45 (m, 1H), 3.45-3.33 (m, 1H), 3.22 (dd, J=7.1, 11.0 Hz, 1H), 2.78-2.60 (m, 1H), 2.10 (dd, J=5.4, 12.2 Hz, 1H), 1.81 (dd, J=8.1, 12.5 Hz, 1H), 1.49 (s, 9H).

Description 41: (R)-tert-butyl 2-(hydroxymethyl)pyrrolidine-1-carboxylate (D41)

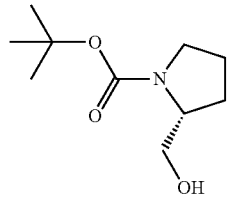

To an ice cooled solution of (R)-(-)-2-(Hydroxymethyl)pyrrolidin (1 g, 9.88 mmol, available at Aldrich#281697) in THF/$H_2O$ (21/21 ml) di-tert-butyldicarbonate (2.58 g, 11.86 mmol) was added portionwise followed by addition of triethylamine (2.96 ml, 21.25 mmol). After completed addiction (10 min), the reaction mixture was stirred for 17 h at room temperature. The solution was diluted with ethylacetate (21 ml) and acidified to pH 5 by addition of 2N HCl (10 ml). The phases were separated and the aqueous phase was extracted with ethylacetate (2×40 ml). The combined organic phases were dried over $Na_2SO_4$ anhydrous, filtrated and the solvent was evaporated under vacuo to afford the title compound (D41) (2.38 g).

The product isolated was denominated 0021/037/1 (white solid).

MS: (ES/+) m/z: 146.1 [M-56H$^+$] C10H19NO3 requires 201.14

$^1$H NMR (400 MHz, CHLOROFORM-d) δ ppm: 4.72 (br. s., 1H), 3.99 (br. s., 1H), 3.72-3.55 (m, 2H), 3.55-3.42 (m, 1H), 3.33 (td, J=6.8, 10.9 Hz, 1H), 2.08-1.98 (m, 1H), 1.84 (tdd, J=6.2, 12.8, 19.3 Hz, 2H), 1.50 (s, 9H).

Description 42: (R)-tert-butyl 2-((3-fluorophenoxy)methyl)pyrrolidine-1-carboxylate (D42)

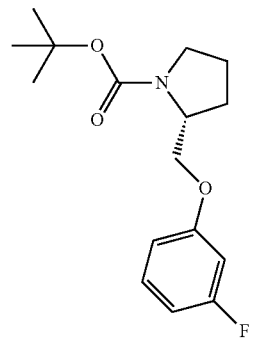 [SMILES: CC(C)(C)OC(=O)N1CCC[C@@H]1COc1cccc(F)c1]

The title compound (D42) (D021/047/1) (252.3 mg) was prepared according to the experimental procedure described in Description 40 starting from (R)-tert-butyl 2-(hydroxymethyl)pyrrolidine-1-carboxylate (D41) (200 mg, 0.993 mmol) and 3-Fluorophenol (0.089 ml, 0.993 mmol).

MS: (ES/+) m/z: 240.2 [M-56H$^+$] C16H22FNO3 requires 295.16

¹H NMR (400 MHz, CHLOROFORM-d) δ ppm: =7.27-7.17 (m, 1H), 6.78-6.61 (m, 3H), 4.14 (d, J=7.3 Hz, 2H), 3.89 (br. s., 1H), 3.41 (br. s., 2H), 2.13-1.83 (m, 4H), 1.50 (s, 9H).

Description 43: (S)-tert-butyl 2-(hydroxymethyl) pyrrolidine-1-carboxylate (D43)

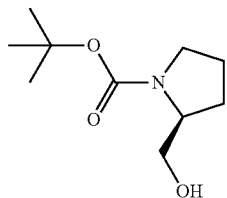

The title compound (D43) (2.43 g mg) was prepared according to the experimental procedure described in Description 41 starting from (S)-(+)-2-(Hydroxymethyl)pyrrolidin (1 g, 9.88 mmol, available at Aldrich#186511).

MS: (ES/+) m/z: 146.1 [M-56H⁺] C10H19NO3 requires 201.14

¹H NMR (400 MHz, CHLOROFORM-d) δ ppm: 4.72 (br. s., 1H), 3.98 (br. s., 1H), 3.72-3.55 (m, 2H), 3.55-3.41 (m, 1H), 3.33 (td, J=6.8, 10.9 Hz, 1H), 2.10-1.97 (m, 1H), 1.92-1.74 (m, 2H), 1.50 (s, 9H).

Description 44: (S)-tert-butyl 2-((3-fluorophenoxy) methyl)pyrrolidine-1-carboxylate (D44)

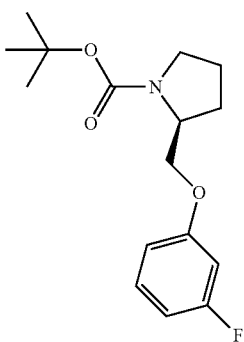 [SMILES: CC(C)(C)OC(=O)N1CCC[C@H]1COc1cccc(F)c1]

The title compound (D44) (239.7 mg) was prepared according to the experimental procedure described in Description 40 starting from (S)-tert-butyl 2-(hydroxymethyl)pyrrolidine-1-carboxylate (D43) (200 mg, 0.993 mmol) and 3-Fluorophenol (0.089 ml, 0.993 mmol).

MS: (ES/+) m/z: 240.2 [M-56H⁺] C16H22FNO3 requires 295.16

¹H NMR (400 MHz, CHLOROFORM-d) δ ppm: =7.26-7.17 (m, 1H), 6.80-6.59 (m, 3H), 4.14 (d, J=6.8 Hz, 2H), 3.88 (br. s., 1H), 3.41 (br. s., 2H), 2.12-1.82 (m, 4H), 1.50 (s, 9H).

Description 45: tert-butyl 3-((3-fluorophenoxy)methyl)piperidine-1-carboxylate (D45)

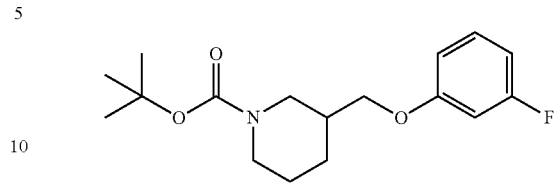

The title compound (D45) (244.9 mg) was prepared according to the experimental procedure described in Description 40 starting from tert-butyl 3-(hydroxymethyl)piperidine-1-carboxylate (200 mg, 0.929 mmol, available at Aldrich#681318) and 3-Fluorophenol (0.083 ml, 0.929 mmol).

MS: (ES/+) m/z: 254.2 [M-56H⁺] C17H24FNO3 requires 309.17

¹H NMR (400 MHz, CHLOROFORM-d) δ ppm: =7.27-7.18 (m, 1H), 6.73-6.58 (m, 3H), 4.08 (d, J=12.7 Hz, 1H), 3.94-3.85 (m, 1H), 3.85-3.77 (m, 2H), 2.93 (t, J=10.8 Hz, 1H), 2.82 (t, J=11.2 Hz, 1H), 2.09-1.96 (m, 1H), 1.95-1.85 (m, 1H), 1.71 (td, J=4.0, 13.1 Hz, 1H), 1.50-1.35 (m, 11H).

Description 46: (S)-tert-butyl 3-(3-fluorophenoxy) pyrrolidine-1-carboxylate (D46)

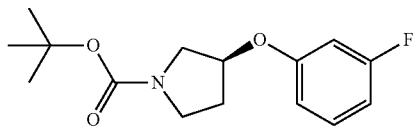 [SMILES: CC(C)(C)OC(=O)N1CC[C@H](Oc2cccc(F)c2)C1]

The title compound (D46) (294.6 mg) was prepared according to the experimental procedure described in Description 40 starting from (R)-tert-butyl 3-hydroxypyrrolidine-1-carboxylate (200 mg, 1.068 mmol, available at Aldrich#532169) and 3-Fluorophenol (0.096 ml, 1.068 mmol).

MS: (ES/+) m/z: 226.1 [M-56H⁺] C15H20FNO3 requires 281.14

¹H NMR (400 MHz, CHLOROFORM-d) δ ppm: =7.27-7.17 (m, 1H), 6.74-6.56 (m, 3H), 4.88 (br. s., 1H), 3.71-3.43 (m, 4H), 2.25-2.05 (m, 2H), 1.49 (s, 9H).

Description 47: (R)-tert-butyl 3-(3-fluorophenoxy) pyrrolidine-1-carboxylate (D47)

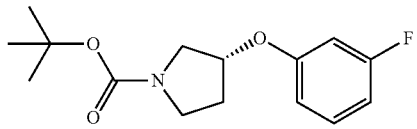

The title compound (D47) (294.6 mg) was prepared according to the experimental procedure described in Description 40 starting from (S)-tert-butyl 3-hydroxypyrrolidine-1-carboxylate (200 mg, 1.068 mmol, available at Aldrich#634786) and 3-Fluorophenol (0.096 ml, 1.068 mmol).

MS: (ES/+) m/z: 226.1 [M-56H⁺] C15H20FNO3 requires 281.14

$^1$H NMR (400 MHz, CHLOROFORM-d) δ ppm: =7.27-7.21 (m, 1H), 6.73-6.64 (m, 2H), 6.64-6.57 (m, 1H), 4.88 (br. s., 1H), 3.70-3.46 (m, 4H), 2.25-2.06 (m, 2H), 1.49 (s, 9H).

Description 48: 3-phenoxyazetidine (D48)

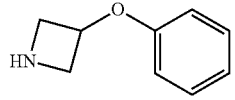 [SMILES: c1ccc(OC2CNC2)cc1]

1-benzhydryl-3-phenoxyazetidine (D20) (2.28 g, 7.23 mmol) was dissolved in ethanol (50 ml) and Pd/C (400 mg, w/w 10%) was added. The mixture was heated at 70° C. under hydrogen atmosphere (50 psi) for 18 hours then filtered off. The filtrate was concentrated to obtain a residue which was recrystallized from diethylether to provide the title compound (D48) (400 mg) as a white solid.

$^1$H NMR (400 MHz, CHLOROFORM-d) δ ppm: δ 7.29-7.28 (2H, m), 6.96 (1H, t, J=7.6 Hz), 6.75 (2H, d, J=8.0 Hz), 5.01 (1H, s), 4.00-3.93 (2H, m), 1.77 (3H, br s).

Description 49: 3-(4-fluorophenoxy)azetidine (D49)

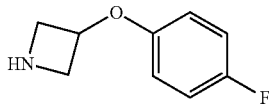 [SMILES: Fc1ccc(OC2CNC2)cc1]

1-chloroethyl chloroformate (0.87 ml, 8.09 mmol) was added to an ice-cooled solution of 1-benzhydryl-3-(4-fluorophenoxy)azetidine (D21) (1.8 g, 5.39 mmol) in 1,2 dichloroethane (18 ml) and the resulting mixture was heated under reflux for 3 hours. The reaction mixture was evaporated in vacuo and the residue was re-dissolved in methanol (10 ml). This solution was heated under reflux overnight then cooled at room temperature and evaporated in vacuo. The obtained residue was loaded on SPE-SCX (20 g) cartridge. The ammonia fractions, after evaporation in vacuo, were loaded on by SPE-Si (5 g) cartridge eluting with a mixture dichloromethane/dichloromethane:NH$_3$ (2M solution in MeOH) (from 100/0 to 80/20). Collected fractions after solvent evaporation afforded the title compound (D49) (0.9 g)

MS: (ES/+) m/z: 168.4 [MH$^+$] C9H10FNO requires 167.18

$^1$H NMR (400 MHz, METHANOL-d$_4$) δ (ppm): 7.07 (t, J=8.8 Hz, 2H), 6.95-6.83 (m, 2H), 5.20-5.09 (m, 1H), 4.57 (dd, J=6.4, 11.7 Hz, 2H), 4.16 (dd, J=4.4, 11.7 Hz, 2H)

Description 50: 3-(3-fluorophenoxy)azetidine (D50)

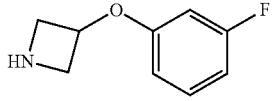

The title compound (D50) (0.95 g) was prepared according to the experimental procedure described in Description 49 starting from 1-benzhydryl-3-(3-fluorophenoxy)azetidine (D22) (1.9 g, 5.698 mmol).

MS: (ES/+) m/z: 168.5 [MH$^+$] C9H10FNO requires 167.18

$^1$H NMR (400 MHz, METHANOL-d$_4$) δ (ppm): 7.43-7.26 (m, 1H), 6.80 (dt, J=2.0, 8.3 Hz, 1H), 6.73-6.63 (m, 2H), 5.25-5.11 (m, 1H), 4.59 (dd, J=6.4, 12.2 Hz, 2H), 4.16 (dd, J=4.4, 12.2 Hz, 2H)

Description 51: 2-(azetidin-3-yloxy)-5-fluoropyrimidine (D51)

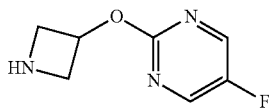 [SMILES: Fc1cnc(OC2CNC2)nc1]

The title compound (D51) (0.57 g) was prepared according to the experimental procedure described in Description 49 starting from 2-((1-benzhydrylazetidin-3-yl)oxy)-5-fluoropyrimidine (D23) (1.1 g, 3.279 mmol).

$^1$H NMR (400 MHz, CHLOROFORM-d) δ (ppm): 8.38 (s, 2H), 5.44 (t, J=6.4 Hz, 1H), 4.00-3.93 (m, 2H), 3.85 (dd, J=5.9, 9.8 Hz, 2H).

Description 52: 3-(4-(trifluoromethyl)phenoxy)azetidine (D52)

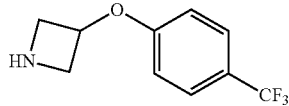

To a solution of 1-Boc-3-hydroxyazetidine (1 g, 5.77 mmol, available from Aldrich #694347) and 4-(Trifluoromethyl)phenol (0.94 g, 5.77 mmol) in dry tetrahydrofuran (10 ml), Triphenylphosphine (1.66 g, 6.35 mmol) and diisopropyl azodicarboxylate (1.25 ml, 6.35 mmol) were added. The mixture was stirred at room temperature for 2 days. Solvents were evaporated in vacuo and the residue was loaded on SPE-Si (25 g) cartridge and purified eluting with a mixture petroleum ether/ethyacetate (from 100/0 to 80/20). Collected fractions gave, after evaporation, a residue that was treated with a mixture dichloromethane/trifluoroacetic acid (0.5 ml/2 ml). The reaction mixture was stirred 1 h at room temperature then solvents were evaporated in vacuo. The residue was loaded on SPE-SCX (25 g) cartridge. Collected ammonia fractions gave, after evaporation, the title compound (D52) (300 mg).

MS: (ES/+) m/z: 218.1 [MH$^+$] C10H10F3NO requires 217.19

Description 53: 3-(3-(trifluoromethyl)phenoxy)azetidine (D53)

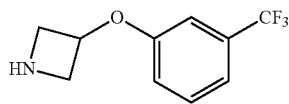 [SMILES: FC(F)(F)c1cccc(OC2CNC2)c1]

The title compound (D53) (100 mg) was prepared according to the experimental procedure described in Description 52 starting from 1-Boc-3-hydroxyazetidine (1 g, 5.77 mmol) and 3-(Trifluoromethyl)phenol (0.69 ml, 5.77 mmol).

MS: (ES/+) m/z: 218.1 [MH⁺] C10H10F3NO requires 217.19

Description 54: N-(4-fluorophenyl)azetidin-3-amine (D54)

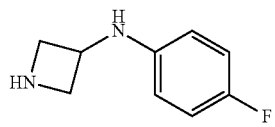 [SMILES: Fc1ccc(NC2CNC2)cc1]

The title compound (D54) (60 mg) was prepared according to the experimental procedure described in Description 49 starting from 1-benzhydryl-N-(4-fluorophenyl)azetidin-3-amine (D24) (0.5 g, 1.5 mmol).

MS: (ES/+) m/z: 167.0 [MH⁺] C9H11FN2 requires 166.22

Description 55:
N-(4-fluoro-2-methylphenyl)azetidin-3-amine (D55)

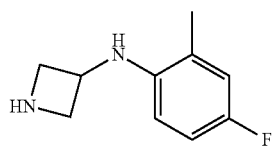

To an ice cooled solution of tert-butyl 3-((4-fluoro-2-methylphenyl)amino)azetidine-1-carboxylate (D30) (300 mg, 1.07 mmol) in dichloromethane (2 ml), a mixture of trifluoroacetic acid/dichloromethane (4.5 ml/1.5 ml) was added and the mixture stirred at room temperature for 1 h. Solvents were evaporated in vacuo and the resulting residue was purified by SPE-SCX cartridge (10 g). Collected ammonia fractions, after solvent evaporation afforded the title compound (D55) (0022/107/1) (190 mg)

MS: (ES/+) m/z: 181.1 [MH⁺] C10H13FN2 requires 180.11

¹H NMR (400 MHz, CHLOROFORM-d) δ (ppm): 6.91-6.74 (m, 2H), 6.32 (dd, J=4.6, 8.6 Hz, 1H), 4.43-4.26 (m, 1H), 4.09-3.92 (m, 2H), 3.75-3.61 (m, 1H), 3.61-3.47 (m, 2H), 2.18 (s, 3H)

Description 56: N-(4-fluoro-2-methylphenyl)-N-methylazetidin-3-amine (D56)

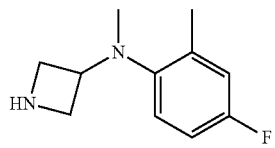

To an ice cooled solution of tert-butyl 3-((4-fluoro-2-methylphenyl)(methyl)amino)azetidine-1-carboxylate (D33) 8170 mg, 0.577 mmol) in dichloromethane (1 ml) trifluoroacetic acid/dichloromethane (3/1 ml) was added and the resulting mixture was stirred at room temperature for 1 h.

Solvents were evaporated under vacuo and the residue was purified by SPE-SCX cartridge (10 g) eluting with methanol and 2N ammonia in methanol. Ammonia fractions were evaporated in vacuo to afford the title compound (D56) (110 mg)

MS: (ES/+) m/z: 195.1 [MH⁺] C11H15FN2 requires 194.12

¹H NMR (400 MHz, CHLOROFORM-d) δ (ppm): 6.92 (dd, J=2.9, 9.3 Hz, 1H), 6.85-6.77 (m, 2H), 4.15 (t, J=6.8 Hz, 1H), 3.78 (t, J=7.6 Hz, 2H), 3.68-3.61 (m, 2H), 2.51 (s, 3H), 2.35 (s, 3H).

Description 57:
3-(4-(trifluoromethyl)phenoxy)pyrrolidine (D57)

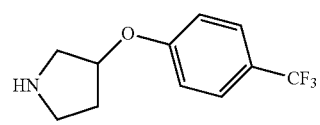 [SMILES: FC(F)(F)c1ccc(OC2CCNC2)cc1]

To an ice cooled solution of tert-butyl 3-(4-(trifluoromethyl)phenoxy)pyrrolidine-1-carboxylate (D34) (1.86 g, 5.613 mmol) in dichloromethane (2 ml), a mixture of trifluoroacetic acid/dichloromethane (4.5 ml/1.5 ml) was added and the mixture stirred at room temperature for 3 h. Solvents were evaporated in vacuo and the resulting residue was purified by SPE-SCX cartridge (10 g). Collected ammonia fractions, after solvent evaporation afforded the title compound (D57) (844 mg)

MS: (ES/+) m/z: 232 [MH⁺] C11H12F3NO requires 231.21

¹H NMR (400 MHz, CHLOROFORM-d) δ (ppm): 7.66-7.47 (m, J=8.8 Hz, 2H), 7.68-7.45 (m, 2H), 7.04-6.85 (m, J=8.8 Hz, 2H), 7.06-6.80 (m, 2H), 4.97-4.80 (m, 1H), 5.00-4.76 (m, 1H), 3.29-3.16 (m, 2H), 3.14-3.05 (m, 1H), 2.97 (ddd, J=5.4, 8.3, 11.2 Hz, 1H), 2.23-2.08 (m, 1H), 2.07-1.86 (m, 1H)

Description 58:
3-(3-(trifluoromethyl)phenoxy)pyrrolidine (D58)

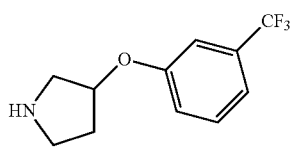 [SMILES: FC(F)(F)c1cccc(OC2CCNC2)c1]

The title compound (D58) (843 mg) was prepared according to the experimental procedure described in Description 57 starting from tert-butyl 3-(3-(trifluoromethyl)phenoxy)pyrrolidine-1-carboxylate (D35) (1.5 g, 4.52 mmol).

MS: (ES/+) m/z: 232 [MH⁺] C11H12F3NO requires 231.21

¹H NMR (400 MHz, CHLOROFORM-d) δ (ppm): 7.40 (t, J=8.1 Hz, 1H), 7.22 (d, J=7.8 Hz, 1H), 7.11 (s, 1H), 7.05 (dd, J=2.0, 8.3 Hz, 1H), 4.94-4.85 (m, 1H), 3.29-3.17 (m, 2H), 3.09 (dd, J=4.6, 12.5 Hz, 1H), 2.97 (ddd, J=5.4, 8.8, 11.2 Hz, 1H), 2.22-2.08 (m, 1H), 2.04-1.97 (m, 1H)

Description 59: 3-(4-fluorophenoxy)pyrrolidine (D59)

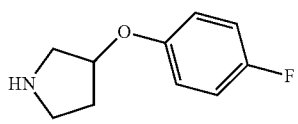 [SMILES: Fc1ccc(OC2CCNC2)cc1]

The title compound (D59) (585 mg) was prepared according to the experimental procedure described in Description 57 starting from tert-butyl 3-(4-fluorophenoxy)pyrrolidine-1-carboxylate (D36) (1.43 g, 5.08 mmol).
MS: (ES/+) m/z: 182.5 [MH$^+$] C10H12FNO requires 181.21
$^1$H NMR (400 MHz, CHLOROFORM-d) δ (ppm): 7.07-6.93 (m, 2H), 6.86-6.73 (m, 2H), 4.84-4.75 (m, 1H), 3.27-3.15 (m, 2H), 3.05 (dd, J=4.6, 12.5 Hz, 1H), 2.96 (ddd, J=5.4, 8.3, 11.2 Hz, 1H), 2.15-2.03 (m, 1H), 2.03-1.98 (m, 1H)

Description 60: 3-(3-fluorophenoxy)pyrrolidine (D60)

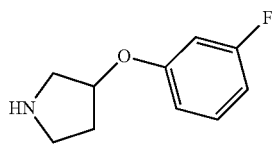 [SMILES: Fc1cccc(OC2CCNC2)c1]

The title compound (D60) (643 mg) was prepared according to the experimental procedure described in Description 57 starting from tert-butyl 3-(3-fluorophenoxy)pyrrolidine-1-carboxylate (D37) (1.26 g, 4.47 mmol).
MS: (ES/+) m/z: 182.5 [MH$^+$] C10H12FNO requires 181.21
$^1$H NMR (400 MHz, CHLOROFORM-d) δ (ppm): 7.23 (dt, J=6.8, 8.3 Hz, 1H), 6.72-6.63 (m, 2H), 6.63-6.53 (m, 1H), 4.84 (dd, J=4.6, 6.1 Hz, 1H), 3.28-3.17 (m, 2H), 3.09 (dd, J=4.9, 12.7 Hz, 1H), 2.98 (ddd, J=5.4, 8.3, 11.2 Hz, 1H), 2.20-2.08 (m, 1H), 2.01 (d, J=7.3 Hz, 1H)

Description 61: 3-(m-tolyloxy)pyrrolidine (D61)

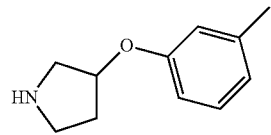

The title compound (D61) (693 mg) was prepared according to the experimental procedure described in Description 57 starting from 3-(m-tolyloxy)pyrrolidine-1-carboxylate (D38) (1.5 g, 5.73 mmol).
MS: (ES/+) m/z: 178.5 [MH$^+$] C10H12FNO requires 177.24
$^1$H NMR (400 MHz, CHLOROFORM-d) δ (ppm): 7.18 (t, J=7.8 Hz, 1H), 6.78 (d, J=7.3 Hz, 1H), 6.73-6.63 (m, 2H), 4.90-4.77 (m, 1H), 3.27-3.14 (m, 2H), 3.04 (dd, J=4.6, 12.5 Hz, 1H), 2.94 (ddd, J=5.6, 8.4, 11.4 Hz, 1H), 2.34 (s, 3H), 2.16-2.05 (m, 1H), 2.04-2.00 (m, 1H)

Description 62: methyl 5-chloro-2-(3-hydroxyazetidin-1-yl)nicotinate (D62)

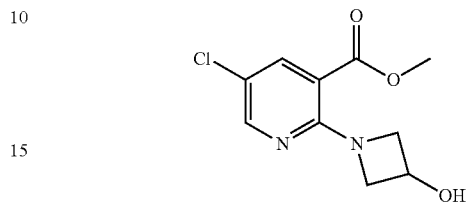

methyl 5-chloro-2-(3-hydroxyazetidin-1-yl)nicotinate (D62) was prepared according to two different procedures described below:
Procedure A
To a solution of azetidin-3-ol hydrochloride (637 mg, 5.82 mmol, commercially available from Matrix Scientific #011272) and trietylamine (1.69 ml, 12.11 mmol) in methanol (10 ml), methyl 2-chloropyridine-3-carboxylate (1 g, 4.84 mmol) was added and the mixture stirred at 150° C. under microwave irradiation 10 min (2 cycles of 5 min each). The residue obtained after solvent evaporation was purified by SPE-Si cartridge (10 g) eluting with a mixture cyclohexane/ethylacetate from 90/10 to 60/40. Collected fractions after solvent evaporation afforded the title compound (D62) (D004/099/1) (800 mg)
MS: (ES/+) m/z: 242.6 [MH$^+$] C10H11ClN2O3 requires 242.04
$^1$H NMR (400 MHz, CHLOROFORM-d) δ (ppm): 8.25 (d, J=2.4 Hz, 1H), 7.98 (d, J=2.4 Hz, 1H), 4.74 (br. s., 1H), 4.37 (dd, J=6.8, 10.3 Hz, 2H), 3.95 (dd, J=3.9, 10.3 Hz, 2H), 3.90 (s, 3H)
Procedure B
To a mixture of 3-Hydroxyazetidine hydrochloride (37.17 g, 0.339 mol) and triethylamine (70.93 ml, 0.508 mol) in tetrahydrofuran/methanol (840/280 ml) Methyl 2,5-dichloronicotinate (70 g, 0.339 mol) was added and the resulting mixture was heated at 75° C. for 4 hours then at 62° C. overnight. 3-Hydroxyazetidine hydrochloride (3.7 g, 0.03 mol) and triethylamine (23.60 ml, 0.16 mol) were added and the reaction mixture was further heated at 80° C. for 28 h. Solvents were evaporated in vacuo. The residue was taken in dichloromethane (400 ml) and water (500 ml). The formed solid was filtered, washed with water (500 ml) and dried in vacuum to afford a first batch of the title compound (D62) (63 g).
The two layer filtrate was separated and the aqueous layer was extracted with dichloromethane (1×300 ml). The two organic layers obtained were collected together and reduced to ¼ of volume. The formed precipitate was filtered off, washed with cyclohexane then treated with water (200 ml) and filtered off to afford a second batch of title compound (D62) (15 g) (by $^1$H NMR spectra 0.56% mol of TEA HCl 6%
MS: (ES/+) m/z: 242.6 [MH$^+$] C10H11ClN2O3 requires 242.04
$^1$H NMR (400 MHz, DMSO-d6) δ (ppm): 8.30 (dd, J=1.2, 2.7 Hz, 1H), 7.91 (dd, J=1.2, 2.7 Hz, 1H), 5.64 (d, J=6.4 Hz, 1H), 4.57-4.41 (m, 1H), 4.16 (dd, J=6.8, 9.8 Hz, 2H), 3.86-3.77 (m, 3H), 3.72 (dd, J=4.4, 9.8 Hz, 2H).

Description 63: methyl 5-chloro-2-(3-((methylsulfonyl)oxy)azetidin-1-yl)nicotinate (D63)

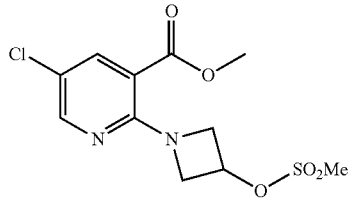 [SMILES: COC(=O)c1cc(Cl)cnc1N1CC(OS(C)(=O)=O)C1]

methyl 5-chloro-2-(3-((methylsulfonyl)oxy)azetidin-1-yl)nicotinate (D63) was prepared according to two different procedures described below Procedure A To a stirred solution of methyl 5-chloro-2-(3-hydroxyazetidin-1-yl)nicotinate (D62) (50 mg, 0.206 mmol) and triethylamine (0.057 ml, 0.412 mmol) in dimethylformamide (0.26 ml) cooled at 0° C., methansulfonyl chloride (0.016 ml, 0.206 mmole) was added dropwise and the reaction mixture stirred at the same temperature for 1 h. After solvent evaporation the obtained residue was purified by SPE-Si (5 g) eluting with a mixture petroleum ether/ethyl acetate from 90/10 to 70/30. Collected fractions, after solvent evaporation, afforded the title compound (D63) (53 mg)

MS: (ES/+) m/z: 321.1 [MH$^+$] C11H13ClN2O5S requires 320.02

$^1$H NMR (400 MHz, CHLOROFORM-d) δ (ppm): 8.25 (d, J=2.45 Hz, 1H) 8.01 (d, J=2.45 Hz, 1H) 5.41-5.24 (m, 1H) 4.47 (ddd, J=11.00, 6.72, 0.86 Hz, 2H) 4.29-4.13 (m, 2H) 3.88 (s, 3H) 3.08 (s, 3H)

Procedure B

To an ice cooled stirred solution of methyl 5-chloro-2-(3-hydroxyazetidin-1-yl)nicotinate (D62) (66 g, 0.27 mol) and triethylamine (56.86 ml, 0.40 mol) in dimethylformamide (500 ml) methanesulfonylchloride (23.15 ml, 0.29 mol) was added dropwise maintaining the temperature at 0° C. The reaction mixture was stirred at 0° C. for 3.5 h then methanesulfonyl chloride (6.3 ml, 0.037 mol) and triethylamine (18.9 ml, 0.135 mol) were added and the reaction mixture was stirred for 3 h at 0° C. After this time the formed solid was filtered off. Water (700 ml) was added to the filtrate. The formed solid was filtered off, washed with water (400 ml) and dried under vacuo to afford the title compound (D63) (80 g).

$^1$H NMR (400 MHz, DMSO-d6) δ (ppm): 8.37 (d, J=2.4 Hz, 1H), 8.01 (d, J=2.4 Hz, 1H), 5.46-5.19 (m, 1H), 4.44-4.31 (m, 2H), 4.10 (td, J=1.7, 10.8 Hz, 2H), 3.83 (s, 3H), 3.27 (s, 3H)

Description 64: 1-(5-chloro-3-(methoxycarbonyl)pyridin-2-yl)azetidine-3-carboxylic acid (D64)

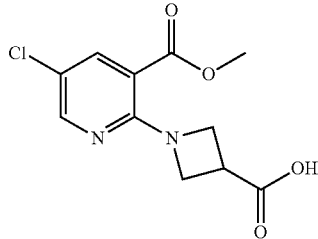 [SMILES: COC(=O)c1cc(Cl)cnc1N1CC(C(=O)O)C1]

To a mixture 3-Azetidinecarboxylic acid (411 mg, 4.06 mmol) and triethylamine (1.17 ml, 8.47 mmol) in methanol (3 ml), methyl 2-chloropyridine-3-carboxylate (700 mg, 3.38 mmol) was added and the mixture was heated at 150° C. under microwave irradiation 10 min (2 cycles of 5 min each). Solvents were evaporated in vacuo and the residue was taken in water (5 ml) and 1M HCl (5 ml) and extracted with ethylacetate (3×5 ml). Collected organics after solvent evaporation afforded the title compound (D64) (880 mg)

MS: (ES/+) m/z: 270.8 [MH$^+$] C11H11ClN2O4 requires 270.04

$^1$H NMR (400 MHz, CHLOROFORM-d) δ ppm 8.23-8.32 (m, 1H) 7.90-8.06 (m, 1H) 4.31-4.45 (m, 2H) 4.17-4.30 (m, 2H) 3.84-3.95 (m, 3H) 3.58 (tt, J=8.93, 6.11 Hz, 1H).

Description 65: methyl 5-chloro-2-(3-(hydroxymethyl)azetidin-1-yl)nicotinate (D65)

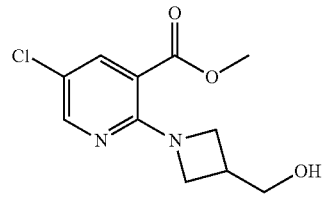 [SMILES: COC(=O)c1cc(Cl)cnc1N1CC(CO)C1]

To a cooled solution of (D64) (340 mg, 1.25 mmol) and N-Methylmorpholine (0.207 ml, 1.88 mmol) in dry tetrahydrofuran (30 ml), isobutyl chloroformate (0.244 ml, 1.88 mmol) was added dropwise and the resulting mixture was stirred 2 h at 0° C. Sodium borohydride (261 mg, 6.90 mmol) was added slowly and the solution stirred 10 min at 0° C. then 30 min at room temperature. The reaction mixture was cooled again to 0° C. then methanol (20 ml) was added and the reaction allowed to reach room temperature. The residue obtained after solvent evaporation was purified by SPE-Si cartridge (10 g) eluting with a mixture dichloromethane/methanol from 100/0 to 98/2. Collected fractions after solvent evaporation afforded the title compound (D65) (0021/004/1) (215.2 mg).

MS: (ES/+) m/z: 257.2 [MH$^+$] C11H13ClN2O3 requires 256.06

$^1$H NMR (400 MHz, METHANOL-d$_4$) δ=8.20 (d, J=2.4 Hz, 1H), 7.95 (d, J=2.9 Hz, 1H), 4.11 (t, J=9.0 Hz, 2H), 3.88 (s, 3H), 3.82 (dd, J=5.4, 9.8 Hz, 2H), 3.72 (d, J=6.4 Hz, 2H), 2.87-2.76 (m, 1H)

Description 66: methyl 2-chloro-5-(trifluoromethyl)nicotinate (D66)

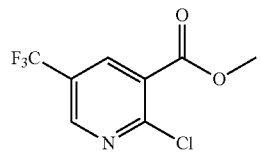

A solution of 2-chloro-5-(trifluoromethyl)nicotinic acid (500 mg, 2.21 mmole, available from Apollo #PC9219) in a mixture diethyl ether/methanol (5 ml)/(15 ml) was cooled to −20° C. then trimethylsilyldiazomethane (2M solution in diethyl ether) (2.15 ml, 4.43 mmol) was added dropwise. The reaction mixture was stirred at −20° C. for 1 h then allowed to warm to room temperature. After solvent evaporation, the obtained residue was loaded on SPE-Si cartridge (10 g) eluting with a mixture cyclohexane/dichloromethane from 80/20 to 60/40. Collected fractions, after solvent evaporation, afforded the title compound (D66) (300 mg)

MS: (ES/+) m/z: 240.1 [MH$^+$] C8H5ClF3NO2 requires 239.00

$^1$H NMR (400 MHz, CHLOROFORM-d) δ (ppm): 8.80 (s, 1H) 8.43 (s, 1H) 4.03 (s, 3H)

Description 67: methyl 2-(3-hydroxyazetidin-1-yl)-5-(trifluoromethyl)nicotinate (D67)

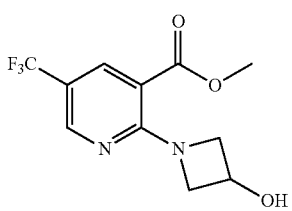 [SMILES: COC(=O)c1cc(C(F)(F)F)cnc1N1CC(O)C1]

The title compound (D67) (4.0 g) was prepared according to the experimental procedure described in Description 62 starting from azetidin-3-ol hydrochloride (2.3 g, 21.03 mmol) and methyl 2-chloro-5-(trifluoromethyl)nicotinate (D66) (4.2 g, 17.53 mmol)

MS: (ES/+) m/z: 277 [MH$^+$] C11H11F3N2O3 requires 276.07

$^1$H NMR (400 MHz, CHLOROFORM-d) δ (ppm): 8.64-8.41 (m, 1H) 8.18 (d, J=2.45 Hz, 1H) 4.75 (dd, J=7.09, 3.18 Hz, 1H) 4.44 (dd, J=11.00, 6.60 Hz, 2H) 4.04 (dd, J=11.13, 4.03 Hz, 2H) 3.91 (s, 3H) 2.15-2.49 (m, 1H)

Description 68: methyl 2-(3-((methylsulfonyl)oxy)azetidin-1-yl)-5-(trifluoromethyl)nicotinate (D68)

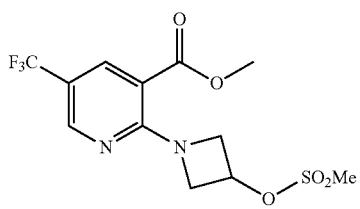 [SMILES: COC(=O)c1cc(C(F)(F)F)cnc1N1CC(OS(C)(=O)=O)C1]

The title compound (D53) (4.85 g) was prepared according to the experimental procedure described in Description 63 starting from methyl 2-(3-hydroxyazetidin-1-yl)-5-(trifluoromethyl)nicotinate (D67) (3.9 g, 14.11 mmol)

MS: (ES/+) m/z: 355 [MH$^+$] C12H13F3N2O5S requires 354.05

$^1$H NMR (400 MHz, CHLOROFORM-d) δ (ppm): 8.53 (d, J=1.96 Hz, 1H) 8.26 (d, J=2.45 Hz, 1H) 5.47-5.22 (m, 1H) 4.58 (dd, J=11.98, 6.60 Hz, 2H) 4.36 (dd, J=11.74, 3.67 Hz, 2H) 3.92 (s, 3H) 3.11 (s, 3H).

Description 69: methyl 2-chloro-5-fluoronicotinate (D69)

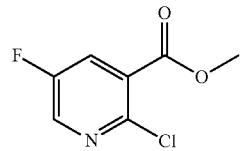

The title compound (D69) (0022/105/1) (1.8 g) was prepared according to the experimental procedure described in Description 66 starting from 2-Chloro-5-fluoronicotinic acid (2 g, 11.39 mmol) and trimethylsilyldiazomethane (2M solution in diethyl ether) (17 ml, 34.18 mmol)

MS: (ES/+) m/z: 190.1 [MH$^+$] C7H5ClFNO2 requires 189.00

$^1$H NMR (400 MHz, CHLOROFORM-d) δ (ppm): 8.41 (d, J=2.9 Hz, 1H), 7.93 (dd, J=3.2, 7.6 Hz, 1H), 3.98 (s, 3H)

Description 70: methyl 5-fluoro-2-(3-hydroxyazetidin-1-yl)nicotinate (D70)

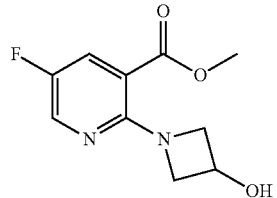 [SMILES: COC(=O)c1cc(F)cnc1N1CC(O)C1]

The title compound (D70) (75 mg) was prepared according to the experimental procedure described in Description 62 starting from azetidin-3-ol hydrochloride (208 mg, 1.89 mmol) and methyl 2-chloro-5-fluoronicotinate (300 mg, 1.58 mmol, commercially available from Adesis#2-482).

MS: (ES/+) m/z: 227.2 [MH$^+$] C10H11FN2O3 requires 226.08

$^1$H NMR (400 MHz, CHLOROFORM-d) δ (ppm): 8.23 (br. s., 1H) 7.92-7.66 (m, 1H) 4.74 (br. s., 1H) 4.36 (br. s., 2H) 4.05-3.70 (m, 4H)

Description 71: methyl 5-fluoro-2-(3-((methylsulfonyl)oxy)azetidin-1-yl)nicotinate (D71)

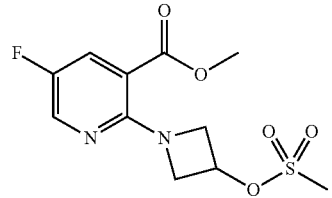 [SMILES: COC(=O)c1cc(F)cnc1N1CC(OS(C)(=O)=O)C1]

The title compound (D71) (90 mg) was prepared according to the experimental procedure described in Description 63 starting from methyl 5-fluoro-2-(3-hydroxyazetidin-1-yl) nicotinate (D70) (73 mg, 0.322 mmol)

MS: (ES/+) m/z: 305.6 [MH$^+$] C11H13FN2O5S requires 304.05

$^1$H NMR (400 MHz, CHLOROFORM-d) δ (ppm): 8.24 (d, J=3.18 Hz, 1H) 7.85 (dd, J=8.44, 3.06 Hz, 1H) 5.36 (tt, J=6.60, 4.16 Hz, 1H) 4.49 (dd, J=11.74, 6.60 Hz, 2H) 4.24 (dd, J=11.74, 4.16 Hz, 2H) 3.91 (s, 3H) 3.10 (s, 3H).

Description 72: methyl 5-chloro-2-(2-phenylpyrrolidin-1-yl)nicotinate (D72)

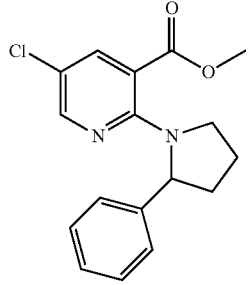 [SMILES: COC(=O)c1cc(Cl)cnc1N1CCCC1c1ccccc1]

To a solution of Methyl 2,5-dichloronicotinate (120 mg, 0.58 mmol,) in isopropanol (10 ml), 2-phenylpyrrolidine (86 mg, 0.58 mmol, available from Matrix Scientific #018619) and N,N-Diisopropylethylamine (90 mg, 0.70 mmol) were added. The mixture was heated under reflux overnight. After cooling to room temperature, the mixture was evaporated and the residue was dissolved in ethyl acetate (10 ml), washed with water (10 ml) and brine (10 ml), dried over $Na_2SO_4$ and evaporated in vacuo. The crude residue was purified by flash chromatography on silica gel eluting with a mixture petroleum ether/ethyl acetate 20:1 to afford the title compound (D72) (167 mg) as colorless oil.

$^1$H NMR (400 MHz, CHLOROFORM-d) δ (ppm): 8.10 (1H, d, J=2.4 Hz), 7.79 (1H, d, J=2.4 Hz), 7.28-7.18 (5H, m), 5.36-5.32 (1H, m), 3.95-3.89 (1H, m), 3.85 (3H, s), 3.33-3.28 (1H, m), 2.52-2.47 (1H, m), 2.07-2.04 (1H, m), 1.92-1.89 (2H, m).

Description 73: methyl 5-chloro-2-(3-phenylpyrrolidin-1-yl)nicotinate (D73)

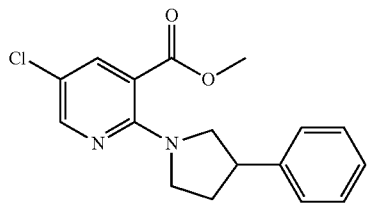 [SMILES: COC(=O)c1cc(Cl)cnc1N1CCC(c2ccccc2)C1]

The title compound (D35) (316 mg) was prepared according to the experimental procedure described in Description 72 starting from methyl 2,5-dichloronicotinate (206 mg, 1.00 mmol) and 3-phenylpyrrolidine (147 mg, 1.00 mmol)

$^1$H NMR (400 MHz, CHLOROFORM-d) δ (ppm): 8.23 (1H, d, J=2.4 Hz), 7.90 (1H, d, J=2.4 Hz), 7.38-7.26 (5H, m), 3.90 (3H, s), 3.74-3.43 (5H, m), 2.39-2.35 (1H, m), 2.15-2.10 (1H, m).

Description 74: methyl 2-(2-benzylpyrrolidin-1-yl)-5-chloronicotinate (D74)

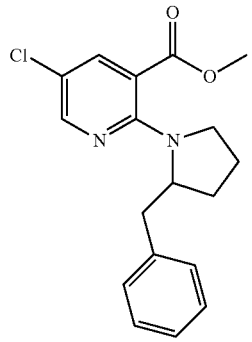 [SMILES: COC(=O)c1cc(Cl)cnc1N1CCCC1Cc1ccccc1]

The title compound (D74) (80 mg) was prepared according to the experimental procedure described in Description 62 starting from Methyl 2-chloropyridine-3-carboxylate (106.62 mg, 0.516 mmol, available from Matrix #037174) and 2-benzylpyrrolidine (100 mg, 0.602 mmol, commercially available from Apollo#OR12512)

MS: (ES/+) m/z: 331.0 [MH$^+$] C18H19ClN2O2 requires 330.81

$^1$H NMR (400 MHz, CHLOROFORM-d) δ (ppm): 8.28 (d, J=2.9 Hz, 1H), 7.91 (d, J=2.4 Hz, 1H), 7.35-7.18 (m, 5H), 4.67-4.53 (m, 1H), 3.90 (s, 2H), 3.54-3.43 (m, 1H), 3.36-3.25 (m, 1H), 2.94-2.83 (m, 1H), 2.76 (d, J=8.3 Hz, 1H), 2.03-1.92 (m, 1H), 1.91-1.81 (m, 1H), 1.79-1.61 (m, 1H)

Description 75: methyl 5-chloro-2-(3-phenoxyazetidin-1-yl)nicotinate (D75)

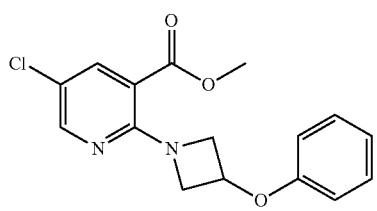 [SMILES: COC(=O)c1cc(Cl)cnc1N1CC(Oc2ccccc2)C1]

To a solution of methyl 2,5-dichloronicotinate (217 mg, 1.05 mmol) in tetrahydrofuran (5 ml), 3-phenoxyazetidine (D48) (149 mg, 1.05 mmol) and triethylamine (117 mg, 1.16 mmol) were added and the mixture was heated at reflux for 18 hours. The resulting mixture was cooled to room temperature, the precipitates were filtered off and the filtrate was concentrated under vacuo. The residue was dissolved in ethyl acetate (5 ml), washed with water (5 ml) and brine (5 ml), dried over $Na_2SO_4$, filtered and concentrated. The crude residue was purified by flash chromatography on silica gel eluting with a mixture petroleum ether/ethyl acetate from 30:1 to 20:1. Collected fractions after solvent evaporation afforded the title compound (D75) (250 mg) as a white solid.

$^1$H NMR (400 MHz, CHLOROFORM-d) δ (ppm): 8.24 (1H, d, J=2.8 Hz), 7.98 (1H, d, J=2.4 Hz), 7.31-7.27 (2H, m), 6.99 (1H, t, J=7.2 Hz), 6.77 (2H, d, J=7.6 Hz), 5.04-5.01 (1H, m), 4.52 (2H, dd, J=10.4, 6.4 Hz), 4.11 (2H, dd, J=10.0, 4.0 Hz), 3.88 (3H, s).

Description 76: methyl 5-chloro-2-(3-(4-fluorophenoxy)azetidin-1-yl)nicotinate (D76)

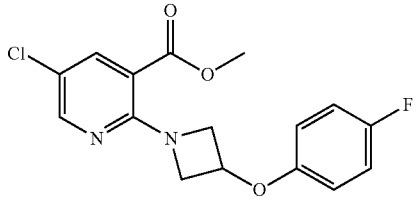 [SMILES: COC(=O)c1cc(Cl)cnc1N1CC(Oc2ccc(F)cc2)C1]

To a mixture of (D49) (243 mg, 1.454 mmol) and triethylamine (0.253 ml, 1.817 mmol) in methanol (3 ml), methyl 2-chloropyridine-3-carboxylate (250 mg, 1.2118 mmol) was added and the resulting mixture was heated 10 min (2 cycles of 5 min each) at 150° C. under microwave irradiation. Solvents were evaporated in vacuo and the residue was purified by SPE-Si cartridge (25 g) eluting with cyclohexane/ethylacetate from 95/5 to 85/15. Collected fractions after solvent evaporation afforded the title compound (D76) (270 mg)

MS: (ES/+) m/z: 337.1 [MH$^+$] C16H14ClFN2O3 requires 336.07

$^1$H NMR (400 MHz, CHLOROFORM-d) δ (ppm): 8.27 (d, J=2.4 Hz, 1H), 8.02 (d, J=2.4 Hz, 1H), 7.06-6.97 (m, 2H), 6.78-6.69 (m, 2H), 4.99 (ddd, J=2.2, 4.2, 6.4 Hz, 1H), 4.53 (ddd, J=1.0, 6.4, 10.3 Hz, 2H), 4.13 (dd, J=3.9, 11.2 Hz, 2H), 3.90 (s, 3H)

Description 77: methyl 5-chloro-2-(3-(3-fluorophenoxy)azetidin-1-yl)nicotinate (D77)

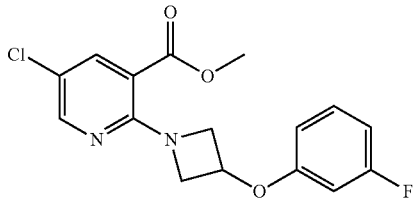 [SMILES: COC(=O)c1cc(Cl)cnc1N1CC(Oc2cccc(F)c2)C1]

methyl 5-chloro-2-(3-(3-fluorophenoxy)azetidin-1-yl)nicotinate (D77) was prepared according to three different procedures reported below
Procedure A
The title compound (D77) (295 mg) was prepared according to the experimental procedure described in Description 76 starting from methyl 2-chloropyridine-3-carboxylate (250 mg, 1.2118 mmol) and (D50) (243 mg, 1.454 mmol).
Procedure B
To a solution of 3-Fluorophenol (0.005 ml, 0.056 mmole) in acetonitrile (1 ml), potassium carbonate (10 mg, 0.0728 mmol) were added followed by the addition of methyl 5-chloro-2-(3-((methylsulfonyl)oxy)azetidin-1-yl)nicotinate (D63) (20 mg, 0.062 mmol). The reaction mixture was heated at 150° C. under microwave irradiation for 10 min (2 cycle of 5 min each) then at 180° C. for 5 min. After solvent evaporation the obtained residue was purified by SPE-Si (10 g) eluting with mixture cyclohexane/ethyl acetate from 95/5 to 90/10. Collected fractions, after solvent evaporation, afforded the title compound D77 (10 mg)

MS: (ES/+) m/z: 337.1 [MH$^+$] C16H14ClFN2O3 requires 336.07

Procedure C To a solution of 3-Fluorophenol (0.139 ml, 1.417 mmole) in acetonitrile (3 ml), potassium carbonate (254.6 mg, 1.842 mmol) were added followed by the addition of methyl 5-chloro-2-(3-((methylsulfonyl)oxy)azetidin-1-yl)nicotinate (D63) (500 mg, 1.558 mmol). The reaction mixture was heated at 160° C. under microwave irradiation for 20 min. After solvent evaporation the obtained residue was diluted in 1M HCl (10 ml) and extracted with ethyl acetate (3×20 ml). Collected organics, after solvent evaporation, afforded a residue that was first purified eluting with a mixture cycloexane/ethy/acetate/methanol from 95/5/0 to 90/10/0 to 90/10/20. Collected fractions, after solvent evaporation, afforded a residue (350 mg) that was further purified by SPE-SCX (20 g) cartridge. The ammonia fractions, after evaporation afforded the title compound (D77) (290 mg).

MS: (ES/+) m/z: 337.1 [MH$^+$] C16H14ClFN2O3 requires 336.07

$^1$H NMR (400 MHz, CHLOROFORM-d) δ (ppm): 8.27 (d, J=2.45 Hz, 1H) 8.02 (d, J=2.93 Hz, 1H) 7.28-7.18 (m, 1H) 6.72 (td, J=8.31, 2.45 Hz, 1H) 6.58 (dd, J=8.31, 1.96 Hz, 1H) 6.51 (dt, J=10.64, 2.26 Hz, 1H) 5.10-4.90 (m, 1H) 4.55 (dd, J=10.76, 6.36 Hz, 2H) 4.14 (dd, J=10.51, 4.16 Hz, 2H) 3.91 (s, 3H).

Description 78: methyl 5-chloro-2-(3-(4-(trifluoromethyl)phenoxy)azetidin-1-yl)nicotinate (D78)

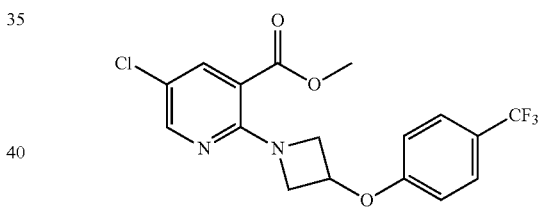

The title compound (D78) (200 mg) was prepared according to the experimental procedure described in Description 62 starting from Methyl 2,5-dichloronicotinate (160 mg, 0.775 mmol) and 3-(4-(trifluoromethyl)phenoxy)azetidine (D52) (202.13 mg, 0.903 mmol).

MS: (ES/+) m/z: 387.5 [MH$^+$] C17H14ClF$_3$N$_2$O3 requires 386.06

Description 79: methyl 5-chloro-2-(3-(3-(trifluoromethyl)phenoxy)azetidin-1-yl)nicotinate (D79)

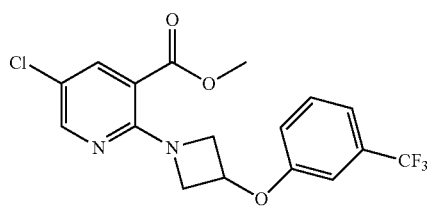 [SMILES: COC(=O)c1cc(Cl)cnc1N1CC(Oc2cccc(C(F)(F)F)c2)C1]

The title compound (D79) (110 mg) was prepared according to the experimental procedure described in Description 62 starting from Methyl 2,5-dichloronicotinate (87 mg, 0.422 mmol) and 3-(3-(trifluoromethyl)phenoxy)azetidine (D53) (110 mg, 0.506 mmol)

MS: (ES/+) m/z: 387.5 [MH$^+$] C17H14ClF$_3$N$_2$O3 requires 386.06

Description 80: methyl 5-chloro-2-(3-(3-fluorophenyl)-3-hydroxyazetidin-1-yl)nicotinate (D80)

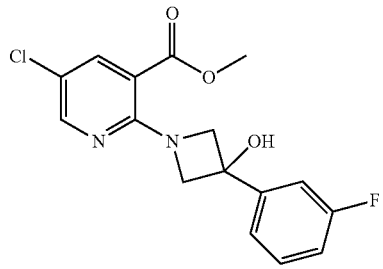 [SMILES: COC(=O)c1cc(Cl)cnc1N1CC(O)(c2cccc(F)c2)C1]

To a cooled (0° C.) solution of tert-butyl 3-(3-fluorophenyl)-3-hydroxyazetidine-1-carboxylate (D28) (100 mg, 0.374 mmol) in dichloromethane (0.5 ml), a mixture 3:1 of trifluoroacetic acid/dichloromethane (1 ml) was added and the mixture was stirred 30 min at room temperature. The residue obtained after solvent evaporation was dissolved in a mixture 3:1 of tetrahydrofuran/methanol (1 ml) and triethylamine (0.156 ml, 1.122 mmol) was added followed by addition of methyl 2,5-dichloronicotinate (77.32 mg, 0.374 mmol). The resulting mixture was heated 15 h at 60° C. After solvent evaporation the residue was taken in NH$_4$Cl sat. sol. (10 ml) and the resulting mixture was extracted with ethylacetate (2×10 ml). The residue obtained after solvet evaporation was purified by SPE-Si cartridge (5 g) eluting with a mixture cyclohexane/ethylacetate from 100/0 to 90:10. Collected fractions, after solvent evaporation afforded the title compound (D80) (71.4 mg)

MS: (ES/+) m/z: 337.2 [MH$^+$] C16H14ClFN2O3 requires 336.75

$^1$H NMR (400 MHz, CHLOROFORM-d) δ=8.29 (d, J=2.9 Hz, 1H), 8.04 (d, J=2.4 Hz, 1H), 7.43-7.30 (m, 3H), 7.07-7.00 (m, 1H), 4.47 (d, J=9.8 Hz, 2H), 4.33 (d, J=9.8 Hz, 2H), 3.91-3.88 (m, 3H).

Description 81: methyl 5-chloro-2-(3-(4-fluorophenyl)-3-hydroxyazetidin-1-yl)nicotinate (D81)

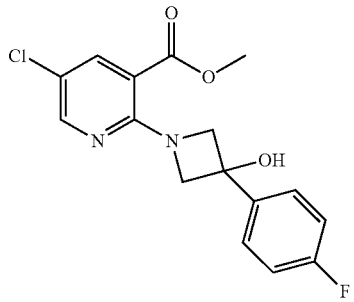 [SMILES: COC(=O)c1cc(Cl)cnc1N1CC(O)(c2ccc(F)cc2)C1]

The title compound (D81) (0021/074/1) (75.9 mg) was prepared according to the experimental procedure described in Description 80 starting from tert-butyl 3-(4-fluorophenyl)-3-hydroxyazetidine-1-carboxylate (D29) (100 mg, 0.374 mmol) and methyl 2,5-dichloronicotinate (77.32 mg, 0.374 mmol).

MS: (ES/+) m/z: 337.2 [MH$^+$] C16H14ClFN2O3 requires 336.75

Description 82: methyl 5-chloro-2-(3-((4-fluorophenoxy)methyl)azetidin-1-yl)nicotinate (D82)

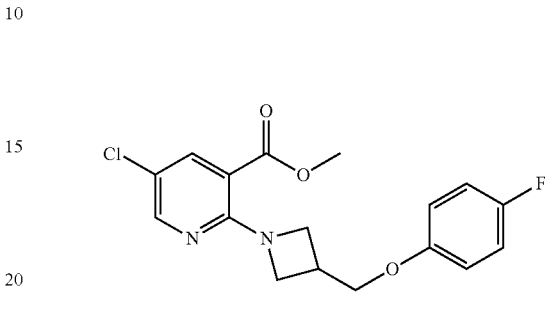

To a solution of methyl 5-chloro-2-(3-(hydroxymethyl)azetidin-1-yl)nicotinate (D65) (59 mg, 0.229 mmol) in dry tetrahydrofuran (1.6 ml) 4-Fluorophenol (25.8 mg, 0.229 mmol) Diisopropyl azodicarboxylate (50 µl, 0.253 mmol) and the triphenylphosphine (66.3 mg, 0.258 mmol) were added. The resulting solution was stirred overnight at room temperature. The residue obtained after solvent evaporation was purified by ISOLUTE SPE-Si cartridge (10 g) eluting with a mixture cyclohexane/ethylacetate from 100/0 to 90/10. Collected fractions, after solvent evaporation afforded the title compound (D82) (53.1 mg)

MS: (ES/+) m/z: 351.3 [MH$^+$] C17H16ClFN2O3 requires 350.08

1H NMR (400 MHz, CHLOROFORM-d) δ=8.25 (d, J=2.4 Hz, 1H), 7.97 (d, J=2.9 Hz, 1H), 7.03-6.92 (m, 2H), 6.88-6.76 (m, 2H), 4.26 (t, J=9.0 Hz, 2H), 4.13 (d, J=6.8 Hz, 2H), 3.96 (dd, J=5.4, 9.8 Hz, 2H), 3.90 (s, 3H), 3.18-3.08 (m, 1H).

Description 83: methyl 5-chloro-2-(3-((3-fluorophenoxy)methyl)azetidin-1-yl)nicotinate (D83)

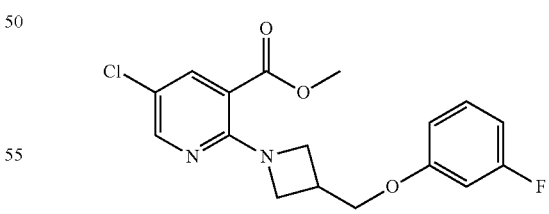

The title compound (D83) (D021/006/3) (66.2 mg) was prepared according to the experimental procedure described in Description 82 starting from methyl 5-chloro-2-(3-(hydroxymethyl)azetidin-1-yl)nicotinate (D65) (37 mg, 0.143 mmol) and 3-Fluorophenol (13 µl, 0.143 mmol).

MS: (ES/+) m/z: 351.3 [MH$^+$] C17H16ClFN2O3 requires 350.08

Description 84: methyl 5-chloro-2-(3-((4-fluorophenyl)amino)azetidin-1-yl)nicotinate (D84)

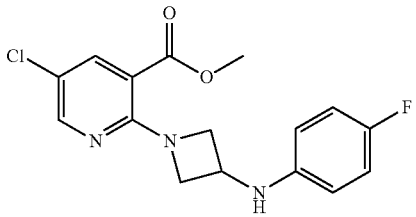 [SMILES: COC(=O)c1cc(Cl)cnc1N1CC(Nc2ccc(F)cc2)C1]

The title compound (D84) (79 mg) was prepared according to the experimental procedure described in Description 62 starting from Methyl 2,5-dichloronicotinate (62.06 mg, 0.3 mmol) and N-(4-fluorophenyl)azetidin-3-amine (D54) (60 mg, 0.361 mmol).

MS: (ES/+) m/z: 336.1 [MH$^+$] C16H15ClFN3O2 requires 335.07

$^1$H NMR (400 MHz, CHLOROFORM-d) δ (ppm): 8.26 (d, J=2.4 Hz, 1H), 8.00 (d, J=2.4 Hz, 1H), 6.94 (t, J=8.8 Hz, 2H), 6.61-6.41 (m, 2H), 4.49 (dd, J=7.6, 9.0 Hz, 2H), 4.31 (s, 1H), 3.96-3.84 (m, 5H)

Description 85: methyl 5-chloro-2-(3-((2,4-difluorophenyl)amino)azetidin-1-yl)nicotinate (D85)

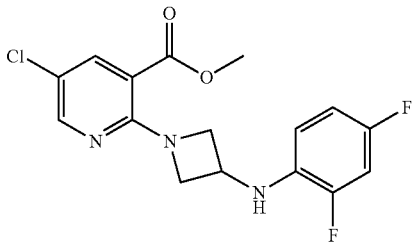 [SMILES: COC(=O)c1cc(Cl)cnc1N1CC(Nc2ccc(F)cc2F)C1]

To a cooled (0° C.) solution of tert-butyl 3-((2,4-difluorophenyl)amino)azetidine-1-carboxylate (D31) (90 mg, 0.316 mmol) in dichloromethane, a mixture of trifluoroacetic acid/dichloromethane (3 ml/1 ml) was added and the reaction mixture was stirred 1 h. The solvents were evaporated in vacuo and the residue was dissolved in tetrahydrofuran/methanol (3/1 ml) triethylamine (0.132 ml, 0.95 mmol) was added followed by the addition of methyl 2,5-dichloronicotinate (52.33 mg, 0.253 mmol) and the resulting mixture was stirred 12 h at 75° C. The residue abtained after solvent evaporation was purified by Biotage SNAP-Si column eluting with cyclohexane/ethyl acetate from 100/0 to 90/10. Collected fractions afforded the title compound (D85) (0022/086/5) (38 mg).

MS: (ES/+) m/z: 354.1 [MH$^+$] C16H14ClF2N3O2 requires 353.07.

$^1$H NMR (400 MHz, CHLOROFORM-d) δ=8.26 (d, J=2.4 Hz, 1H), 8.00 (d, J=2.4 Hz, 1H), 6.89-6.71 (m, 2H), 6.47 (dt, J=5.1, 9.2 Hz, 1H), 4.50 (dd, J=7.3, 9.3 Hz, 2H), 4.33 (br. s., 1H), 4.12 (br. s., 1H), 3.98-3.85 (m, 5H)

Description 86: methyl 5-chloro-2-(3-((2-methyl-4-(trifluoromethyl)phenyl)amino)azetidin-1-yl)nicotinate (D86)

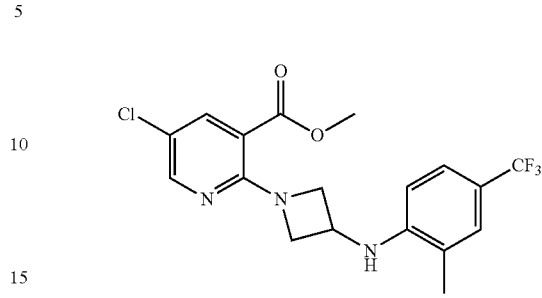

The title compound (D86) (44 mg) was prepared according to the experimental procedure described in Description 85 starting from tert-butyl 3-((2-methyl-4-(trifluoromethyl)phenyl)amino)azetidine-1-carboxylate (D32) (150 mg, 0.454 mmol) and methyl 2,5-dichloronicotinate (74.92 mg, 0.363 mmol)

MS: (ES/+) m/z: 400.2 [MH$^+$] C18H17ClF3N3O2 requires 399.15

$^1$H NMR (400 MHz, CHLOROFORM-d) δ (ppm): 8.27 (d, J=2.4 Hz, 1H), 8.01 (d, J=2.4 Hz, 1H), 7.39 (d, J=8.8 Hz, 1H), 7.34 (s, 1H), 6.42 (d, J=8.3 Hz, 1H), 4.55 (dd, J=7.6, 9.0 Hz, 2H), 4.41 (br. s., 1H), 4.19 (br. s., 1H), 3.95 (dd, J=4.4, 9.8 Hz, 2H), 3.90 (s, 3H), 2.22 (s, 3H)

Description 87: methyl 5-chloro-2-(3-((4-fluoro-2-methylphenyl)(methyl)amino)azetidin-1-yl)nicotinate (D87)

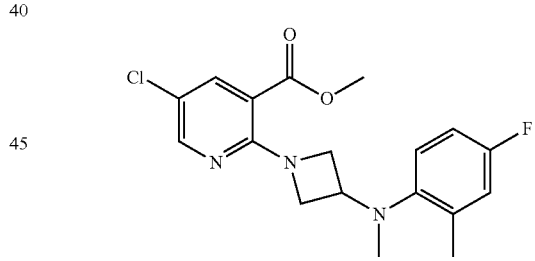

To mixture of N-methyl-N-(2-methyl-4-fluoro-phenyl)azetidin-3-amine (D56) (110 mg, 0.566 mmol) and triethylamine (0.18 ml, 0.849 mmol) in tetrahydrofuran/methanol (3/1 ml) Methyl 2,5-dichloronicotinate (116.82 mg, 0.566 mmol) was added and the mixture was heated at 75° C. for 12 hours. Solvents were evaporated and the residue was purified by SNAP-Si cartridge (10 g) eluting with cyclohexane/ethyl acetate from 100/0 to 90/10. Collected fractions after solvent evaporation afforded the title compound (D87) (170 mg)

MS: (ES/+) m/z: 363.8 [MH$^+$] C18H19ClFN3O2 requires 363.81

$^1$H NMR (400 MHz, CHLOROFORM-d) δ (ppm): 8.25 (br. s, 1H), 8.02 (br. s., 1H), 6.99-6.79 (m, 3H), 4.40-4.21 (m, J=6.4 Hz, 2H), 4.21-4.09 (m, J=6.8 Hz, 1H), 3.97-3.90 (m, 2H), 3.86 (s, 3H), 2.61 (br. s., 3H), 2.35 (s, 3H)

Description 88: methyl 2-(3-((5-methylisoxazol-3-yl)oxy)azetidin-1-yl)-5-(trifluoromethyl)nicotinate (D88)

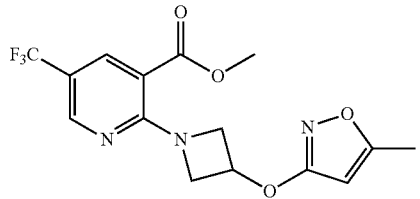 [SMILES: COC(=O)c1cc(C(F)(F)F)cnc1N1CC(Oc2cc(C)on2)C1]

To a solution of 5-methylisoxazol-3-ol (33.48 mg, 0.34 mmol) in acetonitrile (0.7 ml) potassium carbonate (60.85 mg, 0.44 mmol) was added followed by addition of methyl 2-(3-((methylsulfonyl)oxy)azetidin-1-yl)-5-(trifluoromethyl)nicotinate (D68) (120 mg, 0.34 mmol). The reaction mixture was heated at 180° C. under microwave irradiation for 25 min. After solvent evaporation the residue was purified by Biotage SNAP-Si column (10 g) eluting with cycloexane/ethyl acetate from 95/05 to 70/30. Collected fractions were evaporated in vacuo tot afford the title compound (D88) (20 mg)

MS: (ES/+) m/z: 358.2 [MH$^+$] C15H14F3N3O4 requires 357.09

$^1$H NMR (400 MHz, CHLOROFORM-d) δ (ppm): 8.62-8.42 (m, 1H), 8.21 (d, J=2.0 Hz, 1H), 5.67 (d, J=0.7 Hz, 1H), 5.29 (ddd, J=2.6, 3.9, 6.5 Hz, 1H), 4.56 (ddd, J=0.9, 6.5, 11.2 Hz, 2H), 4.25 (dd, J=2.7, 11.2 Hz, 2H), 3.91 (s, 3H), 2.36 (d, J=0.7 Hz, 3H)

Description 89: methyl 5-(trifluoromethyl)-2-(3-((6-(trifluoromethyl)pyridin-2-yl)oxy)azetidin-1-yl)nicotinate (D89)

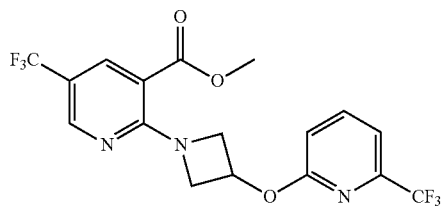 [SMILES: COC(=O)c1cc(C(F)(F)F)cnc1N1CC(Oc2cccc(C(F)(F)F)n2)C1]

The title compound (D89) (25 mg) was prepared according to the experimental procedure described in Description 88 starting from methyl 2-(3-((methylsulfonyl)oxy)azetidin-1-yl)-5-(trifluoromethyl)nicotinate (D68) (120 mg, 0.34 mmol) and 2-Hydroxy-6-(trifluoromethyl)pyridine (55.12 mg, 0.34 mmol, commercially available from Fluorochem#032990).

MS: (ES/+) m/z: 358.2 [MH$^+$] C17H13F6N3O3 requires 421.09

$^1$H NMR (400 MHz, CHLOROFORM-d) δ (ppm): 8.52 (d, J=1.7 Hz, 1H), 8.21 (d, J=2.2 Hz, 1H), 7.78 (t, J=7.9 Hz, 1H), 7.33 (d, J=7.3 Hz, 1H), 7.00 (d, J=8.3 Hz, 1H), 5.65-5.34 (m, 1H), 4.63 (dd, J=6.6, 11.0 Hz, 2H), 4.25 (dd, J=3.9, 11.2 Hz, 2H), 3.92 (s, 3H)

Description 90: methyl 5-fluoro-2-(3-((4-fluoro-2-methylphenyl)amino)azetidin-1-yl)nicotinate (D90)

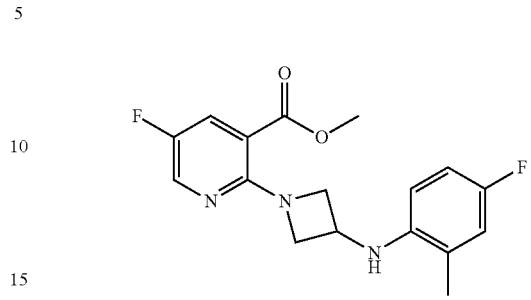

A mixture of methyl 2-chloro-5-fluoronicotinate (D69) (199.85 mg, 1.054 mmol) and potassium carbonate (291 mg, 2.108 mmol) in tetrahydrofuran (2 ml) was stirred under N2 nitrogen 15 min at room temperature. N-(4-fluoro-2-methylphenyl)azetidin-3-amine (D55) (190 mg, 1.054 mmol) was added and the resulting mixture was stirred 1 day at room temperature. The residue obtained after solvent evaporation was purified by Biotage SNAP-Si column eluting with a mixture cyclohexane/ethyl acetate from 100/0 to 80/20. Collected fractions after solvent evaporation afforded the title compound (D90)(155 mg)

MS: (ES/+) m/z: 334.6 [MH$^+$] C17H17F2N3O2 requires 333.33

$^1$H NMR (400 MHz, CHLOROFORM-d) δ=8.24 (d, J=2.9 Hz, 1H), 7.80 (dd, J=2.9, 8.3 Hz, 1H), 6.91-6.75 (m, 2H), 6.32 (dd, J=4.9, 8.3 Hz, 1H), 4.50 (dd, J=7.3, 9.3 Hz, 2H), 4.40-4.27 (m, 1H), 3.97-3.81 (m, 5H), 3.72 (d, J=6.4 Hz, 1H), 2.18 (s, 3H)

Description 91: methyl 5-chloro-2-(3-(4-(trifluoromethyl)phenoxy)pyrrolidin-1-yl)nicotinate (D91)

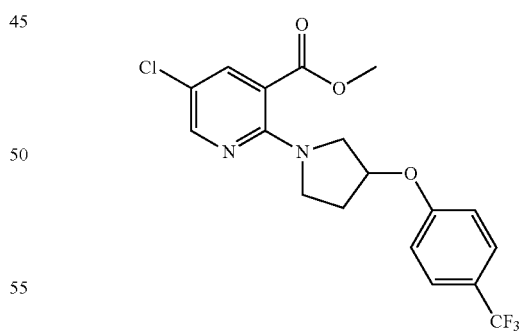

The title compound (D91) (230 mg) was prepared according to the experimental procedure described in Description 62 starting methyl 2,5-dichloronicotinate (180 mg, 0.87 mmol) and 3-(4-(trifluoromethyl)phenoxy)pyrrolidine (D57) (242 mg, 1.05 mmol).

MS: (ES/+) m/z: 401.5 [MH$^+$] C18H16ClF3N2O3 requires 400.08

Description 92: methyl 5-chloro-2-(3-(3-(trifluoromethyl)phenoxy)pyrrolidin-1-yl)nicotinate (D92)

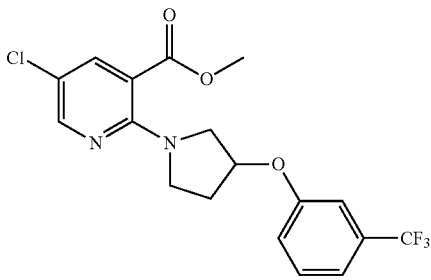 [SMILES: COC(=O)c1cc(Cl)cnc1N1CCC(Oc2cccc(C(F)(F)F)c2)C1]

The title compound (D92) (270 mg) was prepared according to the experimental procedure described in Description 62 starting methyl 2,5-dichloronicotinate (241.37 mg, 1.17 mmol) and from 3-(3-(trifluoromethyl)phenoxy)pyrrolidine (D58) (323 mg, 1.39 mmol).

MS: (ES/+) m/z: 401.5 [MH$^+$] C18H16ClF3N2O3 requires 400.08

Description 93: methyl 5-chloro-2-(3-(4-fluorophenoxy)pyrrolidin-1-yl)nicotinate (D93)

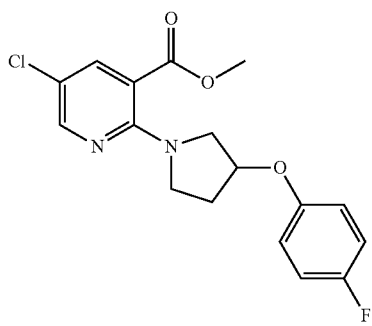 [SMILES: COC(=O)c1cc(Cl)cnc1N1CCC(Oc2ccc(F)cc2)C1]

The title compound (D93) (235 mg) was prepared according to the experimental procedure described in Description 62 starting from methyl 2,5-dichloronicotinate (241.37 mg, 1.17 mmol) and 3-(4-fluorophenoxy)pyrrolidine (D59) (253 mg, 1.39 mmol).

MS: (ES/+) m/z: 351 [MH$^+$] C17H16ClFN2O3 requires 350.08

Description 94: methyl 5-chloro-2-(3-phenoxy)pyrrolidin-1-yl)nicotinate (D94)

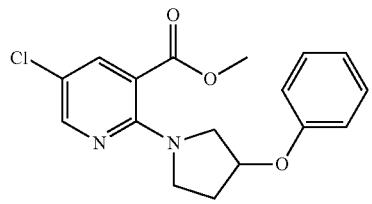 [SMILES: COC(=O)c1cc(Cl)cnc1N1CCC(Oc2ccccc2)C1]

To a solution of methyl 2,5-dichloronicotinate (303 mg, 1.47 mmol) in tetrahydrofuran (10 ml) 3-phenoxy)pyrrolidine (240 mg, 1.47 mmol, available from Tigersci #P67164) and triethylamine (163 mg, 1.62 mmol) were added and the mixture was refluxed 18 hours. After cooling to room temperature, the precipitates were filtered off and the filtrate was concentrated under reduced pressure. The residue was dissolved in ethyl acetate (10 ml), washed with water (10 ml) and brine (10 ml), dried over Na$_2$SO$_4$ and concentrated. The residue was purified by flash chromatography on silica gel eluting with a mixture: petroleum ether/ethyl acetate from 30:1 to 20:1. Collected fractions, after solvent evaporation afforded the title compound (D94) (234 mg) as a colorless oil.

$^1$H NMR (400 MHz, CHLOROFORM-d) δ (ppm): 8.22 (1H, d, J=2.8 Hz), 7.90 (1H, d, J=2.4 Hz), 7.31 (2H, dd, J=8.4, 7.6 Hz), 6.99 (1H, t, J=7.6 Hz), 6.91-6.89 (2H, m), 5.03-5.01 (1H, m), 3.95-3.94 (1H, m), 3.92 (3H, s), 3.86-3.79 (1H, m), 3.53-3.48 (1H, m), 3.41-3.40 (1H, m), 2.36-2.30 (1H, m), 2.24-2.17 (1H, m).

Description 95: methyl 5-chloro-2-(3-(3-fluorophenoxy)pyrrolidin-1-yl)nicotinate (D95)

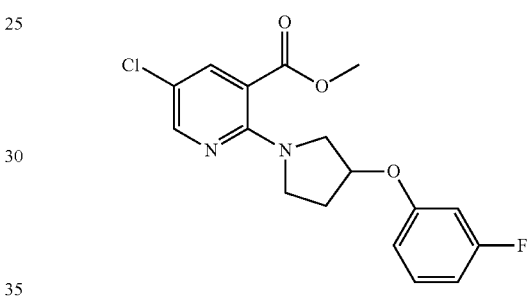

The title compound (D95) (250 mg) was prepared according to the experimental procedure described in Description 62 starting from methyl 2,5-dichloronicotinate (241.37 mg, 1.17 mmol) and 3-(3-fluorophenoxy)pyrrolidine (D60) (253 mg, 1.39 mmol).

MS: (ES/+) m/z: 351 [MH$^+$] C17H16ClFN2O3 requires 350.08

Description 96: methyl 5-chloro-2-(3-(m-tolyloxy)pyrrolidin-1-yl)nicotinate (D96)

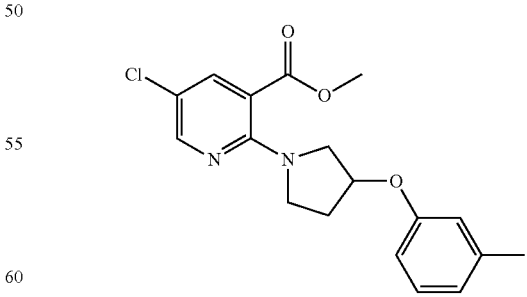

The title compound (D96) (200 mg) was prepared according to the experimental procedure described in Description 62 starting from methyl 2,5-dichloronicotinate (241.37 mg, 1.17 mmol) and 3-(m-tolyloxy)pyrrolidine (D61) (247.7 mg, 1.39 mmol).

Description 97: methyl 4-(1-(2,5-dichloronicotinamido)cyclopropyl)benzoate (D97)

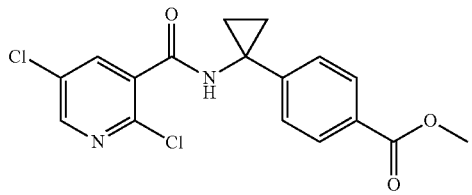 [SMILES: COC(=O)c1ccc(C2(NC(=O)c3cc(Cl)cnc3Cl)CC2)cc1]

To a solution of 2,5-dichloronicotinic acid (1.84 g, 7.06 mmol) in dry dimethylformamide (15 ml) 1-Hydroxybenzotriazole hydrate (1.08 g, 7.06 mmol) and 1-ethyl-3-(3-dimethylaminopropyl) carbodiimide (2.03 g, 10.58 mmol), a solution of methyl 4-(1-aminocyclopropyl)benzoate hydrochloride (D7) (1.67 g, 7.06 mmol) and triethylamine (0.98 ml, 7.06 mmol) in dry dimethylformamide (15 ml) was added and the resulting mixture was stirred 1 h at room temperature. NH$_4$Cl saturated solution (50 ml) was added the mixture was extracted with ethylacetate (3×50 ml). Collected organics, after solvent evaporation, was purified by Biotage column SNAP-Si (50 g) eluting with a mixture dichloromethane/ethylacetate from 100/0 to 95:5. Collected organics after solvent evaporation afforded the title compound (D97) (1.03 mg)

MS: (ES/+) m/z: 365.1 [MH$^+$] C17H14Cl2N2O3 requires 364.4

$^1$H NMR (400 MHz, CHLOROFORM-d) δ=8.46 (d, J=2.4 Hz, 1H), 8.14 (d, J=2.4 Hz, 1H), 8.05-7.99 (m, 2H), 7.41-7.35 (m, 2H), 7.17 (s, 1H), 3.93 (s, 3H), 1.50 (s, 4H).

Description 98:
5-chloro-2-(2-phenylpyrrolidin-1-yl)nicotinic acid
(D98)

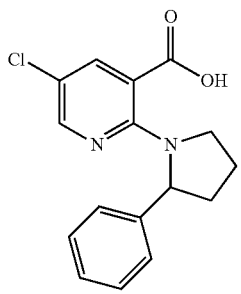 [SMILES: O=C(O)c1cc(Cl)cnc1N1CCCC1c1ccccc1]

To an ice cooled solution of methyl 5-chloro-2-(2-phenylpyrrolidin-1-yl)nicotinate (D72) (165 mg, 0.520 mmol) in methanol (10 ml), 10N NaOH (10 ml) was added. The mixture was heated under reflux overnight. After cooled to room temperature, the mixture was concentrated in vacuo. The residue was diluted with water (10 ml), acidified with 2.5N HCl (pH 1-2), and the resulting mixture was extracted with ethyl acetate (2×10 ml). The organic solution was washed with brine (20 ml), dried over Na$_2$SO$_4$ and evaporated in vacuo to afford the title compound (D98) (170 mg) as a red solid.

Description 99:
5-chloro-2-(3-phenylpyrrolidin-1-yl)nicotinic acid
(D99)

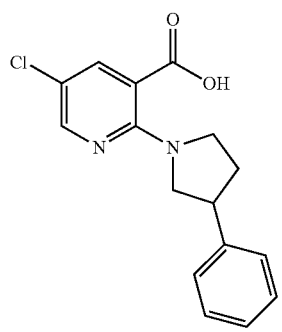 [SMILES: O=C(O)c1cc(Cl)cnc1N1CCC(c2ccccc2)C1]

The title compound (D99) (270 mg) was prepared according to the experimental procedure described in Description 60 starting from methyl 5-chloro-2-(3-phenylpyrrolidin-1-yl)nicotinate (D73) (310 mg, 1.00 mmol)

$^1$H NMR (400 MHz, CHLOROFORM-d) δ (ppm): 8.36 (1H, d, J=2.4 Hz), 8.20 (1H, d, J=2.4 Hz), 7.40-7.27 (5H, m), 3.78-3.52 (5H, m), 2.47-2.42 (1H, m), 2.21-2.10 (1H, m).

Description 100:
2-(2-benzylpyrrolidin-1-yl)-5-chloronicotinic acid
(D100)

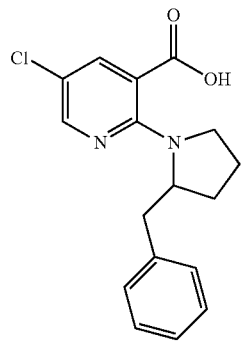 [SMILES: O=C(O)c1cc(Cl)cnc1N1CCCC1Cc1ccccc1]

To methyl 2-(2-benzylpyrrolidin-1-yl)-5-chloronicotinate (D74) (75 mg, 0.226 mmol) in a mixture 1,4-dioxane/water (3 ml/1 ml), lithium hydroxide monohydrate (14.3 mg, 0.34 mmol) was added and the resulting mixture was stirred at 150° C. under microwave irradiation for 10 min (2 cycles of 5 min each). Solvents were evaporated in vacuo. The obtained residue was diluted with water/1M HCl (5 ml/15 ml) and extracted with ethyl acetate (3×30 ml). Collected fractions after solvent evaporation afforded the title compound (D100) (70 mg).

MS: (ES/+) m/z: 317 [MH⁺] C17H17ClN2O2 requires 316.10

Description 101: 5-chloro-2-(3-phenoxyazetidin-1-yl)nicotinic acid (D101)

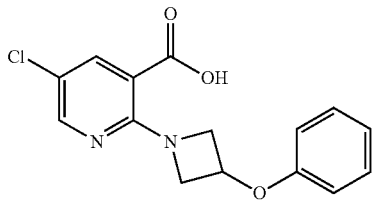 [SMILES: O=C(O)c1cc(Cl)cnc1N1CC(Oc2ccccc2)C1]

Methyl 5-chloro-2-(3-phenoxyazetidin-1-yl)nicotinate (D75) (305 mg, 0.96 mmol) was dissolved in methanol/tetrahydrofuran (10 ml/10 ml), 5N NaOH (10 ml) was added at 0° C. The resulting reaction mixture was heated to 35° C. for 18 hours then cooled to room temperature and concentrated. Water added (10 ml) and the mixture was acidified with 2.5N HCl (pH1-2). The white solid was collected, washed with water and dried to provide compound (D101) (280 mg) as a white solid.

¹H NMR (400 MHz, DMSO-d6): δ (ppm): 8.33 (1H, d, J=2.8 Hz), 7.97 (1H, d, J=2.8 Hz), 7.33 (2H, dd, J=8.4, 7.6 Hz), 6.99 (1H, t, J=7.2 Hz), 6.87 (2H, d, J=7.6 Hz), 5.11-5.07 (1H, m), 4.45 (2H, dd, J=10.4, 6.4 Hz), 3.97 (2H, dd, J=6.4, 3.6 Hz).

Description 102: 5-chloro-2-(3-(4-fluorophenoxy) azetidin-1-yl)nicotinic acid (D102)

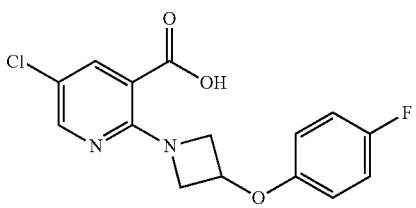 [SMILES: O=C(O)c1cc(Cl)cnc1N1CC(Oc2ccc(F)cc2)C1]

The title compound (D102) (240 mg) was prepared according to the experimental procedure described in Description 100 starting from methyl 5-chloro-2-(3-(4-fluorophenoxy) azetidin-1-yl)nicotinate (D76) (270 mg, 0.801 mmol)

MS: (ES/+) m/z: 323.1 [MH⁺] C15H12ClFN2O3 requires 322.05

¹H NMR (400 MHz, DMSO-d₆) δ (ppm): 13.16 (br. s., 1H), 8.32 (d, J=2.9 Hz, 1H), 8.00-7.93 (m, 1H), 7.20-7.10 (m, 2H), 6.94-6.83 (m, 2H), 5.13-4.99 (m, 1H), 4.44 (dd, J=5.9, 10.8 Hz, 2H), 3.96 (dd, J=3.4, 10.3 Hz, 2H)

Description 103: 5-chloro-2-(3-(3-fluorophenoxy) azetidin-1-yl)nicotinic acid (D103)

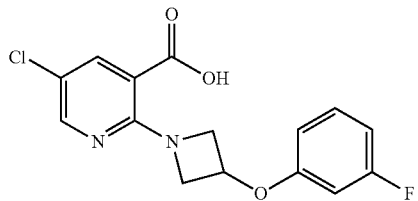 [SMILES: O=C(O)c1cc(Cl)cnc1N1CC(Oc2cccc(F)c2)C1]

5-chloro-2-(3-(3-fluorophenoxy)azetidin-1-yl)nicotinic acid (D103) was prepared according to three different procedures reported below
Procedure A To a solution of 3-Fluorophenol (0.139 ml, 1.417 mmole) in acetonitrile (3 ml), potassium carbonate (254.6 mg, 1.842 mmol) were added followed by the addition of methyl 5-chloro-2-(3-((methylsulfonyl)oxy)azetidin-1-yl)nicotinate (D63) (500 mg, 1.558 mmol). The reaction mixture was heated at 160° C. under microwave irradiation for 25 min. Solvents were evaporated in vacuo and the residue was diluted with 1M sol HCl (20 ml) and extracted with ethyl acetate (3×20 ml). The organics after solvent evaporation were loaded on SPE-SCX cartridge (20 g). Collected ammonia fractions were evaporated in vacuo and the residue was dissolved in 1,4-dioxane/water (3 ml/1 ml) and heated at 150° C. under microwave irradiation for 10 min in the presence of LiOH (59.4 mg, 1.417 mmol). The mixture was evaporated in vacuo, diluted with water/1M HCl (10 ml/20 ml) and extracted with ethyl acetate (3×40 ml). Collected organics, after solvent evaporation, afforded the title compound (D103) (420 mg)

Procedure B

The title compound (D103) (250 mg) was prepared according to the experimental procedure described in Description 100 starting from methyl 5-chloro-2-(3-(3-fluorophenoxy) azetidin-1-yl)nicotinate (D77) (290 mg, 0.861 mmol)

MS: (ES/+) m/z: 323.5 [MH⁺] C15H12ClFN2O3 requires 322.05

¹H NMR (400 MHz, DMSO-d₆) δ (ppm): 13.20 (s, 1H), 8.33 (d, J=2.4 Hz, 1H), 7.97 (d, J=2.7 Hz, 1H), 7.35 (q, J=8.1 Hz, 1H), 6.99-6.30 (m, 3H), 5.11 (tt, J=3.5, 6.4 Hz, 1H), 4.46 (dd, J=6.4, 10.5 Hz, 2H), 3.97 (dd, J=3.3, 10.4 Hz, 2H)

Procedure C

To a solution of 3-fluorophenol (24.6 ml, 0.274 mol) in dimethylformamide (400 ml) anhydrous potassium carbonate (37.87 g, 0.274 mol) was added and the mixture was heated at 80° C. for 4 hours. A solution of 5-chloro-2-(3-((methylsulfonyl)oxy)azetidin-1-yl)nicotinic acid (D63) (80 g, 0.249 mol) in dimethylformamide (160 ml) was added dropwise and the reaction mixture was stirred at 120° C. for 24 hours. The resulting mixture was cooled to room temperature, then 1M NaOH (548 ml) was added and the mixture was left stirring 12 hours at 120° C. The reaction mixture was extracted with diethylether (1 L). The resulting mixture was acidified to pH1 by addition of 2N HCl. A precipitate formed and was filtered off and was washed with water (500 ml). After drying title compound (D103) (60 g) was isolated MS: (ES/+) m/z: 323.5 [MH⁺] C15H12ClFN2O3 requires 322.05

¹H NMR (400 MHz, DMSO-d₆) δ (ppm): 13.18 (br. s., 1H), 8.32 (d, J=2.4 Hz, 1H), 7.97 (d, J=2.4 Hz, 1H), 7.39-7.30 (m, 1H), 6.86-6.62 (m, 3H), 5.11 (tt, J=3.3, 6.5 Hz, 1H), 4.46 (dd, J=6.4, 10.3 Hz, 2H), 3.97 (dd, J=3.4, 10.8 Hz, 2H).

Description 104: 5-chloro-2-(3-(4-(trifluoromethyl)phenoxy)azetidin-1-yl)nicotinic acid (D104)

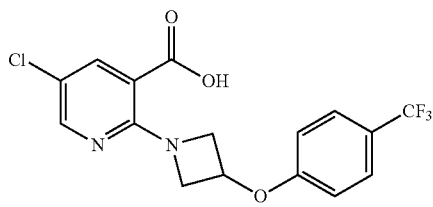 [SMILES: O=C(O)c1cc(Cl)cnc1N1CC(Oc2ccc(C(F)(F)F)cc2)C1]

The title compound (D104) (200 mg) was prepared according to the experimental procedure described in 100 starting from methyl 5-chloro-2-(3-(4-(trifluoromethyl)phenoxy)azetidin-1-yl)nicotinate (D78) (110 mg, 0.284 mmol)

MS: (ES/+) m/z: 373.1 [MH⁺] C16H12ClF3N2O3 requires 372.05

Description 105: 5-chloro-2-(3-(3-(trifluoromethyl)phenoxy)azetidin-1-yl)nicotinic acid (D105)

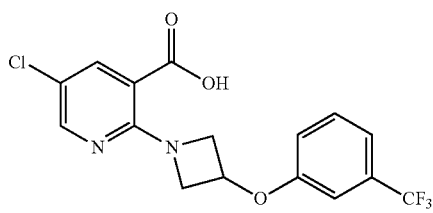 [SMILES: O=C(O)c1cc(Cl)cnc1N1CC(Oc2cccc(C(F)(F)F)c2)C1]

The title compound (D105) (180 mg) was prepared according to the experimental procedure described in 100 starting from methyl 5-chloro-2-(3-(3-(trifluoromethyl)phenoxy)azetidin-1-yl)nicotinate (D79) (110 mg, 0.284 mmol)

MS: (ES/+) m/z: 373.1 [MH⁺] C16H12ClF3N2O3 requires 372.05

Description 106: 5-chloro-2-(3-(4-fluoro-3-(trifluoromethyl)phenoxy)azetidin-1-yl)nicotinic (D106)

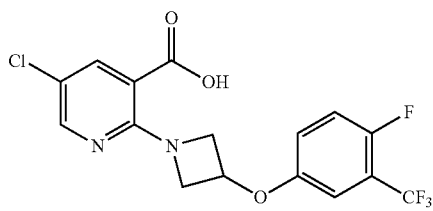

The title compound (D106) (117 mg) was prepared according to the experimental procedure described in Description 103A vero starting from methyl 5-chloro-2-(3-((methylsulfonyl)oxy)azetidin-1-yl)nicotinate (D63) (100 mg, 0.311 mmol) and 4-Fluoro-3-(trifluoromethyl)phenol (51.04 mg, 0.284 mmol).

MS: (ES/+) m/z: 391.2 [MH⁺] C16H11ClF4N2O3 requires 390.04

¹H NMR (400 MHz, DMSO-d6) δ (ppm): 8.32 (d, J=2.45 Hz, 1H) 7.97 (d, J=2.69 Hz, 1H) 7.55-7.45 (m, 1H) 7.30-7.23 (m, 1H) 7.15-7.22 (m, 1H) 5.26-5.12 (m, 1H) 4.46 (dd, J=10.39, 6.72 Hz, 2H) 3.98 (dd, J=10.39, 3.06 Hz, 2H)

Description 107: 5-chloro-2-(3-(3-(trifluoromethoxy)phenoxy)azetidin-1-yl)nicotinic acid (D107)

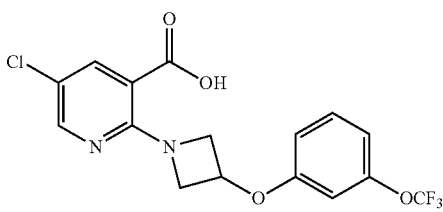 [SMILES: O=C(O)c1cc(Cl)cnc1N1CC(Oc2cccc(OC(F)(F)F)c2)C1]

The title compound (D107) (112 mg) was prepared according to the experimental procedure described in Description 103A starting from methyl 5-chloro-2-(3-((methylsulfonyl)oxy)azetidin-1-yl)nicotinate (D63) (100 mg, 0.311 mmol) and 3-(trifluoromethoxy)phenol (0.036 ml, 0.284 mmol).

MS: (ES/+) m/z: 389.2 [MH⁺] C16H12ClF3N2O4 requires 388.04

¹H NMR (400 MHz, DMSO-d₆) δ (ppm): 13.22 (br. s., 1H), 8.33 (d, J=2.7 Hz, 1H), 7.97 (d, J=2.7 Hz, 1H), 7.45 (t, J=8.3 Hz, 1H), 6.99 (d, J=8.6 Hz, 1H), 6.96-6.83 (m, 2H), 5.24-4.99 (m, 1H), 4.46 (dd, J=6.2, 10.6 Hz, 2H), 3.98 (dd, J=3.4, 10.3 Hz, 2H)

Description 108: 5-chloro-2-(3-(2,4-difluorophenoxy)azetidin-1-yl)nicotinic acid (D108)

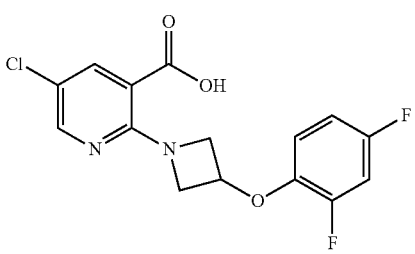 [SMILES: O=C(O)c1cc(Cl)cnc1N1CC(Oc2ccc(F)cc2F)C1]

The title compound (D108) (84 mg) was prepared according to the experimental procedure described in Description 103A starting from methyl 5-chloro-2-(3-((methylsulfonyl)oxy)azetidin-1-yl)nicotinate (D63) (100 mg, 0.311 mmol) and 2,4-Difluorophenol (0.027 ml, 0.284 mmol).

MS: (ES/+) m/z: 341.1 [MH⁺] C15H11ClF2N2O3 requires 340.04

¹H NMR (400 MHz, DMSO-d₆) δ (ppm): 13.21 (br. s., 1H), 8.33 (d, J=2.4 Hz, 1H), 7.98 (d, J=2.4 Hz, 1H), 7.60-7.21 (m, 1H), 7.20-6.77 (m, 2H), 5.12 (td, J=2.9, 6.4 Hz, 1H), 4.44 (dd, J=6.6, 10.5 Hz, 2H), 4.00 (dd, J=3.4, 10.5 Hz, 2H)

Description 109: 5-chloro-2-(3-(3,4-difluorophenoxy)azetidin-1-yl)nicotinic acid (D109)

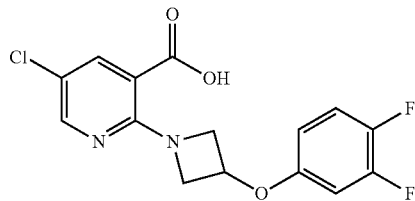 [SMILES: O=C(O)c1cc(Cl)cnc1N1CC(Oc2ccc(F)c(F)c2)C1]

The title compound (D109) (87 mg) was prepared according to the experimental procedure described in Description 103A starting from methyl 5-chloro-2-(3-((methylsulfonyl)oxy)azetidin-1-yl)nicotinate (D63) (100 mg, 0.311 mmol) and 3,4-Difluorophenol (36.87 mg, 0.284 mmol).

MS: (ES/+) m/z: 341.1 [MH$^+$] C15H11ClF2N2O3 requires 340.04

$^1$H NMR (400 MHz, DMSO-d$_6$) δ (ppm): 9.25 (s, 1H), 8.22 (d, J=2.4 Hz, 1H), 7.85 (d, J=8.6 Hz, 2H), 7.77 (d, J=2.4 Hz, 1H), 7.39-7.25 (m, 3H), 6.90 (d, J=7.3 Hz, 1H), 6.81 (br. s., 1H), 6.77-6.67 (m, 2H), 4.27 (d, J=6.1 Hz, 3H), 3.84 (s, 3H), 3.69 (d, J=5.6 Hz, 2H), 1.45-1.24 (m, 4H)

Description 110: 2-(3-(3-(4-(tert-butoxycarbonyl)piperazin-1-yl)phenoxy)azetidin-1-yl)-5-chloronicotinic acid (D110)

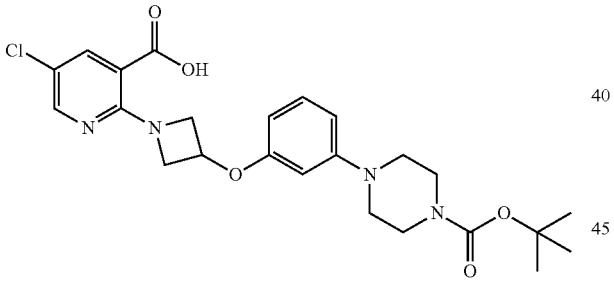

To a solution of tert-butyl 4-(3-hydroxyphenyl)piperazine-1-carboxylate (D18) (143.18 mg, 0.514 mmole) in dimethylformamide (2 ml), potassium carbonate (71 mg, 0.514 mmol) and the reaction mixture was heated 2 h at 80° C. methyl 5-chloro-2-(3-((methylsulfonyl)oxy)azetidin-1-yl)nicotinate (D63) (150 mg, 0.467 mmol) in dimethylformamide (2 ml) was added dropwise and the resulting mixture stirred 21 h at 120° C. After cooling at room temperature, 1M NaOH (0.935 ml) was added and the mixture stirred 1 h at 120° C. After cooling the reaction mixture was extracted with diethylether (2×10 ml) and the aqueous was evaporated in vacuo. The residue was purified by SPE-Si cartridge (5 g) eluting with a mixture dichloromethane/methanol from 100/0 to 80/20. Collected fractions, after solvent evaporation afforde the title compound (D110) (155 mg)

MS: (ES/+) m/z: 489.4 [MH$^+$] C24H29ClN4O5 requires 488.18

$^1$H NMR (400 MHz, DMSO-d$_6$) δ (ppm): 8.28 (br. s., 1H), 7.91 (br. s., 1H), 7.14 (t, J=8.1 Hz, 1H), 6.59 (d, J=8.3 Hz, 1H), 6.41 (s, 1H), 6.28 (d, J=8.3 Hz, 1H), 5.06 (br. s., 1H), 4.43 (dd, J=6.4, 10.3 Hz, 2H), 3.94 (dd, J=3.4, 10.3 Hz, 2H), 3.44 (d, J=4.9 Hz, 4H), 3.15-3.03 (m, 4H), 1.43 (s, 9H).

Description 111: 5-chloro-2-(3-(3-fluorophenyl)-3-hydroxyazetidin-1-yl)nicotinic acid (D111)

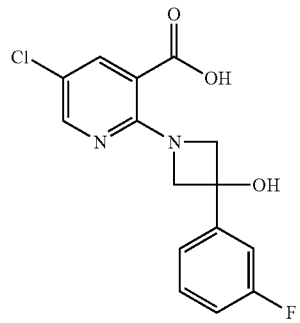 [SMILES: O=C(O)c1cc(Cl)cnc1N1CC(O)(c2cccc(F)c2)C1]

To a solution of methyl 5-chloro-2-(3-(3-fluorophenyl)-3-hydroxyazetidin-1-yl)nicotinate (D80) (70 mg, 0.207 mmol) in a mixture 3:1 1,4-dioxane/water (2 ml), lithium hydroxide monohydrate (133 mg, 0.312 mmol) was added and the resulting mixture was stirred 4 h at 70° C. After solvent evaporation the residue was taken in a mixture water/1M HCl (10 ml/10 ml) and extracted with ethylacetate (2×30 ml). Collected organics after solvent evaporation afforded the title compound (D111) (64.6 mg).

MS: (ES/+) m/z: 323.1 [MH$^+$] C15H12ClFN2O3 requires 322.05

$^1$H NMR (400 MHz, DMSO-d$_6$) δ (ppm): 8.35 (d, J=2.4 Hz, 1H), 7.98 (d, J=2.9 Hz, 1H), 7.48-7.40 (m, 1H), 7.38-7.27 (m, 2H), 7.12 (dt, J=2.0, 8.3 Hz, 1H), 6.42 (s, 1H), 4.26-4.14 (m, 4H).

Description 112: 5-chloro-2-(3-(4-fluorophenyl)-3-hydroxyazetidin-1-yl)nicotinic acid (D112)

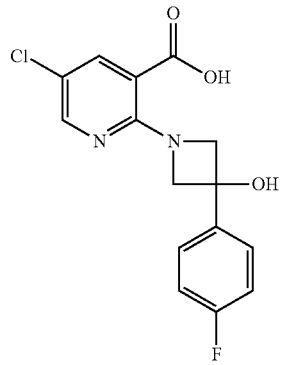 [SMILES: O=C(O)c1cc(Cl)cnc1N1CC(O)(c2ccc(F)cc2)C1]

The title compound (D112) (65.5 mg) was prepared according to the experimental procedure described in Description 111 starting from methyl 5-chloro-2-(3-(4-fluorophenyl)-3-hydroxyazetidin-1-yl)nicotinate (D81) (74 mg, 0.22 mmol).

MS: (ES/+) m/z: 323.1 [MH$^+$] C15H12ClFN2O3 requires 322.05

¹H NMR (400 MHz, DMSO-d₆) δ (ppm): 8.34 (d, J=2.9 Hz, 1H), 7.98 (d, J=2.4 Hz, 1H), 7.55 (dd, J=5.6, 8.6 Hz, 2H), 7.20 (t, J=8.8 Hz, 2H), 6.34 (s, 1H), 4.25-4.14 (m, 4H).

Description 113: 5-chloro-2-(3-((4-fluorophenoxy)methyl)azetidin-1-yl)nicotinic acid (D113)

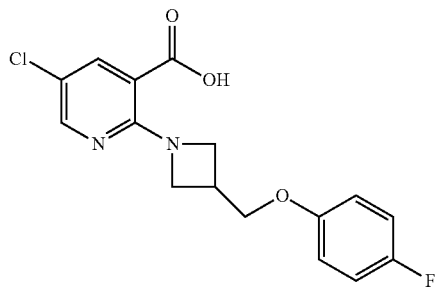 [SMILES: O=C(O)c1cc(Cl)cnc1N1CC(COc2ccc(F)cc2)C1]

To a solution of methyl 5-chloro-2-(3-((4-fluorophenoxy)methyl)azetidin-1-yl)nicotinate (D82) (52.1 mg, 0.148 mmol) in a mixture (3:1) 1,4-dioxane/water (1.6 ml), lithium hydroxide monohydrate (9.3 mg, 0.22 mmol) was added and the resulting mixture was heated under microwave irradiation 6 min at 140° C. After solvent evaporation the residue was taken in a mixture water/1M HCl (20 ml/5 ml) and extracted with ethylacetate (3×20 ml). Collected organics after solvent evaporation afforded the title compound (D113) (55.4 mg).

MS: (ES/+) m/z: 337.2 [MH⁺] C16H14ClFN2O3 requires 336.07

¹H NMR (400 MHz, DMSO-d₆) δ (ppm): 8.29 (d, J=2.9 Hz, 1H), 7.91 (d, J=2.9 Hz, 1H), 7.14-7.08 (m, 2H), 6.98-6.93 (m, 2H), 4.17-4.09 (m, 4H), 3.83 (dd, J=5.4, 8.8 Hz, 2H), 3.11-3.03 (m, 1H).

Description 114: 5-chloro-2-(3-((3-fluorophenoxy)methyl)azetidin-1-yl)nicotinic acid (D114)

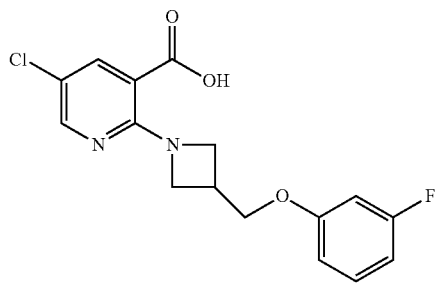 [SMILES: O=C(O)c1cc(Cl)cnc1N1CC(COc2cccc(F)c2)C1]

The title compound (D114) (66.3 mg) was prepared according to the experimental procedure described in Description 113 starting from methyl 5-chloro-2-(3-(3-fluorophenyl)-3-hydroxyazetidin-1-yl)nicotinate (D83) (66.2 mg, 0.188 mmol).

MS: (ES/+) m/z: 337.2 [MH⁺] C16H14ClFN2O3 requires 336.07

¹H NMR (400 MHz, DMSO-d₆) δ (ppm): 8.29 (d, J=2.4 Hz, 1H), 7.91 (d, J=2.4 Hz, 1H), 7.35-7.26 (m, 1H), 6.85-6.73 (m, 3H), 4.22-4.10 (m, 4H), 3.83 (dd, J=5.4, 9.3 Hz, 2H), 3.13-3.03 (m, 1H).

Description 115: 5-chloro-2-(3-((3-(trifluoromethyl)phenyl)amino)azetidin-1-yl)nicotinic acid (D115)

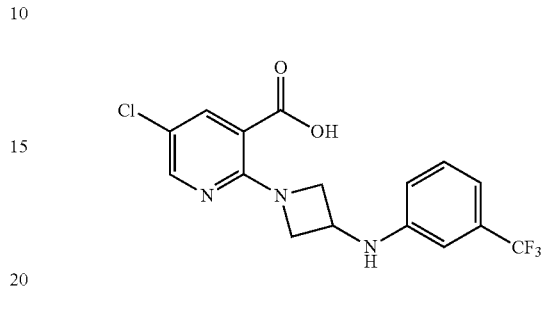

To a solution of 3-(Trifluoromethyl)aniline (0.047 ml, 0.374 mmol) in acetonitrile (0.5 ml), potassium carbonate (67.21 mg, 0.486 mmol) was added followed by the addition of methyl 5-chloro-2-(3-((methylsulfonyl)oxy)azetidin-1-yl)nicotinate (D63)(120 mg, 0.374 mmol). The reaction mixture was heated at 160° C. under microwave irradiation for 25 min. Lithium hydroxide monohydrate (23.54 mg, 0.561 mmol) was added and the resulting reaction mixture was heated at 150° C. under microwave irradiation for 5 min. Solvents were evaporated in vacuo and the residue was diluted with water (5 ml) and HCl 1M (15 ml) and extracted with ethyl acetate (3×20 ml). Collected organics, after solvent evaporation, afforded the title compound (D115) (50 mg)

MS: (ES/+) m/z: 372.1 [MH⁺] C16H13ClF3N3O2 requires 371.06

Description 116: 5-chloro-2-(3-((3-fluorophenyl)amino)azetidin-1-yl)nicotinic acid (D116)

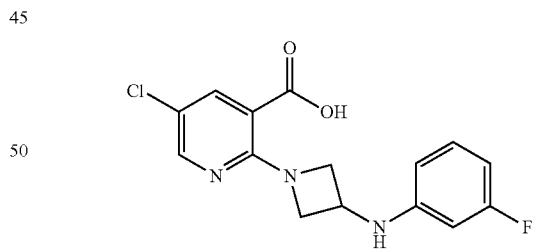

The title compound (D116) (40 mg) was prepared according to the experimental procedure described in Description 115 starting from methyl 5-chloro-2-(3-((methylsulfonyl)oxy)azetidin-1-yl)nicotinate (D63) (120 mg, 0.374 mmol) and 3-Fluoroaniline (0.036 ml, 0.374 mmole).

MS: (ES/+) m/z: 322.1 [MH⁺] C15H13ClFN3O2 requires 321.07

¹H NMR (400 MHz, DMSO-d₆) δ (ppm): 8.30 (d, J=2.7 Hz, 1H), 7.93 (d, J=2.7 Hz, 1H), 7.11 (d, J=7.3 Hz, 1H), 6.42-6.24 (m, 3H), 4.42-4.31 (m, 2H), 4.30-4.21 (m, 1H), 3.79 (dd, J=4.5, 9.4 Hz, 2H)

Description 117: 5-chloro-2-(3-((4-fluorophenyl)amino)azetidin-1-yl)nicotinic acid (D117)

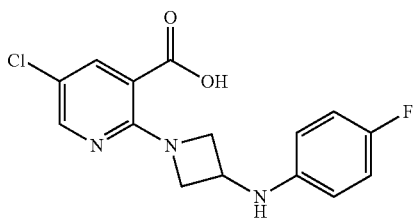 [SMILES: O=C(O)c1cc(Cl)cnc1N1CC(Nc2ccc(F)cc2)C1]

The title compound (D117) (70 mg) was prepared according to the experimental procedure described in Description 100 starting from methyl 5-chloro-2-(3-((4-fluorophenyl)amino)azetidin-1-yl)nicotinate (D84) (76 mg, 0.226 mmol)

MS: (ES/+) m/z: 322.1 [MH$^+$] C15H13ClFN3O2 requires 321.05

Description 118: 5-chloro-2-(3-((2,4-difluorophenyl)amino)azetidin-1-yl)nicotinic acid (D118)

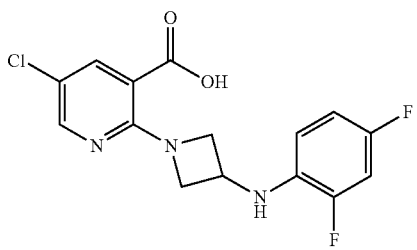 [SMILES: O=C(O)c1cc(Cl)cnc1N1CC(Nc2ccc(F)cc2F)C1]

To a solution of methyl 5-chloro-2-(3-((2,4-difluorophenyl)amino)azetidin-1-yl)nicotinate (D85) (37 mg, 0.104 mmol) in a mixture 3:1 1,4-dioxane/water (4 ml), 1M NaOH (0.157 ml) was added and the resulting mixture was stirred 12 h at 60° C. After cooling the reaction mixture was acidified to pH 1 by addition of 1M HCl. The resulting precipitate was collected by filtration and afforded the title compound (D118) (35 mg).

MS: (ES/+) m/z: 340.1 [MH$^+$] C15H12ClF2N3O2 requires 339.06

$^1$H NMR (400 MHz, DMSO-d$_6$) δ (ppm): 8.29 (d, J=2.9 Hz, 1H), 7.92 (d, J=2.4 Hz, 1H), 7.17-7.03 (m, 1H), 6.93-6.82 (m, 1H), 6.65-6.54 (m, 1H), 4.40-4.32 (m, 2H), 4.28 (d, J=5.9 Hz, 1H), 3.87 (dd, J=4.4, 9.3 Hz, 2H)

Description 119: 5-chloro-2-(3-((2-methyl-4-(trifluoromethyl)phenyl)amino)azetidin-1-yl)nicotinic acid (D119)

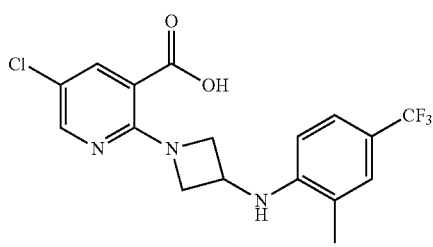 [SMILES: Cc1cc(C(F)(F)F)ccc1NC1CN(c2ncc(Cl)cc2C(=O)O)C1]

The title compound (D119) (40 mg) was prepared according to the experimental procedure described in Description 118 starting from methyl 5-chloro-2-(3-((2-methyl-4-(trifluoromethyl)phenyl)amino)azetidin-1-yl)nicotinate (D86) (44 mg, 0.110 mmol)

MS: (ES/+) m/z: 386.2 [MH$^+$] C17H15ClF3N3O2 requires 385.08

$^1$H NMR (400 MHz, DMSO-d$_6$) δ (ppm): 8.31 (d, J=2.9 Hz, 1H), 7.93 (d, J=2.4 Hz, 1H), 7.36-7.30 (m, 2H), 6.49 (d, J=8.3 Hz, 1H), 6.17-5.90 (m, 1H), 4.44-4.34 (m, 3H), 3.95 (dd, J=3.4, 8.8 Hz, 2H), 2.18 (s, 3H)

Description 120: 5-chloro-2-(3-((4-fluoro-2-methylphenyl)(methyl)amino)azetidin-1-yl)nicotinic acid (D120)

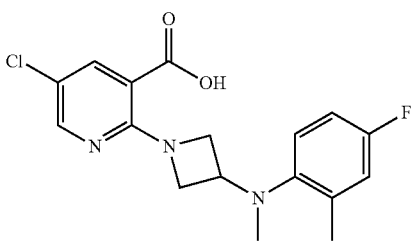 [SMILES: Cc1cc(F)ccc1N(C)C1CN(c2ncc(Cl)cc2C(=O)O)C1]

To a solution of methyl 5-chloro-2-(3-(methyl(2-methyl-4-fluoro-phenyl)amino)azetidin-1-yl)nicotinate (D87) (170 mg, 0.467 mmol) in 1,4 dioxane (3 ml) and water (1 ml) 1M NaOH (0.7 ml) was added. The mixture was stirred at 60° C. for 2 h. Organic solvent was evaporated and remaining aqueous were acidified 2N HCl and extracted with ethylacetate (3×5 ml). The combined organic phases after solvent evaporation afforded the title compound (D120) (156 mg)

MS: (ES/+) m/z: 350.1 [MH$^+$] C17H17ClFN3O2 requires 349.79

1H NMR (400 MHz, DMSO-d6) δ (ppm): 13.06 (s, 1H), 8.27 (d, J=2.4 Hz, 1H), 7.91 (d, J=2.4 Hz, 1H), 7.05 (d, J=9.8 Hz, 1H), 6.99-6.90 (m, 2H), 4.17-4.03 (m, 3H), 3.66 (dd, J=3.4, 8.3 Hz, 2H), 2.49 (s, 3H), 2.26 (s, 3H)

Description 121: 2-(3-(3-fluorophenoxy)azetidin-1-yl)-5-(trifluoromethyl)nicotinic acid (D121)

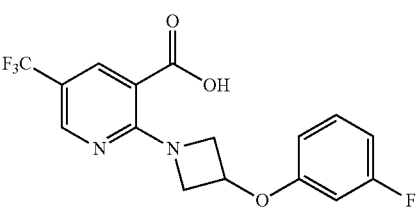 [SMILES: O=C(O)c1cc(C(F)(F)F)cnc1N1CC(Oc2cccc(F)c2)C1]

To a mixture of 3-(3-fluorophenoxy)azetidine) (D50) (106.73 mg, 0.638 mmol) and triethylamine (0.11 ml, 0.798 mmol) in methanol (3 ml), 2-Chloro-5-(trifluoromethyl)nicotinic acid (120 mg, 0.532 mmol) was added and the mixture was heated 10 min (2 cycles of 5 min each) under microwave irradiation at 150° C. After solvent evaporation the residue was purified by SPE-Si cartridge (25 g) eluting with a mixture dichloromethane/methanol from 100/0 to 50/50. Collected fraction after solvent evaporation afforded the title compound (D121) (83 mg)

MS: (ES/+) m/z: 357.1 [MH⁺] C16H12F4N2O3 requires 356.08

¹H NMR (400 MHz, CHLOROFORM-d) δ (ppm): 8.58 (d, J=1.5 Hz, 1H), 8.37 (d, J=2.0 Hz, 1H), 7.28-7.23 (m, 1H), 6.74 (dt, J=1.5, 8.3 Hz, 2H), 6.58 (dd, J=2.2, 8.1 Hz, 1H), 6.53 (td, J=2.3, 10.6 Hz, 1H), 5.13-4.97 (m, 1H), 4.67 (dd, J=6.4, 10.8 Hz, 2H), 4.30 (dd, J=3.9, 10.8 Hz, 2H)

Description 122: 2-(3-(4-fluorophenoxy)azetidin-1-yl)-5-(trifluoromethyl)nicotinic acid (D122)

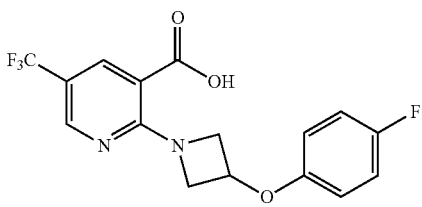 [SMILES: O=C(O)c1cc(C(F)(F)F)cnc1N1CC(Oc2ccc(F)cc2)C1]

The title compound (D122) (180 mg) was prepared according to the experimental procedure described in Description 121 starting from 3-(4-fluorophenoxy)azetidine) (D49) (177.89 mg, 1.064 mmol) and 2-chloro-5-(trifluoromethyl)nicotinic acid (200 mg, 0.886 mmol)

MS: (ES/+) m/z: 357.1 [MH⁺] C16H12F4N2O3 requires 356.08

¹H NMR (400 MHz, CHLOROFORM-d) δ (ppm): 8.57 (d, J=2.0 Hz, 1H), 8.36 (d, J=2.4 Hz, 1H), 7.09-6.92 (m, 2H), 6.83-6.57 (m, 2H), 5.08-4.96 (m, 1H), 4.64 (dd, J=6.4, 10.8 Hz, 2H), 4.28 (dd, J=3.9, 11.2 Hz, 2H)

Description 123: 2-(3-(4-chlorophenoxy)azetidin-1-yl)-5-(trifluoromethyl)nicotinic acid (D123)

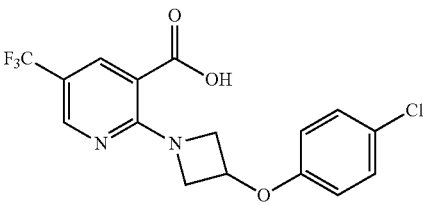 [SMILES: O=C(O)c1cc(C(F)(F)F)cnc1N1CC(Oc2ccc(Cl)cc2)C1]

The title compound (D123) (125 mg) was prepared according to the experimental procedure described in Description 103A vero starting from methyl 2-(3-((methylsulfonyl)oxy)azetidin-1-yl)-5-(trifluoromethyl)nicotinate (D68) (100 mg, 0.258 mmol) and 4-Chlorophenol (0.033 ml, 0.338 mmol).

MS: (ES/+) m/z: 373.2 [MH⁺] C16H12ClF3N2O3 requires 372.05

¹H NMR (400 MHz, DMSO-d₆) δ (ppm): 9.71 (s, 1H), 8.61 (s, 1H), 8.16 (d, J=2.4 Hz, 1H), 7.37 (d, J=8.8 Hz, 2H), 6.92 (d, J=8.8 Hz, 1H), 5.11 (br. s., 1H), 4.63-4.38 (m, 2H), 4.16-3.95 (m, 2H)

Description 124: 2-(3-(3-chlorophenoxy)azetidin-1-yl)-5-(trifluoromethyl)nicotinic acid (D124)

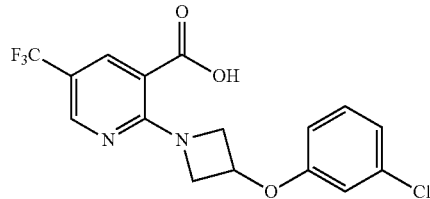 [SMILES: O=C(O)c1cc(C(F)(F)F)cnc1N1CC(Oc2cccc(Cl)c2)C1]

The title compound (D124) (85 mg) was prepared according to the experimental procedure described in Description 103A starting from methyl 2-(3-((methylsulfonyl)oxy)azetidin-1-yl)-5-(trifluoromethyl)nicotinate (D68) (100 mg, 0.258 mmol) and 3-Chlorophenol (0.035 ml, 0.338 mmol).

MS: (ES/+) m/z: 373.2 [MH⁺] C16H12ClF3N2O3 requires 372.05

¹H NMR (400 MHz, DMSO-d₆) δ (ppm): 8.61 (d, J=1.7 Hz, 1H), 8.16 (d, J=2.2 Hz, 1H), 7.40-7.32 (m, 1H), 7.06 (d, J=8.1 Hz, 1H), 6.98 (t, J=2.0 Hz, 1H), 6.91-6.85 (m, 1H), 5.15 (qd, J=3.0, 6.1 Hz, 1H), 4.56 (dd, J=6.5, 10.6 Hz, 2H), 4.15-4.05 (m, 2H)

Description 125: 2-(3-(4-fluoro-3-(trifluoromethyl)phenoxy)azetidin-1-yl)-5-(trifluoromethyl)nicotinic acid (D125)

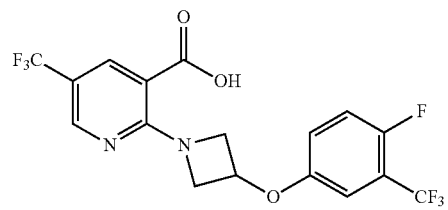

The title compound (D125) (108 mg) was prepared according to the experimental procedure described in Description 103A starting from methyl 2-(3-((methylsulfonyl)oxy)azetidin-1-yl)-5-(trifluoromethyl)nicotinate (D68) (100 mg, 0.258 mmol) and 4-Fluoro-3-(trifluoromethyl)phenol (60.98 mg, 0.338 mmol).

MS: (ES/+) m/z: 425 [MH⁺] C17H11F7N2O3 requires 424.07

¹H NMR (400 MHz, DMSO-d₆) δ (ppm): 8.61 (d, J=1.5 Hz, 1H), 8.16 (d, J=2.4 Hz, 1H), 7.53-7.45 (m, 1H), 7.31-7.17 (m, 2H), 5.21 (dd, J=3.3, 6.2 Hz, 1H), 4.57 (dd, J=6.5, 10.1 Hz, 2H), 4.15-4.05 (m, 2H)

Description 126: 2-(3-(3-(trifluoromethoxy)phenoxy)azetidin-1-yl)-5-(trifluoromethyl)nicotinic acid (D126)

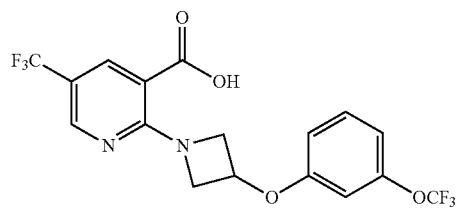 [SMILES: O=C(O)c1cc(C(F)(F)F)cnc1N1CC(Oc2cccc(OC(F)(F)F)c2)C1]

The title compound (D126) (110 mg) was prepared according to the experimental procedure described in Description 103A starting from methyl 2-(3-((methylsulfonyl)oxy)azetidin-1-yl)-5-(trifluoromethyl)nicotinate (D68) (100 mg, 0.258 mmol) and 3-(trifluoromethoxy)phenol (0.043 ml, 0.338 mmol).

MS: (ES/+) m/z: 423 [MH$^+$] C17H12F6N2O4 requires 422.07

$^1$H NMR (400 MHz, DMSO-d$_6$) δ (ppm): 13.32 (br. s., 1H), 8.62 (d, J=2.0 Hz, 1H), 8.16 (d, J=2.2 Hz, 1H), 7.46 (t, J=8.2 Hz, 1H), 7.00 (d, J=8.3 Hz, 1H), 6.94 (dd, J=2.2, 8.3 Hz, 1H), 6.91 (s, 1H), 5.17 (td, J=3.0, 6.4 Hz, 1H), 4.57 (dd, J=6.2, 10.6 Hz, 2H), 4.09 (dd, J=3.2, 10.8 Hz, 2H)

Description 127: 2-(3-(2,4-difluorophenoxy)azetidin-1-yl)-5-(trifluoromethyl)nicotinic acid (D127)

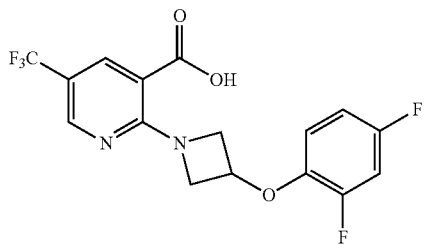 [SMILES: O=C(O)c1cc(C(F)(F)F)cnc1N1CC(Oc2ccc(F)cc2F)C1]

The title compound (D127) (95 mg) was prepared according to the experimental procedure described in Description 103A starting from methyl 2-(3-((methylsulfonyl)oxy)azetidin-1-yl)-5-(trifluoromethyl)nicotinate (D68) (100 mg, 0.258 mmol) and 2,4-Difluorophenol (0.032 ml, 0.338 mmol).

MS: (ES/+) m/z: 375 [MH$^+$] C16H11F5N2O3 requires 374.07

$^1$H NMR (400 MHz, DMSO-d$_6$) δ (ppm): 13.32 (br. s., 1H), 8.62 (d, J=1.7 Hz, 1H), 8.16 (d, J=2.4 Hz, 1H), 7.44-7.28 (m, 1H), 7.12-6.92 (m, 2H), 5.15 (td, J=3.1, 6.5 Hz, 1H), 4.55 (dd, J=6.1, 11.0 Hz, 2H), 4.11 (dd, J=3.3, 10.9 Hz, 2H).

Description 128: 2-(3-(3,4-difluorophenoxy)azetidin-1-yl)-5-(trifluoromethyl)nicotinic acid (D128)

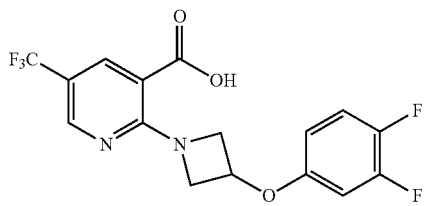 [SMILES: O=C(O)c1cc(C(F)(F)F)cnc1N1CC(Oc2ccc(F)c(F)c2)C1]

The title compound (D128) (100 mg) was prepared according to the experimental procedure described in Description 103A starting from methyl 2-(3-((methylsulfonyl)oxy)azetidin-1-yl)-5-(trifluoromethyl)nicotinate (D68) (100 mg, 0.258 mmol) and 3,4-Difluorophenol (44.06 mg, 0.338 mmol).

MS: (ES/+) m/z: 375 [MH$^+$] C16H11F5N2O3 requires 374.07

$^1$H NMR (400 MHz, DMSO-d$_6$) δ (ppm): 13.30 (br. s., 1H), 8.63-8.58 (m, 1H), 8.61 (d, J=1.7 Hz, 1H), 8.16 (d, J=2.4 Hz, 1H), 7.46-7.31 (m, 1H), 7.06 (ddd, J=2.9, 6.7, 12.4 Hz, 1H), 6.79-6.62 (m, 1H), 5.11 (tt, J=3.4, 6.4 Hz, 1H), 4.55 (dd, J=6.5, 10.9 Hz, 2H), 4.06 (dd, J=3.1, 11.4 Hz, 2H)

Description 129: 2-(3-((5-methylisoxazol-3-yl)oxy)azetidin-1-yl)-5-(trifluoromethyl)nicotinic acid (D129)

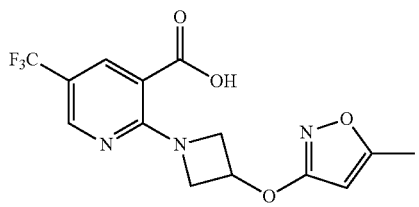 [SMILES: Cc1cc(OC2CN(c3ncc(C(F)(F)F)cc3C(=O)O)C2)no1]

To a solution of methyl 2-(3-((5-methylisoxazol-3-yl)oxy)azetidin-1-yl)-5-(trifluoromethyl)nicotinate (D88) (20 mg, 0.056 mmol) in 1,4-dioxane/water (3 ml/1 ml), lithium hydroxide monohydrate (3.52 mg, 0.084 mmol) and the resulting mixture was heated at 130° C. under microwave irradiation 10 min (2 cycles of 5 min each). Solvents were evaporated in vacuo and the residue was taken in a mixture water/1M HCl (5 ml/15 ml) and extracted with ethyl acetate (3×20 ml). Collected organics, after solvent evaporation, afforded the title compound (D129) (19 mg)

MS: (ES/+) m/z: 344.2 [MH$^+$] C14H12F3N3O4 requires 343.08

$^1$H NMR (400 MHz, DMSO-d$_6$) δ (ppm): 13.32 (br. s., 1H), 8.61 (d, J=1.5 Hz, 1H), 8.16 (d, J=2.2 Hz, 1H), 6.06 (d, J=1.0 Hz, 1H), 5.21 (br. s., 1H), 4.47 (dd, J=6.5, 11.1 Hz, 2H), 4.12 (dd, J=2.3, 11.1 Hz, 2H), 2.34 (d, J=0.5 Hz, 3H)

Description 130: 5-(trifluoromethyl)-2-(3-((6-(trifluoromethyl)pyridin-2-yl)oxy)azetidin-1-yl)nicotinic acid (D130)

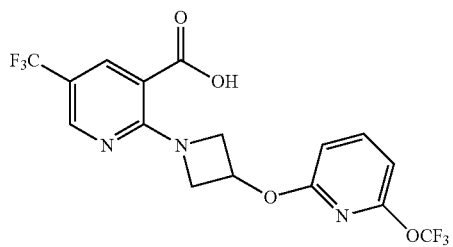 [SMILES: O=C(O)c1cc(C(F)(F)F)cnc1N1CC(Oc2cccc(OC(F)(F)F)n2)C1]

The title compound (D130) (77 mg) was prepared according to the experimental procedure described in Description 129 starting methyl 5-(trifluoromethyl)-2-(3-((6-(trifluoromethyl)pyridin-2-yl)oxy)azetidin-1-yl)nicotinate (D89) (80 mg, 0.19 mmol) and 2-Hydroxy-6-(trifluoromethyl)pyridine (55.12 mg, 0.34 mmol).

MS: (ES/+) m/z: 408.6 [MH$^+$] C16H11F6N3O3 requires 407.07

$^1$H NMR (400 MHz, DMSO-d$_6$) δ (ppm): 13.71-12.69 (m, 1H), 8.66-8.49 (m, 1H), 8.20-8.11 (m, 1H), 8.10-7.96 (m, 1H), 7.61-7.49 (m, 1H), 7.33-7.18 (m, 1H), 5.53-5.32 (m, 1H), 4.62-4.43 (m, 2H), 4.22-4.05 (m, 2H)

Description 131: 2-(3-((5-fluoropyrimidin-2-yl)oxy) azetidin-1-yl)-5-(trifluoromethyl)nicotinic acid (D131)

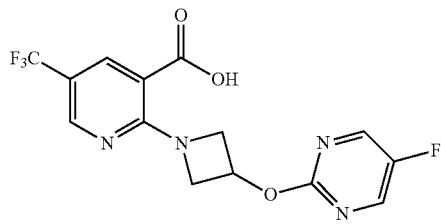 [SMILES: O=C(O)c1cc(C(F)(F)F)cnc1N1CC(Oc2ncc(F)cn2)C1]

To a mixture of 2-(azetidin-3-yloxy)-5-fluoropyrimidine (D51) (108 mg, 0.638 mmol) and triethylamine (0.11 ml, 0.798 mmol) in methanol (1 ml) and tetrahydrofuran (2 ml), 2-chloro-5-(trifluoromethyl)nicotinic acid (120 mg, 0.532 mmol) was added and the mixture was heated 2 h at 80° C. After solvent evaporation the residue was purified by SPE-Si cartridge (25 g) eluting with a mixture dichloromethane/methanol from 95/5 to 80/20. Collected fraction after solvent evaporation afforded the title compound (D131) (44 mg)

MS: (ES/+) m/z: 359.3 [MH$^+$] C14H10F4N4O3 requires 358.07

$^1$H NMR (400 MHz, CHLOROFORM-d) δ (ppm): 8.74 (s, 2H), 8.59 (d, J=2.0 Hz, 1H), 8.13 (d, J=2.4 Hz, 1H), 5.38 (s, 1H), 4.52 (dd, J=6.4, 11.2 Hz, 2H), 4.14 (dd, J=3.4, 11.2 Hz, 2H)

Description 132: 5-fluoro-2-(3-(3-fluorophenoxy) azetidin-1-yl)nicotinic acid (D132)

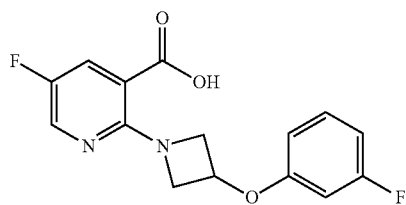 [SMILES: O=C(O)c1cc(F)cnc1N1CC(Oc2cccc(F)c2)C1]

The title compound (D132) (108 mg) was prepared according to the experimental procedure described in Description 115 starting from methyl 5-fluoro-2-(3-((methylsulfonyl)oxy)azetidin-1-yl)nicotinate (D71) (90 mg, 0.295 mmol) and 3-Fluorophenol (0.029 ml, 0.295 mmol).

MS: (ES/+) m/z: 307.2 [MH$^+$] C15H12F2N2O3 requires 306.08

$^1$H NMR (400 MHz, DMSO-d$_6$) δ (ppm): 13.18 (br. s., 1H), 8.35 (d, J=3.2 Hz, 1H), 7.93-7.81 (m, 1H), 7.35 (q, J=8.1 Hz, 1H), 6.82 (dt, J=2.4, 8.6 Hz, 1H), 6.79-6.68 (m, 2H), 5.11 (tt, J=3.4, 6.4 Hz, 1H), 4.43 (dd, J=6.4, 10.0 Hz, 2H), 3.94 (dd, J=3.3, 9.9 Hz, 2H)

Description 133: 2-(3-(3-chlorophenoxy)azetidin-1-yl)-5-fluoronicotinic acid (133)

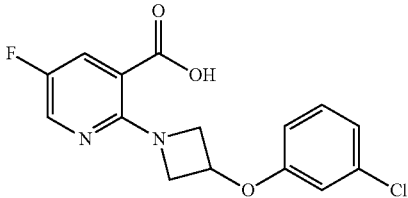 [SMILES: O=C(O)c1cc(F)cnc1N1CC(Oc2cccc(Cl)c2)C1]

To a solution of 3-chlorophenol (0.035 ml, 0.328 mmol) in dimethylformamide (1 ml), potassium carbonate (45.42 mg, 0.328 mmol) and the reaction mixture was stirred 2 h at 80° C. Methyl 5-fluoro-2-(3-((methylsulfonyl)oxy)azetidin-1-yl) nicotinate (D71) (100 mg, 0.328 mmol) was added and the resulting reaction mixture was heated 12 h at 160° C. After cooling at room temperature 1N NaOH (0.656 ml, 0.656 mmol) was added and the reaction mixture heated 2 h at 120° C. Solvents were evaporated in vacuo and the residue was loaded on SPE-SCX cartridge (5 g). Ammonia fractions after solvent evaporation afforded a residue that was further purified by Biotage column SNAP-C18 (30 g) eluting with water/acetic acid (0.1%)/acetonitrile-acetic acid (0.1%) from 70/30 to 0/100.

Collected fractions, after solvent evaporation, afforded the title compound (D133) (14 mg)

MS: (ES/+) m/z: 323.1 [MH$^+$] C15H12ClFN2O3 requires 322.05

$^1$H NMR (400 MHz, DMSO-d$_6$) δ (ppm 13.19 (br. s., 1H), 8.34 (d, J=2.9 Hz, 1H), 7.85 (dd, J=2.9, 8.8 Hz, 1H), 7.40-7.29 (m, 1H), 7.08-7.01 (m, 1H), 6.96 (t, J=2.2 Hz, 1H), 6.91-6.83 (m, 1H), 5.17-5.08 (m, 1H), 4.43 (dd, J=6.4, 9.8 Hz, 2H), 3.93 (dd, J=3.4, 10.3 Hz, 2H))

Description 134: 5-fluoro-2-(3-(3-(trifluoromethoxy) phenoxy)azetidin-1-yl)nicotinic acid (D134)

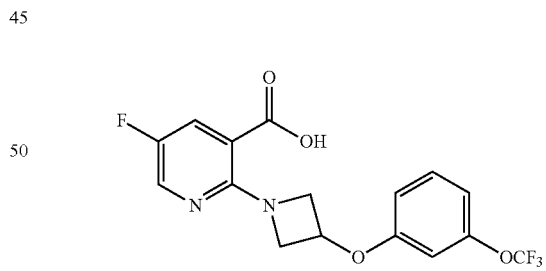

The title compound (D134) (27 mg) was prepared according to the experimental procedure described in Description 133 starting from Methyl 5-fluoro-2-(3-((methylsulfonyl)oxy)azetidin-1-yl)nicotinate (D71) (100 mg, 0.328 mmol) and 3-(trifluoromethoxy)phenol (0.042 ml, 0.328 mmol).

MS: (ES/+) m/z: 372.6 [MH$^+$] C16H12F4N2O4 requires 372.7

$^1$H NMR (400 MHz, DMSO-d$_6$) δ (ppm): 13.17 (br. s., 1H), 8.34 (d, J=2.9 Hz, 1H), 7.86 (dd, J=2.9, 8.8 Hz, 1H), 7.45 (t, J=8.3 Hz, 1H), 6.99 (d, J=7.3 Hz, 1H), 6.93 (dd, J=2.4, 8.3 Hz, 1H), 6.88 (s, 1H), 5.19-4.99 (m, 1H), 4.44 (dd, J=6.4, 9.8 Hz, 2H), 3.95 (dd, J=3.4, 10.3 Hz, 2H)

Description 135: 5-fluoro-2-(3-((4-fluoro-2-methylphenyl)amino)azetidin-1-yl)nicotinic acid (D135)

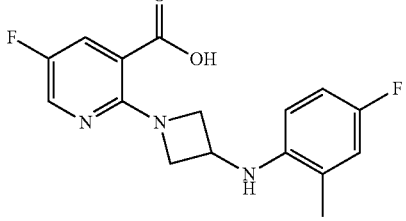

To a solution of methyl 5-fluoro-2-(3-((4-fluoro-2-methylphenyl)amino)azetidin-1-yl)nicotinate (D90) (150 mg, 0.450 mmol) in 1,4-dioxane/water (3 ml/1 ml), 1M NaOH (0.675 ml, 0.657 mmol) was added and the resulting mixture was stirred 2 h at 60° C. Organic solvent was evaporated. The remaining aqueous were washed with dichloromethane (5 ml) then acidified to pH2 by addition of 2M HCl and extracted with ethylacetate (3×20 ml). Collected organics, after solvent evaporation afforded the title compound (D135) (140 mg).

MS: (ES/+) m/z: 321.1 [MH$^+$] C16H15F2N3O2 requires 319.11

$^1$H NMR (400 MHz, DMSO-d$_6$) δ (ppm): 8.32 (d, J=2.9 Hz, 1H), 7.82 (dd, J=2.9, 8.8 Hz, 1H), 6.93-6.78 (m, 2H), 6.34 (dd, J=5.1, 8.6 Hz, 1H), 4.39-4.31 (m, 2H), 4.27-4.19 (m, 1H), 3.83 (dd, J=4.9, 9.3 Hz, 2H), 2.13 (s, 3H).

Description 136: lithium 5-chloro-2-(3-(4-(trifluoromethyl)phenoxy)pyrrolidin-1-yl)nicotinate (D136)

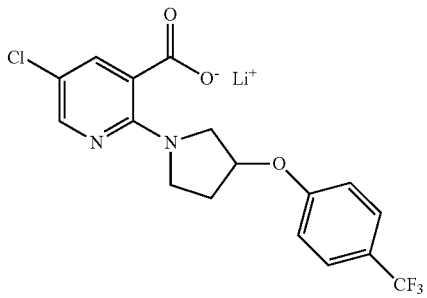 [SMILES: O=C([O-])c1cc(Cl)cnc1N1CCC(Oc2ccc(C(F)(F)F)cc2)C1 ; [Li+]]

To a mixture of methyl 5-chloro-2-(3-(4-(trifluoromethyl)phenoxy)pyrrolidin-1-yl)nicotinate (D91) (220 mg, 0.548 mmol) in a mixture 1,4-dioxane/water (2 ml/1 ml), lithium hydroxide monohydrate (34.55 mg, 0.823 mmol) was added and the resulting mixture was stirred at 150° C. under microwave irradiation for 10 min (2 cycles of 5 min each). Solvents were evaporated in vacuo to afford the title compound (D136) 265 mg MS: (ES/+) m/z: 387.4 [MH$^+$] (free acid) C17H14ClF3N2O3 requires 386.07

Description 137: 5-chloro-2-(3-(3-(trifluoromethyl)phenoxy)pyrrolidin-1-yl)nicotinic acid (D137)

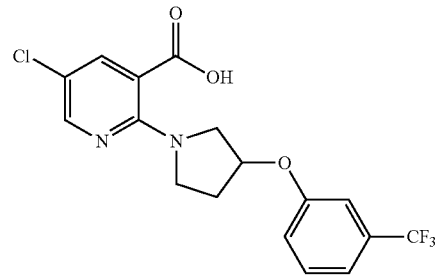 [SMILES: O=C(O)c1cc(Cl)cnc1N1CCC(Oc2cccc(C(F)(F)F)c2)C1]

The title compound (D137) (240 mg) was prepared according to the experimental procedure described in Description 100 starting from methyl 5-chloro-2-(3-(3-(trifluoromethyl)phenoxy)pyrrolidin-1-yl)nicotinate (D92) (270 mg, 0.673 mmol)

MS: (ES/+) m/z: 387 [MH$^+$] C17H14ClF3N2O3 requires 386.06

Description 138: 5-chloro-2-(3-(4-fluorophenoxy)pyrrolidin-1-yl)nicotinic acid (D138)

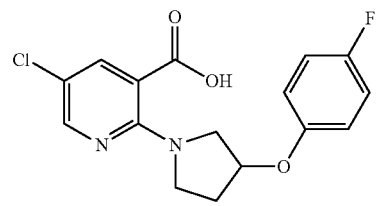 [SMILES: O=C(O)c1cc(Cl)cnc1N1CCC(Oc2ccc(F)cc2)C1]

The title compound (D138) (220 mg) was prepared according to the experimental procedure described in Description 100 starting from methyl 5-chloro-2-(3-(4-fluorophenoxy)pyrrolidin-1-yl)nicotinate (D93) (235 mg, 0.669 mmol)

MS: (ES/+) m/z: 337 [MH$^+$] C16H14ClFN2O3 requires 336.06

Description 139: 5-chloro-2-(3-phenoxy)pyrrolidin-1-yl)nicotinic acid (D139)

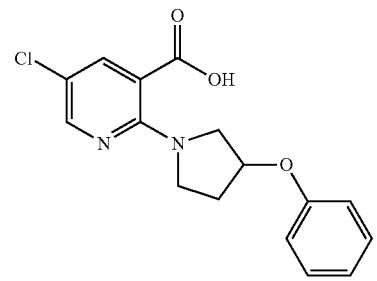 [SMILES: O=C(O)c1cc(Cl)cnc1N1CCC(Oc2ccccc2)C1]

Methyl 5-chloro-2-(3-phenoxy)pyrrolidin-1-yl)nicotinate (D94) (230 mg, 0.69 mmol) was dissolved in methanol (10 ml), 10N NaOH (10 ml) was added at 0° C. The reaction mixture was heated to reflux for 18 hours. After cooling to room temperature, methanol was evaporated then water (10 ml) was added and the mixture was acidified to pH1-2 by addition of 2.5N HCl at 0° C. The mixture was stirred at 0° C. for 30 min. The white solid was collected by filtration, washed with water, dried to provide compound (D139) (210 mg) as a white solid.

$^1$H NMR (400 MHz, DMSO-d6): δ (ppm): 13.23 (1H, br s), 8.26 (1H, d, J=2.4 Hz), 7.88 (1H, d, J=2.0 Hz), 7.32-7.28 (2H, m), 6.97-6.94 (3H, m), 5.13 (1H, s), 3.87-3.82 (1H, m), 3.70-3.63 (1H, m), 3.34-3.31 (2H, m), 2.24-2.14 (2H, m).

Description 140: 5-chloro-2-(3-(3-fluorophenoxy)pyrrolidin-1-yl)nicotinic acid (D140)

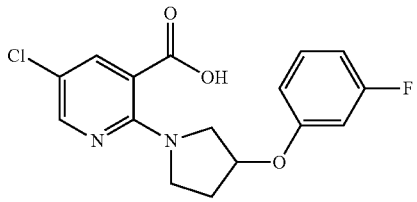 [SMILES: O=C(O)c1cc(Cl)cnc1N1CCC(Oc2cccc(F)c2)C1]

The title compound (D140) (228 mg) was prepared according to the experimental procedure described in Description 100 starting from methyl 5-chloro-2-(3-(3-fluorophenoxy)pyrrolidin-1-yl)nicotinate (D95)) (250 mg, 0.712 mmol)

MS: (ES/+) m/z: 337 [MH$^+$] C16H14ClFN2O3 requires 336.06

Description 141: 5-chloro-2-(3-(m-tolyloxy)pyrrolidin-1-yl)nicotinic acid (D141)

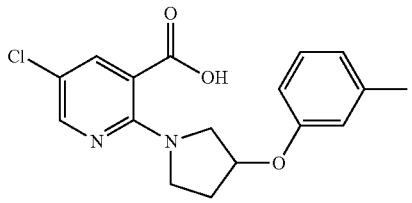 [SMILES: Cc1cccc(OC2CCN(c3ncc(Cl)cc3C(=O)O)C2)c1]

The title compound (D141) (180 mg) was prepared according to the experimental procedure described in Description 100 starting from methyl 5-chloro-2-(3-(m-tolyloxy)pyrrolidin-1-yl)nicotinate (D96) (250 mg, 0.712 mmol)

MS: (ES/+) m/z: 333 [MH$^+$] C17H17ClN2O3 requires 332.09

Description 142: methyl 4-(1-(5-chloro-2-(2-phenylpyrrolidin-1-yl)nicotinamido)cyclopropyl)benzoate (D142)

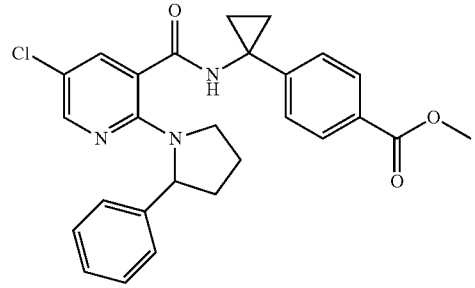 [SMILES: COC(=O)c1ccc(C2(NC(=O)c3cc(Cl)cnc3N3CCCC3c3ccccc3)CC2)cc1]

A solution of 5-chloro-2-(2-phenylpyrrolidin-1-yl)nicotinic acid (D98) (150 mg, 0.5 mmol), methyl 4-(1-aminocyclopropyl)benzoate hydrochloride (D7) (114 mg, 0.5 mmol) and N,N-Diisopropylethylamine (194 mg, 1.5 mmol) in dimethylformamide (10 ml) was stirred 1 h at room temperature, then benzotriazol-1-yl-oxytripyrrolidinophosphonium hexafluorophosphate (PyBOP) (312 mg, 0.6 mmol) was added. The mixture was stirred at room temperature overnight, then poured into ice-water (20 ml) and extracted with ethyl acetate (2×20 ml). The organic solution was washed with brine (40 ml), dried over Na$_2$SO$_4$ and concentrated to obtain a residue which was purified by flash chromatography on silica gel eluting with a mixture petroleum ether/ethyl acetate (4:1). Collected fractions after solvent evaporation afforded the title compound (D142) (189 mg) as a yellow solid.

$^1$H NMR (400 MHz, CHLOROFORM-d) δ (ppm): 8.10 (1H, d, J=2.4 Hz) 8.03-8.00 (2H, m) 7.74 (1H, d, J=2.4 Hz) 7.67 (1H, s) 7.41 (2H, d, J=8.0 Hz) 7.28-7.18 (5H, m) 5.36-5.32 (1H, m) 3.91 (3H, s) 3.69-3.63 (1H, m) 3.16-3.11 (1H, m) 2.43-2.37 (1H, m) 1.97-1.87 (3H, m) 1.49-1.39 (4H, m)

Description 143: methyl 4-(1-(5-chloro-2-(3-phenylpyrrolidin-1-yl)nicotinamido)cyclopropyl)benzoate (D143)

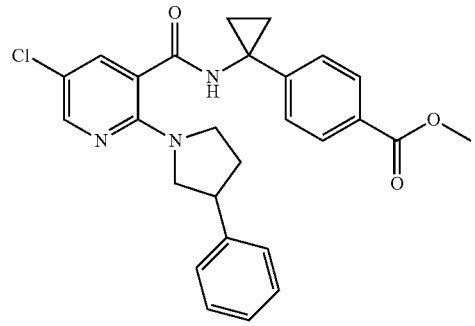 [SMILES: COC(=O)c1ccc(C2(NC(=O)c3cc(Cl)cnc3N3CCC(c4ccccc4)C3)CC2)cc1]

The title compound (D143) (210 mg) was prepared according to the experimental procedure described in Description 142 starting from 5-chloro-2-(3-phenylpyrrolidin-1-yl)nicotinic acid (D99) (260 mg, 0.860 mmol) and methyl 4-(1-aminocyclopropyl)benzoate hydrochloride (D7) (195 mg, 0.86 mmol).

¹H NMR (400 MHz, CHLOROFORM-d) δ (ppm): 8.20 (1H, d, J=2.4 Hz) 7.90 (1H, d, J=8.0 Hz) 7.65 (1H, d, J=2.4 Hz) 7.40-7.20 (7H, m) 6.81 (1H, s) 3.93 (3H, s) 3.70-3.37 (5H, m) 2.34-2.27 (1H, m) 2.08-2.01 (1H, m) 1.45-1.37 (4H, m)

Description 144: methyl 4-(1-(2-(2-benzylpyrrolidin-1-yl)-5-chloronicotinamido)cyclopropyl)benzoate (D144)

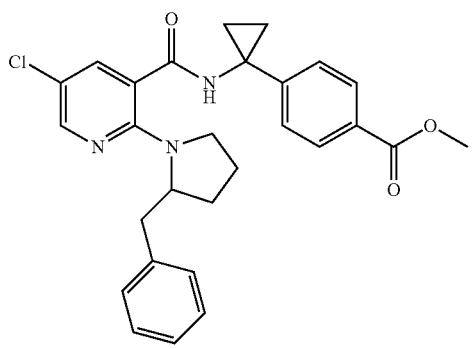 [SMILES: COC(=O)c1ccc(C2(NC(=O)c3cc(Cl)cnc3N3CCCC3Cc3ccccc3)CC2)cc1]

A mixture of 2-(2-benzylpyrrolidin-1-yl)-5-chloronicotinic acid (D100) (70 mg, 0.22 mmol), methyl 4-(1-aminocyclopropyl)benzoate (D7) (50.31 mg, 0.22 mmol) and N,N-Diisopropylethylamine (0.115 ml, 0.66 mmol) in dimethylformamide (5 ml) was stirred at room temperature for 1 h. (Benzotriazol-1-yloxy)tripyrrolidinophosphonium hexafluorophosphate (PyBOP) (137.9 mg, 0.265 mmol) was added and the resulting mixture was stirred overnight at room temperature. The reaction mixture was poured into ice-water and extracted with diethyl ether (3×15 ml). The combined organic layers were washed with brine (2×10 ml), dried over $Na_2SO_4$, filtered and concentrated. The crude residue was purified by Biotage column (10 g) eluting with a mixture dichloromethane/ethylacetate from 100/0 to 90/10. Collected fractions, after solvent evaporation, afforded the title compound (D144) (66 mg)

MS: (ES/+) m/z: 490.2 [MH⁺] C28H28ClN3O3 requires 489.18

¹H NMR (400 MHz, CHLOROFORM-d) δ (ppm): 8.32-8.24 (m, 1H), 8.03-7.96 (m, 2H), 7.94-7.85 (m, 1H), 7.27-7.21 (m, 3H), 7.20-7.07 (m, 3H), 7.03-6.96 (m, 1H), 4.64-4.52 (m, 1H), 3.95-3.90 (m, 3H), 3.04-2.96 (m, 2H), 2.91-2.81 (m, 1H), 2.12-1.99 (m, 1H), 1.88-1.60 (m, 4H), 1.48-1.39 (m, 1H), 1.39-1.27 (m, 2H), 1.04-0.94 (m, 1H)

Description 145: methyl 4-(1-(5-chloro-2-(3-phenoxyazetidin-1-yl)nicotinamido)cyclopropyl)benzoate (D145)

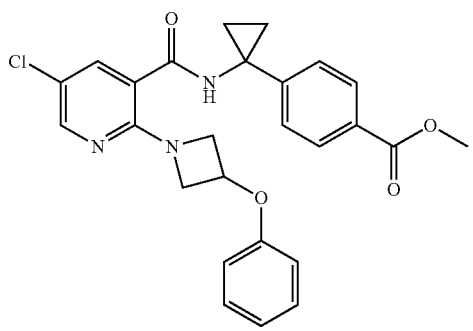 [SMILES: COC(=O)c1ccc(C2(NC(=O)c3cc(Cl)cnc3N3CC(Oc4ccccc4)C3)CC2)cc1]

The title compound (D145) (225 mg) was prepared according to the experimental procedure described in Description 142 starting from 5-chloro-2-(3-phenoxyazetidin-1-yl)nicotinic acid (D101) (140 mg, 0.46 mmol) and methyl 4-(1-aminocyclopropyl)benzoate hydrochloride (D7) (104 mg, 0.40 mmol).

¹H NMR (400 MHz, CHLOROFORM-d) δ (ppm): 8.23 (1H, d, J=2.4 Hz) 7.96 (2H, d, J=8.0 Hz) 7.77 (1H, d, J=2.4 Hz) 7.41 (2H, d, J=8.0 Hz) 7.32 (2H, t, J=7.6 Hz) 7.07 (1H, s) 7.03 (1H, t, J=7.6 Hz) 6.71 (2H, d, J=8.0 Hz) 4.95-4.92 (1H, m) 4.35 (2H, dd, J=10.0, 2.4 Hz) 4.00 (2H, dd, J=10.0, 4.0 Hz) 3.94 (3H, s), 1.43-1.41 (4H, m)

Description 146: (S)-methyl 4-(1-(5-chloro-2-(3-(4-fluorophenoxy)azetidin-1-yl)nicotinamido)ethyl)benzoate (D146)

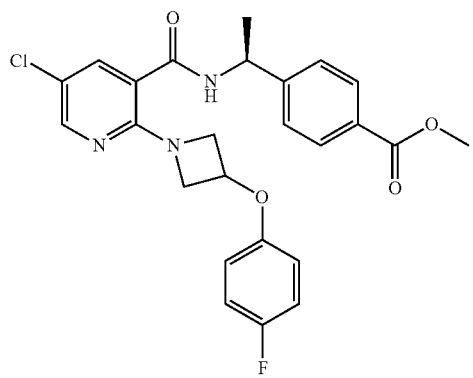 [SMILES: COC(=O)c1ccc([C@H](C)NC(=O)c2cc(Cl)cnc2N2CC(Oc3ccc(F)cc3)C2)cc1]

A mixture of 5-chloro-2-(3-(4-fluorophenoxy)azetidin-1-yl)nicotinic acid (D102) (75 mg, 0.232 mmol) 1-Hydroxybenzotriazole hydrate (31.34 mg, 0.232 mmol) and 1-Ethyl-3-(3-dimethylaminopropyl)carbodiimide hydrochloride (66.8 mg, 0.35 mmol) in dichloromethane (3 ml) was stirred 1 h at room temperature. A solution (S)-methyl 4-(1-aminoethyl)benzoate (D3) (50 mg, 0.232 mmol) and triethylamine (0.03 ml, 0.232 mmol) in dichloromethane (1 ml) was added and the resulting mixture was stirred overnight at room temperature. $NaHCO_3$ sat. sol. (5 ml) was added and the mixture was extracted with dichloromethane (3×10 ml). Collected organics, after solvent evaporation were purified by SPE-Si (10 g) eluting with a mixture Cyclohexane/ethylacetate from 95/05 to 60/40. Collected fractions, after solvent evaporation, afforded the title compound (D146) (100 mg).

MS: (ES/+) m/z: 484 [MH⁺] C25H23ClFN3O4 requires 483.14

¹H NMR (400 MHz, CHLOROFORM-d) δ (ppm): 8.22 (d, J=2.4 Hz, 1H), 8.04-8.00 (m, J=8.3 Hz, 2H), 7.76 (d, J=2.4 Hz, 1H), 7.48-7.43 (m, J=8.3 Hz, 2H), 7.03-6.95 (m, 2H), 6.65-6.58 (m, 3H), 5.37 (quin, J=7.2 Hz, 1H), 4.87-4.78 (m, 1H), 4.29 (ddd, J=6.6, 9.8, 16.4 Hz, 2H), 4.01 (dd, J=4.2, 9.5 Hz, 1H), 3.95 (s, 3H), 3.91 (dd, J=3.9, 9.8 Hz, 1H), 1.61 (d, J=6.8 Hz, 3H)

Description 147: (S)-methyl 4-(1-(5-chloro-2-(3-(3-fluorophenoxy)azetidin-1-yl)nicotinamido)ethyl)benzoate (D147)

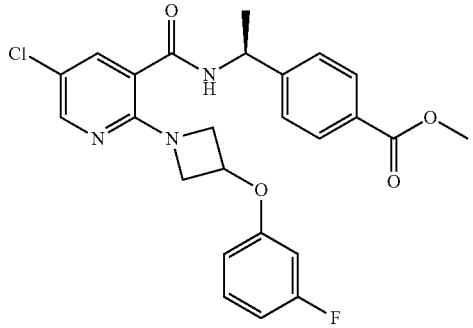 [SMILES: COC(=O)c1ccc([C@H](C)NC(=O)c2cc(Cl)cnc2N2CC(Oc3cccc(F)c3)C2)cc1]

The title compound (D147) (90 mg) was prepared according to the experimental procedure described in Description 146 starting from 5-chloro-2-(3-(3-fluorophenoxy)azetidin-1-yl)nicotinic acid (D103) (75 mg, 0.232 mmol) and (S)-methyl 4-(1-aminoethyl)benzoate (D3) (50 mg, 0.232 mmol).

MS: (ES/+) m/z: 484 [MH$^+$] C25H23ClFN3O4 requires 483.14

$^1$H NMR (400 MHz, CHLOROFORM-d) δ (ppm): 8.22 (d, J=2.4 Hz, 1H), 8.05-8.00 (m, J=7.8 Hz, 2H), 7.77 (d, J=2.4 Hz, 1H), 7.48-7.43 (m, J=8.3 Hz, 2H), 7.28-7.15 (m, 1H), 6.79-6.68 (m, 1H), 6.68-6.58 (m, 1H), 6.50-6.34 (m, 2H), 5.47-5.31 (m, 1H), 4.94-4.80 (m, 1H), 4.45-4.24 (m, 2H), 4.10-3.98 (m, 1H), 3.94 (s, 4H), 1.61 (d, J=6.8 Hz, 3H)

Description 148: methyl 4-(1-(5-chloro-2-(3-(4-(trifluoromethyl)phenoxy)azetidin-1-yl)nicotinamido)cyclopropyl)benzoate (D148)

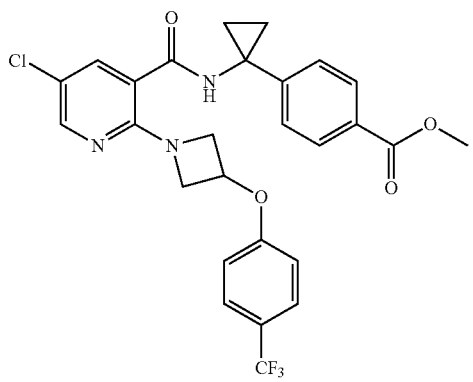 [SMILES: COC(=O)c1ccc(C2(NC(=O)c3cc(Cl)cnc3N3CC(Oc4ccc(C(F)(F)F)cc4)C3)CC2)cc1]

To a mixture of 5-chloro-2-(3-(4-(trifluoromethyl)phenoxy)azetidin-1-yl)nicotinic acid (D104) (200 mg, 0.53 mmol), methyl 4-(1-aminocyclopropyl)benzoate (D7) (144.31 mg, 0.634 mmol) and N,N-diisopropylethylamine (0.291 ml, 1.674 mmol) in dichloromethane (8 ml), ®T3P (1-Propanephosphonic acid cyclic anhydride) (403 mg, 0.633 mmol) was added and the mixture stirred under microwave irradiation at 110° C. for 10 min (2 cycle of 5 min each). 1M NaOH (5 ml) was added and the mixture extracted with dichloromethane (3×20 ml). Collected organics, after solvent evaporation, afforded a crude material that was purified by SPE-Si cartridge (10 g) eluting with a mixture cyclohexane/ethyl acetate from 100/0 to 60/40. Collected fractions, after solvent evaporation, afforded the title compound (D148) (140 mg)

MS: (ES/+) m/z: 546.2 [MH$^+$] C27H23ClF3N3O4 requires 545.13

$^1$H NMR (400 MHz, CHLOROFORM-d) δ (ppm): 8.23 (d, J=2.4 Hz, 1H), 7.99 (d, J=8.3 Hz, 2H), 7.75 (d, J=2.4 Hz, 1H), 7.63-7.55 (m, J=8.3 Hz, 2H), 7.50-7.40 (m, J=8.3 Hz, 2H), 7.05-6.95 (m, 1H), 6.76 (d, J=8.8 Hz, 2H), 5.04-4.89 (m, 1H), 4.43-4.29 (m, 2H), 4.07-3.97 (m, 2H), 3.94 (s, 3H), 1.42 (d, J=8.8 Hz, 4H)

Description 149: methyl 4-(1-(5-chloro-2-(3-(3-(trifluoromethyl)phenoxy)azetidin-1-yl)nicotinamido)cyclopropyl)benzoate (D149)

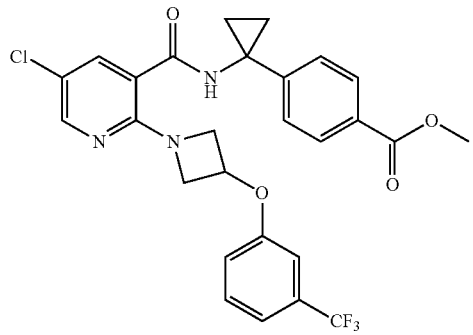 [SMILES: COC(=O)c1ccc(C2(NC(=O)c3cc(Cl)cnc3N3CC(Oc4cccc(C(F)(F)F)c4)C3)CC2)cc1]

The title compound (D149) (20 mg) was prepared according to the experimental procedure described in Description 148 starting from 5-chloro-2-(3-(3-(trifluoromethyl)phenoxy)azetidin-1-yl)nicotinic acid (D105) (160 mg, 0.423 mmol) and methyl 4-(1-aminocyclopropyl)benzoate (D7) (115.45 mg, 0.507 mmol). The residue obtained from SPE-Si cartridge purification (38 mg) dissolved in a mixture of chloroform/ethanol/n-hexane (70/15/15) (1 ml) was separated by chiral HPLC [Phenomenex Lux1 column (250×20 mm, 5 μm particle size). Mobile phase: isocratic premixed mixture of (hexane 75%, ethanol 25%) containing 0.1% of diethylamine. Flow rate=10 ml/min. UV detection: 235 nm]. Collected fractions, after solvent evaporation afforded the title compound (D149) (20 mg)

MS: (ES/+) m/z: 546.3 [MH$^+$] C27H23ClF3N3O4 requires 545.13

Description 150: methyl 4-(1-(5-chloro-2-(3-(4-fluorophenoxy)azetidin-1-yl)nicotinamido)cyclopropyl)benzoate (D150)

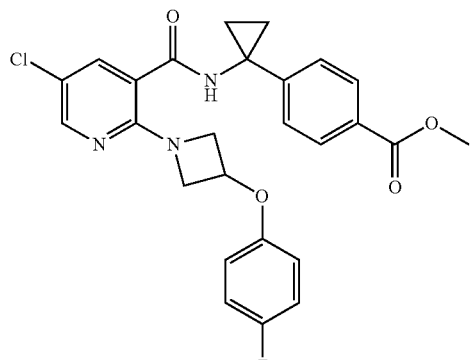

The title compound (D150) (75 mg) was prepared according to the experimental procedure described in Description 146 starting from 5-chloro-2-(3-(4-fluorophenoxy)azetidin-1-yl)nicotinic acid (D102) (70 mg, 0.216 mmol) and solution methyl 4-(1-aminocyclopropyl)benzoate (D7) (49.18 mg, 0.216 mmol).

MS: (ES/+) m/z: 496.2 [MH$^+$] C26H23ClFN3O4 requires 495.14

$^1$H NMR (400 MHz, CHLOROFORM-d) δ (ppm): 8.28-8.19 (m, 1H), 7.98-7.91 (m, 2H), 7.78-7.71 (m, 1H), 7.46-7.39 (m, 2H), 7.07-6.94 (m, 3H), 6.69-6.59 (m, 2H), 4.91-4.81 (m, 1H), 4.36-4.27 (m, 2H), 3.94 (s, 5H), 1.46-1.37 (m, 4H)

Description 151: methyl 4-(1-(5-chloro-2-(3-(3-fluorophenoxy)azetidin-1-yl)nicotinamido)cyclopropyl)benzoate (D151)

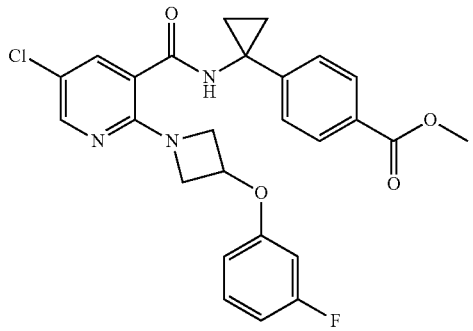 [SMILES: COC(=O)c1ccc(C2(NC(=O)c3cc(Cl)cnc3N3CC(Oc4cccc(F)c4)C3)CC2)cc1]

methyl 4-(1-(5-chloro-2-(3-(3-fluorophenoxy)azetidin-1-yl)nicotinamido)cyclopropyl)benzoate (D151) was prepared according to two different procedures reported below Procedure A The title compound (D151) (56 mg) was prepared according to the experimental procedure described in Description 146 starting from 5-chloro-2-(3-(3-fluorophenoxy)azetidin-1-yl)nicotinic acid (D103) (70 mg, 0.216 mmol) and methyl 4-(1-aminocyclopropyl)benzoate (D7) (49.18 mg, 0.216 mmol).

MS: (ES/+) m/z: 496.2 [MH$^+$] C26H23ClFN3O4 requires 495.14

$^1$H NMR (400 MHz, CHLOROFORM-d) δ (ppm): 8.23 (d, J=2.4 Hz, 1H), 8.00-7.91 (m, J=8.8 Hz, 2H), 7.76 (d, J=2.4 Hz, 1H), 7.49-7.38 (m, J=8.3 Hz, 2H), 7.28-7.17 (m, 1H), 7.02 (s, 1H), 6.81-6.65 (m, 1H), 6.47 (d, J=5.9 Hz, 2H), 5.01-4.80 (m, 1H), 4.34 (d, J=5.9 Hz, 2H), 4.04-3.96 (m, 2H), 3.93 (s, 3H), 1.42 (d, J=7.3 Hz, 4H)

Procedure B

A mixture of 5-chloro-2-(3-(3-fluorophenoxy)azetidin-1-yl)nicotinic acid (D103) (30 g, 0.0929 mol), 1-Hydroxybenzotriazole hydrate (14.2 g, 0.0929 mol) 1-Ethyl-3-(3-dimethylaminopropyl)carbodiimide hydrochloride (26.7 g, 0.1394 mol) in dimethylformamide (230 ml) was stirred 40 min at room temperature. A solution of methyl 4-(1-aminocyclopropyl)benzoate (D7) (21.16 g, 0.0929 mol) and triethylamine (12.94 ml, 0.0929 mol) in dimethylformamide (75 ml) was added and the resulting mixture was stirred 3 hours at room temperature. Water (500 ml) was added and the formed precipitate was filtered off and washed with water. After drying it afford the title compound (D151) (41 g)

$^1$H NMR (400 MHz, DMSO-d$_6$) δ (ppm): 9.26 (s, 1H), 8.23 (d, J=2.4 Hz, 1H), 7.84 (d, J=8.3 Hz, 2H), 7.79 (d, J=2.4 Hz, 1H), 7.38-7.27 (m, 3H), 6.88-6.77 (m, 1H), 6.77-6.64 (m, 2H), 5.09 (td, J=3.0, 6.2 Hz, 1H), 4.35 (dd, J=6.4, 9.8 Hz, 2H), 3.90-3.72 (m, 5H), 1.33 (d, J=7.8 Hz, 4H)

Description 152: methyl 4-(1-(5-chloro-2-(3-(4-fluoro-3-(trifluoromethyl)phenoxy)azetidin-1-yl)nicotinamido)cyclopropyl)benzoate (D152)

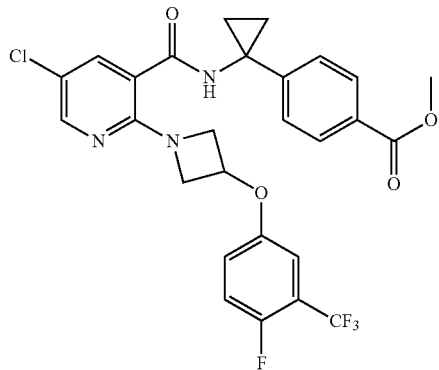 [SMILES: COC(=O)c1ccc(C2(NC(=O)c3cc(Cl)cnc3N3CC(Oc4ccc(F)c(C(F)(F)F)c4)C3)CC2)cc1]

The title compound (D152) (28 mg) was prepared according to the experimental procedure described in Description 144 starting from 5-chloro-2-(3-(4-fluoro-3-(trifluoromethyl)phenoxy)azetidin-1-yl)nicotinic (D106) (115 mg, 0.295 mmol) and methyl 4-(1-aminocyclopropyl)benzoate (D7) (67.01 mg, 0.295 mmol).

MS: (ES/+) m/z: 564.4 [MH$^+$] C26H23ClFN3O4 requires 563.12

$^1$H NMR (400 MHz, CHLOROFORM-d) δ (ppm): 8.23 (d, J=2.4 Hz, 1H), 7.96 (d, J=8.3 Hz, 2H), 7.75 (d, J=2.4 Hz, 1H), 7.42 (d, J=8.3 Hz, 2H), 7.15 (t, J=9.2 Hz, 1H), 7.04-6.91 (m, 2H), 6.88-6.66 (m, 1H), 5.05-4.74 (m, 1H), 4.36 (dd, J=6.2, 9.9 Hz, 2H), 3.98 (dd, J=4.0, 9.9 Hz, 2H), 3.93 (s, 3H), 1.42 (d, J=10.0 Hz, 4H)

Description 153: methyl 4-(1-(5-chloro-2-(3-(3-(trifluoromethoxy)phenoxy)azetidin-1-yl)nicotinamido)cyclopropyl)benzoate (D153)

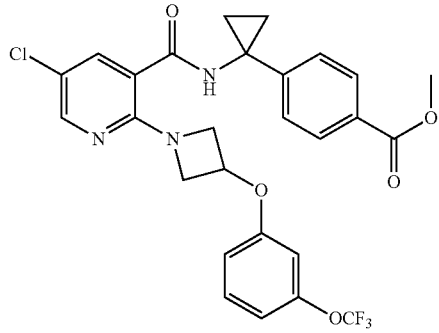 [SMILES: COC(=O)c1ccc(C2(NC(=O)c3cc(Cl)cnc3N3CC(Oc4cccc(OC(F)(F)F)c4)C3)CC2)cc1]

The title compound (D153) (120 mg) was prepared according to the experimental procedure described in Description 144 starting from 5-chloro-2-(3-(3-(trifluoromethoxy)phenoxy)azetidin-1-yl)nicotinic acid (D107) (110 mg, 0.282 mmol) and methyl 4-(1-aminocyclopropyl)benzoate (D7) (64.43 mg, 0.282 mmol).

MS: (ES/+) m/z: 562.4 [MH+] C27H23ClF3N3O5 requires 561.13

1H NMR (400 MHz, CHLOROFORM-d) δ (ppm): 8.23 (d, J=2.7 Hz, 1H), 7.96 (d, J=8.6 Hz, 2H), 7.76 (d, J=2.4 Hz, 1H), 7.41 (d, J=8.3 Hz, 2H), 7.32 (t, J=8.3 Hz, 1H), 7.02 (s, 1H), 6.89 (d, J=8.1 Hz, 1H), 6.64 (s, 1H), 6.60 (d, J=8.1 Hz, 1H), 5.04-4.83 (m, 1H), 4.36 (dd, J=6.2, 9.9 Hz, 2H), 4.00 (dd, J=4.0, 9.9 Hz, 2H), 3.92 (s, 3H), 1.50-1.31 (m, 4H)

Description 154: methyl 4-(1-(5-chloro-2-(3-(2,4-difluorophenoxy)azetidin-1-yl)nicotinamido)cyclopropyl)benzoate (D154)

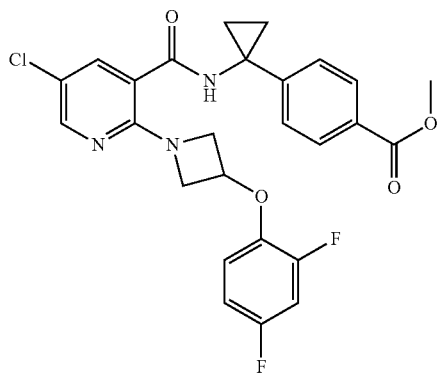 [SMILES: COC(=O)c1ccc(C2(NC(=O)c3cc(Cl)cnc3N3CC(Oc4ccc(F)cc4F)C3)CC2)cc1]

The title compound (D154) (55 mg) was prepared according to the experimental procedure described in Description 144 starting from 5-chloro-2-(3-(2,4-difluorophenoxy)azetidin-1-yl)nicotinic acid (D108) (82 mg, 0.240 mmol) and methyl 4-(1-aminocyclopropyl)benzoate (D7) (54.79 mg, 0.240 mmol).

MS: (ES/+) m/z: 514.13 [MH+] C26H22ClF2N3O4 requires 513.13

1H NMR (400 MHz, CHLOROFORM-d) δ (ppm): 8.23 (d, J=2.4 Hz, 1H), 7.96 (d, J=8.3 Hz, 2H), 7.75 (d, J=2.4 Hz, 1H), 7.43 (d, J=8.3 Hz, 2H), 7.02 (s, 1H), 6.91 (ddd, J=2.9, 8.3, 11.1 Hz, 1H), 6.79 (t, J=8.3 Hz, 1H), 6.58 (dt, J=5.0, 9.1 Hz, 1H), 5.03-4.80 (m, 1H), 4.31 (dd, J=6.2, 9.9 Hz, 2H), 4.02 (dd, J=3.8, 9.9 Hz, 2H), 3.94 (s, 3H), 1.50-1.35 (m, 4H)

Description 155: methyl 4-(1-(5-chloro-2-(3-(3,4-difluorophenoxy)azetidin-1-yl)nicotinamido)cyclopropyl)benzoate (D155)

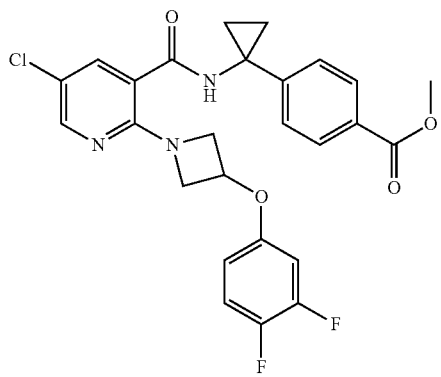 [SMILES: COC(=O)c1ccc(C2(NC(=O)c3cc(Cl)cnc3N3CC(Oc4ccc(F)c(F)c4)C3)CC2)cc1]

The title compound (D155) (50 mg) was prepared according to the experimental procedure described in Description 144 starting from 5-chloro-2-(3-(3,4-difluorophenoxy)azetidin-1-yl)nicotinic acid (D109) (87 mg, 0.255 mmol) and methyl 4-(1-aminocyclopropyl)benzoate (D7) (58.14 mg, 0.255 mmol).

MS: (ES/+) m/z: 514.13 [MH+] C26H22ClF2N3O4 requires 513.13

1H NMR (400 MHz, CHLOROFORM-d) δ (ppm): 8.23 (br. s., 1H), 7.95 (br. s., 2H), 7.74 (br. s., 1H), 7.44 (br. s., 2H), 7.09 (d, J=8.6 Hz, 1H), 6.98 (br. s., 1H), 6.56 (br. s., 1H), 6.36 (br. s., 1H), 4.85 (br. s., 1H), 4.32 (br. s., 2H), 3.97 (br. s., 5H), 1.42 (d, J=8.3 Hz, 4H)

Description 156: methyl 4-(1-(5-chloro-2-(3-(3-(piperazin-1-yl)phenoxy)azetidin-1-yl)nicotinamido)cyclopropyl)benzoate (D156)

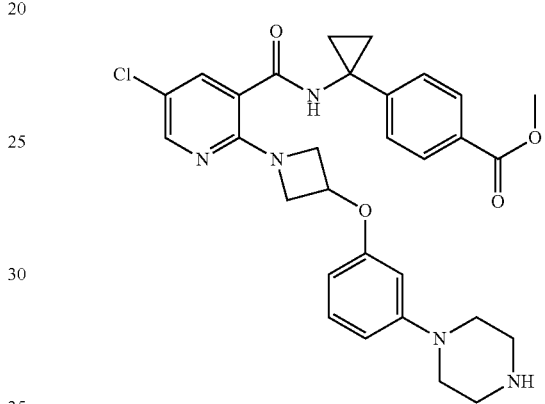

A suspension of 2-(3-(3-(4-(tert-butoxycarbonyl)piperazin-1-yl)phenoxy)azetidin-1-yl)-5-chloronicotinic acid (D110) (150 mg, 0.306 mmol), 1-Hydroxybenzotriazole hydrate (47 mg, 0.306 mmol) and 1-Ethyl-3-(3-dimethylaminopropyl)carbodiimide hydrochloride (88 mg, 0.46 mmol) in dimethylformamide (2 ml) was stirred 40 min at room temperature. A solution of methyl 4-(1-aminocyclopropyl)benzoate (D7) (68.9 mg, 0.306 mmol) and triethylamine (0.042 ml, 0.306 mmol) in dimethylformamide (2 ml) was added and the resulting mixture was stirred 40 min at room temperature. Water (2 ml) was added and the resulting precipitate was collected by filtration and purified by Biotage column (10 g) eluting with a mixture dichloromethane/ethylacetate from 100/0 to 80/20. Collected fractions, after solvent evaporation, afforded tert-butyl 4-(3-((1-(5-chloro-3-((1-(4-(methoxycarbonyl)phenyl)cyclopropyl)carbamoyl)pyridin-2-yl)azetidin-3-yl)oxy)phenyl)piperazine-1-carboxylate (135 mg)

MS: (ES/+) m/z: 662.5 [MH+] C35H40ClN5O6 requires 661.27

1H NMR (400 MHz, DMSO-d6) δ=9.25 (s, 1H), 8.23 (d, J=2.4 Hz, 1H), 7.85 (d, J=8.3 Hz, 2H), 7.79 (d, J=2.4 Hz, 1H), 7.33 (d, J=8.8 Hz, 2H), 7.13 (t, J=8.3 Hz, 1H), 6.59 (d, J=7.8 Hz, 1H), 6.38 (s, 1H), 6.20 (d, J=5.9 Hz, 1H), 5.04 (br. s., 1H), 4.32 (dd, J=6.4, 9.8 Hz, 2H), 3.86 (s, 3H), 3.80 (dd, J=3.7, 10.0 Hz, 2H), 3.43 (d, J=4.9 Hz, 4H), 3.14-3.04 (m, 4H), 1.42 (s, 9H), 1.33 (d, J=2.9 Hz, 4H)

To a cooled solution of tert-butyl 4-(3-((1-(5-chloro-3-((1-(4-(methoxycarbonyl)phenyl)cyclopropyl)carbamoyl)pyridin-2-yl)azetidin-3-yl)oxy)phenyl)piperazine-1-carboxylate (130 mg, 0.196 mmol) in dichloromethane (1 ml) a mixture trifluoroacetic acid/dichloromethane (3 ml/1 ml) was added and the resulting mixture stirred for 15 min. Solvents were evaporated in vacuo to afford a residue that was loaded on SPE-SCX (5 g) cartridge. Ammonia fractions after solvent evaporation afforded the title compound (D156) (105 mg)

MS: (ES/+) m/z: 562.4 [MH$^+$] C30H32ClN5O4 requires 561.21

$^1$H NMR (400 MHz, DMSO-d6) δ=9.25 (s, 1H), 8.23 (d, J=2.4 Hz, 1H), 7.89-7.81 (m, J=8.3 Hz, 2H), 7.79 (d, J=2.4 Hz, 1H), 7.39-7.29 (m, J=8.3 Hz, 2H), 7.11 (t, J=8.3 Hz, 1H), 6.56 (d, J=8.8 Hz, 1H), 6.33 (s, 1H), 6.17 (d, J=8.3 Hz, 1H), 5.03 (br. s., 1H), 4.32 (dd, J=6.4, 9.8 Hz, 2H), 3.86 (s, 3H), 3.80 (dd, J=3.2, 10.0 Hz, 2H), 3.10-2.99 (m, 4H), 2.88-2.78 (m, 4H), 1.33 (s, 4H)

Description 157 methyl 4-((5-chloro-2-(3-(3-fluorophenoxy)azetidin-1-yl)nicotinamido)methyl)benzoate (D157)

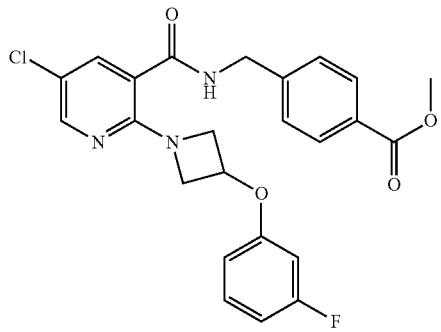 [SMILES: COC(=O)c1ccc(CNC(=O)c2cc(Cl)cnc2N2CC(Oc3cccc(F)c3)C2)cc1]

The title compound (D157) (55 mg) was prepared according to the experimental procedure described in Description 144 starting from 5-chloro-2-(3-(3-fluorophenoxy)azetidin-1-yl)nicotinic acid (D103) (50 mg, 0.154 mmol) and Methyl 4-(aminomethyl)benzoate hydrochloride (31.24 mg, 0.154 mmol, available at Aldrich#328383).

MS: (ES/+) m/z: 470.3 [MH$^+$] C24H21ClFN3O4 requires 469.12

$^1$H NMR (400 MHz, CHLOROFORM-d) δ (ppm): 8.23 (br. s., 1H), 8.02 (d, J=7.8 Hz, 2H), 7.83 (br. s., 1H), 7.43 (d, J=7.3 Hz, 2H), 7.32-7.16 (m, 7H), 6.74 (d, J=7.8 Hz, 2H), 6.53-6.35 (m, 2H), 4.91 (br. s., 1H), 4.69 (br. s., 2H), 4.39 (br. s., 2H), 4.09-3.99 (m, 2H), 3.95 (br. s., 3H)

Description 158: ethyl 6-((5-chloro-2-(3-(3-fluorophenoxy)azetidin-1-yl)nicotinamido)methyl)nicotinate (D158)

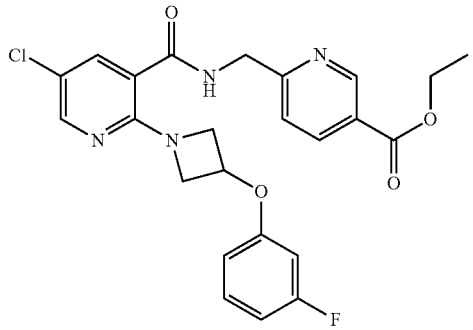 [SMILES: CCOC(=O)c1ccc(CNC(=O)c2cc(Cl)cnc2N2CC(Oc3cccc(F)c3)C2)nc1]

The title compound (D158) (59 mg) was prepared according to the experimental procedure described in Description 144 starting from 5-chloro-2-(3-(3-fluorophenoxy)azetidin-1-yl)nicotinic acid (D103) (50 mg, 0.154 mmol) and ethyl 6-(aminomethyl)nicotinate hydrochloride (33.56 mg, 0.154 mmol, commercially available at Chemimpex#23882).

MS: (ES/+) m/z: 485.3 [MH$^+$] C24H22ClFN4O4 requires 484.13

$^1$H NMR (400 MHz, CHLOROFORM-d) δ (ppm): 9.18 (d, J=1.7 Hz, 1H), 8.38 (d, J=8.1 Hz, 1H), 8.24 (d, J=2.4 Hz, 1H), 7.88 (d, J=2.4 Hz, 1H), 7.83-7.66 (m, 1H), 7.49 (d, J=8.1 Hz, 1H), 7.27-7.14 (m, 1H), 6.70 (d, J=2.2 Hz, 1H), 6.52 (dd, J=2.2, 8.3 Hz, 1H), 6.47 (td, J=2.3, 10.6 Hz, 1H), 5.07-4.93 (m, 1H), 4.85 (d, J=4.6 Hz, 2H), 4.56-4.37 (m, 4H), 4.13 (dd, J=4.4, 10.3 Hz, 2H), 1.50-1.37 (m, 3H)

Description 159: methyl 6-(1-(5-chloro-2-(3-(3-fluorophenoxy)azetidin-1-yl)nicotinamido)cyclopropyl)nicotinate (D159)

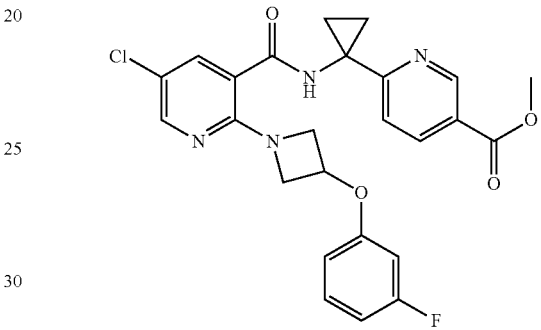

The title compound (D159) (22.4 mg) was prepared according to the experimental procedure described in Description 146 starting from 5-chloro-2-(3-(3-fluorophenoxy)azetidin-1-yl)nicotinic acid (D103) (60 mg, 0.186 mmol) and methyl 6-(1-aminocyclopropyl)nicotinate hydrochloride (D12) (28.5 mg, 0.186 mmol).

MS: (ES/+) m/z: 497.2 [MH$^+$] C25H22ClFN4O4 requires 496.13

$^1$H NMR (400 MHz, CHLOROFORM-d) δ (ppm): 9.32 (s, 1H), 8.94 (d, J=2.0 Hz, 1H), 8.26 (d, J=2.4 Hz, 1H), 8.13 (dd, J=2.0, 8.3 Hz, 1H), 7.89 (d, J=2.4 Hz, 1H), 7.57 (d, J=8.8 Hz, 1H), 7.34 (d, J=6.8 Hz, 1H), 6.83 (s, 1H), 6.78-6.70 (m, 2H), 5.15-5.09 (m, 1H), 4.41 (dd, J=6.1, 10.0 Hz, 2H), 3.92-3.85 (m, 5H), 1.62-1.57 (m, 2H), 1.38-1.34 (m, 2H).

Description 160: methyl 4-(1-(5-chloro-2-(3-(3-fluorobenzoyl)azetidin-1-yl)nicotinamido)cyclopropyl)benzoate (D160)

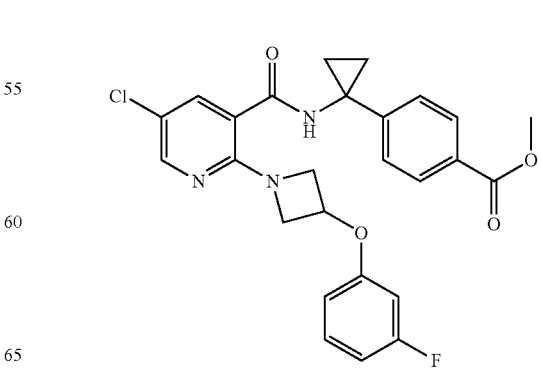

A solution of tert-butyl 3-(3-fluorobenzoyl)azetidine-1-carboxylate (D27) (100 mg, 0.358 mmol) in a 3:1 mixture of trifluoroacetic acid/dichloromethane (0.5 ml) was stirred 30 min at room temperature. After solvent evaporation the residue was dissolved in tetrahydrofuran/methanol 3:1 (1 ml) then triethylamine (0.15 ml, 1.074 mmol) and methyl 4-(1-(2,5-dichloronicotinamido)cyclopropyl)benzoate (D97) (130.8 mg, 0.358 mmol) were added and the resulting mixture was heated at 75° C. for 5 h, then overnight at 80° C. The reaction mixture was loaded on SPE-SCX cartridge (2 g). Collected ammonia fractions afforded, after solvent evaporation, a residue that was washed with a mixture dichloromethane/methanol and filtered off to afford the title compound (D160) (40.5 mg)

MS: (ES/+) m/z: 508.4 [MH$^+$] C27H23ClFN3O4 requires 507.14

$^1$H NMR (400 MHz, CHLOROFORM-d) δ (ppm).

Description 161: methyl 4-(1-(5-chloro-2-(3-(3-fluorophenyl)-3-hydroxyazetidin-1-yl)nicotinamido)cyclopropyl)benzoate (D161)

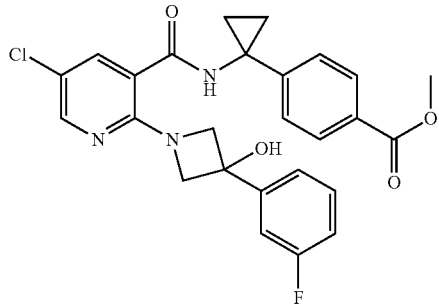 [SMILES: COC(=O)c1ccc(C2(NC(=O)c3cc(Cl)cnc3N3CC(O)(c4cccc(F)c4)C3)CC2)cc1]

The title compound (D161) (64.7 mg) was prepared according to the experimental procedure described in Description 146 (reaction time 1 h) starting from 5-chloro-2-(3-(3-fluorophenyl)-3-hydroxyazetidin-1-yl)nicotinic acid (D111) (63 mg, 0.195 mmol) and methyl 4-(1-aminocyclopropyl)benzoate hydrochloride (D7) (44.4 mg, 0.195 mmol).

MS: (ES/+) m/z: 496.2 [MH$^+$] C26H23ClFN3O4 requires 495.14

$^1$H NMR (400 MHz, CHLOROFORM-d) δ (ppm): 8.25 (d, J=2.4 Hz, 1H), 7.95 (d, J=8.3 Hz, 2H), 7.80 (d, J=2.4 Hz, 1H), 7.43-7.35 (m, 3H), 7.27-7.18 (m, 2H), 7.16 (s, 1H), 7.06 (dt, J=2.4, 8.3 Hz, 1H), 4.25-4.20 (m, 4H), 4.15 (d, J=8.8 Hz, 2H), 3.92 (s, 3H), 1.43-1.33 (m, 4H).

Description 162: methyl 4-(1-(5-chloro-2-(3-(4-fluorophenyl)-3-hydroxyazetidin-1-yl)nicotinamido)cyclopropyl)benzoate (D162)

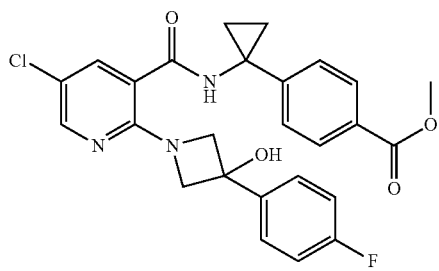 [SMILES: COC(=O)c1ccc(C2(NC(=O)c3cc(Cl)cnc3N3CC(O)(c4ccc(F)cc4)C3)CC2)cc1]

The title compound (D162) (76.7 mg) was prepared according to the experimental procedure described in Description 146 (reaction time 1 h) starting from 5-chloro-2-(3-(4-fluorophenyl)-3-hydroxyazetidin-1-yl)nicotinic acid (D112) (64 mg, 0.198 mmol) and methyl 4-(1-aminocyclopropyl)benzoate hydrochloride (D7) (45 mg, 0.198 mmol).

MS: (ES/+) m/z: 496.2 [MH$^+$] C26H23ClFN3O4 requires 495.14

$^1$H NMR (400 MHz, CHLOROFORM-d) δ (ppm): =8.25 (d, J=2.4 Hz, 1H), 7.99-7.94 (m, J=8.3 Hz, 2H), 7.79 (d, J=2.4 Hz, 1H), 7.44 (dd, J=5.1, 8.6 Hz, 2H), 7.41-7.36 (m, J=8.3 Hz, 2H), 7.15 (s, 1H), 7.11 (t, J=8.8 Hz, 2H), 4.24 (d, J=9.3 Hz, 2H), 4.15 (d, J=9.3 Hz, 2H), 3.92 (s, 2H), 1.44-1.33 (m, 4H).

Description 163: methyl 4-(1-(5-chloro-2-(3-((4-fluorophenoxy)methyl)azetidin-1-yl)nicotinamido)cyclopropyl)benzoate (D163)

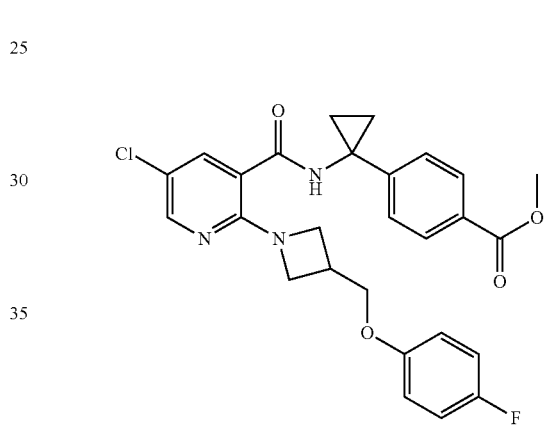

A mixture of 5-chloro-2-(3-((4-fluorophenoxy)methyl)azetidin-1-yl)nicotinic acid (D113) (55.4 mg, 0.161 mmol), O-(6-Chlorobenzotriazol-1-yl)-N,N,N',N'-tetramethyluronium hexafluorophosphate (HCTU) (66.8 mg, 0.161 mmol) and N,N-disopropylethylamine (0.072 ml, 0.403 mmol) was stirred 30 min at room temperature. Methyl 4-(1-aminocyclopropyl)benzoate hydrochloride (D7) (37.8 mg, 0.161 mmol) was added and the reaction mixture stirred overnight at room temperature. NH$_4$Cl saturated solution (20 ml) was added and the mixture was extracted with ethylacetate (3×10 ml). The residue obtained after solvent evaporation was purified by SPE-Si cartridge (10 g) eluting dichloromethane. Collected fractions, after solvent evaporation, afforded the title compound (D163) (52.6 mg).

MS: (ES/+) m/z: 510.4 [MH$^+$] C27H25ClFN3O4 requires 509.97

$^1$H NMR (400 MHz, CHLOROFORM-d) δ=8.23 (d, J=2.4 Hz, 1H), 8.00-7.96 (m, 2H), 7.78 (d, J=2.4 Hz, 1H), 7.42-7.37 (m, 2H), 7.07 (s, 1H), 7.03-6.97 (m, 2H), 6.87-6.81 (m, 2H), 4.14-4.04 (m, 4H), 3.92 (s, 3H), 3.82 (dd, J=5.4, 8.8 Hz, 2H), 3.07-3.01 (m, 1H), 1.42 (s, 4H).

Description 164: methyl 4-(1-(5-chloro-2-(3-(3-fluorophenyl)-3-hydroxyazetidin-1-yl)nicotinamido)cyclopropyl)benzoate (D164)

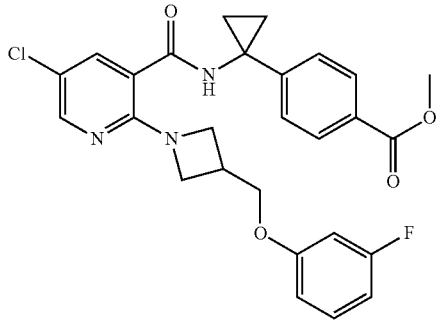 [SMILES: COC(=O)c1ccc(C2(NC(=O)c3cc(Cl)cnc3N3CC(COc4cccc(F)c4)C3)CC2)cc1]

The title compound (D164) (62 mg) was prepared according to the experimental procedure described in Description 163 starting from 5-chloro-2-(3-((3-fluorophenoxy)methyl)azetidin-1-yl)nicotinic acid (D114) (65 mg, 0.193 mmol) and methyl 4-(1-aminocyclopropyl)benzoate hydrochloride (D7) (44 mg, 0.193 mmol).

MS: (ES/+) m/z: 510.4 [MH$^+$] C27H25ClFN3O4 requires 509.97

$^1$H NMR (400 MHz, CHLOROFORM-d) δ (ppm): 8.23 (d, J=2.4 Hz, 1H), 8.01-7.95 (m, 2H), 7.78 (d, J=2.9 Hz, 1H), 7.42-7.38 (m, 2H), 7.27-7.22 (m, 1H), 7.07 (s, 1H), 6.74-6.66 (m, 2H), 6.62 (td, J=2.4, 10.8 Hz, 1H), 4.14-4.06 (m, 4H), 3.92 (s, 3H), 3.82 (dd, J=5.4, 8.8 Hz, 2H), 3.09-3.00 (m, 1H), 1.42 (s, 4H)

Description 165: methyl 4-(1-(5-chloro-2-(3-((3-(trifluoromethyl)phenyl)amino)azetidin-1-yl)nicotinamido)cyclopropyl)benzoate (D165)

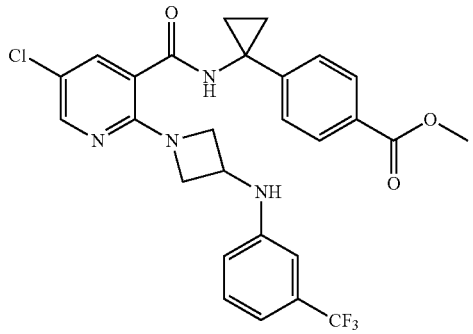 [SMILES: COC(=O)c1ccc(C2(NC(=O)c3cc(Cl)cnc3N3CC(Nc4cccc(C(F)(F)F)c4)C3)CC2)cc1]

The title compound (D165) (17 mg) was prepared according to the experimental procedure described in Description 144 starting from 5-chloro-2-(3-((3-(trifluoromethyl)phenyl)amino)azetidin-1-yl)nicotinic acid (D115) (50 mg, 0.135 mmol) and methyl 4-(1-aminocyclopropyl)benzoate (D7) (30.62 mg, 0.135 mmol).

MS: (ES/+) m/z: 545.3 [MH$^+$] C27H24ClF3N4O3 requires 544.15

$^1$H NMR (400 MHz, DMSO-d6) δ (ppm): 9.25 (s, 1H), 8.22 (d, J=2.4 Hz, 1H), 7.85 (d, J=8.6 Hz, 2H), 7.77 (d, J=2.4 Hz, 1H), 7.39-7.25 (m, 3H), 6.90 (d, J=7.3 Hz, 1H), 6.81 (br. s., 1H), 6.77-6.67 (m, 2H), 4.27 (d, J=6.1 Hz, 3H), 3.84 (s, 3H), 3.69 (d, J=5.6 Hz, 2H), 1.45-1.24 (m, 4H)

Description 166: methyl 4-(1-(5-chloro-2-(3-((3-fluorophenyl)amino)azetidin-1-yl)nicotinamido)cyclopropyl)benzoate (D166)

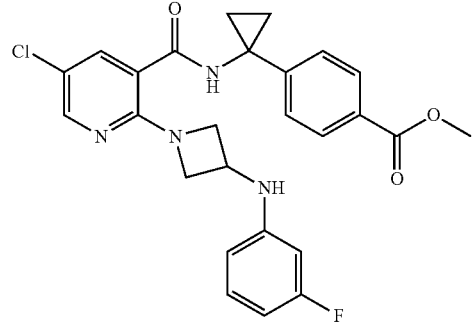 [SMILES: COC(=O)c1ccc(C2(NC(=O)c3cc(Cl)cnc3N3CC(Nc4cccc(F)c4)C3)CC2)cc1]

The title compound (D166) (17 mg) was prepared according to the experimental procedure described in Description 144 starting from 5-chloro-2-(3-((3-fluorophenyl)amino)azetidin-1-yl)nicotinic acid (D116) (40 mg, 0.124 mmol) and methyl 4-(1-aminocyclopropyl)benzoate (D7) (28.3 mg, 0.124 mmol).

MS: (ES/+) m/z: 495.2 [MH$^+$] C26H24ClFN4O3 requires 494.15

$^1$H NMR (400 MHz, CHLOROFORM-d) δ (ppm): 8.18 (d, J=2.2 Hz, 1H), 7.97 (d, J=8.3 Hz, 2H), 7.73 (d, J=2.4 Hz, 1H), 7.43 (d, J=8.3 Hz, 2H), 7.21-7.08 (m, 1H), 6.62-6.36 (m, 1H), 6.33-6.10 (m, 2H), 4.48-4.27 (m, 2H), 3.92 (s, 3H), 3.86-3.73 (m, 2H), 1.41 (d, J=7.8 Hz, 4H), 1.28 (s, 1H).

Description 167: methyl 4-(1-(5-chloro-2-(3-((4-fluorophenyl)amino)azetidin-1-yl)nicotinamido)cyclopropyl)benzoate (D167)

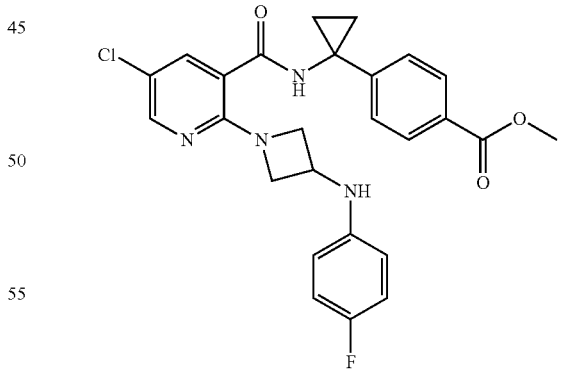

The title compound (D167) (43 mg) was prepared according to the experimental procedure described in Description 146 starting from 5-chloro-2-(3-((4-fluorophenyl)amino)azetidin-1-yl)nicotinic acid (D117) (70 mg, 0.217 mmol) and methyl 4-(1-aminocyclopropyl)benzoate (D7) (50 mg, 0.217 mmol).

MS: (ES/+) m/z: 495.3 [MH$^+$] C26H24ClFN4O3 requires 494.15

¹H NMR (400 MHz, DMSO-d₆) δ (ppm): 9.25 (s, 1H), 8.21 (d, J=2.4 Hz, 1H), 7.91-7.82 (m, 2H), 7.75 (d, J=2.4 Hz, 1H), 7.39-7.27 (m, 2H), 6.94 (t, J=9.0 Hz, 2H), 6.45 (dd, J=4.4, 8.8 Hz, 2H), 6.23 (d, J=5.9 Hz, 1H), 4.27-4.08 (m, 3H), 3.88-3.77 (m, 3H), 3.65 (dd, J=4.2, 8.6 Hz, 2H), 1.41-1.28 (m, 3H)

Description 168: methyl 4-(1-(5-chloro-2-(3-((4-fluoro-2-methylphenyl)amino)azetidin-1-yl)nicotinamido)cyclopropyl)benzoate (D168)

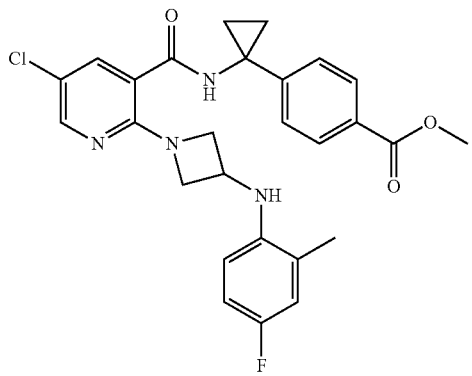 [SMILES: COC(=O)c1ccc(C2(NC(=O)c3cc(Cl)cnc3N3CC(Nc4ccc(F)cc4C)C3)CC2)cc1]

To a solution of N-(4-fluoro-2-methylphenyl)azetidin-3-amine (D55) and triethylamine (0.14 ml, 1.04 mmol) in tetrahydrofuran/methanol (3 ml/1 ml) methyl 4-(1-(2,5-dichloronicotinamido)cyclopropyl)benzoate (D97) (253 mg, 0.693 mmol) was added and the resulting mixture was heated 24 h at 75° C. The residue obtained after solvent evaporation, was purified by Biotage SNAP-Si (10 g) cartridge eluting with eluting with a mixture dichloromethane/ethylacetate from 95/5 to 80/20. Collected fractions, after solvent evaporation afforded the title compound (D168) (105 mg).

MS: (ES/+) m/z: 509.3 [MH⁺] C27H26ClFN4O3 requires 508.17

¹H NMR (400 MHz, DMSO-d6) δ=9.23 (s, 1H), 8.21 (d, J=2.4 Hz, 1H), 7.93-7.82 (m, J=8.3 Hz, 2H), 7.74 (d, J=2.4 Hz, 1H), 7.41-7.24 (m, J=8.3 Hz, 2H), 6.89 (dd, J=2.9, 9.8 Hz, 1H), 6.85-6.68 (m, 1H), 6.22 (dd, J=4.9, 8.8 Hz, 1H), 5.34 (d, J=5.9 Hz, 1H), 4.31-4.12 (m, 3H), 3.86 (s, 3H), 3.76 (dd, J=4.2, 8.6 Hz, 2H), 2.13 (s, 3H), 1.34 (d, J=8.3 Hz, 4H)

Description 169: methyl 4-(1-(5-chloro-2-(3-((2,4-difluorophenyl)amino)azetidin-1-yl)nicotinamido)cyclopropyl)benzoate (D169)

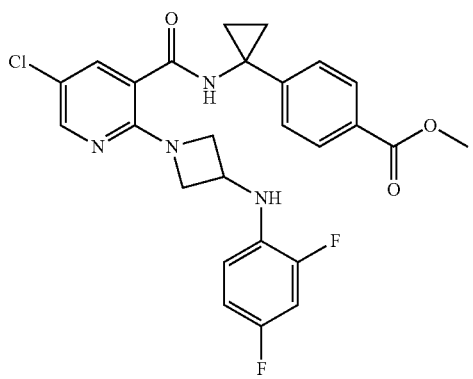 [SMILES: COC(=O)c1ccc(C2(NC(=O)c3cc(Cl)cnc3N3CC(Nc4ccc(F)cc4F)C3)CC2)cc1]

A mixture of 5-chloro-2-(3-((2,4-difluorophenyl)amino)azetidin-1-yl)nicotinic acid (D118) (40 mg, 0.118 mmol), 1-Hydroxybenzotriazole hydrate (18 mg, 0.118 mmol) and 1-Ethyl-3-(3-dimethylaminopropyl)carbodiimide hydrochloride (34 mg, 0.177 mmol) in dimethylformamide (5 ml) was stirred 10 min at room temperature. A solution of methyl 4-(1-aminocyclopropyl)benzoate hydrochloride (D7) (32.2 mg, 0.141 mmol) and triethylamine (0.02 ml, 0.141 mmol) in dry dimethylformamide (2 ml) was added and the mixture was stirred 24 h at room temperature. After solvent evaporation, water (10 ml) was added and the formed precipitate was filtered off and purified by Biotage SNAP-Si (10 g) cartridge eluting with a mixture dichloromethane/methanol from 100/0 to 80/20. Collected fractions, after solvent evaporation afforded the title compound (D169) (105 mg).

MS: (ES/+) m/z: 513.2 [MH⁺] C26H23ClF2N4O3 requires 512.14

¹H NMR (400 MHz, DMSO-d6) δ=9.23 (s, 1H), 8.21 (d, J=2.4 Hz, 1H), 7.91-7.80 (m, J=8.3 Hz, 2H), 7.74 (d, J=2.4 Hz, 1H), 7.40-7.29 (m, J=8.3 Hz, 2H), 7.18-7.06 (m, 1H), 6.85 (t, J=8.6 Hz, 1H), 6.48 (d, J=5.4 Hz, 1H), 6.03 (br. s., 1H), 4.22 (d, J=3.9 Hz, 3H), 3.86 (s, 3H), 3.76 (d, J=4.9 Hz, 2H), 1.34 (d, J=9.3 Hz, 4H)

Description 170: methyl 4-(1-(5-chloro-2-(3-((2-methyl-4-(trifluoromethyl)phenyl)amino)azetidin-1-yl)nicotinamido)cyclopropyl)benzoate (D170)

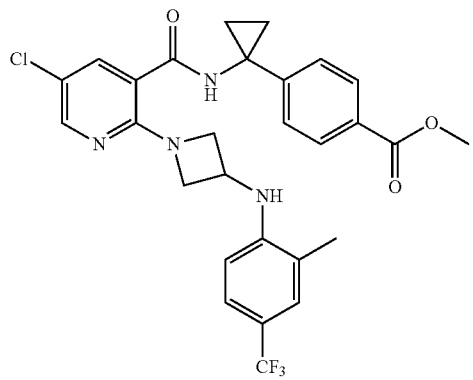

The title compound (D170) (43 mg) was prepared according to the experimental procedure described in Description 169 starting from 5-chloro-2-(3-((2-methyl-4-(trifluoromethyl)phenyl)amino)azetidin-1-yl)nicotinic acid (D119) (40 mg, 0.103 mmol) and methyl 4-(1-aminocyclopropyl)benzoate (D7) (23.6 mg, 0.103 mmol).

MS: (ES/+) m/z: 559.3 [MH⁺] C28H26ClF3N4O3 requires 558.16

¹H NMR (400 MHz, DMSO-d₆) δ (ppm): =9.26 (s, 1H), 8.22 (d, J=2.4 Hz, 1H), 7.90 (d, J=8.8 Hz, 2H), 7.76 (d, J=2.4 Hz, 1H), 7.40-7.25 (m, 4H), 6.38 (d, J=8.3 Hz, 1H), 6.05 (d, J=4.4 Hz, 1H), 4.37-4.17 (m, 3H), 3.85 (s, 5H), 2.18 (s, 3H), 1.34 (d, J=9.8 Hz, 4H)

Description 171: methyl 4-(1-(5-chloro-2-(3-((4-fluoro-2-methylphenyl)(methyl)amino)azetidin-1-yl)nicotinamido)cyclopropyl)benzoate (D171)

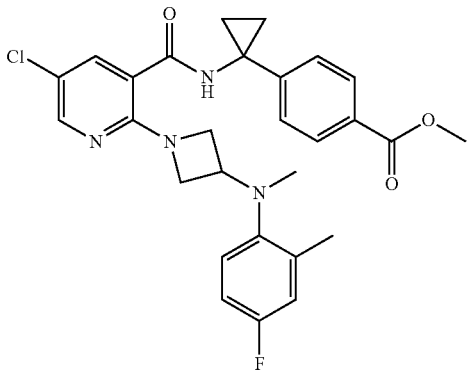 [SMILES: COC(=O)c1ccc(C2(NC(=O)c3cc(Cl)cnc3N3CC(N(C)c4ccc(F)cc4C)C3)CC2)cc1]

The title compound (D171) (58 mg) was prepared according to the experimental procedure described in Description 169 (reaction time 2 h) starting from 5-chloro-2-(3-((4-fluoro-2-methylphenyl)(methyl)amino)azetidin-1-yl)nicotinic acid (D120) (55 mg, 0.157 mmol) and methyl 4-(1-aminocyclopropyl)benzoate (D7) (35.8 mg, 0.157 mmol).

MS: (ES/+) m/z: 523.3 [MH$^+$] C28H28ClFN4O3 requires 522.18

$^1$H NMR (400 MHz, DMSO-d$_6$) δ (ppm): 9.20 (s, 1H), 8.18 (d, J=2.4 Hz, 1H), 7.82 (d, J=8.8 Hz, 2H), 7.71 (d, J=2.4 Hz, 1H), 7.30 (d, J=8.3 Hz, 2H), 7.04 (d, J=9.3 Hz, 1H), 6.91 (d, J=6.8 Hz, 2H), 4.09-4.03 (m, 1H), 4.02-3.94 (m, 2H), 3.86 (s, 3H), 3.52 (dd, J=4.4, 8.8 Hz, 2H), 2.43 (s, 3H), 2.26 (s, 3H), 1.28 (s, 4H)

Description 172: methyl 4-(1-(2-(3-(3-fluorophenoxy)azetidin-1-yl)-5-(trifluoromethyl)nicotinamido)cyclopropyl)benzoate (D172)

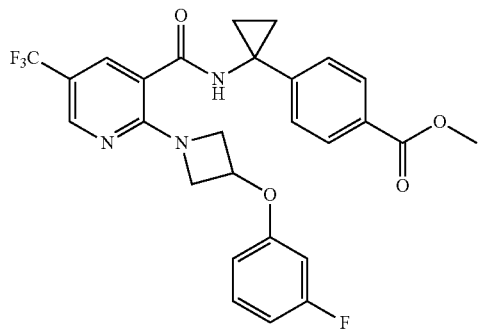 [SMILES: COC(=O)c1ccc(C2(NC(=O)c3cc(C(F)(F)F)cnc3N3CC(Oc4cccc(F)c4)C3)CC2)cc1]

The title compound (D172) (60 mg) was prepared according to the experimental procedure described in Description 146 starting from 2-(3-(3-fluorophenoxy)azetidin-1-yl)-5-(trifluoromethyl)nicotinic acid (D121) (50 mg, 0.14 mmol) and methyl 4-(1-aminocyclopropyl)benzoate (D7) (31.95 mg, 0.14 mmol).

MS: (ES/+) m/z: 530.2 [MH$^+$] C27H23F4N3O4 requires 529.16

$^1$H NMR (400 MHz, CHLOROFORM-d) δ (ppm): 8.48 (s, 1H), 8.04 (s, 2H), 8.01-7.93 (m, J=8.3 Hz, 2H), 7.81 (d, J=2.0 Hz, 1H), 7.49-7.40 (m, J=8.3 Hz, 2H), 6.79 (s, 1H), 6.78-6.71 (m, 1H), 6.46 (d, J=7.8 Hz, 2H), 5.00-4.87 (m, 1H), 4.43 (br. s., 2H), 4.08 (d, J=3.9 Hz, 2H), 3.93 (s, 3H), 1.43 (d, J=3.4 Hz, 3H)

Description 173: methyl 4-(1-(2-(3-(4-fluorophenoxy)azetidin-1-yl)-5-(trifluoromethyl)nicotinamido)cyclopropyl)benzoate (D173)

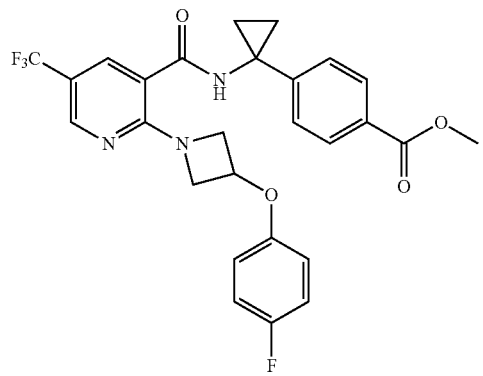 [SMILES: COC(=O)c1ccc(C2(NC(=O)c3cc(C(F)(F)F)cnc3N3CC(Oc4ccc(F)cc4)C3)CC2)cc1]

The title compound (D173) (80 mg) was prepared according to the experimental procedure described in Description 146 starting from 2-(3-(4-fluorophenoxy)azetidin-1-yl)-5-(trifluoromethyl)nicotinic acid (D122) (90 mg, 0.252 mmol) and methyl 4-(1-aminocyclopropyl)benzoate (D7) (57.51 mg, 0.252 mmol).

MS: (ES/+) m/z: 530.2 [MH$^+$] C27H23F4N3O4 requires 529.16

$^1$H NMR (400 MHz, CHLOROFORM-d) δ (ppm): 8.50-8.46 (m, 1H), 7.99-7.93 (m, J=8.3 Hz, 2H), 7.80 (d, J=2.4 Hz, 1H), 7.47-7.41 (m, J=8.3 Hz, 2H), 7.00 (t, J=8.6 Hz, 2H), 6.72 (s, 1H), 6.67-6.60 (m, 2H), 4.88 (s, 1H), 4.40 (dd, J=5.9, 10.3 Hz, 2H), 4.04 (dd, J=3.9, 10.3 Hz, 2H), 3.95 (s, 3H), 1.43 (d, J=2.9 Hz, 4H)

Description 174: methyl 4-(1-(2-(3-(4-chlorophenoxy)azetidin-1-yl)-5-(trifluoromethyl)nicotinamido)cyclopropyl)benzoate (D174)

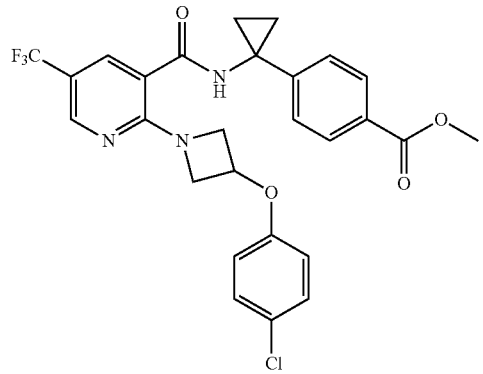 [SMILES: COC(=O)c1ccc(C2(NC(=O)c3cc(C(F)(F)F)cnc3N3CC(Oc4ccc(Cl)cc4)C3)CC2)cc1]

The title compound (D174) (25 mg) was prepared according to the experimental procedure described in Description 144 starting from 2-(3-(4-chlorophenoxy)azetidin-1-yl)-5-(trifluoromethyl)nicotinic acid (D123) (125 mg, 0.335 mmol) and methyl 4-(1-aminocyclopropyl)benzoate (D7) (76.35 mg, 0.335 mmol).

MS: (ES/+) m/z: 546.3 [MH⁺] C27H23ClF3N3O4 requires 545.13

¹H NMR (400 MHz, CHLOROFORM-d) δ (ppm): 8.47 (s, 1H), 7.99 (d, J=8.3 Hz, 2H), 7.80 (s, 1H), 7.45 (d, J=8.3 Hz, 2H), 7.26 (m, 2H), 6.73 (br. s., 1H), 6.61 (d, J=8.8 Hz, 2H), 5.00-4.78 (m, 1H), 4.42 (dd, J=6.4, 10.0 Hz, 2H), 4.06 (dd, J=3.3, 10.1 Hz, 2H), 3.96 (s, 3H), 1.43 (d, J=4.9 Hz, 4H)

Description 175: methyl 4-(1-(2-(3-(3-chlorophenoxy)azetidin-1-yl)-5-(trifluoromethyl)nicotinamido)cyclopropyl)benzoate (D175)

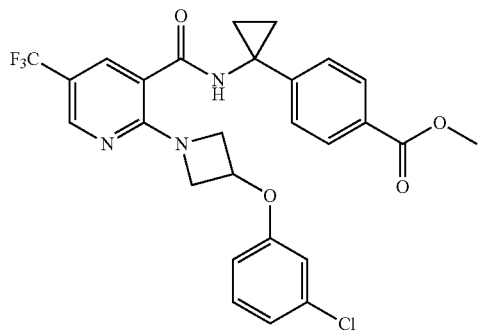 [SMILES: COC(=O)c1ccc(C2(NC(=O)c3cc(C(F)(F)F)cnc3N3CC(Oc4cccc(Cl)c4)C3)CC2)cc1]

The title compound (D175) (14 mg) was prepared according to the experimental procedure described in Description 144 starting from 2-(3-(3-chlorophenoxy)azetidin-1-yl)-5-(trifluoromethyl)nicotinic acid (D124) (85 mg, 0.228 mmol) and methyl 4-(1-aminocyclopropyl)benzoate (D7) (51.92 mg, 0.228 mmol).

MS: (ES/+) m/z: 546.3 [MH⁺] C27H23ClF3N3O4 requires 545.14

¹H NMR (400 MHz, CHLOROFORM-d) δ (ppm): 8.48 (s, 1H), 7.97 (d, J=8.3 Hz, 2H), 7.82 (d, J=2.2 Hz, 1H), 7.43 (d, J=8.3 Hz, 2H), 7.27-7.17 (m, 1H), 7.02 (d, J=6.1 Hz, 1H), 6.74 (t, J=2.2 Hz, 2H), 6.57 (dd, J=2.6, 8.2 Hz, 1H), 4.93 (br. s., 1H), 4.62-4.31 (m, 2H), 4.08 (d, J=7.6 Hz, 2H), 3.93 (s, 3H), 1.44 (d, J=4.9 Hz, 4H)

Description 176: methyl 4-(1-(2-(3-(4-fluoro-3-(trifluoromethyl)phenoxy)azetidin-1-yl)-5-(trifluoromethyl)nicotinamido)cyclopropyl)benzoate (D176)

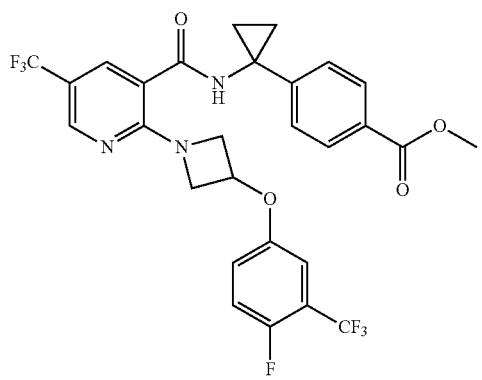

The title compound (D176) (52 mg) was prepared according to the experimental procedure described in Description 144 starting from 2-(3-(4-fluoro-3-(trifluoromethyl)phenoxy)azetidin-1-yl)-5-(trifluoromethyl)nicotinic acid (D125) (108 mg, 0.254 mmol) and methyl 4-(1-aminocyclopropyl)benzoate (D7) (57.95 mg, 0.254 mmol).

MS: (ES/+) m/z: 598.4 [MH⁺] C28H22F7N3O4 requires 597.15

¹H NMR (400 MHz, CHLOROFORM-d) δ (ppm): 8.48 (s, 1H), 7.97 (d, J=8.6 Hz, 2H), 7.81 (d, J=2.2 Hz, 1H), 7.44 (d, J=8.3 Hz, 2H), 7.16 (t, J=9.4 Hz, 1H), 6.97 (dd, J=3.2, 5.6 Hz, 1H), 6.79 (d, J=9.0 Hz, 1H), 6.72 (s, 1H), 4.93 (s, 1H), 4.46 (dd, J=6.4, 10.5 Hz, 2H), 4.07 (dd, J=3.5, 10.4 Hz, 2H), 3.93 (s, 3H), 1.44 (d, J=6.4 Hz, 4H)

Description 177: methyl 4-(1-(2-(3-(3-(trifluoromethoxy)phenoxy)azetidin-1-yl)-5-(trifluoromethyl)nicotinamido)cyclopropyl)benzoate (D177)

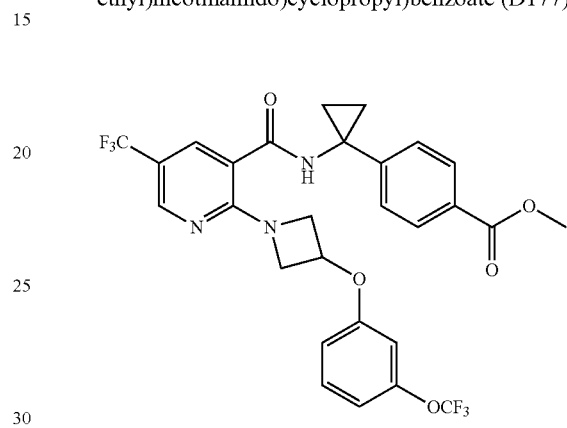

The title compound (D177) (113 mg) was prepared according to the experimental procedure described in Description 144 starting from 2-(3-(3-(trifluoromethoxy)phenoxy)azetidin-1-yl)-5-(trifluoromethyl)nicotinic acid (D126) (110 mg, 0.26 mmol) and methyl 4-(1-aminocyclopropyl)benzoate (D7) (59.31 mg, 0.26 mmol).

MS: (ES/+) m/z: 596.4 [MH⁺] C28H23F6N3O5 requires 595.15

¹H NMR (400 MHz, CHLOROFORM-d) δ (ppm): 8.48 (s, 1H), 7.97 (d, J=8.3 Hz, 2H), 7.82 (d, J=2.2 Hz, 1H), 7.43 (d, J=8.3 Hz, 2H), 7.33 (t, J=8.4 Hz, 1H), 6.90 (d, J=8.1 Hz, 1H), 6.74 (s, 1H), 6.67-6.62 (m, 1H), 6.61-6.54 (m, 1H), 5.05-4.85 (m, 1H), 4.46 (dd, J=6.5, 10.4 Hz, 2H), 4.08 (dd, J=3.9, 10.3 Hz, 2H), 3.96-3.86 (m, 3H), 1.48-1.36 (m, 4H)

Description 178: methyl 4-(1-(2-(3-(2,4-difluorophenoxy)azetidin-1-yl)-5-(trifluoromethyl)nicotinamido)cyclopropyl)benzoate (D178)

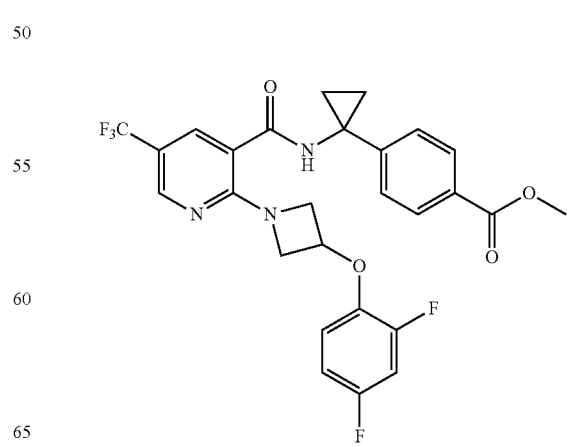

The title compound (D178) (106 mg) was prepared according to the experimental procedure described in Description 144 starting from 2-(3-(2,4-difluorophenoxy)azetidin-1-yl)-5-(trifluoromethyl)nicotinic acid (D127) (95 mg, 0.253 mmol) and methyl 4-(1-aminocyclopropyl)benzoate (D7) (57.79 mg, 0.253 mmol).

MS: (ES/+) m/z: 548.4 [MH⁺] C28H23F6N3O5 requires 547.14

¹H NMR (400 MHz, CHLOROFORM-d) δ (ppm): 8.48 (s, 1H), 7.98 (s, 2H), 7.81 (d, J=2.2 Hz, 1H), 7.45 (d, J=8.3 Hz, 2H), 6.92 (ddd, J=2.9, 8.4, 11.2 Hz, 1H), 6.86-6.76 (m, 1H), 6.75 (s, 1H), 6.59 (dt, J=5.0, 9.1 Hz, 1H), 5.00-4.75 (m, 1H), 4.41 (dd, J=6.4, 10.3 Hz, 2H), 4.11 (dd, J=3.8, 10.4 Hz, 2H), 3.94 (s, 3H), 1.43 (s, 4H)

Description 179: methyl 4-(1-(2-(3-(3,4-difluorophenoxy)azetidin-1-yl)-5-(trifluoromethyl)nicotinamido)cyclopropyl)benzoate (D179)

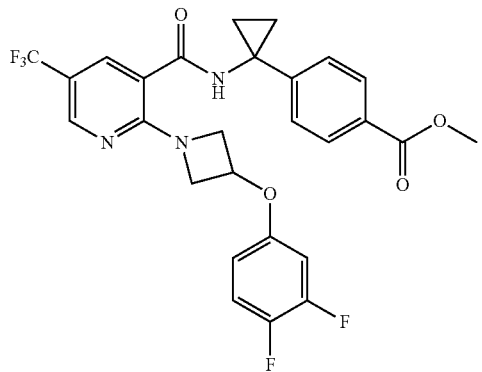 [SMILES: COC(=O)c1ccc(C2(NC(=O)c3cc(C(F)(F)F)cnc3N3CC(Oc4ccc(F)c(F)c4)C3)CC2)cc1]

The title compound (D179) (80 mg) was prepared according to the experimental procedure described in Description 144 starting from 2-(3-(3,4-difluorophenoxy)azetidin-1-yl)-5-(trifluoromethyl)nicotinic acid (D128) (100 mg, 0.267 mmol) and methyl 4-(1-aminocyclopropyl)benzoate (D7) (60.83 mg, 0.267 mmol).

MS: (ES/+) m/z: 548.4 [MH⁺] C28H23F6N3O5 requires 547.15

¹H NMR (400 MHz, CHLOROFORM-d) δ (ppm): 8.48 (s, 1H), 7.98 (s, 2H), 7.81 (d, J=2.2 Hz, 1H), 7.45 (d, J=8.3 Hz, 2H), 6.92 (ddd, J=2.9, 8.4, 11.2 Hz, 1H), 6.86-6.76 (m, 1H), 6.75 (s, 1H), 6.59 (dt, J=5.0, 9.1 Hz, 1H), 5.00-4.75 (m, 1H), 4.41 (dd, J=6.4, 10.3 Hz, 2H), 4.11 (dd, J=3.8, 10.4 Hz, 2H), 3.94 (s, 3H), 1.43 (s, 4H)

Description 180: methyl 4-(1-(2-(3-((5-methylisoxazol-3-yl)oxy)azetidin-1-yl)-5-(trifluoromethyl)nicotinamido)cyclopropyl)benzoate (D180)

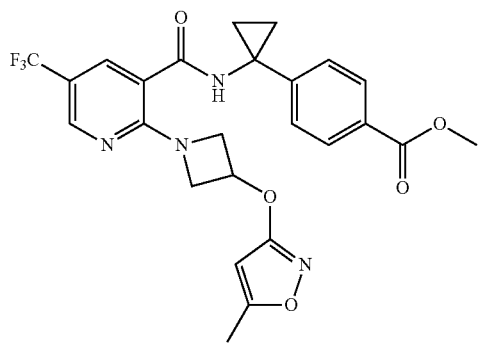 [SMILES: COC(=O)c1ccc(C2(NC(=O)c3cc(C(F)(F)F)cnc3N3CC(Oc4cc(C)on4)C3)CC2)cc1]

The title compound (D180) (20 mg) was prepared according to the experimental procedure described in Description 144 starting from 2-(3-((5-methylisoxazol-3-yl)oxy)azetidin-1-yl)-5-(trifluoromethyl)nicotinic acid (D129) (19 mg, 0.055 mmol) and methyl 4-(1-aminocyclopropyl)benzoate hydrochloride (D7) (12.6 mg, 0.055 mmol).

MS: (ES/+) m/z: 517.4 [MH⁺] C25H23F3N4O5 requires 516.16

¹H NMR (400 MHz, CHLOROFORM-d) δ (ppm): 8.46 (s, 1H), 8.00 (d, J=8.3 Hz, 2H), 7.83 (d, J=2.2 Hz, 1H), 7.43 (d, J=8.6 Hz, 2H), 6.83 (br. s., 1H), 5.65 (d, J=1.0 Hz, 1H), 5.21 (t, J=3.8 Hz, 1H), 4.44 (dd, J=6.1, 10.5 Hz, 2H), 4.13 (dd, J=3.3, 10.9 Hz, 2H), 3.93 (s, 3H), 2.38 (d, J=0.7 Hz, 3H), 1.44 (s, 4H)

Description 181: methyl 4-(1-(5-(trifluoromethyl)-2-(3-((6-(trifluoromethyl) pyridin-2-yl)oxy)azetidin-1-yl)nicotinamido)cyclopropyl)benzoate (D181)

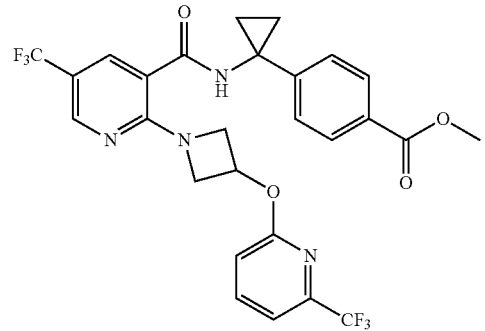 [SMILES: COC(=O)c1ccc(C2(NC(=O)c3cc(C(F)(F)F)cnc3N3CC(Oc4cccc(C(F)(F)F)n4)C3)CC2)cc1]

The title compound (D181) (75 mg) was prepared according to the experimental procedure described in Description 144 starting from 5-(trifluoromethyl)-2-(3-((6-(trifluoromethyl)pyridin-2-yl)oxy)azetidin-1-yl)nicotinic acid (D130) (77 mg, 0.189 mmol) and methyl 4-(1-aminocyclopropyl)benzoate hydrochloride (D7) (43.04 mg, 0.189 mmol).

MS: (ES/+) m/z: 581.04 [MH⁺] C27H22F6N4O4 requires 580.15

¹H NMR (400 MHz, CHLOROFORM-d) δ (ppm): 8.48 (d, J=1.5 Hz, 1H), 8.02-7.93 (m, 2H), 7.85 (d, J=2.0 Hz, 1H), 7.79 (t, J=7.9 Hz, 1H), 7.39 (d, J=8.8 Hz, 2H), 7.36-7.31 (m, 1H), 6.99 (d, J=8.3 Hz, 1H), 6.77 (s, 1H), 5.54-5.34 (m, 1H), 4.52 (dd, J=7.1, 10.5 Hz, 2H), 4.21-4.06 (m, 2H), 3.92 (s, 3H), 1.44 (d, J=2.7 Hz, 4H)

Description 182: methyl 4-(1-(2-(3-((5-fluoropyrimidin-2-yl)oxy)azetidin-1-yl)-5-(trifluoromethyl)nicotinamido)cyclopropyl)benzoate (D182)

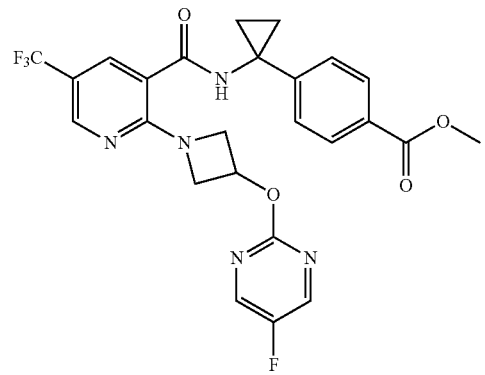

The title compound (D182) (36 mg) was prepared according to the experimental procedure described in Description (D169) starting from 2-(3-((5-fluoropyrimidin-2-yl)oxy)azetidin-1-yl)-5-(trifluoromethyl)nicotinic acid (D131) (42 mg, 0.117 mmol) and methyl 4-(1-aminocyclopropyl)benzoate hydrochloride (D7) (27 mg, 0.117 mmol).

MS: (ES/+) m/z: 532.04 [MH$^+$] C25H21F4N5O4 requires 531.15

$^1$H NMR (400 MHz, CHLOROFORM-d) δ (ppm): 9.34 (s, 1H), 8.70 (s, 2H), 8.52 (s, 1H), 7.94 (d, J=2.0 Hz, 1H), 7.85-7.80 (m, J=8.8 Hz, 2H), 7.39-7.33 (m, J=8.3 Hz, 2H), 5.39-5.27 (m, 1H), 4.40 (dd, J=6.4, 10.8 Hz, 2H), 3.96 (dd, J=3.4, 10.3 Hz, 2H), 3.86 (s, 3H), 1.34 (d, J=12.7 Hz, 4H)

Description 183: methyl 4-(1-(2-(3-((3-fluorophenyl)amino)azetidin-1-yl)-5-(trifluoromethyl)nicotinamido)cyclopropyl)benzoate (D183)

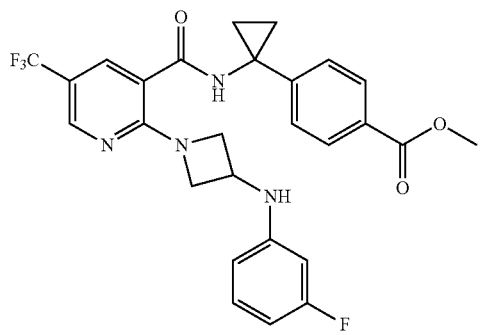 [SMILES: COC(=O)c1ccc(C2(NC(=O)c3cc(C(F)(F)F)cnc3N3CC(Nc4cccc(F)c4)C3)CC2)cc1]

To a solution of 3-Fluoroaniline (0.032 ml, 0.34 mmol) in acetonitrile (0.5 ml), potassium carbonate (61 mg, 0.044 mmol) was added followed by the addition of methyl 2-(3-((methylsulfonyl)oxy)azetidin-1-yl)-5-(trifluoromethyl)nicotinate (D68) (120 mg, 0.374 mmol). The reaction mixture was stirred under microwave irradiation for 50 min at 200° C. (2 cycles of 25 min each). Lithium hydroxide monohydrate (14.26 mg, 0.34 mmol) and a mixture 1,4-dioxane/water (3/1 ml) was added and the mixture was stirred under microwave irradiation for 5 min at 150° C. The mixture was evaporated in vacuo, diluted with water (5 ml)/1M HCl (15 ml) and extracted with ethylacetate (3×20 ml). After solvent evaporation, the residue was dissolved in dimethylformamide (2.5 ml) then (Benzotriazol-1-yloxy)tripyrrolidinophosphonium hexafluorophosphate (PyBOP) (307.55 mg, 0.59 mmol) and N,N-Disopropylethylamine (0.27 ml, 1.57 mmol) were added and the mixture stirred at room temperature for 1 h. Methyl 4-(1-aminocyclopropyl)benzoate hydrochloride (D7) (89.7 mg, 0.394 mmol) was added and the resulting mixture was stirred at room temperature overnight then poured into ice-water and extracted with diethylether (3×20 ml). The combined organic layers were washed with brine, dried over Na$_2$SO$_4$, filtered and concentrated. The crude residue obtained after solvent evaporation was loaded on SNAP-Si cartridge (10 g) and eluted with a mixture cyclohexane/dichloromethane from 30/70 to 0/100 then dichloromethane/ethylacetate from 100/0 to 80/20. Collected fractions, after solvent evaporation afforded the title compound (D183) (16 mg)

MS: (ES/+) m/z: 529.4 [MH$^+$] C27H24F4N4O3 requires 528.18

$^1$H NMR (400 MHz, CHLOROFORM-d) δ (ppm): 8.45 (s, 1H), 7.97 (d, J=8.8 Hz, 2H), 7.77 (d, J=2.0 Hz, 1H), 7.41 (d, J=8.3 Hz, 2H), 7.20-7.11 (m, 1H), 6.82 (s, 1H), 6.49 (dt, J=2.2, 8.4 Hz, 1H), 6.23 (dd, J=1.7, 8.1 Hz, 1H), 6.20-6.08 (m, 1H), 4.38 (dd, J=7.6, 9.0 Hz, 2H), 4.28-4.18 (m, 1H), 3.94-3.89 (m, 3H), 3.82 (dd, J=4.6, 9.5 Hz, 2H), 1.41 (d, J=3.9 Hz, 4H)

Description 184: methyl 4-(1-(2-(3-((4-fluorophenyl)amino)azetidin-1-yl)-5-(trifluoromethyl)nicotinamido)cyclopropyl)benzoate (D184)

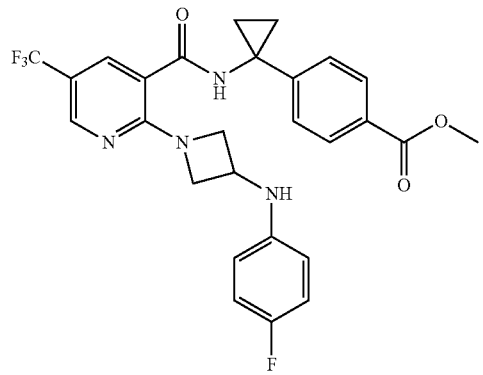 [SMILES: COC(=O)c1ccc(C2(NC(=O)c3cc(C(F)(F)F)cnc3N3CC(Nc4ccc(F)cc4)C3)CC2)cc1]

The title compound (D184) (35 mg) was prepared according to the experimental procedure described in Description 183 starting from methyl 2-(3-((methylsulfonyl)oxy)azetidin-1-yl)-5-(trifluoromethyl)nicotinate (D68) (120 mg, 0.374 mmol) and 4-Fluoroaniline (0.032 ml, 0.34 mmol)

MS: (ES/+) m/z: 529.4 [MH$^+$] C27H24F4N4O3 requires 528.18

$^1$H NMR (400 MHz, CHLOROFORM-d) δ (ppm): 8.43 (s, 1H), 8.01-7.93 (m, 2H), 7.78 (d, J=2.2 Hz, 1H), 7.44 (d, J=8.3 Hz, 2H), 6.95 (t, J=8.7 Hz, 2H), 6.50 (br. s., 2H), 4.43-4.31 (m, 2H), 4.26-4.16 (m, 1H), 3.97-3.87 (m, 5H), 1.38 (br. s., 4H)

Description 185: ethyl 4-(1-(2-(3-((4-fluoro-2-methylphenyl)amino)azetidin-1-yl)-5-(trifluoromethyl)nicotinamido)cyclopropyl)benzoate (D185)

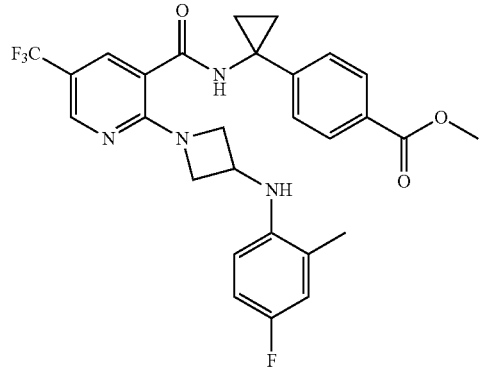

The title compound (D185) (20 mg) was prepared according to the experimental procedure described in Description 183 starting from methyl 2-(3-((methylsulfonyl)oxy)azetidin-1-yl)-5-(trifluoromethyl)nicotinate (D68) (120 mg, 0.374 mmol) and 4-Fluoro-2-methylaniline (0.037 ml, 0.34 mmol)

MS: (ES/+) m/z: 543.5 [MH⁺] C28H26F4N4O3 requires 542.19

¹H NMR (400 MHz, CHLOROFORM-d) δ (ppm): 8.45 (s, 1H), 7.97 (d, J=8.6 Hz, 2H), 7.77 (d, J=2.2 Hz, 1H), 7.45 (d, J=8.3 Hz, 2H), 6.91-6.85 (m, 1H), 6.84-6.79 (m, 1H), 6.27-6.09 (m, 1H), 4.47-4.37 (m, 2H), 4.26-4.19 (m, 1H), 3.99-3.86 (m, 5H), 2.18 (s, 3H), 1.46 (br. s., 4H)

Description 186: methyl 4-(1-(2-(3-((2,4-difluorophenyl)amino)azetidin-1-yl)-5-(trifluoromethyl)nicotinamido)cyclopropyl)benzoate (D186)

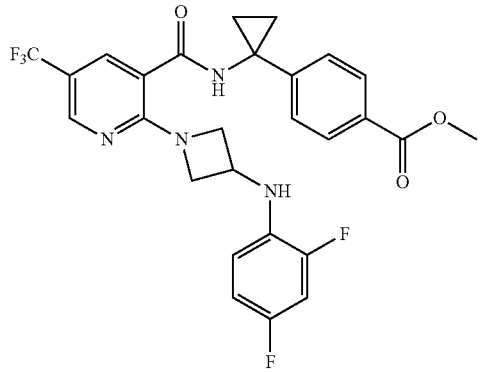 [SMILES: COC(=O)c1ccc(C2(NC(=O)c3cc(C(F)(F)F)cnc3N3CC(Nc4ccc(F)cc4F)C3)CC2)cc1]

The title compound (D186) (9 mg) was prepared according to the experimental procedure described in Description 183 starting from methyl 2-(3-((methylsulfonyl)oxy)azetidin-1-yl)-5-(trifluoromethyl)nicotinate (D68) (120 mg, 0.374 mmol) and 2,4-Difluoroaniline (0.032 ml, 0.34 mmol)

MS: (ES/+) m/z: 547.4 [MH⁺] C27H23F5N4O3 requires 546.17

¹H NMR (400 MHz, CHLOROFORM-d) δ (ppm): 8.46 (s, 1H), 7.98 (s, 2H), 7.77 (d, J=2.0 Hz, 1H), 7.44 (d, J=8.3 Hz, 2H), 6.84 (ddd, J=2.7, 8.4, 11.4 Hz, 1H), 6.80-6.72 (m, 2H), 6.27 (dt, J=5.4, 9.0 Hz, 1H), 4.38 (dd, J=7.3, 9.3 Hz, 2H), 4.22 (t, J=5.6 Hz, 1H), 3.92 (s, 3H), 3.84 (dd, J=4.6, 9.5 Hz, 2H), 1.42 (d, J=3.4 Hz, 4H)

Description 187: methyl 4-(1-(5-fluoro-2-(3-(3-fluorophenoxy)azetidin-1-yl)nicotinamido)cyclopropyl)benzoate (D187)

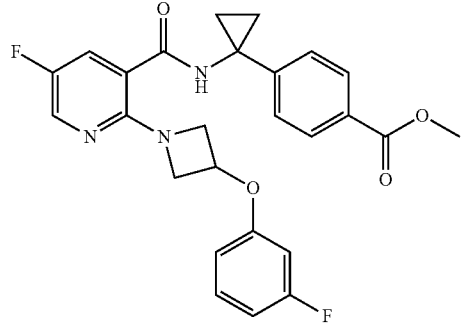 [SMILES: COC(=O)c1ccc(C2(NC(=O)c3cc(F)cnc3N3CC(Oc4cccc(F)c4)C3)CC2)cc1]

The title compound (D187) (45 mg) was prepared according to the experimental procedure described in Description 144 starting from 5-fluoro-2-(3-(3-fluorophenoxy)azetidin-1-yl)nicotinic acid (D132) (50 mg, 0.228 mmol) and methyl 4-(1-aminocyclopropyl)benzoate (D7) (52.04 mg, 0.228 mmol).

MS: (ES/+) m/z: 480.3 [MH⁺] C26H23F2N3O4 requires 479.17

¹H NMR (400 MHz, CHLOROFORM-d) δ (ppm): 8.19 (d, J=2.7 Hz, 1H), 7.96 (d, J=8.3 Hz, 2H), 7.72 (dd, J=2.9, 8.1 Hz, 1H), 7.52 (s, 1H), 7.42 (d, J=8.3 Hz, 2H), 7.27-7.19 (m, 1H), 6.81-6.66 (m, 1H), 6.53-6.40 (m, 2H), 4.96-4.81 (m, 1H), 4.31 (dd, J=6.2, 9.7 Hz, 2H), 3.98 (dd, J=4.2, 9.8 Hz, 2H), 3.93 (s, 3H), 1.42 (d, J=7.3 Hz, 4H)

Description 188: methyl 4-(1-(2-(3-(3-chlorophenoxy)azetidin-1-yl)-5-fluoronicotinamido)cyclopropyl)benzoate (D188)

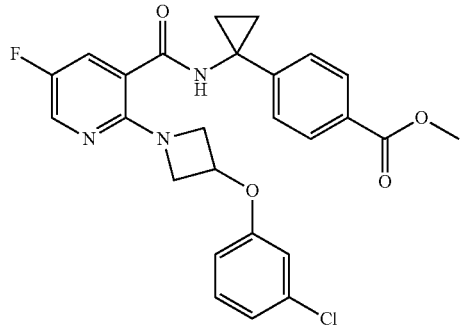 [SMILES: COC(=O)c1ccc(C2(NC(=O)c3cc(F)cnc3N3CC(Oc4cccc(Cl)c4)C3)CC2)cc1]

The title compound (D188) (12 mg) was prepared according to the experimental procedure described in Description 169 starting from 2-(3-(3-chlorophenoxy)azetidin-1-yl)-5-fluoronicotinic acid (D133) (14 mg, 0.043 mmol) and methyl 4-(1-aminocyclopropyl)benzoate hydrochloride (D7) (9.85 mg, 0.043 mmol).

MS: (ES/+) m/z: 496.2 [MH⁺] C26H23ClFN3O4 requires 495.14

¹H NMR (400 MHz, CHLOROFORM-d) δ (ppm): 9.23 (s, 1H), 8.24 (d, J=2.9 Hz, 1H), 7.84 (d, J=8.3 Hz, 2H), 7.72 (dd, J=2.9, 8.3 Hz, 1H), 7.37-7.27 (m, 3H), 7.05 (d, J=7.3 Hz, 1H), 6.91 (t, J=2.2 Hz, 1H), 6.81 (dd, J=2.4, 8.3 Hz, 1H), 5.10 (br. s., 1H), 4.32 (dd, J=6.4, 9.8 Hz, 2H), 3.85 (s, 3H), 3.79 (dd, J=3.4, 9.8 Hz, 2H), 1.34 (d, J=2.0 Hz, 4H)

Description 189: methyl 4-(1-(5-fluoro-2-(3-(3-(trifluoromethoxy)phenoxy)azetidin-1-yl)nicotinamido)cyclopropyl)benzoate (D189)

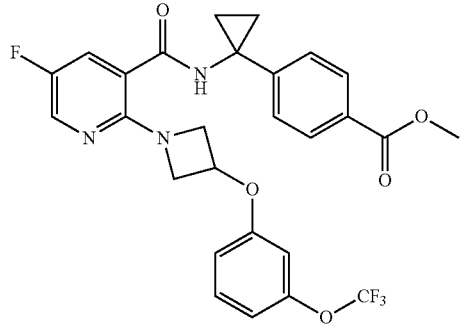 [SMILES: COC(=O)c1ccc(C2(NC(=O)c3cc(F)cnc3N3CC(Oc4cccc(OC(F)(F)F)c4)C3)CC2)cc1]

The title compound (D189) (39 mg) was prepared according to the experimental procedure described in Description 169 starting from 5-fluoro-2-(3-(3-(trifluoromethoxy)phenoxy)azetidin-1-yl)nicotinic acid (D134) (27 mg, 0.072 mmol) and methyl 4-(1-aminocyclopropyl)benzoate hydrochloride (D7) (16.5 mg, 0.072 mmol).

MS: (ES/+) m/z: 546.2 [MH⁺] C27H23F4N3O5 requires 545.16

¹H NMR (400 MHz, CHLOROFORM-d) δ (ppm): 9.23 (s, 1H), 8.24 (d, J=2.9 Hz, 1H), 7.88-7.81 (m, J=8.3 Hz, 2H), 7.73 (dd, J=2.9, 8.8 Hz, 1H), 7.43 (t, J=8.1 Hz, 1H), 7.37-7.29 (m, J=8.3 Hz, 2H), 6.99 (d, J=8.8 Hz, 1H), 6.90-6.83 (m, 2H), 5.23-5.03 (m, 1H), 4.33 (dd, J=6.1, 9.5 Hz, 2H), 3.85 (s, 3H), 3.80 (dd, J=3.4, 9.8 Hz, 2H), 1.33 (s, 4H)

Description 190: methyl 4-(1-(5-fluoro-2-(3-((4-fluoro-2-methylphenyl)amino)azetidin-1-yl)nicotinamido)cyclopropyl)benzoate (D190)

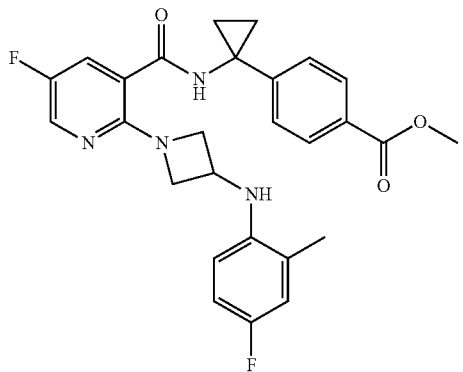 [SMILES: COC(=O)c1ccc(C2(NC(=O)c3cc(F)cnc3N3CC(Nc4ccc(F)cc4C)C3)CC2)cc1]

The title compound (D190) (26 mg) was prepared according to the experimental procedure described in Description 169 starting from 5-fluoro-2-(3-((4-fluoro-2-methylphenyl)amino)azetidin-1-yl)nicotinic acid (D135) (70 mg, 0.219 mmol) and methyl 4-(1-aminocyclopropyl)benzoate hydrochloride (D7) (50 mg, 0.219 mmol).

MS: (ES/+) m/z: 493.3 [MH$^+$] C27H26F2N4O3 requires 492.2

$^1$H NMR (400 MHz, CHLOROFORM-d) δ (ppm): 9.20 (s, 1H), 8.21 (d, J=2.9 Hz, 1H), 7.90-7.82 (m, J=8.3 Hz, 2H), 7.67 (dd, J=2.9, 8.8 Hz, 1H), 7.38-7.30 (m, J=8.3 Hz, 2H), 6.89 (dd, J=2.9, 9.8 Hz, 1H), 6.86-6.73 (m, 1H), 6.22 (dd, J=4.9, 8.8 Hz, 1H), 5.31 (d, J=5.4 Hz, 1H), 4.27-4.12 (m, 3H), 3.86 (s, 3H), 3.78-3.67 (m, 2H), 2.13 (s, 3H), 1.34 (d, J=3.9 Hz, 4H)

Description 191: methyl 4-((1S)-1-(5-chloro-2-(3-(4-(trifluoromethyl)phenoxy)pyrrolidin-1-yl)nicotinamido)ethyl)benzoate (D191)

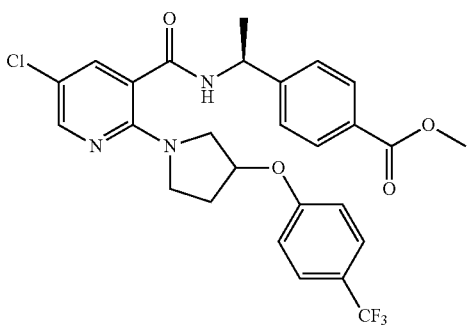 [SMILES: COC(=O)c1ccc([C@H](C)NC(=O)c2cc(Cl)cnc2N2CCC(Oc3ccc(C(F)(F)F)cc3)C2)cc1]

The title compound (D191) (50 mg) was prepared according to the experimental procedure described in Description 148 starting from lithium 5-chloro-2-(3-(4-(trifluoromethyl)phenoxy)pyrrolidin-1-yl)nicotinate (D136) (130 mg, 0.331 mmol) and (S)-methyl 4-(1-aminoethyl)benzoate (D3) (71.19 mg, 0.331 mmol)

MS: (ES/+) m/z: 548.3 [MH$^+$] C27H25ClF3N3O4 requires 547.15

Description 192: methyl 4-((1S)-1-(5-chloro-2-(3-(3-(trifluoromethyl)phenoxy)pyrrolidin-1-yl)nicotinamido)ethyl)benzoate (D192)

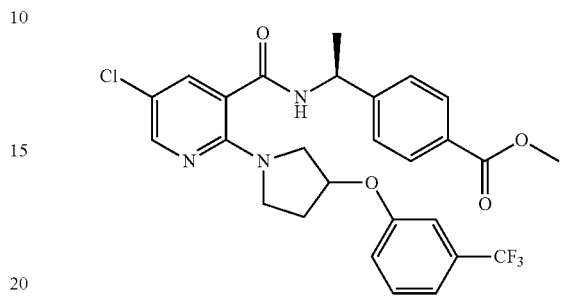

The title compound (D192) (64 mg) was prepared according to the experimental procedure described in Description 146 starting from 5-chloro-2-(3-(3-(trifluoromethyl)phenoxy)pyrrolidin-1-yl)nicotinic acid (D137) (120 mg, 0.305 mmol) and (S)-methyl 4-(1-aminoethyl)benzoate (D3) (65.7 mg, 0.305 mmol)

MS: (ES/+) m/z: 548.2 [MH$^+$] C27H25ClF3N3O4 requires 547.15

$^1$H NMR (400 MHz, CHLOROFORM-d) δ (ppm): 8.20 (d, J=2.9 Hz, 1H), 8.03 (d, J=8.3 Hz, 2H), 7.71 (s, 1H), 7.49 (s, 3H), 7.27-7.22 (m, 1H), 7.10-7.05 (m, 1H), 7.03-6.96 (m, 1H), 6.79-6.71 (m, 1H), 5.42-5.29 (m, 1H), 4.97-4.91 (m, 1H), 3.92 (d, J=5.9 Hz, 3H), 3.84-3.77 (m, 1H), 3.76-3.49 (m, 2H), 3.47-3.38 (m, 1H), 2.26-2.08 (m, 2H), 1.61 (dd, J=7.1, 19.3 Hz, 3H)

Description 193: methyl 4-((1S)-1-(5-chloro-2-(3-(4-fluorophenoxy)pyrrolidin-1-yl)nicotinamido)ethyl)benzoate (D193)

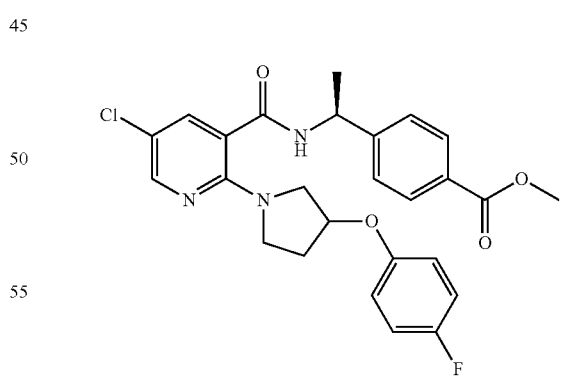

The title compound (D193) (64 mg) was prepared according to the experimental procedure described in Description 146 starting from 5-chloro-2-(3-(4-fluorophenoxy)pyrrolidin-1-yl)nicotinic acid (D138) (110 mg, 0.320 mmol), and (S)-methyl 4-(1-aminoethyl)benzoate (D3) (68.82 mg, 0.320 mmol) MS: (ES/+) m/z: 499.2 [MH$^+$] C26H25ClFN3O4 requires 497.15

Description 194: methyl 4-(1-(5-chloro-2-(3-phenoxy)pyrrolidin-1-yl)nicotinamido)cyclopropyl)benzoate (D194)

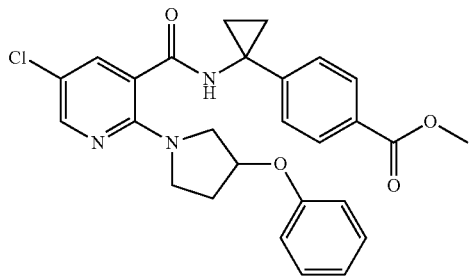 [SMILES: COC(=O)c1ccc(C2(NC(=O)c3cc(Cl)cnc3N3CCC(Oc4ccccc4)C3)CC2)cc1]

The title compound (D194) (100 mg) was prepared according to the experimental procedure described in Description 144 starting from 5-chloro-2-(3-phenoxy)pyrrolidin-1-yl) nicotinic acid (D139) (127 mg, 0.40 mmol), and methyl 4-(1-aminocyclopropyl)benzoate hydrochloride (D7) (91 mg, 0.40 mmol) (column eluting system: dichloromethane/methanol from 100/1 to 50/1)

$^1$H NMR (400 MHz, CHLOROFORM-d) δ (ppm): 8.17 (1H, d, J=2.0 Hz), 7.96 (2H, d, J=8.4 Hz), 7.70 (1H, d, J=2.0 Hz), 7.39 (2H, d, J=8.4 Hz), 7.30-7.28 (2H, m), 7.20-7.18 (1H, m), 6.97 (1H, t, J=7.2 Hz), 6.81 (2H, d, J=8.0 Hz), 4.90 (1H, s), 3.89 (3H, s), 3.72 (1H, dd, J=12.0, 4.4 Hz), 3.60 (1H, dd, J=17.2, 9.6 Hz), 3.43-3.37 (2H, m), 2.18-2.12 (2H, m), 1.45-1.34 (4H, m).

Description 195: methyl 4-(1-(5-chloro-2-(3-(3-(trifluoromethyl)phenoxy)pyrrolidin-1-yl)nicotinamido) cyclopropyl)benzoate (D195)

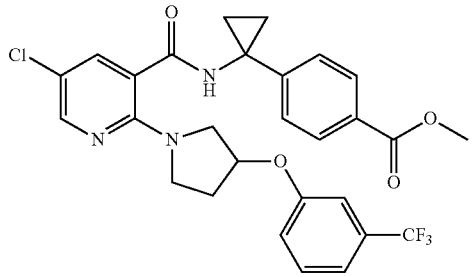 [SMILES: COC(=O)c1ccc(C2(NC(=O)c3cc(Cl)cnc3N3CCC(Oc4cccc(C(F)(F)F)c4)C3)CC2)cc1]

The title compound (D195) (150 mg) was prepared according to the experimental procedure described in Description 146 starting from 5-chloro-2-(3-(3-(trifluoromethyl)phenoxy)pyrrolidin-1-yl)nicotinic acid (D137) (120 mg, 0.305 mmol) and methyl 4-(1-aminocyclopropyl)benzoate (D7) (65.57 mg, 0.305 mmol).

MS: (ES/+) m/z: 560.2 [MH$^+$] C28H25ClF3N3O4 requires 559.15

Description 196: methyl 4-(1-(5-chloro-2-(3-(4-fluorophenoxy)pyrrolidin-1-yl)nicotinamido)cyclopropyl)benzoate (D196)

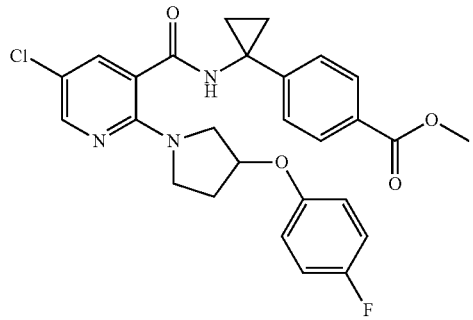 [SMILES: COC(=O)c1ccc(C2(NC(=O)c3cc(Cl)cnc3N3CCC(Oc4ccc(F)cc4)C3)CC2)cc1]

The title compound (D196) (50 mg) was prepared according to the experimental procedure described in Description 146 starting from 5-chloro-2-(3-(4-fluorophenoxy)pyrrolidin-1-yl)nicotinic acid (D138) (110 mg, 0.320 mmol) and methyl 4-(1-aminocyclopropyl)benzoate (D7) (72.86 mg, 0.320 mmol).

MS: (ES/+) m/z: 510.2 [MH$^+$] C27H25ClFN3O4 requires 509.15

Description 197: methyl 4-(1-(5-chloro-2-(3-(3-fluorophenoxy)pyrrolidin-1-yl)nicotinamido)cyclopropyl)benzoate (D197)

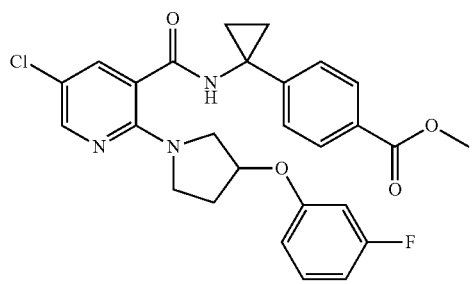 [SMILES: COC(=O)c1ccc(C2(NC(=O)c3cc(Cl)cnc3N3CCC(Oc4cccc(F)c4)C3)CC2)cc1]

The title compound (D197) (180 mg) was prepared according to the experimental procedure described in Description 146 starting from 5-chloro-2-(3-(3-fluorophenoxy)pyrrolidin-1-yl)nicotinic acid (D140) (225 mg, 0.656 mmol) and methyl 4-(1-aminocyclopropyl)benzoate (D7) (149.36 mg, 0.656 mmol).

MS: (ES/+) m/z: 510.2 [MH$^+$] C27H25ClFN3O4 requires 509.15

$^1$H NMR (400 MHz, CHLOROFORM-d) δ (ppm): 8.20 (d, J=2.4 Hz, 1H), 8.03-7.95 (m, J=8.3 Hz, 2H), 7.72 (d, J=2.4 Hz, 1H), 7.48-7.41 (m, J=8.3 Hz, 2H), 7.24 (d, J=6.8 Hz, 1H), 7.17 (s, 1H), 6.73-6.65 (m, 1H), 6.63-6.51 (m, 2H), 4.95-4.81 (m, 1H), 3.91 (s, 3H), 3.78-3.70 (m, 1H), 3.65-3.54 (m, 1H), 3.41 (d, J=12.2 Hz, 2H), 2.18 (br. s., 2H), 1.49-1.37 (m, 4H)

Description 198: methyl 4-(1-(5-chloro-2-(3-(m-tolyloxy)pyrrolidin-1-yl)nicotinamido)cyclopropyl)benzoate (D198)

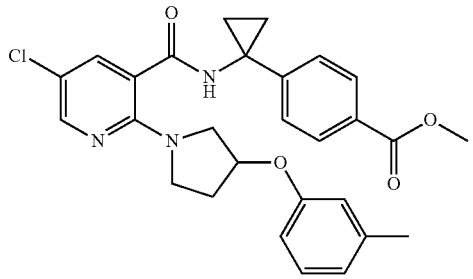 [SMILES: COC(=O)c1ccc(C2(NC(=O)c3cc(Cl)cnc3N3CCC(Oc4cccc(C)c4)C3)CC2)cc1]

The title compound (D198) (12 mg) was prepared according to the experimental procedure described in Description 146 starting from 5-chloro-2-(3-(m-tolyloxy)pyrrolidin-1-yl) nicotinic acid (D141) (160 mg, 0.472 mmol) and methyl 4-(1-aminocyclopropyl)benzoate (D7) (107.46 mg, 0.472 mmol). The residue (50 mg) obtained from SPE-Si cartridge purification (50 mg) dissolved in a mixture of chloroform/ethanol (1/1) (1 ml) was separated by chiral HPLC [Phenomenex Lux1 column (250×20 mm, 5 μm particle size). Mobile phase: isocratic premixed mixture of (hexane 80%, ethanol 20%) containing 0.1% of diethylamine. Flow rate=10 ml/min. UV detection: 245 nm]. Collected fractions, after solvent evaporation, afforded the title compound (D198) (12 mg)

MS: (ES/+) m/z: 506.3 [MH$^+$] C28H28ClN3O4 requires 505.18

Description 199: methyl 4-(1-(5-chloro-2-(3-(4-(trifluoromethyl)phenoxy)pyrrolidin-1-yl)nicotinamido)cyclopropyl)benzoate (D199)

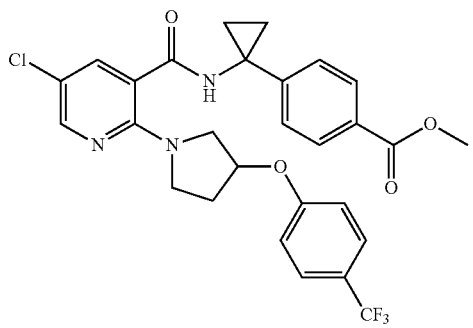 [SMILES: COC(=O)c1ccc(C2(NC(=O)c3cc(Cl)cnc3N3CCC(Oc4ccc(C(F)(F)F)cc4)C3)CC2)cc1]

The title compound (D199) (24 mg) was prepared according to the experimental procedure described in Description 148 starting from lithium 5-chloro-2-(3-(4-(trifluoromethyl)phenoxy)pyrrolidin-1-yl)nicotinate (D136) (130 mg, 0.331 mmol) and methyl 4-(1-aminocyclopropyl)benzoate (D7) (75.36 mg, 0.331 mmol).

MS: (ES/+) m/z: 560.3 [MH$^+$] C28H25ClF3N3O4 requires 559.15

Description 200: methyl 4-(1-(5-chloro-2-(3-((3-fluorophenoxy)methyl)pyrrolidin-1-yl)nicotinamido) cyclopropyl)benzoate (D200)

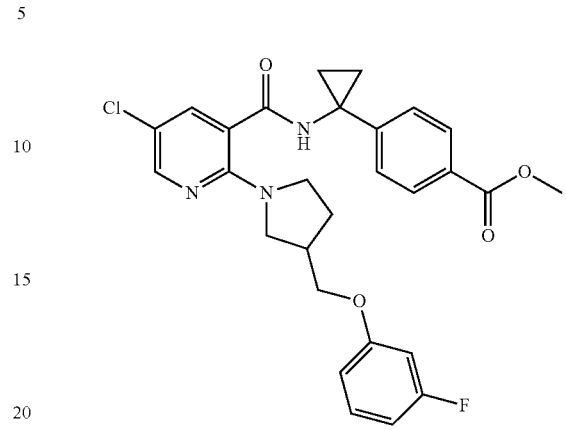

The title compound (D200) (38 mg) was prepared according to the experimental procedure described in Description 160 starting from tert-butyl 3-((3-fluorophenoxy)methyl) pyrrolidine-1-carboxylate (D40) (100 mg, 0.338 mmol) and reacting in the second step with methyl 4-(1-(2,5-dichloronicotinamido)cyclopropyl)benzoate (D97) (61.8 mg, 0.169 mmol).

MS: (ES/+) m/z: 524.4 [MH$^+$] C28H27ClFN3O4 requires 523.17

$^1$H NMR (400 MHz, CHLOROFORM-d) δ (ppm): 8.18 (d, J=2.4 Hz, 1H), 8.01-7.97 (m, J=8.3 Hz, 2H), 7.65 (d, J=2.4 Hz, 1H), 7.46-7.42 (m, J=8.3 Hz, 2H), 7.25-7.20 (m, 1H), 6.74-6.64 (m, 2H), 6.59 (td, J=2.4, 10.9 Hz, 1H), 3.96-3.91 (m, 1H), 3.90 (s, 3H), 3.88-3.81 (m, 1H), 3.53 (dd, J=7.3, 10.8 Hz, 1H), 3.45 (t, J=6.8 Hz, 2H), 3.31 (dd, J=7.3, 10.8 Hz, 1H), 2.75-2.65 (m, 1H), 2.12 (dd, J=6.4, 12.2 Hz, 1H), 1.80 (dd, J=7.8, 12.2 Hz, 1H), 1.45-1.38 (m, 4H).

Description 201: (R)-methyl 4-(1-(5-chloro-2-(2-((3-fluorophenoxy)methyl)pyrrolidin-1-yl)nicotinamido) cyclopropyl)benzoate (D201)

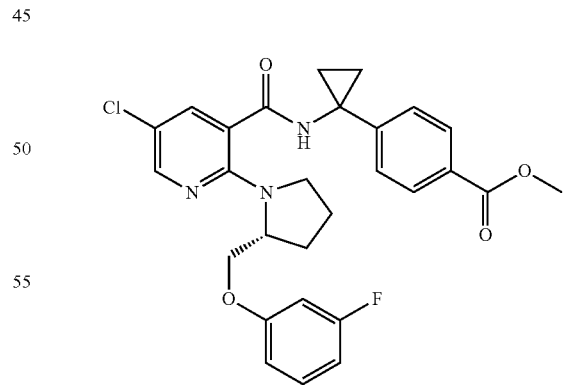

The title compound (D201) (80 mg) was prepared according to the experimental procedure described in Description 160 starting from (R)-tert-butyl 2-((3-fluorophenoxy)methyl)pyrrolidine-1-carboxylate (D42) (100 mg, 0.338 mmol) and reacting in the second step with methyl 4-(1-(2,5-dichloronicotinamido)cyclopropyl)benzoate (D97) (61.8 mg, 0.169 mmol).

MS: (ES/+) m/z: 524.4 [MH+] C28H27ClFN3O4 requires 523.17

Description 202: (S)-methyl 4-(1-(5-chloro-2-(2-((3-fluorophenoxy)methyl)pyrrolidin-1-yl)nicotinamido)cyclopropyl)benzoate (D202)

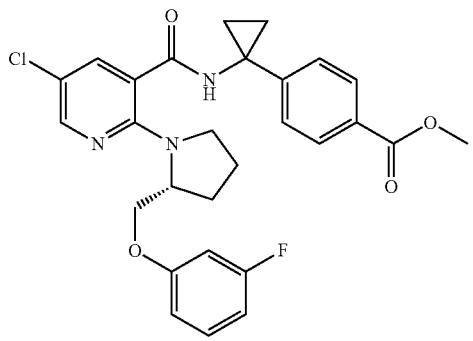 [SMILES: COC(=O)c1ccc(C2(NC(=O)c3cc(Cl)cnc3N3CCC[C@@H]3COc3cccc(F)c3)CC2)cc1]

The title compound (D202) (89 mg) was prepared according to the experimental procedure described in Description 160 starting from (S)-tert-butyl 2-((3-fluorophenoxy)methyl)pyrrolidine-1-carboxylate (D44) (100 mg, 0.338 mmol) and reacting in the second step with methyl 4-(1-(2,5-dichloronicotinamido)cyclopropyl)benzoate (D97) (61.8 mg, 0.169 mmol).

MS: (ES/+) m/z: 524.4 [MH+] C28H27ClFN3O4 requires 523.17

Description 203: methyl 4-(1-(5-chloro-2-(3-((3-fluorophenoxy)methyl)piperidin-1-yl)nicotinamido)cyclopropyl)benzoate (D203)

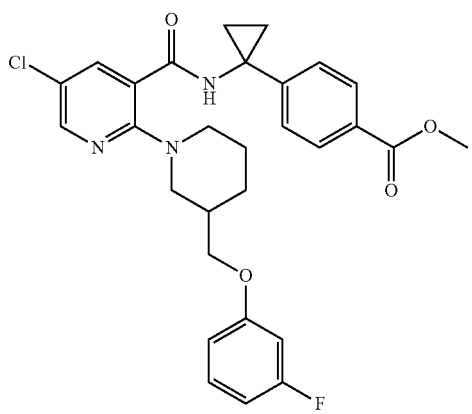 [SMILES: COC(=O)c1ccc(C2(NC(=O)c3cc(Cl)cnc3N3CCCC(COc4cccc(F)c4)C3)CC2)cc1]

The title compound (D203) (97 mg) was prepared according to the experimental procedure described in Description 160 starting from tert-butyl 3-((3-fluorophenoxy)methyl)piperidine-1-carboxylate (D45) (100 mg, 0.323 mmol) and reacting in the second step with methyl 4-(1-(2,5-dichloronicotinamido)cyclopropyl)benzoate (D97) (59 mg, 0.161 mmol).

MS: (ES/+) m/z: 538.4 [MH+] C29H29ClFN3O4 requires 537.18

Description 204: (S)-methyl 4-(1-(5-chloro-2-(3-(3-fluorophenoxy)pyrrolidin-1-yl)nicotinamido)cyclopropyl)benzoate (D204)

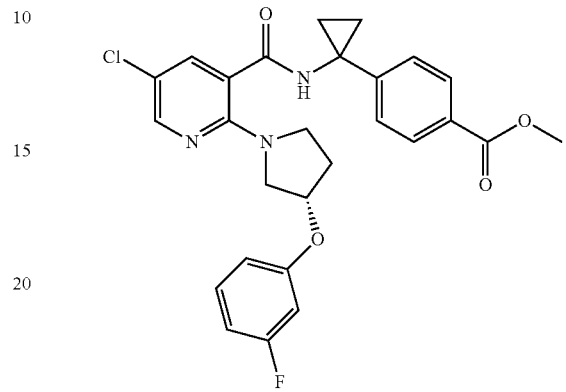

The title compound (D204) (101 mg) was prepared according to the experimental procedure described in Description 160 starting from (S)-tert-butyl 3-(3-fluorophenoxy)pyrrolidine-1-carboxylate (D46) (100 mg, 0.355 mmol) and reacting in the second step with methyl 4-(1-(2,5-dichloronicotinamido)cyclopropyl)benzoate (D) (D021/056/3) (65 mg, 0.177 mmol).

MS: (ES/+) m/z: 510.4 [MH+] C27H25ClFN3O4 requires 509.9

$^1$H NMR (400 MHz, CHLOROFORM-d) δ (ppm): 8.24-8.17 (m, 1H), 8.01-7.94 (m, 2H), 7.75-7.68 (m, 1H), 7.47-7.41 (m, 2H), 7.27-7.21 (m, 2H), 6.75-6.66 (m, 1H), 6.64-6.52 (m, 2H), 4.91-4.82 (m, 1H), 3.91 (s, 3H), 3.79-3.69 (m, 1H), 3.66-3.55 (m, 1H), 3.50-3.35 (m, 2H), 2.23-2.13 (m, 2H), 1.45-1.35 (m, J=7.3, 7.3 Hz, 4H)

Description 205: (R)-methyl 4-(1-(5-chloro-2-(3-(3-fluorophenoxy)pyrrolidin-1-yl)nicotinamido)cyclopropyl)benzoate (D205)

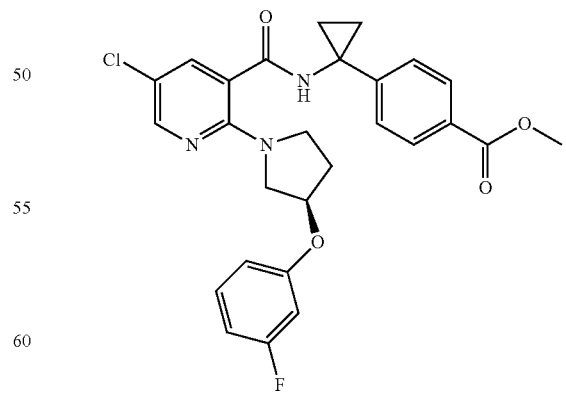

The title compound (D205) (96 mg) was prepared according to the experimental procedure described in Description 160 starting from (R)-tert-butyl 3-(3-fluorophenoxy)pyrrolidine-1-carboxylate (D47) (100 mg, 0.355 mmol) and reacting in the second step with methyl 4-(1-(2,5-dichloronicotinamido)cyclopropyl)benzoate (D97) (D021/056/3) (65 mg, 0.177 mmol).

MS: (ES/+) m/z: 510.4 [MH$^+$] C27H25ClFN3O4 requires 509.9

$^1$H NMR (400 MHz, CHLOROFORM-d) δ (ppm): 8.20 (d, J=2.4 Hz, 1H), 8.00-7.94 (m, J=8.3 Hz, 2H), 7.72 (d, J=2.4 Hz, 1H), 7.45-7.39 (m, J=8.8 Hz, 2H), 7.27-7.20 (m, 2H), 6.74-6.65 (m, 1H), 6.63-6.53 (m, 2H), 4.91-4.86 (m, 1H), 3.91 (s, 3H), 3.78-3.70 (m, 0H), 3.64-3.54 (m, 0H), 3.43 (s, 2H), 2.40-2.23 (m, 2H), 1.40-1.34 (m, 4H)

EXAMPLES

In the following Examples the relative stereochemistry is derived from the stereochemistry of the previous intermediates from which the compounds were synthesised.

Examples 1, 2 and 3

4-(1-(5-chloro-2-(2-phenylpyrrolidin-1-yl)nicotinamido)cyclopropyl)benzoic acid (racemic mixture) (E1)

4-(1-(5-chloro-2-(2-phenylpyrrolidin-1-yl)nicotinamido)cyclopropyl)benzoic acid (enantiomer 1) (E2)

4-(1-(5-chloro-2-(2-phenylpyrrolidin-1-yl)nicotinamido)cyclopropyl)benzoic acid (enantiomer 2) (E3)

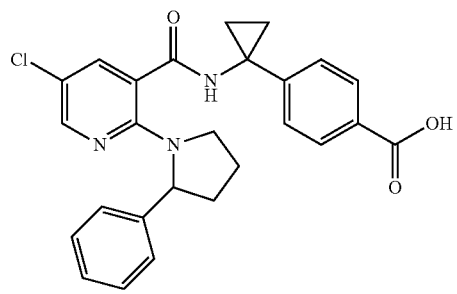 [SMILES: O=C(O)c1ccc(C2(NC(=O)c3cc(Cl)cnc3N3CCCC3c3ccccc3)CC2)cc1]

To an ice cooled solution of methyl 4-(1-(5-chloro-2-(2-phenylpyrrolidin-1-yl)nicotinamido)cyclopropyl)benzoate (D142) (189 mg, 0.40 mmol). in a mixture methanol/tetrahydrofuran (10 ml/10 ml), 2N NaOH (10 ml) was added. The reaction mixture was heated to 40° C. for 2 hours then cooled to 0° C., acidified with 2.5N HCl (pH=1-2) and stirred at 0° C. for 10 min. The formed solid was collected by filtration and dried to provide title compound (E1) (112 mg).

MS: (ES/+) m/z: 462 [MH$^+$] C26H24ClN3O3 requires 461.15

$^1$H NMR (400 MHz, DMSO-d6) δ (ppm): 9.35 (1H, s), 7.99 (1H, d, J=2.8 Hz), 7.90 (2H, d, J=8.8 Hz), 7.40 (2H, d, J=8.0 Hz), 7.30 (1H, d, J=2.8 Hz), 7.24-7.13 (5H, m), 5.35 (1H, t, J=7.2 Hz), 3.61-3.56 (1H, m), 3.14-3.11 (1H, m), 2.36-2.34 (1H, m), 1.83-1.65 (3H, m), 1.36-1.32 (4H, m)

(E1)) (14 mg) dissolved in ethanol (1.5 ml) was separated by chiral HPLC [Daicel Chiralpack IC column (2×25 cm, 5 μm particle size). Mobile phase: isocratic premixed mixture of hexane 80%, ethanol 20% containing 0.2% of trifluoroacetic acid. Flow rate=10 ml/min. UV detection: 270 nm]. Collected fractions after solvent evaporation of the separated peaks, gave the title compounds (E2) (8 mg) and (E3) (8 mg) as single enantiomers.

(E2): (single enantiomer 1)

MS: (ES/+) m/z: 462 [MH$^+$] C26H24ClN3O3 requires 461.15

$^1$H NMR (400 MHz, DMSO-d6) δ (ppm): 9.31 (s, 1H), 7.98 (d, J=2.4 Hz, 1H), 7.93-7.85 (m, J=8.3 Hz, 2H), 7.71 (d, J=2.4 Hz, 1H), 7.45-7.35 (m, J=8.3 Hz, 2H), 7.27-7.16 (m, 4H), 7.14 (d, J=6.4 Hz, 1H), 5.35 (t, J=7.1 Hz, 1H), 3.57 (d, J=9.8 Hz, 1H), 3.23-3.05 (m, 1H), 2.40-2.29 (m, 1H), 1.90-1.75 (m, 2H), 1.66 (dd, J=7.6, 12.0 Hz, 1H), 1.44-1.29 (m, 4H).

(E3): (single enantiomer 2)

MS: (ES/+) m/z: 462 [MH$^+$] C26H24ClN3O3 requires 461.15

$^1$H NMR (400 MHz, DMSO-d6) δ (ppm): 9.31 (s, 1H), 7.98 (d, J=2.4 Hz, 1H), 7.93-7.84 (m, J=8.3 Hz, 2H), 7.71 (d, J=2.4 Hz, 1H), 7.46-7.36 (m, J=8.3 Hz, 2H), 7.26-7.16 (m, 4H), 7.16-7.09 (m, 1H), 5.35 (t, J=7.1 Hz, 1H), 3.60-3.54 (m, 1H), 3.13 (d, J=4.4 Hz, 1H), 2.37-2.30 (m, 1H), 1.90-1.75 (m, 2H), 1.66 (dd, J=7.3, 11.7 Hz, 1H), 1.35 (d, J=7.3 Hz, 4H)

Examples 4, 5 and 6

4-(1-(5-chloro-2-(3-phenylpyrrolidin-1-yl)nicotinamido)cyclopropyl)benzoic acid (E4)

4-(1-(5-chloro-2-(3-phenylpyrrolidin-1-yl)nicotinamido)cyclopropyl)benzoic acid (E5) (enantiomer 1)

4-(1-(5-chloro-2-(3-phenylpyrrolidin-1-yl)nicotinamido)cyclopropyl)benzoic acid (E6) (enantiomer 2)

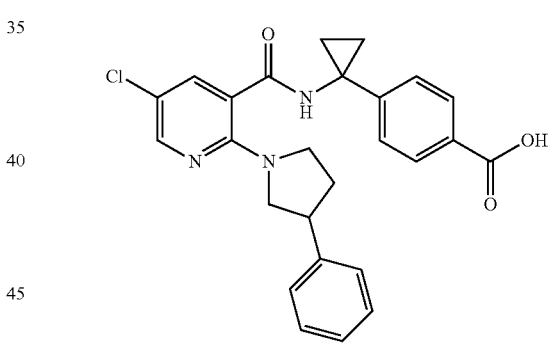

The title compound (E4) (53 mg) was prepared according to the experimental procedure described in Example 1 starting from methyl 4-(1-(5-chloro-2-(3-phenylpyrrolidin-1-yl)nicotinamido)cyclopropyl)benzoate (D143) (210 mg, 0.440 mmol)

MS: (ES/+) m/z: 462 [MH$^+$] C26H24ClN3O3 requires 461.15

$^1$H NMR (400 MHz, DMSO-d6) δ (ppm): 9.31 (1H, s), 8.20 (1H, d, J=2.4 Hz), 7.79 (1H, d, J=8.0 Hz), 7.72 (1H, d, J=2.4 Hz), 7.34-7.22 (7H, m), 3.63-2.51 (5H, m), 2.29-2.25 (1H, m), 2.01-1.96 (1H, m), 1.36-1.24 (4H, m)

(E4) (25 mg) dissolved in ethanol/chloroform (7.5 ml/0.5 ml) was separated by chiral HPLC [Daicel Chiralpack AD-H column (2×25 cm, 5 μm particle size). Mobile phase: isocratic premixed mixture of heptane 70%, ethanol 30% containing 0.1% of trifluoroacetic acid. Flow rate=10 ml/min. UV detection: 270 nm]. Collected fractions after solvent evaporation of the separated peaks, gave the title compounds (E5) (3 mg) and (E6) (3 mg) as single enantiomers.

Examples 7, 8 and 9

4-(1-(2-(2-benzylpyrrolidin-1-yl)-5-chloronicotinamido)cyclopropyl)benzoic acid (racemic mixture) (E7)

4-(1-(2-(2-benzylpyrrolidin-1-yl)-5-chloronicotinamido)cyclopropyl)benzoic acid (enantiomer 1) (E8)

4-(1-(2-(2-benzylpyrrolidin-1-yl)-5-chloronicotinamido)cyclopropyl)benzoic acid (enantiomer 2) (E9)

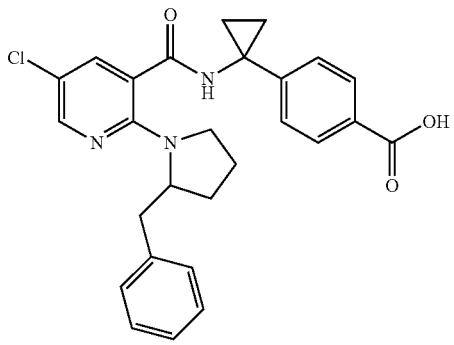 [SMILES: O=C(O)c1ccc(C2(NC(=O)c3cc(Cl)cnc3N3CCCC3Cc3ccccc3)CC2)cc1]

To a solution of methyl 4-(1-(2-(2-benzylpyrrolidin-1-yl)-5-chloronicotinamido)cyclopropyl)benzoate (D144) (60 mg, 0.122 mmol) in 1,4-dioxane (3 ml) and water (1 ml) lithium hydroxide monohydrate (7.7 mg, 0.18 mmol) was added and the resulting mixture was stirred at 150° C. under microwave irradiation for 10 min (2 cycles of 5 min each). Solvents were evaporated in vacuo, and the residue was diluted with water (5 ml) and 1M HCl (15 ml) and extracted with ethylacetate (3×20 ml). Collected organics, after solvent evaporation, afforded the title compound (E7) (racemic mixture) (47 mg).

MS: (ES/+) m/z: 476.2 [MH$^+$] C27H26ClN3O3 requires 475.17

$^1$H NMR (400 MHz, DMSO-d6) δ (ppm): 12.79 (br. s., 1H) 9.24 (s, 1H) 8.26 (d, J=2.45 Hz, 1H) 7.88 (d, J=8.31 Hz, 2H) 7.71 (d, J=2.93 Hz, 1H) 7.38 (d, J=8.31 Hz, 2H) 7.09-7.33 (m, 5H) 4.43 (d, J=5.87 Hz, 1H) 3.17-3.30 (m, 1H) 3.11 (dd, J=12.72, 2.93 Hz, 1H) 2.89-3.04 (m, 1H) 2.54-2.61 (m, 1H) 1.75 (d, J=5.38 Hz, 2H) 1.52-1.70 (m, 2H) 1.32 (s, 4H)

(E7) (20.5 mg) dissolved in ethanol (1.5 ml) was separated by chiral HPLC [Daicel Chiralpack AD-H column (2×25 cm, 5 µm particle size). Mobile phase: isocratic premixed mixture of heptane 70%, ethanol 20% containing 0.1% of trifluoroacetic acid. Flow rate=10 ml/min. UV detection: 275 nm]. Collected fractions after solvent evaporation of the separated peaks, gave the title compounds (E8) (13 mg) (0022/057/1) and (E9) (14 mg) (0022/057/2) as single enantiomers.

(E8): (single enantiomer 1)
MS: (ES/+) m/z: 476.2 [MH$^+$] C27H26ClN3O3 requires 475.17

$^1$H NMR (400 MHz, DMSO-d6) δ (ppm): 9.23 (s, 1H), 8.26 (d, J=2.4 Hz, 1H), 7.91-7.84 (m, J=8.3 Hz, 2H), 7.71 (d, J=2.4 Hz, 1H), 7.42-7.35 (m, J=8.8 Hz, 2H), 7.31-7.14 (m, 5H), 4.43 (br. s., 1H), 3.29-3.18 (m, 1H), 3.10 (dd, J=3.4, 12.7 Hz, 1H), 2.99 (d, J=6.4 Hz, 1H), 2.61-2.54 (m, 1H), 1.75 (d, J=5.4 Hz, 2H), 1.69-1.55 (m, 2H), 1.32 (s, 4H)

(E9): (single enantiomer 2)
MS: (ES/+) m/z: 476.2 [MH$^+$] C27H26ClN3O3 requires 475.17

$^1$H NMR (400 MHz, DMSO-d6) δ (ppm): 9.23 (s, 1H), 8.26 (d, J=2.4 Hz, 1H), 7.92-7.83 (m, J=8.8 Hz, 2H), 7.71 (d, J=2.9 Hz, 1H), 7.42-7.34 (m, J=8.3 Hz, 2H), 7.31-7.13 (m, 5H), 4.43 (d, J=5.9 Hz, 1H), 3.31-3.18 (m, 1H), 3.10 (dd, J=3.2, 13.0 Hz, 1H), 2.99 (d, J=5.9 Hz, 1H), 2.61-2.54 (m, 1H), 1.75 (d, J=4.9 Hz, 2H), 1.69-1.54 (m, 2H), 1.32 (s, 4H)

Example 10

4-(1-(5-chloro-2-(3-phenoxyazetidin-1-yl)nicotinamido)cyclopropyl)benzoic acid (E10)

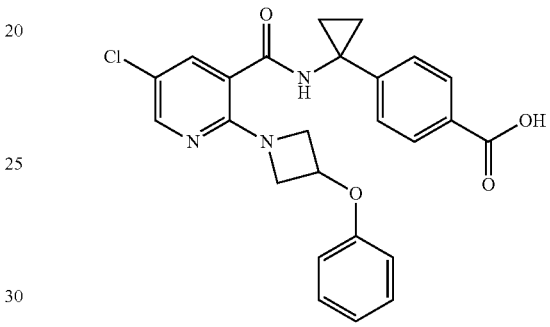

The title compound (E10) (160 mg) was prepared according to the experimental procedure described in Example 1 starting from methyl 4-(1-(5-chloro-2-(3-phenoxyazetidin-1-yl)nicotinamido)cyclopropyl) benzoate (D145) (220 mg, 0.46 mmol MS: (ES/+) m/z: 464 [MH$^+$] C25H22ClN3O4 requires 463.13

$^1$H NMR (400 MHz, DMSO-d6) δ (ppm): 9.31 (1H, s), 8.23 (1H, d, J=2.8 Hz), 7.85 (2H, d, J=8.4 Hz), 7.80 (1H, d, J=2.8 Hz), 7.34-7.30 (4H, m), 6.98 (1H, t, J=7.2 Hz), 6.80 (2H, d, J=8.0 Hz), 5.09-5.04 (1H, m), 4.35-4.31 (2H, m), 3.83-3.80 (2H, m), 1.33-1.25 (4H, m)

Example 11

(S)-4-(1-(5-chloro-2-(3-(4-fluorophenoxy)azetidin-1-yl)nicotinamido)ethyl)benzoic acid (E11)

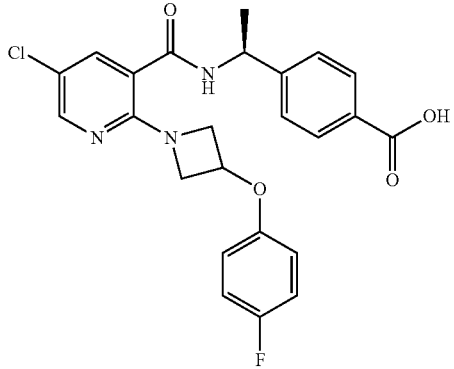 [SMILES: C[C@H](NC(=O)c1cc(Cl)cnc1N1CC(Oc2ccc(F)cc2)C1)c1ccc(C(=O)O)cc1]

The title compound (E11) (88 mg) was prepared according to the experimental procedure described in Example 7 starting from (S)-methyl 4-(1-(5-chloro-2-(3-(4-fluorophenoxy)azetidin-1-yl)nicotinamido)ethyl)benzoate (D146) (100 mg, 0.206 mmol).

MS: (ES/+) m/z: 470.2 [MH$^+$] C24H21ClFN3O4 requires 469.12

$^1$H NMR (400 MHz, DMSO-d6) δ (ppm): 12.88 (br. s., 1H), 9.04 (d, J=7.8 Hz, 1H), 8.21 (d, J=2.4 Hz, 1H), 7.90 (d, J=8.3 Hz, 2H), 7.70 (d, J=2.4 Hz, 1H), 7.48 (d, J=8.3 Hz, 2H), 7.21-7.02 (m, 2H), 6.86-6.65 (m, 2H), 5.07 (t, J=7.3 Hz, 1H), 4.97 (td, J=3.0, 6.2 Hz, 1H), 4.27 (dd, J=6.4, 9.8 Hz, 1H), 4.14 (dd, J=5.9, 9.8 Hz, 1H), 3.81-3.60 (m, 2H), 1.44 (d, J=6.8 Hz, 3H)

Example 12

(S)-4-(1-(5-chloro-2-(3-(3-fluorophenoxy)azetidin-1-yl)nicotinamido)ethyl)benzoic acid (E12)

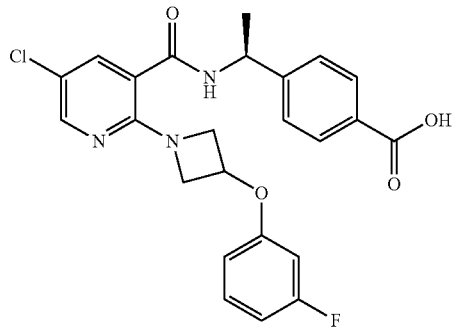 [SMILES: C[C@H](NC(=O)c1cc(Cl)cnc1N1CC(Oc2cccc(F)c2)C1)c1ccc(C(=O)O)cc1]

The title compound (E12) (80 mg) was prepared according to the experimental procedure described in Example 7 starting from (S)-methyl 4-(1-(5-chloro-2-(3-(3-fluorophenoxy)azetidin-1-yl)nicotinamido)ethyl)benzoate (D147) (90 mg, 0.186 mmol).

MS: (ES/+) m/z: 470.2 [MH$^+$] C24H21ClFN3O4 requires 469.12

$^1$H NMR (400 MHz, DMSO-d6) δ (ppm): 12.83 (br. s., 1H), 9.03 (d, J=7.8 Hz, 1H), 8.27-8.16 (m, 1H), 7.95-7.83 (m, 2H), 7.69 (d, J=2.4 Hz, 1H), 7.52-7.43 (m, 2H), 7.39-7.21 (m, 1H), 6.80 (dt, J=2.2, 8.4 Hz, 1H), 6.68 (td, J=2.3, 11.1 Hz, 1H), 6.58 (dd, J=2.0, 8.3 Hz, 1H), 5.19-4.89 (m, 2H), 4.30 (dd, J=6.4, 9.8 Hz, 1H), 4.22 (dd, J=6.1, 10.0 Hz, 1H), 3.83-3.62 (m, 2H), 1.50-1.34 (m, 3H)

Example 13

4-(1-(5-chloro-2-(3-(4-(trifluoromethyl)phenoxy)azetidin-1-yl)nicotinamido)cyclopropyl)benzoic acid (E13)

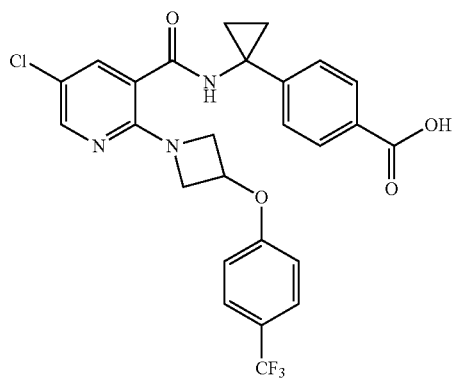 [SMILES: O=C(O)c1ccc(C2(NC(=O)c3cc(Cl)cnc3N3CC(Oc4ccc(C(F)(F)F)cc4)C3)CC2)cc1]

The title compound (E13) (133 mg) was prepared according to the experimental procedure described in Example 7 starting from methyl 4-(1-(5-chloro-2-(3-(4-(trifluoromethyl)phenoxy)azetidin-1-yl)nicotinamido)cyclopropyl)benzoate (D148) (140 mg, 0.25 mmol).

MS: (ES/+) m/z: 532.2 [MH$^+$] C26H21ClF3N3O4 requires 531.12

$^1$H NMR (400 MHz, DMSO-d6) δ (ppm): 12.83 (br. s., 1H), 9.29 (s, 1H), 8.24 (d, J=2.4 Hz, 1H), 7.88 (d, J=8.8 Hz, 2H), 7.81 (d, J=2.4 Hz, 1H), 7.68 (d, J=8.8 Hz, 2H), 7.38-7.28 (m, 2H), 7.02 (d, J=8.3 Hz, 2H), 5.16 (td, J=2.8, 5.7 Hz, 1H), 4.36 (dd, J=6.4, 9.8 Hz, 2H), 3.84 (dd, J=3.2, 10.0 Hz, 2H), 1.39-1.25 (m, 4H)

Example 14

4-(1-(5-chloro-2-(3-(3-(trifluoromethyl)phenoxy)azetidin-1-yl)nicotinamido)cyclopropyl)benzoic acid (E14)

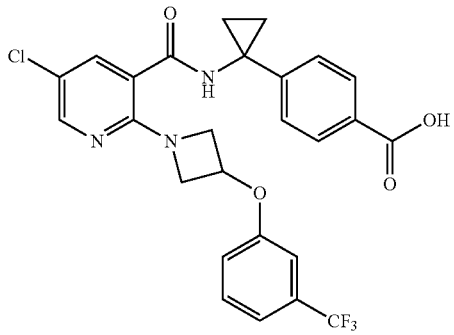 [SMILES: O=C(O)c1ccc(C2(NC(=O)c3cc(Cl)cnc3N3CC(Oc4cccc(C(F)(F)F)c4)C3)CC2)cc1]

The title compound (E14) (12 mg) was prepared according to the experimental procedure described in Example 7 starting from methyl 4-(1-(5-chloro-2-(3-(3-(trifluoromethyl)phenoxy)pyrrolidin-1-yl)nicotinamido)cyclopropyl)benzoate (D149) (20 mg, 0.036 mmol)

MS: (ES/+) m/z: 532.2 [MH$^+$] C26H21ClF3N3O4 requires 531.12

$^1$H NMR (400 MHz, DMSO-d6) δ (ppm): 12.78 (br. s., 1H), 9.27 (s, 1H), 8.24 (d, J=2.4 Hz, 1H), 7.93-7.72 (m, 3H), 7.62-7.47 (m, 1H), 7.41-7.24 (m, 3H), 7.22-7.02 (m, 2H), 5.28-5.08 (m, 1H), 4.37 (dd, J=6.1, 10.0 Hz, 2H), 3.84 (dd, J=2.9, 9.8 Hz, 2H), 1.32 (s, 4H)

Example 15

4-(1-(5-chloro-2-(3-(4-fluorophenoxy)azetidin-1-yl)nicotinamido)cyclopropyl)benzoic acid (E15)

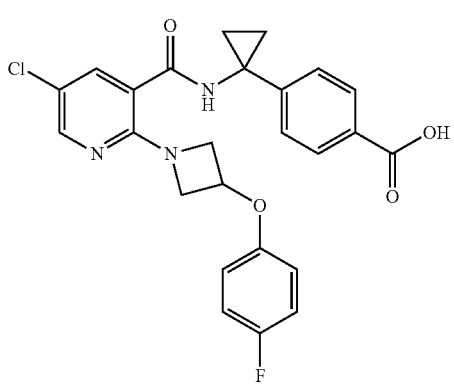 [SMILES: O=C(O)c1ccc(C2(NC(=O)c3cc(Cl)cnc3N3CC(Oc4ccc(F)cc4)C3)CC2)cc1]

The title compound (E15) (50 mg) was prepared according to the experimental procedure described in Example 7 starting from methyl 4-(1-(5-chloro-2-(3-(4-fluorophenoxy)azetidin-1-yl)nicotinamido)cyclopropyl)benzoate (D150) (75 mg, 0.151 mmol).

MS: (ES/+) m/z: 482.2 [MH$^+$] C25H21ClFN3O4 requires 481.12

$^1$H NMR (400 MHz, DMSO-d6) δ (ppm): 12.83 (br. s., 1H), 9.27 (s, 1H), 8.23 (d, J=2.4 Hz, 1H), 7.86 (d, J=8.3 Hz, 2H), 7.79 (d, J=2.4 Hz, 1H), 7.32 (d, J=8.3 Hz, 2H), 7.13 (t, J=8.8 Hz, 2H), 6.89-6.75 (m, 2H), 5.11-4.94 (m, 1H), 4.31 (dd, J=6.4, 9.8 Hz, 2H), 3.80 (dd, J=3.4, 10.3 Hz, 2H), 1.32 (d, J=4.9 Hz, 4H)

Example 16

4-(1-(5-chloro-2-(3-(3-fluorophenoxy)azetidin-1-yl)nicotinamido)cyclopropyl)benzoic acid (E16)

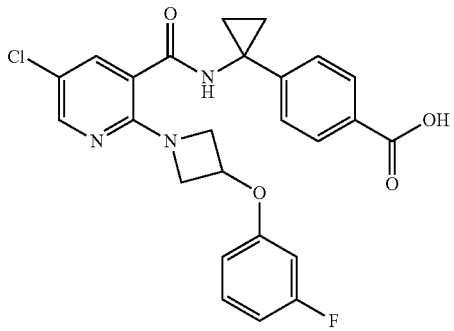 [SMILES: O=C(O)c1ccc(C2(NC(=O)c3cc(Cl)cnc3N3CC(Oc4cccc(F)c4)C3)CC2)cc1]

4-(1-(5-chloro-2-(3-(3-fluorophenoxy)azetidin-1-yl)nicotinamido)cyclopropyl)benzoic acid (E16) was prepared according to two different experimental procedures described below Procedure A The title compound (E16) (47 mg) was prepared according to the experimental procedure described in Example 7 starting from methyl 4-(1-(5-chloro-2-(3-(3-fluorophenoxy)azetidin-1-yl)nicotinamido)cyclopropyl)benzoate (D151) (56 mg, 0.113 mmol).

$^1$H NMR (400 MHz, DMSO-d6) δ (ppm): 12.77 (br. s., 1H) 9.26 (s, 1H) 8.23 (d, J=2.45 Hz, 1H) 7.84 (d, J=8.80 Hz, 2H) 7.80 (d, J=2.45 Hz, 1H) 7.19-7.47 (m, 3H) 6.81 (td, J=8.56, 1.96 Hz, 1H) 6.73 (dt, J=11.13, 2.26 Hz, 1H) 6.66 (dd, J=8.07, 2.20 Hz, 1H) 5.09 (dt, J=6.24, 3.00 Hz, 1H) 4.35 (dd, J=9.78, 6.36 Hz, 2H) 3.82 (dd, J=10.03, 3.18 Hz, 2H) 1.32 (d, J=3.91 Hz, 4H)

Procedure B

To an ice cooled solution of methyl 4-(1-(5-chloro-2-(3-(3-fluorophenoxy)azetidin-1-yl)nicotinamido)cyclopropyl)benzoate (D151) (3 g, 6.049 mmol) in a mixture 1-4-dioxane/water (30 ml/10 ml), 1N NaOH (9.07 ml) was added. The reaction mixture was heated to 60° C. for 12 hours then cooled to 0° C., acidified with 1N HCl (pH=1) and stirred at 0° C. for 10 min. The formed solid was collected by filtration and dried to provide title compound (E16) (2.46 g).

MS: (ES/+) m/z: 482.2 [MH$^+$] C25H21ClFN3O4 requires 481.12

$^1$H NMR (400 MHz, DMSO-d6) δ (ppm): 12.76 (br. s., 1H), 9.25 (s, 1H), 8.23 (d, J=2.4 Hz, 1H), 7.91-7.72 (m, 3H), 7.44-7.31 (m, 3H), 6.89-6.60 (m, 3H), 5.09 (br. s., 1H), 4.35 (dd, J=6.1, 10 Hz, 2H), 3.82 (dd, J=3.2, 10.0 Hz, 2H), 1.32 (d, J=3.9 Hz, 4H)

Example 17

4-(1-(5-chloro-2-(3-(4-fluoro-3-(trifluoromethyl)phenoxy)azetidin-1-yl)nicotinamido)cyclopropyl)benzoic acid (E17)

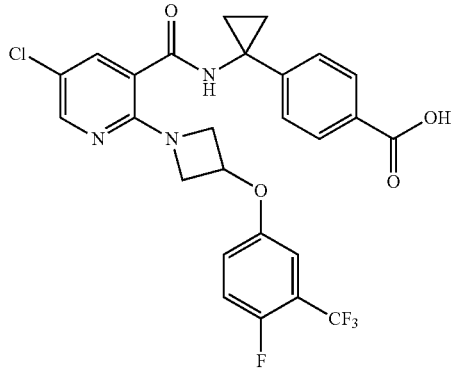 [SMILES: O=C(O)c1ccc(C2(NC(=O)c3cc(Cl)cnc3N3CC(Oc4ccc(F)c(C(F)(F)F)c4)C3)CC2)cc1]

The title compound (E17) (24 mg) was prepared according to the experimental procedure described in Example 7 starting from methyl 4-(1-(5-chloro-2-(3-(4-fluoro-3-(trifluoromethyl)phenoxy)azetidin-1-yl)nicotinamido)cyclopropyl)benzoate (D152) (25 mg, 0.044 mmol).

MS: (ES/+) m/z: 550.3 [MH$^+$] C26H20ClF4N3O4 requires 549.11

$^1$H NMR (400 MHz, DMSO-d6) δ (ppm): 9.48 (s, 1H), 8.45 (d, J=2.4 Hz, 1H), 8.11-7.96 (m, 3H), 7.67 (t, J=10.0 Hz, 1H), 7.52 (d, J=8.3 Hz, 2H), 7.45-7.34 (m, 2H), 5.37 (d, J=3.4 Hz, 1H), 4.56 (dd, J=6.5, 9.9 Hz, 2H), 4.04 (dd, J=3.1, 9.9 Hz, 2H), 1.53 (br. s., 4H)

Example 18

4-(1-(5-chloro-2-(3-(3-(trifluoromethoxy)phenoxy)azetidin-1-yl)nicotinamido)cyclopropyl)benzoic acid (E18)

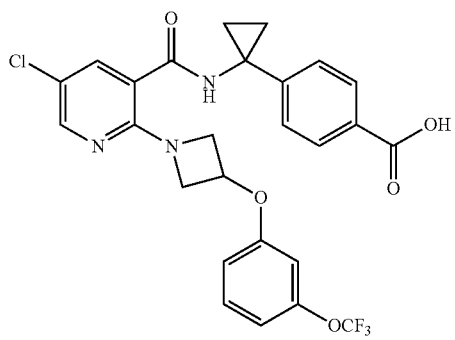

The title compound (E18) (107 mg) was prepared according to the experimental procedure described in Example 7 starting from methyl 4-(1-(5-chloro-2-(3-(3-(trifluoromethoxy)phenoxy)azetidin-1-yl)nicotinamido)cyclopropyl)benzoate (D153) (115 mg, 0.204 mmol).

MS: (ES/+) m/z: 548.3 [MH+] C26H21ClF3N3O5 requires 547.11

¹H NMR (400 MHz, DMSO-d₆) δ (ppm): 12.77 (br. s., 1H), 9.26 (s, 1H), 8.24 (d, J=2.4 Hz, 1H), 7.84 (d, J=8.3 Hz, 2H), 7.81 (d, J=2.4 Hz, 1H), 7.48-7.38 (m, 1H), 7.31 (d, J=8.3 Hz, 2H), 6.98 (d, J=8.3 Hz, 1H), 6.90-6.83 (m, 2H), 5.19-5.03 (m, 1H), 4.35 (dd, J=6.4, 10.0 Hz, 2H), 3.83 (dd, J=3.3, 9.9 Hz, 2H), 1.32 (s, 4H)

Example 19

4-(1-(5-chloro-2-(3-(2,4-difluorophenoxy)azetidin-1-yl)nicotinamido)cyclopropyl)benzoic acid (E19)

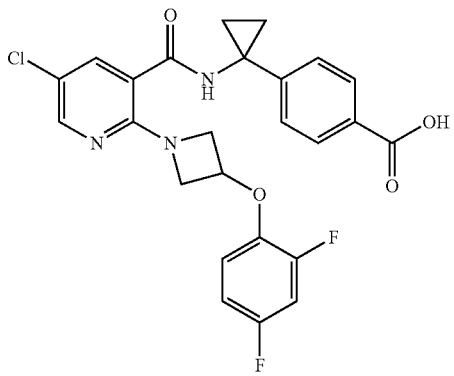 [SMILES: O=C(O)c1ccc(C2(NC(=O)c3cc(Cl)cnc3N3CC(Oc4ccc(F)cc4F)C3)CC2)cc1]

The title compound (E19) (48 mg) was prepared according to the experimental procedure described in Example 7 starting from methyl 4-(1-(5-chloro-2-(3-(2,4-difluorophenoxy)azetidin-1-yl)nicotinamido)cyclopropyl)benzoate (D154) (50 mg, 0.097 mmol).

MS: (ES/+) m/z: 500.3 [MH+] C25H20ClF2N3O4 requires 499.11

¹H NMR (400 MHz, DMSO-d₆) δ (ppm): 12.82 (br. s., 1H), 9.28 (s, 1H), 8.24 (s, 1H), 7.85 (d, J=8.1 Hz, 2H), 7.80 (s, 1H), 7.38-7.28 (m, 3H), 7.05-6.86 (m, 2H), 5.10 (br. s., 1H), 4.38-4.27 (m, 2H), 3.84 (dd, J=2.8, 10.4 Hz, 2H), 1.32 (d, J=6.1 Hz, 4H)

Example 20

4-(1-(5-chloro-2-(3-(3,4-difluorophenoxy)azetidin-1-yl)nicotinamido)cyclopropyl)benzoic acid (E20)

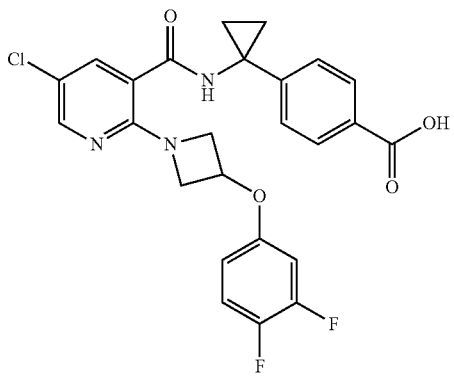 [SMILES: O=C(O)c1ccc(C2(NC(=O)c3cc(Cl)cnc3N3CC(Oc4ccc(F)c(F)c4)C3)CC2)cc1]

The title compound (E20) (28 mg) was prepared according to the experimental procedure described in Example 7 starting from methyl 4-(1-(5-chloro-2-(3-(3,4-difluorophenoxy)azetidin-1-yl)nicotinamido)cyclopropyl)benzoate (D155) (48 mg, 0.093 mmol).

MS: (ES/+) m/z: 500.3 [MH+] C25H20ClF2N3O4 requires 499.11

¹H NMR (400 MHz, DMSO-d₆) δ (ppm): 9.26 (s, 1H), 8.23 (s, 1H), 7.83 (d, J=7.8 Hz, 2H), 7.80 (s, 1H), 7.42-7.26 (m, 3H), 6.65 (d, J=8.6 Hz, 1H), 5.06 (br. s., 1H), 4.33 (dd, J=6.1, 10.0 Hz, 2H), 3.80 (dd, J=2.8, 9.9 Hz, 2H), 1.33 (br. s., 4H)

Example 21

4-(1-(5-chloro-2-(3-(3-(piperazin-1-yl)phenoxy)azetidin-1-yl)nicotinamido)cyclopropyl)benzoic acid (E21)

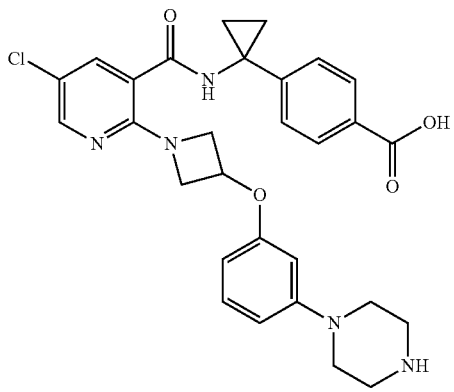 [SMILES: O=C(O)c1ccc(C2(NC(=O)c3cc(Cl)cnc3N3CC(Oc4cccc(N5CCNCC5)c4)C3)CC2)cc1]

To a solution of methyl 4-(1-(5-chloro-2-(3-(3-(piperazin-1-yl)phenoxy)azetidin-1-yl)nicotinamido)cyclopropyl)benzoate (D156) (105 mg, 0.186 mmol) in a mixture 1-4-dioxane/water (3 ml/1 ml), 1N NaOH (0.28 ml) was added. The reaction mixture was heated to 60° C. overnight. After cooling at room temperature, the reaction mixture was acidified with 1N HCl (pH=1) and the solvents were evaporated in vacuo. The residue was loaded on Porapak RXN RP cartridge (5 g) eluting with water+0.1% acetic acid/acetonitrile+0.1% acetic acid from 90/10 to 0/100. Collected fractions after solvente evaporation afforded the title compound (E21) (79 mg).

MS: (ES/+) m/z: 548.3 [MH+] C29H30ClN5O4 requires 547.20

¹H NMR (400 MHz, DMSO-d₆) δ (ppm): 9.25 (s, 1H), 8.23 (d, J=2.4 Hz, 1H), 7.88-7.81 (m, J=8.8 Hz, 2H), 7.78 (d, J=2.4 Hz, 1H), 7.33-7.23 (m, J=8.3 Hz, 2H), 7.15 (t, J=8.3 Hz, 1H), 6.60 (d, J=8.8 Hz, 1H), 6.35 (s, 1H), 6.26 (dd, J=1.7, 8.1 Hz, 1H), 5.07 (br. s., 1H), 4.30 (dd, J=6.4, 9.8 Hz, 2H), 3.80 (dd, J=2.7, 10.0 Hz, 2H), 3.31-3.20 (m, 4H), 3.17-3.08 (m, 4H), 1.31 (d, J=7.3 Hz, 4H)

Example 22

4-((5-chloro-2-(3-(3-fluorophenoxy)azetidin-1-yl)nicotinamido)methyl)benzoic acid (E22)

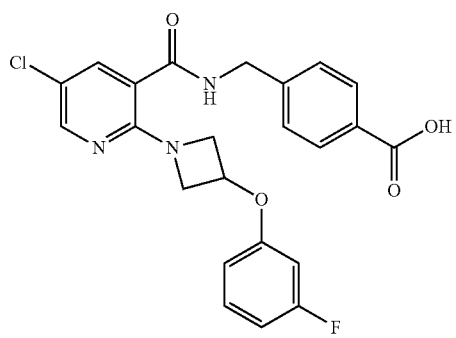 [SMILES: O=C(O)c1ccc(CNC(=O)c2cc(Cl)cnc2N2CC(Oc3cccc(F)c3)C2)cc1]

The title compound (E22) (46 mg) was prepared according to the experimental procedure described in Example 7 starting from methyl 4-((5-chloro-2-(3-(3-fluorophenoxy)azetidin-1-yl)nicotinamido)methyl)benzoate (D157) (47 mg, 0.1 mmol).

MS: (ES/+) m/z: 456.3 [MH$^+$] C23H19ClFN3O4 requires 455.10

$^1$H NMR (400 MHz, DMSO-d$_6$) δ (ppm): 9.08 (br. s., 1H), 8.22 (d, J=2.2 Hz, 1H), 7.89 (d, J=7.8 Hz, 2H), 7.72 (s, 1H), 7.44 (d, J=8.1 Hz, 2H), 7.34 (d, J=7.8 Hz, 1H), 6.81 (t, J=8.8 Hz, 1H), 6.72 (d, J=10.5 Hz, 1H), 6.65 (d, J=8.1 Hz, 1H), 5.08 (br. s., 1H), 4.47 (d, J=5.9 Hz, 2H), 4.34 (dd, J=6.5, 9.9 Hz, 2H), 3.82 (dd, J=3.1, 10.1 Hz, 2H)

Example 23

6-((5-chloro-2-(3-(3-fluorophenoxy)azetidin-1-yl)nicotinamido)methyl)nicotinic acid (E23)

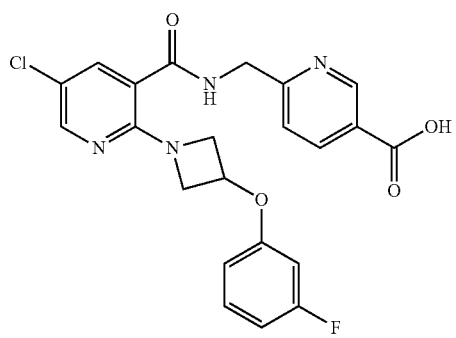 [SMILES: O=C(O)c1ccc(CNC(=O)c2cc(Cl)cnc2N2CC(Oc3cccc(F)c3)C2)nc1]

The title compound (E23) (46 mg) was prepared according to the experimental procedure described in Example 7 starting from ethyl 6-((5-chloro-2-(3-(3-fluorophenoxy)azetidin-1-yl)nicotinamido)methyl)nicotinate (D158) (59 mg, 0.121 mmol).

MS: (ES/+) m/z: 457.3 [MH$^+$] C22H18ClFN4O4 requires 456.10

$^1$H NMR (400 MHz, DMSO-d$_6$) δ (ppm): 12.43-13.66 (m, 1H) 9.15 (t, J=5.87 Hz, 1H) 8.94 (d, J=1.96 Hz, 1H) 8.07-8.29 (m, 2H) 7.76 (d, J=2.45 Hz, 1H) 7.50 (d, J=8.31 Hz, 1H) 7.16-7.42 (m, 1H) 6.80 (td, J=8.44, 2.20 Hz, 1H) 6.67-6.75 (m, 1H) 6.55-6.67 (m, 1H) 5.09 (dt, J=6.24, 3.00 Hz, 1H) 4.56 (d, J=5.87 Hz, 2H) 4.36 (dd, J=10.27, 6.36 Hz, 2H) 3.85 (dd, J=10.27, 3.42 Hz, 2H)

Example 24

6-((5-chloro-2-(3-(3-fluorophenoxy)azetidin-1-yl)nicotinamido)methyl)nicotinic acid (E24)

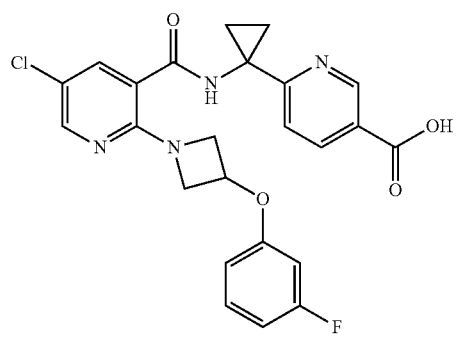

To a solution of methyl 6-((5-chloro-2-(3-(3-fluorophenoxy)azetidin-1-yl)nicotinamido)methyl)nicotinate (D159) (22 mg, 0.045 mmol) in a mixture 1-4dioxane/water (1.5 ml/0.5 ml), lithium hydroxide hydrate (2.8 mg, 0.067 mmol) was added. The reaction mixture was heated to 70° C. for 1 h. After solvent evaporation the residue was taken in water (10 ml) and 1M HCl (10 ml) and extracted with ethylacetate (2×20 ml). Collected aorganics after solvent evaporation afforded the title compound (E24) (19 mg)

MS: (ES/+) m/z: 483.2 [MH$^+$] C24H20ClFN4O4 requires 482.12

$^1$H NMR (400 MHz, DMSO-d$_6$) δ (ppm): 9.32 (s, 1H), 8.92 (d, J=2.4 Hz, 1H), 8.25 (d, J=2.4 Hz, 1H), 8.13 (dd, J=2.4, 8.3 Hz, 1H), 7.89 (d, J=2.4 Hz, 1H), 7.55 (d, J=7.8 Hz, 1H), 7.38-7.31 (m, 1H), 6.84-6.70 (m, 3H), 5.12 (d, J=2.4 Hz, 1H), 4.41 (dd, J=6.6, 10.0 Hz, 2H), 3.88 (dd, J=2.9, 10.3 Hz, 2H), 1.62-1.57 (m, 2H), 1.36-1.32 (m, 2H).

Example 25

4-(1-(5-chloro-2-(3-(3-fluorobenzoyl)azetidin-1-yl)nicotinamido)cyclopropyl)benzoic acid (E25)

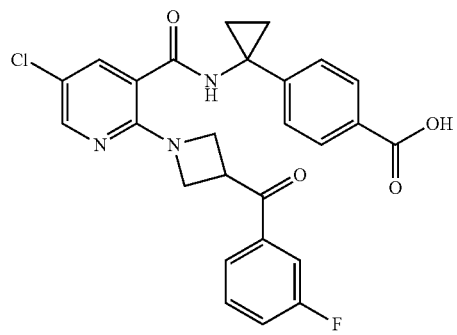 [SMILES: O=C(O)c1ccc(C2(NC(=O)c3cc(Cl)cnc3N3CC(C(=O)c4cccc(F)c4)C3)CC2)cc1]

To a solution of methyl 6-((5-chloro-2-(3-(3-fluorophenoxy)azetidin-1-yl)nicotinamido)methyl)nicotinate (D160) (40.5 mg, 0.079 mmol) in a mixture 1-4 dioxane/water (1.5 ml/0.5 ml), lithium hydroxide hydrate (10 mg, 0.24 mmol) was added. The reaction mixture was heated to 70° C. under microwave irradiation for 20 min (4 cycles of 5 min each). After solvent evaporation the residue was taken in water (5 ml) and 1M HCl (5 ml) and extracted with ethylacetate (3×10 ml). Collected organics after solvent evaporation afforded the title compound (E25) (29 mg)

MS: (ES/+) m/z: 494.2 [MH+] C26H21ClFN3O4 requires 493.12

¹H NMR (400 MHz, DMSO-d₆) δ (ppm): 9.22 (s, 1H), 8.22 (d, J=2.4 Hz, 1H), 7.79 (d, J=8.3 Hz, 2H), 7.76 (d, J=2.9 Hz, 1H), 7.74-7.60 (m, 3H), 7.55-7.49 (m, 1H), 7.25 (d, J=8.3 Hz, 2H), 4.56-4.47 (m, 1H), 4.22 (t, J=8.8 Hz, 2H), 4.03 (dd, J=6.1, 8.6 Hz, 2H), 1.30 (d, J=6.4 Hz, 4H).

Example 26

4-(1-(5-chloro-2-(3-((3-fluorophenyl)(methoxyimino)methyl)azetidin-1-yl)nicotinamido)cyclopropyl) benzoic acid (isomers mixture) (E26)

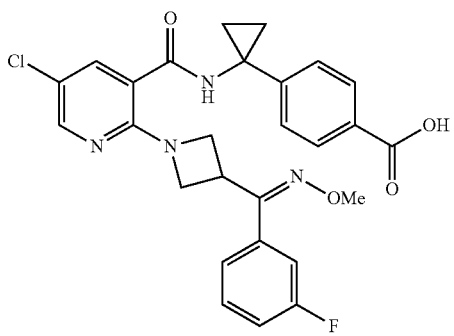 [SMILES: CO/N=C(\c1cccc(F)c1)C1CN(c2ncc(Cl)cc2C(=O)NC2(c3ccc(C(=O)O)cc3)CC2)C1]

4-(1-(5-chloro-2-(3-(3-fluorobenzoyl)azetidin-1-yl)nicotinamido)cyclopropyl)benzoic acid (E25) (12.6 mg, 0.025 mmol) was dissolved in dry pyridine (1.2 ml) then O-methylhydroxylamine hydrochloride (4.3 mg, 0.051 mmol) was added and the resulting mixture was stirred at room temperature for 60 h. Solvents were evaporated in vacuo, and the residue was diluted with water (5 ml) and extracted with ethylacetate (3×20 ml). Collected organics, after solvent evaporation, afforded a residue that was washed with methanol and dried in vacuo to afford the title compound (E26) (D021/092/2) (3 mg).

MS: (ES/+) m/z: 523.3 [MH+] C27H24ClFN4O4 requires 522.15

¹H NMR (400 MHz, DMSO-d₆) δ (ppm): 9.20-9.14 (m, 1H), 8.20-8.15 (m, 1H), 7.87-7.78 (m, 2H), 7.73 (d, J=2.4 Hz, 1H), 7.50-7.42 (m, 1H), 7.31-7.18 (m, 5H), 4.28-4.10 (m, 3H), 3.89-3.81 (m, 3H), 3.72 (t, J=7.8 Hz, 2H), 1.32-1.23 (m, 4H).

Example 27

4-(1-(5-chloro-2-(3-(3-fluorophenyl)-3-hydroxyazetidin-1-yl)nicotinamido)cyclopropyl)benzoic acid (E27)

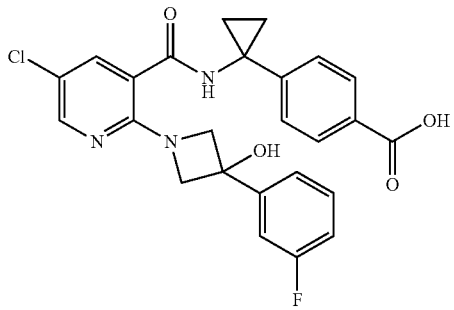 [SMILES: O=C(O)c1ccc(C2(NC(=O)c3cc(Cl)cnc3N3CC(O)(c4cccc(F)c4)C3)CC2)cc1]

The title compound (E27) (55 mg) was prepared according to the experimental procedure described in Example 24 starting from methyl 4-(1-(5-chloro-2-(3-(3-fluorophenyl)-3-hydroxyazetidin-1-yl)nicotinamido)cyclopropyl)benzoate (D161) (63 mg, 0.127 mmol).

MS: (ES/+) m/z: 482.2 [MH+] C25H21ClFN3O4 requires 481.12

¹H NMR (400 MHz, DMSO-d₆) δ (ppm): 12.76 (br. s., 1H), 9.28 (s, 1H), 8.25 (d, J=2.4 Hz, 1H), 7.84-7.80 (m, 3H), 7.47-7.40 (m, 1H), 7.32 (d, J=8.3 Hz, 3H), 7.26 (d, J=10.3 Hz, 1H), 7.15-7.09 (m, 1H), 6.40 (s, 1H), 4.12-4.00 (m, 3H), 1.31 (s, 4H).

Example 28

4-(1-(5-chloro-2-(3-(4-fluorophenyl)-3-hydroxyazetidin-1-yl)nicotinamido)cyclopropyl)benzoic acid (E28)

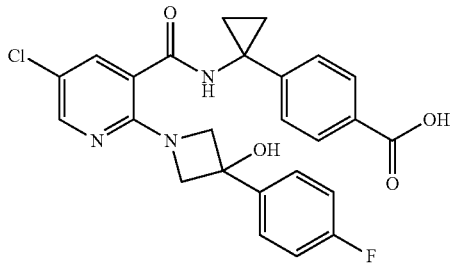 [SMILES: O=C(O)c1ccc(C2(NC(=O)c3cc(Cl)cnc3N3CC(O)(c4ccc(F)cc4)C3)CC2)cc1]

The title compound (E28) (62 mg) was prepared according to the experimental procedure described in Example 24 starting from methyl 4-(1-(5-chloro-2-(3-(4-fluorophenyl)-3-hydroxyazetidin-1-yl)nicotinamido)cyclopropyl)benzoate) (D162) (75 mg, 0.151 mmol).

MS: (ES/+) m/z: 482.2 [MH+] C25H21ClFN3O4 requires 481.12

¹H NMR (400 MHz, DMSO-d₆) δ (ppm): 12.75 (br. s., 1H), 9.27 (s, 1H), 8.24 (d, J=2.4 Hz, 1H), 7.86-7.81 (m, J=8.3 Hz, 2H), 7.80 (d, J=2.4 Hz, 1H), 7.49 (dd, J=5.4, 8.8 Hz, 2H), 7.35-7.31 (m, J=8.3 Hz, 2H), 7.20 (t, J=8.8 Hz, 2H), 6.31 (s, 1H), 4.05 (s, 4H), 1.31 (s, 4H).

Example 29

4-(1-(5-chloro-2-(3-((4-fluorophenoxy)methyl)azetidin-1-yl)nicotinamido)cyclopropyl)benzoic acid (E29)

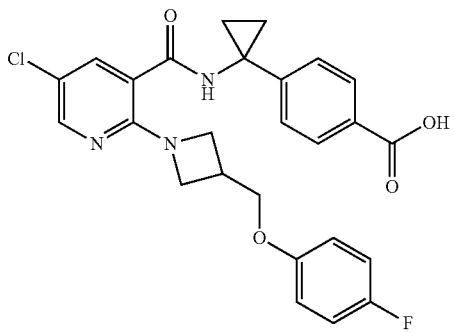 [SMILES: O=C(O)c1ccc(C2(NC(=O)c3cc(Cl)cnc3N3CC(COc4ccc(F)cc4)C3)CC2)cc1]

To a solution of 4-(1-(5-chloro-2-(3-((4-fluorophenoxy)methyl)azetidin-1-yl)nicotinamido)cyclopropyl)benzoic acid (D163) (51.6 mg, 0.101 mmol) in 3:1 mixture 1,4-dioxane/water (2 ml), lithium hydroxide monohydrate (6.4 mg, 0.151 mmol) was added. The mixture was stirred at 120° C. under microwaves irradiation (2 cycles of 6 min each) then 6 min at 140° C. Lithium hydroxide monohydrate (2.1 mg, 0.05 mmol) was added and the mixture was stirred at 140° C. for 3 min under microwaves irradiation. After solvent evaporation the organics were diluted with water (20 ml) and 1M HCl (5 ml) and extracted with ethylacetate (3×20 ml). Collected organics, after solvent evaporation afforded the title compound (E29) (42 mg).

MS: (ES/+) m/z: 496.4 [MH+] C26H23ClFN3O4 requires 495.14

$^1$H NMR (400 MHz, DMSO-$d_6$) δ (ppm): 9.21 (s, 1H), 8.20 (d, J=2.4 Hz, 1H), 7.90-7.83 (m, J=8.3 Hz, 2H), 7.74 (d, J=2.4 Hz, 1H), 7.36-7.29 (m, J=8.8 Hz, 2H), 7.15-7.06 (m, 2H), 7.00-6.92 (m, 2H), 4.11 (d, J=6.8 Hz, 2H), 4.00 (t, J=8.6 Hz, 2H), 3.71 (dd, J=5.4, 8.8 Hz, 2H), 3.04 (d, J=5.9 Hz, 1H), 1.32 (s, 4H).

Example 30

4-(1-(5-chloro-2-(3-((4-fluorophenoxy)methyl)azetidin-1-yl)nicotinamido)cyclopropyl)benzoic acid (E30)

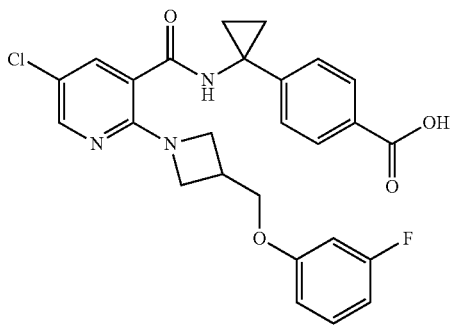 [SMILES: O=C(O)c1ccc(C2(NC(=O)c3cc(Cl)cnc3N3CC(COc4cccc(F)c4)C3)CC2)cc1]

The title compound (E30) (57 mg) was prepared according to the experimental procedure described in Example 29 starting from methyl 4-(1-(5-chloro-2-(3-(3-fluorophenyl)-3-hydroxyazetidin-1-yl)nicotinamido)cyclopropyl)benzoate) (D164) (61 mg, 0.119 mmol).

MS: (ES/+) m/z: 496.4 [MH+] C26H23ClFN3O4 requires 495.14

$^1$H NMR (400 MHz, DMSO-$d_6$) δ (ppm): 9.21 (s, 1H), 8.20 (d, J=2.4 Hz, 1H), 7.86 (d, J=8.3 Hz, 2H), 7.74 (d, J=2.4 Hz, 1H), 7.36-7.26 (m, 3H), 6.86-6.73 (m, 3H), 4.15 (d, J=6.8 Hz, 2H), 4.00 (t, J=8.6 Hz, 2H), 3.71 (dd, J=5.4, 8.8 Hz, 2H), 3.09-3.00 (m, 1H), 1.32 (s, 4H).

Example 31

4-(1-(5-chloro-2-(3-((3-(trifluoromethyl)phenyl)amino)azetidin-1-yl)nicotinamido)cyclopropyl)benzoic acid (E31)

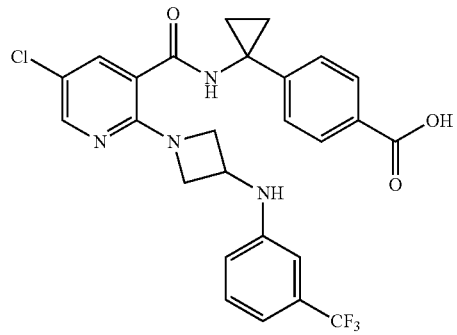

The title compound (E31) (15 mg) was prepared according to the experimental procedure described in Example 7 starting from methyl 4-(1-(5-chloro-2-(3-((3-(trifluoromethyl)phenyl)amino)azetidin-1-yl)nicotinamido)cyclopropyl)benzoate (D165) (16 mg, 0.029 mmol).

MS: (ES/+) m/z: 531.2 [MH+] C26H22ClF3N4O3 requires 530.13

$^1$H NMR (400 MHz, DMSO-$d_6$) δ (ppm): 9.25 (s, 1H), 8.22 (s, 1H), 7.85 (d, J=7.8 Hz, 2H), 7.80-7.79 (m, 1H), 7.77 (s, 1H), 7.38-7.26 (m, 3H), 6.88 (d, J=8.1 Hz, 1H), 6.82 (br. s., 1H), 6.76 (s, 1H), 6.71 (d, J=8.1 Hz, 1H), 4.33-4.18 (m, 3H), 3.70 (d, J=4.6 Hz, 2H), 3.37 (br. s., 1H), 1.32 (s, 4H)

Example 32

4-(1-(5-chloro-2-(3-((3-fluorophenyl)amino)azetidin-1-yl)nicotinamido)cyclopropyl)benzoic acid (E32)

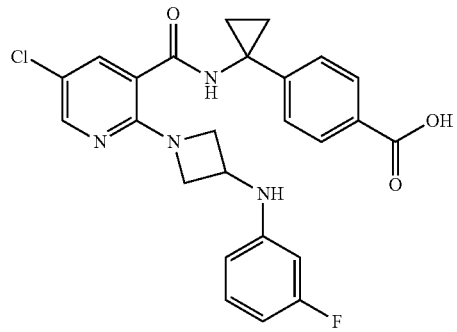

The title compound (E32) (15 mg) was prepared according to the experimental procedure described in Example 7 starting from methyl 4-(1-(5-chloro-2-(3-((3-fluorophenyl)amino)azetidin-1-yl)nicotinamido)cyclopropyl)benzoate (D166) (16 mg, 0.032 mmol).

MS: (ES/+) m/z: 481.2 [MH⁺] C25H22ClFN4O3 requires 480.14

¹H NMR (400 MHz, DMSO-d₆) δ (ppm): 12.76 (br. s., 1H), 9.25 (s, 1H), 8.21 (s, 1H), 7.85 (d, J=7.3 Hz, 2H), 7.80-7.71 (m, 1H), 7.31 (d, J=8.1 Hz, 2H), 7.16-7.04 (m, 1H), 6.63 (d, J=4.6 Hz, 1H), 6.40-6.31 (m, 1H), 6.31-6.21 (m, 2H), 4.31-4.17 (m, 3H), 3.69 (d, J=5.1 Hz, 2H), 1.33 (s, 4H)

Example 33

4-(1-(5-chloro-2-(3-((4-fluorophenyl)amino)azetidin-1-yl)nicotinamido)cyclopropyl)benzoic acid (E33)

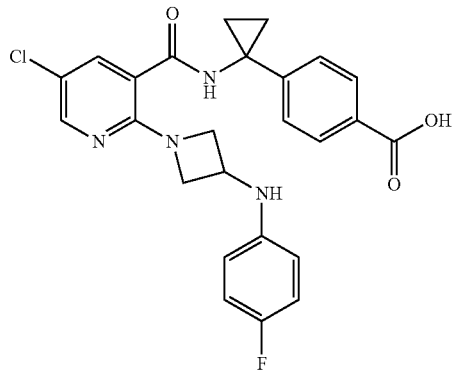 [SMILES: O=C(O)c1ccc(C2(NC(=O)c3cc(Cl)cnc3N3CC(Nc4ccc(F)cc4)C3)CC2)cc1]

The title compound (E33) (37 mg) was prepared according to the experimental procedure described in Example 7 starting from methyl 4-(1-(5-chloro-2-(3-((4-fluorophenyl)amino)azetidin-1-yl)nicotinamido)cyclopropyl)benzoate (D167) (42 mg, 0.092 mmol).

MS: (ES/+) m/z: 481.3 [MH⁺] C25H22ClFN4O3 requires 480.14

¹H NMR (400 MHz, DMSO-d₆) δ (ppm): 12.82 (br. s., 1H), 9.25 (s, 1H), 8.20 (d, J=2.4 Hz, 1H), 7.87 (s, 2H), 7.75 (d, J=2.4 Hz, 1H), 7.32 (d, J=8.8 Hz, 2H), 6.95 (t, J=8.8 Hz, 2H), 6.54-6.40 (m, 2H), 6.23 (br. s., 1H), 4.33-4.06 (m, 3H), 3.66 (dd, J=3.9, 8.8 Hz, 2H), 1.41-1.24 (m, 4H)

Example 34

4-(1-(5-chloro-2-(3-((4-fluoro-2-methylphenyl)amino)azetidin-1-yl)nicotinamido)cyclopropyl)benzoic acid (E34)

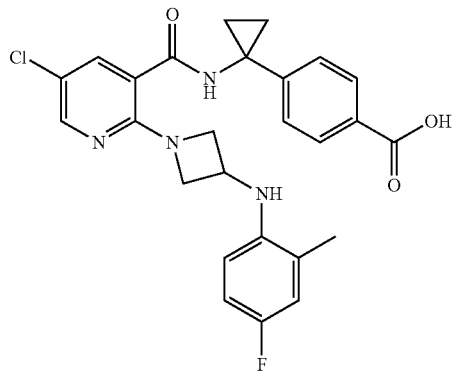 [SMILES: Cc1cc(F)ccc1NC1CN(c2ncc(Cl)cc2C(=O)NC2(c3ccc(C(=O)O)cc3)CC2)C1]

To a solution of methyl 4-(1-(5-chloro-2-(3-((4-fluoro-2-methylphenyl)amino)azetidin-1-yl)nicotinamido)cyclopropyl)benzoate (D168) (105 mg, 0.206 mmol) in a mixture 1-4 dioxane/water (3 ml/1 ml), 1N NaOH (0.309 ml) was added. The reaction mixture was stirred at room temperature overnight. Organic solvent was evaporated in vacuo and the reaction mixture was acidified with 2N HCl (pH=5-6). The solid obtained was filtered off and dried to afford the title (E34) (65 mg MS: (ES/+) m/z: 495.3 [MH⁺] C26H24ClFN4O3 requires 494.15

¹H NMR (400 MHz, DMSO-d₆) δ (ppm): 12.81 (br. s., 1H), 9.23 (s, 1H), 8.20 (d, J=2.4 Hz, 1H), 7.90-7.83 (m, J=8.3 Hz, 2H), 7.74 (d, J=2.4 Hz, 1H), 7.37-7.27 (m, J=8.3 Hz, 2H), 6.92-6.78 (m, 2H), 6.21 (dd, J=4.9, 8.8 Hz, 1H), 5.34 (d, J=5.9 Hz, 1H), 4.29-4.09 (m, 3H), 3.77 (dd, J=4.2, 8.6 Hz, 2H), 2.13 (s, 3H), 1.37-1.29 (m, 4H).

Example 35

4-(1-(5-chloro-2-(3-((2,4-difluorophenyl)amino)azetidin-1-yl)nicotinamido)cyclopropyl)benzoic acid (E35)

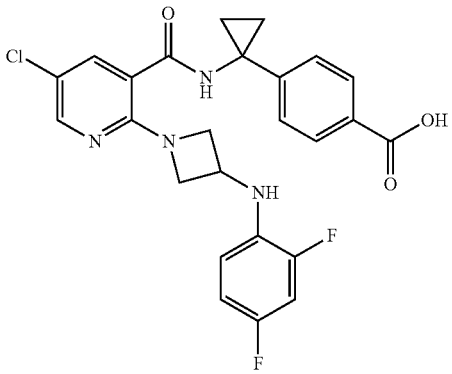 [SMILES: O=C(O)c1ccc(C2(NC(=O)c3cc(Cl)cnc3N3CC(Nc4ccc(F)cc4F)C3)CC2)cc1]

To a solution of methyl 4-(1-(5-chloro-2-(3-((2,4-difluorophenyl)amino)azetidin-1-yl)nicotinamido)cyclopropyl)benzoate (D169) (12 mg, 0.024 mmol) in a mixture 1-4 dioxane/water (3 ml/1 ml), 1N NaOH (0.036 ml) was added. The reaction mixture was stirred 12 h at 60° C. Organic solvent was evaporated in vacuo and the reaction mixture was acidified with 2N HCl (pH=2) and the resulting mixture was extracted with ethylacetate (3×5 ml). Combined organics were evaporated in vacuo and the residue was loaded on SNAP-C18 gold cartridge (15 g) eluting with H2O-AcOH (0.1%)/CH3CN—AcOH (0.1%) from 10/90 to 0/100. Collected fractions were evaporated in vacuo to afford the title (E35) (5 mg)

MS: (ES/+) m/z: 499.2 [MH⁺] C25H21ClF2N4O3 requires 498.13

¹H NMR (400 MHz, DMSO-d₆) δ (ppm): 13.05-12.53 (m, 1H), 9.23 (s, 1H), 8.20 (d, J=2.4 Hz, 1H), 7.90-7.81 (m, J=8.3 Hz, 2H), 7.74 (d, J=2.4 Hz, 1H), 7.37-7.27 (m, J=7.8 Hz, 2H), 7.16-7.04 (m, 1H), 6.88 (t, J=7.8 Hz, 1H), 6.52-6.41 (m, 1H), 6.04 (br. s., 1H), 4.21 (d, J=4.9 Hz, 3H), 3.77 (d, J=4.9 Hz, 2H), 1.38-1.28 (m, 4H)

Example 36

4-(1-(5-chloro-2-(3-((2-methyl-4-(trifluoromethyl)phenyl)amino) azetidin-1-yl)nicotinamido)cyclopropyl)benzoic acid (E36)

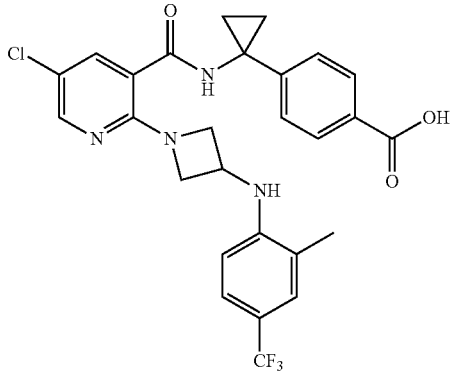 [SMILES: Cc1cc(C(F)(F)F)ccc1NC1CN(c2ncc(Cl)cc2C(=O)NC2(c3ccc(C(=O)O)cc3)CC2)C1]

The title compound (E36) (16 mg) was prepared according to the experimental procedure described in Example 35 (reaction time=2 h) starting from methyl 4-(1-(5-chloro-2-(3-((2-methyl-4-trifluoromethyl)phenyl)amino)azetidin-1-yl)nicotinamido)cyclopropyl)benzoate (D170) (27 mg, 0.048 mmol).

MS: (ES/+) m/z: 545.2 [MH$^+$] C27H24ClF3N4O3 requires 544.15

$^1$H NMR (400 MHz, DMSO-d$_6$) δ (ppm): 12.86-12.65 (m, 1H), 9.29-9.14 (m, 1H), 8.28-8.17 (m, 1H), 7.98-7.82 (m, 2H), 7.78-7.67 (m, 1H), 7.43-7.25 (m, 4H), 6.46-6.32 (m, 1H), 6.14-5.99 (m, 1H), 4.38-4.18 (m, 3H), 3.93-3.84 (m, 2H), 2.25-2.13 (m, 3H), 1.41-1.24 (m, 4H)

Example 37

4-(1-(5-chloro-2-(3-((4-fluoro-2-methylphenyl)(methyl)amino)azetidin-1-yl)nicotinamido)cyclopropyl)benzoic acid (E37)

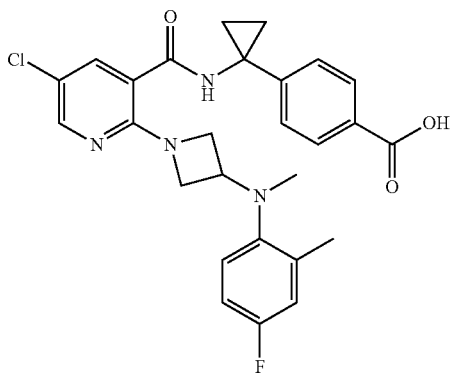 [SMILES: Cc1cc(F)ccc1N(C)C1CN(c2ncc(Cl)cc2C(=O)NC2(c3ccc(C(=O)O)cc3)CC2)C1]

To a solution of starting from methyl 4-(1-(5-chloro-2-(3-((4-fluoro-2-methylphenyl)(methyl)amino)azetidin-1-yl)nicotinamido)cyclopropyl)benzoate (D171) (56 mg, 0.107 mmol). in a mixture 1-4 dioxane/water (3 ml/1 ml), 1N NaOH (0.16 ml) was added. The reaction mixture was stirred 2 h at 60° C. Organic solvent was evaporated in vacuo and the reaction mixture was acidified with 2N HCl (pH=2) and the resulting mixture was extracted with ethylacetate (3×5 ml). Combined organics were evaporated in vacuo to afford the title (E37) (53 mg).

MS: (ES/+) m/z: 509.2 [MH$^+$] C27H26ClFN4O3 requires 508.17

$^1$H NMR (400 MHz, DMSO-d$_6$) δ (ppm): 12.78 (br. s., 1H), 9.20 (s, 1H), 8.17 (d, J=2.4 Hz, 1H), 7.87-7.78 (m, J=8.3 Hz, 2H), 7.71 (d, J=2.4 Hz, 1H), 7.35-7.25 (m, J=8.8 Hz, 2H), 7.03 (dd, J=2.9, 9.8 Hz, 1H), 6.98-6.83 (m, 2H), 4.12-3.92 (m, 3H), 3.53 (dd, J=4.4, 8.8 Hz, 2H), 2.44 (s, 3H), 2.25 (s, 3H), 1.34-1.20 (m, 4H)

Example 38

4-(1-(2-(3-(3-fluorophenoxy)azetidin-1-yl)-5-(trifluoromethyl)nicotinamido)cyclopropyl)benzoic acid (E38)

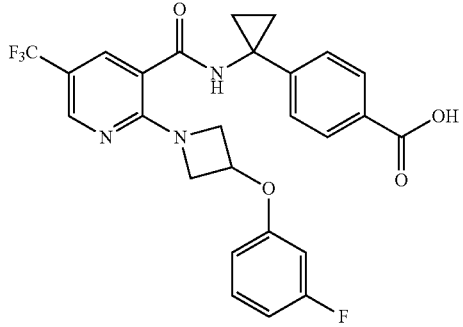 [SMILES: O=C(O)c1ccc(C2(NC(=O)c3cc(C(F)(F)F)cnc3N3CC(Oc4cccc(F)c4)C3)CC2)cc1]

The title compound (E38) (41 mg) was prepared according to the experimental procedure described in Example 7 starting from methyl 4-(1-(2-(3-(3-fluorophenoxy)azetidin-1-yl)-5-(trifluoromethyl)nicotinamido)cyclopropyl)benzoate (D172) (60 mg, 0.113 mmol).

MS: (ES/+) m/z: 516.2 [MH$^+$] C26H21F4N3O4 requires 515.15

$^1$H NMR (400 MHz, DMSO-d$_6$) δ (ppm): 12.78 (br. s., 1H), 9.36 (s, 1H), 8.52 (s, 1H), 7.95 (d, J=2.0 Hz, 1H), 7.85 (s, 2H), 7.41-7.27 (m, 3H), 6.81 (dt, J=2.0, 8.3 Hz, 1H), 6.78-6.70 (m, 1H), 6.66 (dd, J=2.2, 8.1 Hz, 1H), 5.17-5.05 (m, 1H), 4.44 (dd, J=6.1, 10.5 Hz, 2H), 3.91 (dd, J=3.2, 10.5 Hz, 2H), 1.41-1.28 (m, 4H)

Example 39

4-(1-(2-(3-(4-fluorophenoxy)azetidin-1-yl)-5-(trifluoromethyl)nicotinamido)cyclopropyl)benzoic acid (E39)

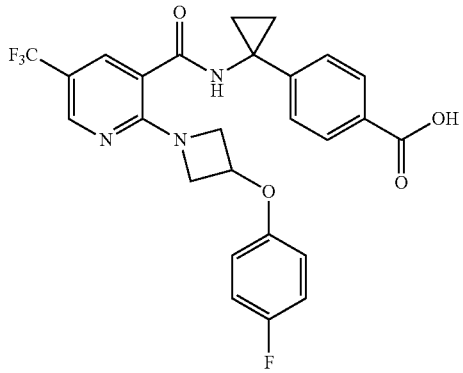 [SMILES: O=C(O)c1ccc(C2(NC(=O)c3cc(C(F)(F)F)cnc3N3CC(Oc4ccc(F)cc4)C3)CC2)cc1]

The title compound (E39) (70 mg) was prepared according to the experimental procedure described in Example 7 starting from methyl 4-(1-(2-(3-(4-fluorophenoxy)azetidin-1-yl)-5-(trifluoromethyl)nicotinamido)cyclopropyl)benzoate (D173) (75 mg, 0.141 mmol).

MS: (ES/+) m/z: 516.2 [MH$^+$] C26H21F4N3O4 requires 515.15

$^1$H NMR (400 MHz, DMSO-d$_6$) δ (ppm): 12.84 (s, 1H), 9.37 (s, 1H), 8.52 (s, 1H), 7.94 (d, J=2.0 Hz, 1H), 7.87 (d, J=8.3 Hz, 2H), 7.34 (d, J=8.3 Hz, 2H), 7.14 (t, J=8.8 Hz, 2H), 6.95-6.73 (m, 2H), 5.14-4.89 (m, 1H), 4.41 (dd, J=6.4, 10.3 Hz, 2H), 3.89 (dd, J=3.4, 10.3 Hz, 2H), 1.43-1.22 (m, 4H)

Example 40

4-(1-(2-(3-(4-chlorophenoxy)azetidin-1-yl)-5-(trifluoromethyl)nicotinamido)cyclopropyl)benzoic acid (E40)

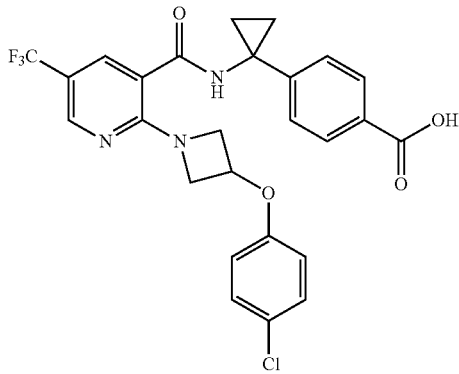 [SMILES: O=C(O)c1ccc(C2(NC(=O)c3cc(C(F)(F)F)cnc3N3CC(Oc4ccc(Cl)cc4)C3)CC2)cc1]

The title compound (E40) (17 mg) was prepared according to the experimental procedure described in Example 7 starting from methyl 4-(1-(2-(3-(4-chlorophenoxy)azetidin-1-yl)-5-(trifluoromethyl)nicotinamido)cyclopropyl)benzoate (D174) (23 mg, 0.042 mmol).

MS: (ES/+) m/z: 532.3 [MH$^+$] C26H21ClF3N3O4 requires 531.12

$^1$H NMR (400 MHz, DMSO-d$_6$) δ (ppm): 12.85 (br. s., 1H), 9.37 (s, 1H), 8.52 (s, 1H), 7.95 (d, J=2.2 Hz, 1H), 7.87 (s, 2H), 7.46-7.26 (m, 4H), 6.95-6.77 (m, 2H), 5.16-4.84 (m, 1H), 4.42 (dd, J=6.4, 10.3 Hz, 2H), 3.90 (dd, J=2.8, 10.1 Hz, 2H), 1.44-1.28 (m, 4H)

Example 41

4-(1-(2-(3-(3-chlorophenoxy)azetidin-1-yl)-5-(trifluoromethyl)nicotinamido)cyclopropyl)benzoic acid (E41)

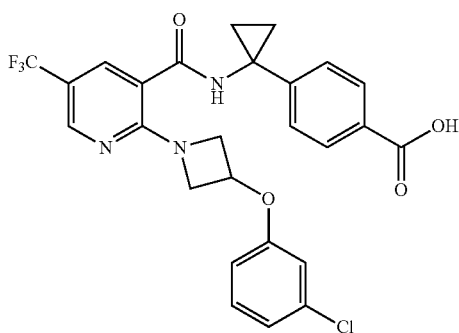

The title compound (E41) (10 mg) was prepared according to the experimental procedure described in Example 7 starting from methyl 4-(1-(2-(3-(3-chlorophenoxy)azetidin-1-yl)-5-(trifluoromethyl)nicotinamido)cyclopropyl)benzoate (D175) (12 mg, 0.0219 mmol).

MS: (ES/+) m/z: 532.3 [MH$^+$] C26H21ClF3N3O4 requires 531.12

$^1$H NMR (400 MHz, DMSO-d$_6$) δ (ppm): 12.77 (br. s., 1H), 9.36 (s, 1H), 8.52 (s, 1H), 7.96 (d, J=2.0 Hz, 1H), 7.85 (d, J=8.3 Hz, 2H), 7.39-7.24 (m, 3H), 7.09-7.00 (m, 1H), 6.93 (t, J=2.2 Hz, 1H), 6.80 (dd, J=2.2, 8.1 Hz, 1H), 5.21-5.02 (m, 1H), 4.44 (dd, J=6.1, 10.5 Hz, 2H), 3.99-3.83 (m, 2H), 1.42-1.28 (m, 4H)

Example 42

4-(1-(2-(3-(4-fluoro-3-(trifluoromethyl)phenoxy)azetidin-1-yl)-5-(trifluoromethyl)nicotinamido)cyclopropyl)benzoic acid (E42)

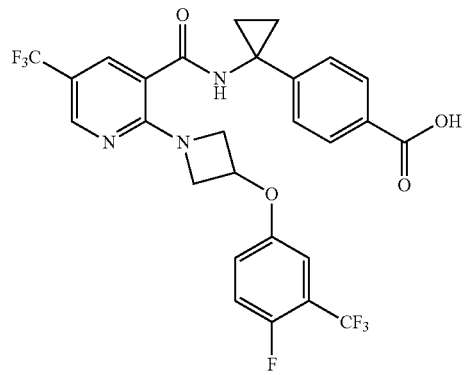 [SMILES: O=C(O)c1ccc(C2(NC(=O)c3cc(C(F)(F)F)cnc3N3CC(Oc4ccc(F)c(C(F)(F)F)c4)C3)CC2)cc1]

The title compound (E42) (41 mg) was prepared according to the experimental procedure described in Example 7 starting from methyl 4-(1-(2-(3-(4-fluoro-3-(trifluoromethyl)phenoxy)azetidin-1-yl)-5-(trifluoromethyl)nicotinamido)cyclopropyl)benzoate (D176) (50 mg, 0.083 mmol).

MS: (ES/+) m/z: 584.4 [MH$^+$] C27H20F7N3O4 requires 583.13

$^1$H NMR (400 MHz, DMSO-d$_6$) δ (ppm): 12.80 (br. s., 1H), 9.36 (s, 1H), 8.52 (d, J=1.5 Hz, 1H), 7.96 (d, J=2.2 Hz, 1H), 7.84 (d, J=8.6 Hz, 2H), 7.46 (t, J=10.1 Hz, 1H), 7.33 (d, J=8.6 Hz, 2H), 7.19 (dd, J=2.8, 5.7 Hz, 2H), 5.18 (td, J=2.9, 6.2 Hz, 1H), 4.45 (dd, J=6.2, 10.6 Hz, 2H), 3.93 (dd, J=3.1, 10.4 Hz, 2H), 1.41-1.27 (m, 4H)

Example 43

4-(1-(2-(3-(3-(trifluoromethoxy)phenoxy)azetidin-1-yl)-5-(trifluoromethyl)nicotinamido)cyclopropyl)benzoic acid (E43)

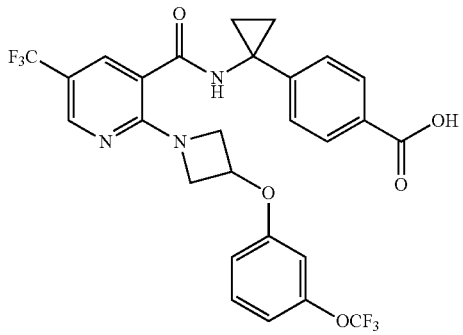 [SMILES: O=C(O)c1ccc(C2(NC(=O)c3cc(C(F)(F)F)cnc3N3CC(Oc4cccc(OC(F)(F)F)c4)C3)CC2)cc1]

The title compound (E43) (106 mg) was prepared according to the experimental procedure described in Example 7 starting from methyl 4-(1-(2-(3-(3-(trifluoromethoxy)phenoxy)azetidin-1-yl)-5-(trifluoromethyl)nicotinamido)cyclopropyl)benzoate (D177) (113 mg, 0.189 mmol).

MS: (ES/+) m/z: 582.4 [MH$^+$] C27H21F6N3O5 requires 581.14

$^1$H NMR (400 MHz, DMSO-d$_6$) δ (ppm): 12.78 (br. s., 1H), 9.36 (s, 1H), 8.52 (d, J=1.2 Hz, 1H), 7.96 (d, J=2.2 Hz, 1H), 7.84 (d, J=8.3 Hz, 2H), 7.44 (t, J=8.3 Hz, 1H), 7.33 (d, J=8.6 Hz, 2H), 6.98 (d, J=7.8 Hz, 1H), 6.86 (s, 2H), 5.23-5.02 (m, 1H), 4.45 (dd, J=6.2, 10.4 Hz, 2H), 3.92 (dd, J=2.9, 10.3 Hz, 2H), 1.41-1.26 (m, 4H)

Example 44

4-(1-(2-(3-(2,4-difluorophenoxy)azetidin-1-yl)-5-(trifluoromethyl)nicotinamido)cyclopropyl)benzoic acid (E44)

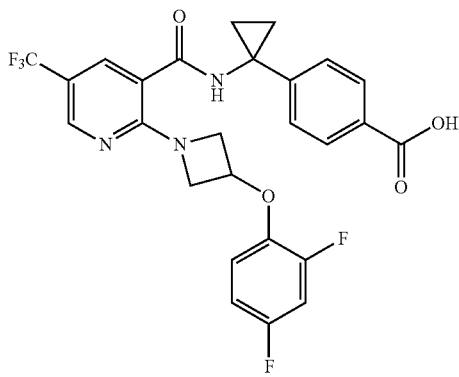 [SMILES: O=C(O)c1ccc(C2(NC(=O)c3cc(C(F)(F)F)cnc3N3CC(Oc4ccc(F)cc4F)C3)CC2)cc1]

The title compound (E44) (98 mg) was prepared according to the experimental procedure described in Example 7 starting from methyl 4-(1-(2-(3-(2,4-difluorophenoxy)azetidin-1-yl)-5-(trifluoromethyl)nicotinamido)cyclopropyl)benzoate (D178) (106 mg, 0.193 mmol).

MS: (ES/+) m/z: 534.3 [MH$^+$] C26H20F5N3O4 requires 533.14

$^1$H NMR (400 MHz, DMSO-d$_6$) δ (ppm): 12.82 (br. s., 1H), 9.37 (s, 1H), 8.53 (d, J=1.5 Hz, 1H), 7.96 (d, J=2.2 Hz, 1H), 7.86 (d, J=8.6 Hz, 2H), 7.42-7.29 (m, 3H), 7.06-6.97 (m, 1H), 6.97-6.86 (m, 1H), 5.23-4.93 (m, 1H), 4.42 (dd, J=6.2, 10.6 Hz, 2H), 3.93 (dd, J=3.1, 10.6 Hz, 2H), 1.45-1.27 (m, 4H)

Example 45

4-(1-(2-(3-(3,4-difluorophenoxy)azetidin-1-yl)-5-(trifluoromethyl)nicotinamido)cyclopropyl)benzoic acid (E45)

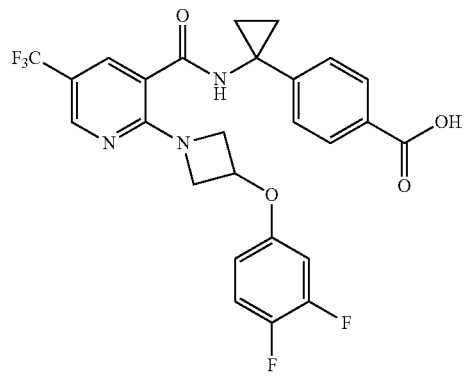 [SMILES: O=C(O)c1ccc(C2(NC(=O)c3cc(C(F)(F)F)cnc3N3CC(Oc4ccc(F)c(F)c4)C3)CC2)cc1]

The title compound (E45) (75 mg) was prepared according to the experimental procedure described in Example 7 starting from methyl 4-(1-(2-(3-(3,4-difluorophenoxy)azetidin-1-yl)-5-(trifluoromethyl)nicotinamido)cyclopropyl)benzoate (D179) (79 mg, 0.144 mmol).

MS: (ES/+) m/z: 534.3 [MH$^+$] C26H20F5N3O4 requires 533.14

$^1$H NMR (400 MHz, DMSO-d$_6$) δ (ppm): 12.80 (br. s., 1H), 9.36 (s, 1H), 8.52 (s, 1H), 7.95 (d, J=2.2 Hz, 1H), 7.84 (d, J=8.3 Hz, 2H), 7.43-7.19 (m, 3H), 7.01 (ddd, J=3.1, 6.6, 12.3 Hz, 1H), 6.65 (d, J=8.1 Hz, 1H), 5.08 (td, J=2.8, 6.1 Hz, 1H), 4.43 (dd, J=6.0, 10.4 Hz, 2H), 3.89 (dd, J=3.2, 10.5 Hz, 2H), 1.42-1.26 (m, 4H)

Example 46

4-(1-(2-(3-((5-methylisoxazol-3-yl)oxy)azetidin-1-yl)-5-(trifluoromethyl)nicotinamido)cyclopropyl)benzoic acid (E46)

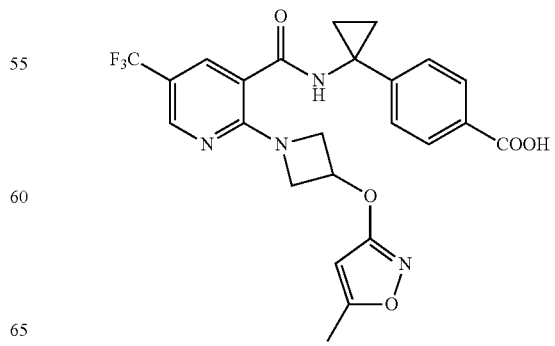

The title compound (E46) (18 mg) was prepared according to the experimental procedure described in Example 7 starting from methyl 4-(1-(5-chloro-2-(3-((5-methylisoxazol-3-yl)oxy)azetidin-1-yl)nicotinamido)cyclopropyl)benzoate (D180) (20 mg, 0.039 mmol).

MS: (ES/+) m/z: 503.3 [MH+] C24H21F3N4O5 requires 502.15

$^1$H NMR (400 MHz, DMSO-d$_6$) δ (ppm): 12.78 (s, 1H), 9.34 (s, 1H), 8.52 (d, J=1.5 Hz, 1H), 7.96 (d, J=2.0 Hz, 1H), 7.84 (d, J=8.6 Hz, 2H), 7.32 (d, J=8.3 Hz, 2H), 6.04 (d, J=1.0 Hz, 1H), 5.19 (br. s., 1H), 4.36 (dd, J=6.6, 10.3 Hz, 2H), 3.96 (dd, J=2.7, 10.5 Hz, 2H), 2.34 (d, J=0.7 Hz, 3H), 1.34 (d, J=4.2 Hz, 4H)

Example 47

4-(1-(5-(trifluoromethyl)-2-(3-((6-(trifluoromethyl)pyridin-2-yl)oxy)azetidin-1-yl)nicotinamido)cyclopropyl)benzoic acid (E47)

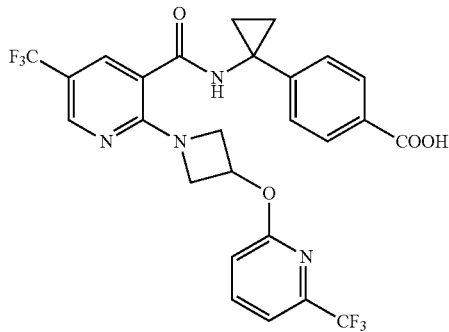 [SMILES: O=C(O)c1ccc(C2(NC(=O)c3cc(C(F)(F)F)cnc3N3CC(Oc4cccc(C(F)(F)F)n4)C3)CC2)cc1]

The title compound (E47) (62 mg) was prepared according to the experimental procedure described in Example 7 starting from methyl 4-(1-(5-chloro-2-(3-((5-methylisoxazol-3-yl)oxy)azetidin-1-yl)nicotinamido)cyclopropyl)benzoate (D181) (75 mg, 0.131 mmol).

MS: (ES/+) m/z: 567.3 [MH+] C26H20F6N4O4 requires 566.14

$^1$H NMR (400 MHz, DMSO-d$_6$) δ (ppm): 12.74 (s, 1H), 9.34 (s, 1H), 8.52 (d, J=1.5 Hz, 1H), 8.04 (t, J=7.9 Hz, 1H), 7.96 (d, J=2.0 Hz, 1H), 7.82 (d, J=8.6 Hz, 2H), 7.54 (d, J=7.3 Hz, 1H), 7.31 (d, J=8.6 Hz, 2H), 7.25 (d, J=8.3 Hz, 1H), 5.51-5.30 (m, 1H), 4.43 (dd, J=6.7, 10.6 Hz, 2H), 3.99 (dd, J=3.3, 10.9 Hz, 2H), 1.32 (s, 4H)

Example 48

4-(1-(2-(3-((5-fluoropyrimidin-2-yl)oxy)azetidin-1-yl)-5-(trifluoromethyl)nicotinamido)cyclopropyl)benzoic acid (E48)

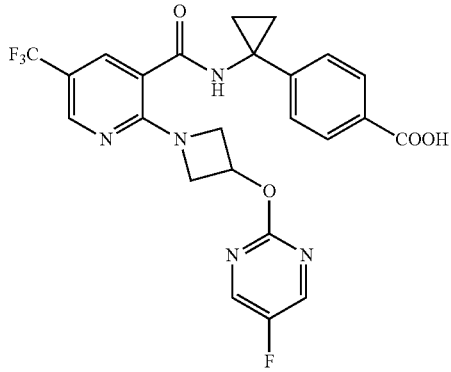 [SMILES: O=C(O)c1ccc(C2(NC(=O)c3cc(C(F)(F)F)cnc3N3CC(Oc4ncc(F)cn4)C3)CC2)cc1]

To a solution of methyl 4-(1-(2-(3-((5-fluoropyrimidin-2-yl)oxy)azetidin-1-yl)-5-(trifluoromethyl)nicotinamido)cyclopropyl)benzoate (D182) (35 mg, 0.065 mmol) in a mixture 1-4 dioxane/water (3 ml/1 ml) 1M NaOH (0.098 ml, 0.098 mmol) was added. The mixture stirred 24 h at room temperature. After solvent evaporation, 1N HCl solution was added up to pH2. The solid precipitate was filtered off and washed with diethylether to afford the title compound (E48) (27 mg)

MS: (ES/+) m/z: 518.2 [MH+] C24H19F4N5O4 requires 517.14

$^1$H NMR (400 MHz, DMSO-d$_6$) δ (ppm): 12.82 (br. s., 1H), 9.35 (s, 1H), 8.70 (s, 2H), 8.52 (s, 1H), 7.94 (d, J=2.0 Hz, 1H), 7.85-7.73 (m, J=8.3 Hz, 2H), 7.39-7.30 (m, J=8.3 Hz, 2H), 5.34 (td, J=2.9, 6.5 Hz, 1H), 4.40 (dd, J=6.4, 10.8 Hz, 2H), 3.96 (dd, J=3.2, 10.5 Hz, 2H), 1.41-1.27 (m, 4H).

Example 49

4-(1-(2-(3-((3-fluorophenyl)amino)azetidin-1-yl)-5-(trifluoromethyl)nicotinamido)cyclopropyl)benzoic acid (E49)

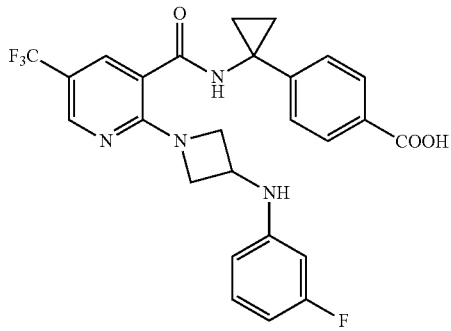 [SMILES: O=C(O)c1ccc(C2(NC(=O)c3cc(C(F)(F)F)cnc3N3CC(Nc4cccc(F)c4)C3)CC2)cc1]

The title compound (E49) (14.5 mg) was prepared according to the experimental procedure described in Example 7 starting from methyl 4-(1-(2-(3-((3-fluorophenyl)amino)azetidin-1-yl)-5-(trifluoromethyl)nicotinamido)cyclopropyl)benzoate (D183) (16 mg, 0.030 mmol).

MS: (ES/+) m/z: 515.14 [MH⁺] C26H22F4N4O3 requires 514.16

¹H NMR (400 MHz, DMSO-d₆) δ (ppm): 12.78 (br. s., 1H), 9.35 (s, 1H), 8.50 (d, J=1.5 Hz, 1H), 7.92 (d, J=2.4 Hz, 1H), 7.86 (d, J=8.3 Hz, 2H), 7.32 (d, J=8.8 Hz, 2H), 7.17-7.05 (m, 1H), 6.67 (d, J=5.9 Hz, 1H), 6.42-6.33 (m, 1H), 6.32-6.20 (m, 2H), 4.39-4.29 (m, 2H), 4.24 (d, J=5.9 Hz, 1H), 3.78 (dd, J=4.2, 9.5 Hz, 2H), 1.34 (d, J=6.8 Hz, 4H)

Example 50

4-(1-(2-(3-((4-fluorophenyl)amino)azetidin-1-yl)-5-(trifluoromethyl)nicotinamido)cyclopropyl)benzoic acid (E50)

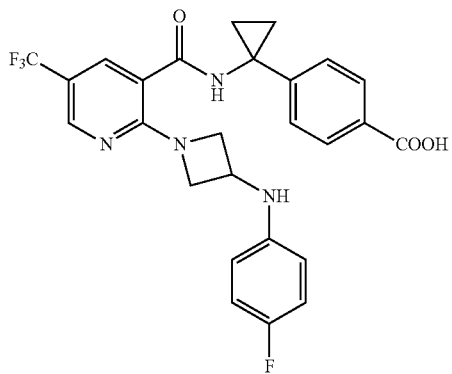 [SMILES: O=C(O)c1ccc(C2(NC(=O)c3cc(C(F)(F)F)cnc3N3CC(Nc4ccc(F)cc4)C3)CC2)cc1]

The title compound (E50) (34 mg) was prepared according to the experimental procedure described in Example 7 starting from methyl 4-(1-(2-(3-((4-fluorophenyl)amino)azetidin-1-yl)-5-(trifluoromethyl)nicotinamido)cyclopropyl)benzoate (D184) (35 mg, 0.066 mmol).

MS: (ES/+) m/z: 515.14 [MH⁺] C26H22F4N4O3 requires 514.16

¹H NMR (400 MHz, DMSO-d₆) δ (ppm): 12.82 (br. s., 1H), 9.34 (s, 1H), 8.49 (s, 1H), 7.94-7.82 (m, 3H), 7.33 (d, J=8.3 Hz, 2H), 6.95 (t, J=8.8 Hz, 2H), 6.45 (dd, J=4.4, 8.8 Hz, 2H), 6.26 (br. s., 1H), 4.39-4.25 (m, 2H), 4.18 (br. s., 1H), 3.74 (dd, J=4.2, 9.0 Hz, 2H), 1.42-1.25 (m, 4H)

Example 51

4-(1-(2-(3-((4-fluoro-2-methylphenyl)amino)azetidin-1-yl)-5-(trifluoromethyl)nicotinamido)cyclopropyl)benzoic acid (E51)

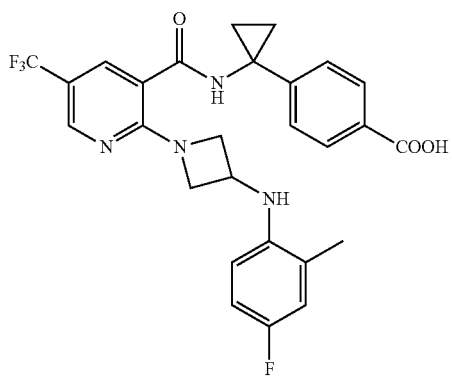 [SMILES: Cc1cc(F)ccc1NC1CN(c2ncc(C(F)(F)F)cc2C(=O)NC2(c3ccc(C(=O)O)cc3)CC2)C1]

The title compound (E51) (19 mg) was prepared according to the experimental procedure described in Example 7 starting from methyl 4-(1-(2-(3-((4-fluoro-2-methylphenyl)amino)azetidin-1-yl)-5-(trifluoromethyl)nicotinamido)cyclopropyl) benzoate (D185) (20 mg, 0.036 mmol).

MS: (ES/+) m/z: 529.4 [MH⁺] C27H24F4N4O3 requires 528.18

¹H NMR (400 MHz, DMSO-d₆) δ (ppm): 12.83 (br. s., 1H), 9.48-9.20 (m, 1H), 8.50 (s, 1H), 7.95-7.82 (m, 3H), 7.34 (d, J=8.3 Hz, 2H), 6.98-6.71 (m, 2H), 6.21 (dd, J=4.9, 8.8 Hz, 1H), 5.40 (br. s., 1H), 4.40-4.28 (m, 2H), 4.21 (br. s., 1H), 3.91-3.79 (m, 2H), 2.13 (s, 3H), 1.40-1.27 (m, 4H)

Example 52

4-(1-(2-(3-((2,4-difluorophenyl)amino)azetidin-1-yl)-5-(trifluoromethyl)nicotinamido)cyclopropyl) benzoic acid (E52)

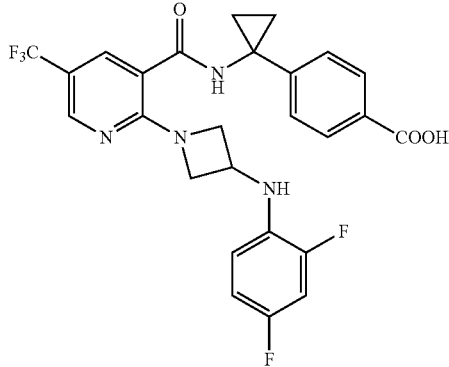 [SMILES: O=C(O)c1ccc(C2(NC(=O)c3cc(C(F)(F)F)cnc3N3CC(Nc4ccc(F)cc4F)C3)CC2)cc1]

The title compound (E52) (34 mg) was prepared according to the experimental procedure described in Example 7 starting from methyl 4-(1-(2-(3-((2,4-difluorophenyl)amino)azetidin-1-yl)-5-(trifluoromethyl)nicotinamido)cyclopropyl) benzoate (D186) (9 mg, 0.016 mmol).

MS: (ES/+) m/z: 533.4 [MH⁺] C26H21F5N4O3 requires 532.15

¹H NMR (400 MHz, DMSO-d₆) δ (ppm): 12.83 (br. s., 1H), 9.41-9.27 (m, 1H), 8.56-8.43 (m, 1H), 7.94-7.81 (m, 3H), 7.42-7.29 (m, 2H), 7.11 (ddd, J=2.7, 8.9, 11.9 Hz, 1H), 6.87 (t, J=8.8 Hz, 1H), 6.47 (dt, J=5.6, 9.4 Hz, 1H), 6.09 (br. s., 1H), 4.36-4.28 (m, 2H), 4.26 (br. s., 1H), 3.86 (dd, J=3.7, 9.0 Hz, 2H), 1.41-1.28 (m, 4H)

Example 53

4-(1-(5-fluoro-2-(3-(3-fluorophenoxy)azetidin-1-yl)nicotinamido)cyclopropyl)benzoic acid (E53)

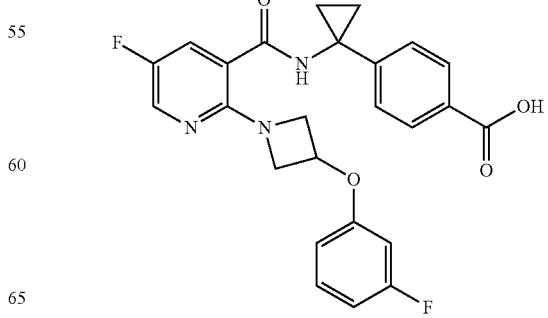

The title compound (E53) (33 mg) was prepared according to the experimental procedure described in Example 7 starting from methyl 4-(1-(5-fluoro-2-(3-(3-fluorophenoxy)azetidin-1-yl)nicotinamido)cyclopropyl)benzoate (D187) (43 mg, 0.089 mmol).

MS: (ES/+) m/z: 466.3 [MH$^+$] C25H21F2N3O4 requires 465.15

$^1$H NMR (400 MHz, DMSO-d$_6$) δ (ppm): 12.78 (br. s., 1H), 9.23 (s, 1H), 8.24 (d, J=2.9 Hz, 1H), 7.84 (d, J=8.3 Hz, 2H), 7.72 (dd, J=2.7, 8.6 Hz, 1H), 7.44-7.21 (m, 3H), 6.85-6.77 (m, 1H), 6.77-6.70 (m, 1H), 6.66 (dd, J=2.0, 8.3 Hz, 1H), 5.14-5.01 (m, 1H), 4.32 (dd, J=6.4, 9.8 Hz, 2H), 3.79 (dd, J=3.4, 9.8 Hz, 2H), 1.32 (s, 4H)

Example 54

4-(1-(5-fluoro-2-(3-(3-chlorophenoxy)azetidin-1-yl)nicotinamido)cyclopropyl)benzoic acid (E54)

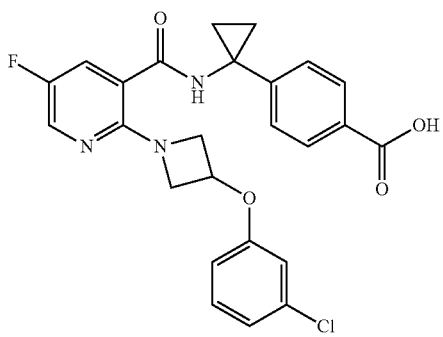 [SMILES: O=C(O)c1ccc(C2(NC(=O)c3cc(F)cnc3N3CC(Oc4cccc(Cl)c4)C3)CC2)cc1]

The title compound (E54) (11.6 mg) was prepared according to the experimental procedure described in Example 37 starting from methyl 4-(1-(5-fluoro-2-(3-(3-chlorophenoxy)azetidin-1-yl)nicotinamido)cyclopropyl)benzoate (D188) (12 mg, 0.024 mmol).

MS: (ES/+) m/z: 482.2 [MH$^+$] C25H21ClFN3O4 requires 481.12

$^1$H NMR (400 MHz, DMSO-d$_6$) δ (ppm): 12.77 (br. s., 1H), 9.22 (s, 1H), 8.24 (d, J=2.4 Hz, 1H), 7.84 (d, J=8.3 Hz, 2H), 7.72 (dd, J=2.9, 8.3 Hz, 1H), 7.37-7.27 (m, 3H), 7.03 (d, J=7.8 Hz, 1H), 6.92 (s, 1H), 6.80 (dd, J=2.4, 8.3 Hz, 1H), 5.10 (d, J=2.9 Hz, 1H), 4.32 (dd, J=6.1, 9.5 Hz, 2H), 3.80 (dd, J=3.4, 9.8 Hz, 2H), 1.33 (s, 4H)

Example 55

4-(1-(5-fluoro-2-(3-(3-(trifluoromethoxy)phenoxy)azetidin-1-yl)nicotinamido)cyclopropyl)benzoic acid (E55)

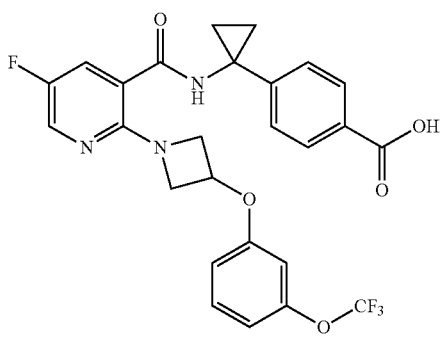 [SMILES: O=C(O)c1ccc(C2(NC(=O)c3cc(F)cnc3N3CC(Oc4cccc(OC(F)(F)F)c4)C3)CC2)cc1]

The title compound (E55) (24 mg) was prepared according to the experimental procedure described in Example 37 starting from methyl 4-(1-(5-fluoro-2-(3-(3-(trifluoromethoxy)phenoxy)azetidin-1-yl)nicotinamido)cyclopropyl)benzoate (D189) (39 mg, 0.071 mmol).

MS: (ES/+) m/z: 532.2 [MH$^+$] C26H21F4N3O5 requires 531.14

$^1$H NMR (400 MHz, DMSO-d$_6$) δ (ppm): 9.23 (s, 1H), 8.24 (d, J=2.9 Hz, 1H), 7.88-7.81 (m, J=8.3 Hz, 2H), 7.73 (dd, J=2.9, 8.3 Hz, 1H), 7.44 (t, J=8.6 Hz, 1H), 7.35-7.29 (m, J=8.3 Hz, 2H), 6.97 (d, J=8.3 Hz, 1H), 6.90-6.84 (m, 2H), 5.13 (t, J=3.4 Hz, 1H), 4.33 (dd, J=6.4, 9.8 Hz, 2H), 3.81 (dd, J=3.4, 9.8 Hz, 2H), 1.32 (s, 4H)

Example 56

4-(1-(5-fluoro-2-(3-((4-fluoro-2-methylphenyl)amino)azetidin-1-yl)nicotinamido)cyclopropyl)benzoic acid (E56)

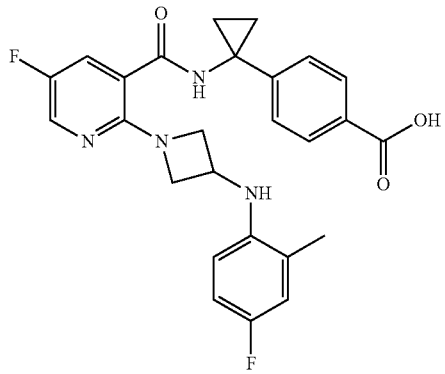 [SMILES: Cc1cc(F)ccc1NC1CN(c2ncc(F)cc2C(=O)NC2(c3ccc(C(=O)O)cc3)CC2)C1]

The title compound (E56) (18 mg) was prepared according to the experimental procedure described in Example 37 starting from methyl 4-(1-(5-fluoro-2-(3-((4-fluoro-2-methylphenyl)amino)azetidin-1-yl)nicotinamido)cyclopropyl)benzoate (D190) (25 mg, 0.051 mmol)

MS: (ES/+) m/z: 479.2 [MH$^+$] C26H24F2N4O3 requires 478.18

$^1$H NMR (400 MHz, DMSO-d$_6$) δ (ppm): 12.80 (br. s., 1H), 9.20 (s, 1H), 8.21 (d, J=2.9 Hz, 1H), 7.92-7.80 (m, J=8.3 Hz, 2H), 7.66 (dd, J=2.9, 8.3 Hz, 1H), 7.37-7.27 (m, J=8.3 Hz, 2H), 6.93-6.77 (m, 2H), 6.21 (dd, J=4.9, 8.8 Hz, 1H), 5.30 (d, J=5.4 Hz, 1H), 4.27-4.10 (m, 3H), 3.74 (dd, J=4.2, 8.1 Hz, 2H), 2.12 (s, 3H), 1.33 (s, 4H)

Example 57

4-((1S)-1-(5-chloro-2-(3-(4-(trifluoromethyl)phenoxy)pyrrolidin-1-yl)nicotinamido)ethyl)benzoic acid (E57)

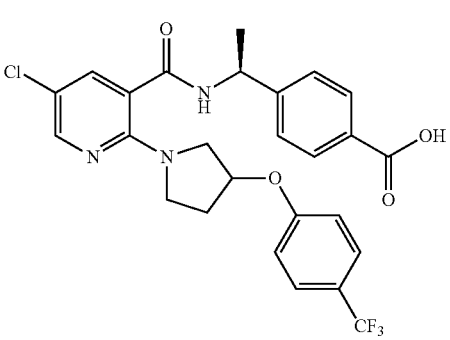 [SMILES: C[C@H](NC(=O)c1cc(Cl)cnc1N1CCC(Oc2ccc(C(F)(F)F)cc2)C1)c1ccc(C(=O)O)cc1]

To a solution of methyl 4-((1S)-1-(5-chloro-2-(3-(4-(trifluoromethyl)phenoxy)pyrrolidin-1-yl)nicotinamido)ethyl)benzoate (D191) (50 mg, 0.091 mmol) in 1,4-dioxane (3 ml) and water (1 ml) lithium hydroxide monohydrate (5.8 mg, 0.14 mmol) was added and the resulting mixture was stirred at room temperature for 2 days. Solvents were evaporated in vacuo. The residue was diluted with water (5 ml) and 1M HCl (15 ml) and extracted with ethylacetate (3×20 ml). Collected organics, after solvent evaporation, afforded the title compound (E57) (40 mg).

MS: (ES/+) m/z: 534.2 [MH$^+$] C26H23ClF3N3O4 requires 533.13

Example 58

4-((1S)-1-(5-chloro-2-(3-(3-(trifluoromethyl)phenoxy)pyrrolidin-1-yl)nicotinamido)ethyl)benzoic acid (E58)

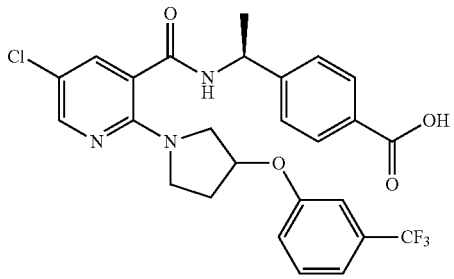 [SMILES: C[C@H](NC(=O)c1cc(Cl)cnc1N1CCC(Oc2cccc(C(F)(F)F)c2)C1)c1ccc(C(=O)O)cc1]

The title compound (E58) (61 mg) was prepared according to the experimental procedure described in Example 7 starting from methyl 4-((1S)-1-(5-chloro-2-(3-(3-(trifluoromethyl)phenoxy)pyrrolidin-1-yl)nicotinamido)ethyl)benzoate (D192) (110 mg, 0.2 mmol)

MS: (ES/+) m/z: 534 [MH$^+$] C26H23ClF3N3O4 requires 533.13

$^1$H NMR (400 MHz, DMSO-d$_6$) δ (ppm): 12.84 (br. s., 2H), 9.06 (dd, J=4.2, 7.6 Hz, 2H), 8.23-8.13 (m, 2H), 7.91 (dd, J=8.3, 10.3 Hz, 4H), 7.61 (d, J=2.4 Hz, 1H), 7.57-7.44 (m, 7H), 7.30 (d, J=7.8 Hz, 2H), 7.27-7.14 (m, 4H), 5.21 (br. s., 1H), 5.16-5.02 (m, 3H), 3.77 (dd, J=4.4, 12.2 Hz, 1H), 3.66 (dd, J=4.4, 12.7 Hz, 1H), 3.58-3.39 (m, 4H), 3.30-3.28 (m, 2H), 2.33-1.90 (m, 4H), 1.46 (d, J=6.8 Hz, 3H), 1.39 (d, J=6.8 Hz, 3H)

Example 59

4-((1S)-1-(5-chloro-2-(3-(4-fluorophenoxy)pyrrolidin-1-yl)nicotinamido)ethyl)benzoic acid (E59)

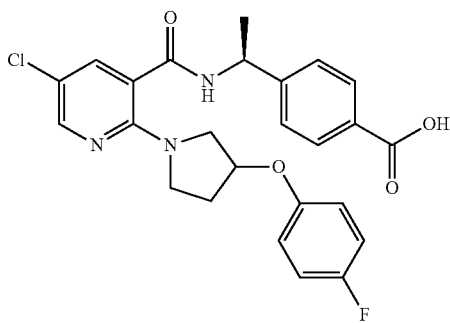 [SMILES: C[C@H](NC(=O)c1cc(Cl)cnc1N1CCC(Oc2ccc(F)cc2)C1)c1ccc(C(=O)O)cc1]

The title compound (E59) (62 mg) was prepared according to the experimental procedure described in Example 7 starting from methyl 4-((1S)-1-(5-chloro-2-(3-(4-fluorophenoxy)pyrrolidin-1-yl)nicotinamido)ethyl)benzoate (D193) (64 mg, 0.128 mmol)

MS: (ES/+) m/z: 484 [MH$^+$] C25H23ClFN3O4 requires 483.14

$^1$H NMR (400 MHz, DMSO-d$_6$) δ (ppm): 9.07 (d, J=7.8 Hz, 2H), 8.16 (d, J=2.4 Hz, 2H), 7.99-7.85 (m, 4H), 7.61 (d, J=2.9 Hz, 1H), 7.58-7.44 (m, 5H), 7.10 (dt, J=6.4, 8.8 Hz, 4H), 6.97-6.79 (m, 4H), 5.17-5.05 (m, 2H), 5.00 (br. s., 1H), 4.91 (br. s., 1H), 3.69 (dd, J=4.4, 12.2 Hz, 1H), 3.62-3.55 (m, 1H), 3.53-3.26 (m, 5H), 3.20 (d, J=12.7 Hz, 1H), 2.22-1.95 (m, 4H), 1.46 (d, J=6.8 Hz, 3H), 1.41 (d, J=6.8 Hz, 3H)

Example 60, 61 and 62

4-(1-(5-chloro-2-(3-phenoxy)pyrrolidin-1-yl)nicotinamido)cyclopropyl)benzoic acid (racemic mixture) (E60)

4-(1-(5-chloro-2-(3-phenoxy)pyrrolidin-1-yl)nicotinamido)cyclopropyl)benzoic acid (enantiomer 1) (E61)

4-(1-(5-chloro-2-(3-phenoxy)pyrrolidin-1-yl)nicotinamido)cyclopropyl)benzoic acid (enantiomer 2) (E62)

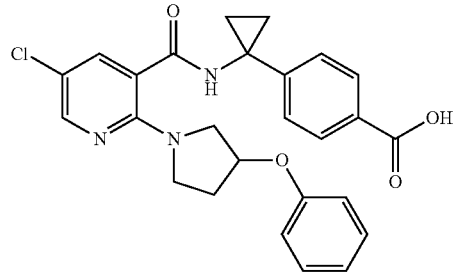 [SMILES: O=C(O)c1ccc(C2(NC(=O)c3cc(Cl)cnc3N3CCC(Oc4ccccc4)C3)CC2)cc1]

To an ice cooled solution of methyl 4-(1-(5-chloro-2-(3-phenoxy)pyrrolidin-1-yl)nicotinamido)cyclopropyl)benzoate (D194) (100 mg, 0.20 mmol) in a mixture methanol/tetrahydrofuran (10 ml/10 ml) 2N NaOH (10 ml). The reaction mixture was heated to 40° C. for 3 hours then cooled to room temperature. Methanol was evaporated and water was added (10 ml). After cooling to 0° C., the mixture was acidified with 2.5N HCl (pH=1-2), then stirred at 0° C. for 30 min. The pale yellow solid was collected by filtration, washed with water, dried and washed with DCM/MeOH (v/v, 20:1), filtered and dried to provide the title compound (E60) (36 mg) as a white solid.

MS: (ES/+) m/z: 478 [MH$^+$] C26H24ClN3O4 requires 477.14

$^1$HNMR (400 MHz, METHANOL-d$_4$) δ (ppm): 8.13 (1H, d, J=2.0 Hz), 7.99 (2H, d, J=8.4 Hz), 7.63 (1H, d, J=2.0 Hz), 7.47 (2H, d, J=8.0 Hz), 7.29 (2H, t, J=7.6 Hz), 6.96 (1H, t, J=7.6 Hz), 6.86 (2H, d, J=8.4 Hz), 4.99 (1H, s), 3.66-3.70 (2H, m), 3.50-3.51 (1H, m), 3.37 (1H, s), 2.18 (2H, s), 1.32-1.41 (4H, m).

(E60) (23 mg) dissolved in ethanol (4.5 ml) was separated by chiral HPLC [Daicel Chiralpack IC column (2×25 cm, 5 μm particle size). Mobile phase: isocratic premixed mixture of heptane 70%, ethanol 30% containing 0.1% of trifluoroacetic acid. Flow rate=10 ml/min. UV detection: 270 nm]. Collected fractions after solvent evaporation of the separated peaks, gave the title compounds (E61) (9 mg) and (E62) (9 mg) as single enantiomers.

(E61): (single enantiomer 1)
MS: (ES/+) m/z: 478 [MH$^+$] C26H24ClN3O4 requires 477.14
$^1$H NMR (400 MHz, DMSO-d$_6$) δ (ppm): 9.27 (s, 1H), 8.18 (d, J=2.4 Hz, 1H), 7.92-7.84 (m, 2H), 7.69 (d, J=2.9 Hz, 1H), 7.35 (d, J=8.8 Hz, 2H), 7.32-7.26 (m, 2H), 6.95 (t, J=7.3 Hz, 1H), 6.90 (d, J=7.8 Hz, 2H), 5.08 (br. s., 1H), 3.70 (dd, J=4.4, 12.2 Hz, 1H), 3.60-3.51 (m, 1H), 3.51-3.44 (m, 1H), 3.31 (d, J=12.2 Hz, 1H), 2.15 (d, J=12.7 Hz, 2H), 1.36-1.24 (m, 4H).

(E62): (single enantiomer 2)
MS: (ES/+) m/z: 478 [MH$^+$] C26H24ClN3O4 requires 477.14
$^1$H NMR (400 MHz, DMSO-d$_6$) δ (ppm): 9.27 (s, 1H), 8.18 (d, J=2.4 Hz, 1H), 7.92-7.84 (m, 2H), 7.69 (d, J=2.9 Hz, 1H), 7.35 (d, J=8.8 Hz, 2H), 7.32-7.26 (m, 2H), 6.95 (t, J=7.3 Hz, 1H), 6.90 (d, J=7.8 Hz, 2H), 5.08 (br. s., 1H), 3.70 (dd, J=4.4, 12.2 Hz, 1H), 3.60-3.51 (m, 1H), 3.51-3.44 (m, 1H), 3.31 (d, J=12.2 Hz, 1H), 2.15 (d, J=12.7 Hz, 2H), 1.36-1.24 (m, 4H).

Example 63, 64 and 65

4-(1-(5-chloro-2-(3-(3-(trifluoromethyl)phenoxy)pyrrolidin-1-yl)nicotinamido)cyclopropyl)benzoic acid (racemic mixture) (E63) (0004/052/1)

4-(1-(5-chloro-2-(3-(3-(trifluoromethyl)phenoxy)pyrrolidin-1-yl)nicotinamido)cyclopropyl)benzoic acid (enantiomer 1) (E64)

4-(1-(5-chloro-2-(3-(3-(trifluoromethyl)phenoxy)pyrrolidin-1-yl)nicotinamido)cyclopropyl)benzoic acid (enantiomer 2) (E65)

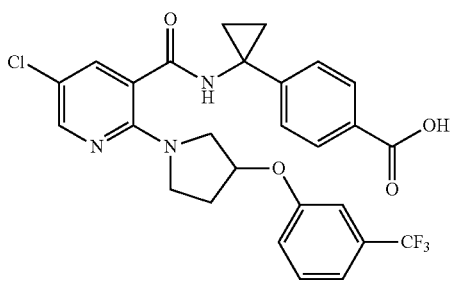

The title compound (E63) (88 mg) was prepared according to the experimental procedure described in Example 7 starting from methyl 4-(1-(5-chloro-2-(3-(3-(trifluoromethyl)phenoxy)pyrrolidin-1-yl)nicotinamido)cyclopropyl)benzoate (D195) (50 mg, 0.098 mmol).
MS: (ES/+) m/z: 546.2 [MH$^+$] C27H23ClF3N3O4 requires 545.13
$^1$H NMR (400 MHz, DMSO-d$_6$) δ (ppm): 12.78 (br. s., 1H), 9.29 (s, 1H), 8.19 (d, J=2.4 Hz, 1H), 7.86 (d, J=8.3 Hz, 2H), 7.72 (d, J=2.4 Hz, 1H), 7.57-7.47 (m, 1H), 7.39-7.29 (m, 3H), 7.28-7.18 (m, 2H), 5.24 (br. s., 1H), 3.75 (dd, J=4.2, 12.0 Hz, 1H), 3.62-3.50 (m, 1H), 3.50-3.41 (m, 1H), 3.38-3.35 (m, 1H), 2.28-2.16 (m, 2H), 2.11 (d, J=13.7 Hz, 2H), 1.39-1.17 (m, 4H).

(E63) (27.3 mg) dissolved in chloroform (150 ul) ethanol (115 ul) and heptane (350 ul) was separated by chiral HPLC [Daicel Chiralpack IC column (2×25 cm, 5 μm particle size). Mobile phase: isocratic premixed mixture of heptane 70%, ethanol 30% containing 0.1% of trifluoroacetic acid. Flow rate=10 ml/min. UV detection: 270 nm]. Collected fractions after solvent evaporation of the separated peaks, gave the title compounds (E64) (11 mg) and (E65) (7 mg) as single enantiomers.

(E64): (single enantiomer 1)
MS: (ES/+) m/z: 546.2 [MH$^+$] C27H23ClF3N3O4 requires 545.13
$^1$H NMR (400 MHz, DMSO-d$_6$) δ (ppm): 13.07-12.43 (m, 1H), 9.27 (s, 1H), 8.27-8.10 (m, 1H), 7.90-7.82 (m, J=8.3 Hz, 2H), 7.76-7.66 (m, 1H), 7.59-7.47 (m, 1H), 7.35 (d, J=8.3 Hz, 3H), 7.27-7.21 (m, 2H), 5.30-5.15 (m, 1H), 3.78-3.71 (m, 1H), 3.60-3.50 (m, 1H), 3.50-3.42 (m, 1H), 3.38-3.30 (m, 1H), 2.29-2.04 (m, 2H), 1.40-1.20 (m, 4H)

(E65): (single enantiomer 2)
MS: (ES/+) m/z: 546.2 [MH$^+$] C27H23ClF3N3O4 requires 545.13
$^1$H NMR (400 MHz, DMSO-d$_6$) δ (ppm): 12.74 (br. s., 1H), 9.27 (s, 1H), 8.19 (d, J=2.4 Hz, 1H), 7.86 (d, J=8.3 Hz, 2H), 7.71 (d, J=2.4 Hz, 1H), 7.58-7.47 (m, 1H), 7.40-7.28 (m, 3H), 7.27-7.20 (m, 2H), 5.24 (br. s., 1H), 3.74 (dd, J=3.9, 12.2 Hz, 1H), 3.59-3.50 (m, 1H), 3.50-3.43 (m, 1H), 3.34 (d, J=11.7 Hz, 1H), 2.21 (dd, J=4.6, 9.0 Hz, 1H), 2.12 (br. s., 1H), 1.39-1.18 (m, 4H)

Example 66, 67 and 68

4-(1-(5-chloro-2-(3-(4-fluorophenoxy)pyrrolidin-1-yl)nicotinamido)cyclopropyl)benzoic acid (racemic mixture) (E66)

4-(1-(5-chloro-2-(3-(4-fluorophenoxy)pyrrolidin-1-yl)nicotinamido)cyclopropyl)benzoic acid (enantiomer 1) (E67)

4-(1-(5-chloro-2-(3-(4-fluorophenoxy)pyrrolidin-1-yl)nicotinamido)cyclopropyl)benzoic acid (enantiomer 2) (E68)

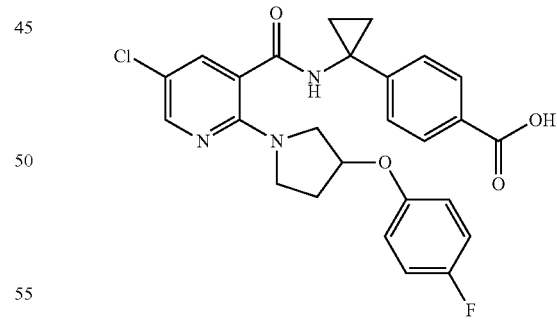

The title compound (E66) (23 mg) was prepared according to the experimental procedure described in Example 7 starting from methyl 4-(1-(5-chloro-2-(3-(4-fluorophenoxy)pyrrolidin-1-yl)nicotinamido)cyclopropyl)benzoate (D196) (50 mg, 0.098 mmol).
MS: (ES/+) m/z: 496.2 [MH$^+$] C26H23ClFN3O4 requires 495.14
$^1$H NMR (400 MHz, DMSO-d$_6$) δ (ppm): 12.79 (br. s., 1H), 9.29 (s, 1H), 8.19 (d, J=2.4 Hz, 1H), 7.87 (d, J=8.6 Hz, 2H), 7.71 (d, J=2.4 Hz, 1H), 7.39-7.24 (m, 3H), 6.91-6.69 (m, 3H), 5.13 (br. s., 1H), 3.72 (dd, J=4.3, 12.1 Hz, 1H), 3.60-3.40 (m, 2H), 3.31-3.29 (m, 1H), 2.27-2.04 (m, 2H), 1.42-1.17 (m, 4H)

(E66) (15 mg) dissolved in chloroform (300 ul) and ethanol (2.2 ml) was separated by chiral HPLC [Daicel Chiralpack IC column (2×25 cm, 5 μm particle size). Mobile phase: isocratic premixed mixture of heptane 70%, ethanol 30% containing 0.1% of trifluoroacetic acid. Flow rate=10 ml/min. UV detection: 270 nm]. Collected fractions after solvent evaporation of the separated peaks, gave the title compounds (E67) (3 mg) and (E68) (3 mg) as single enantiomers.

(E67): (single enantiomer 1)
MS: (ES/+) m/z: 496.2 [MH$^+$] C26H23ClFN3O4 requires 495.14
$^1$H NMR (400 MHz, DMSO-d$_6$) δ (ppm): 12.78 (br. s., 1H), 9.27 (s, 1H), 8.18 (d, J=2.4 Hz, 1H), 7.87 (d, J=8.8 Hz, 2H), 7.70 (d, J=2.9 Hz, 1H), 7.35 (d, J=8.3 Hz, 2H), 7.16-7.05 (m, 2H), 6.99-6.81 (m, 2H), 5.03 (br. s., 1H), 3.68 (dd, J=4.4, 12.2 Hz, 1H), 3.58-3.40 (m, 2H), 3.34-3.26 (m, 1H, under water peak), 2.26-1.98 (m, 2H), 1.39-1.19 (m, 4H)

(E68): (single enantiomer 2)
MS: (ES/+) m/z: 496.2 [MH$^+$] C26H23ClFN3O4 requires 495.14
$^1$H NMR (400 MHz, DMSO-d$_6$) δ (ppm): 12.78 (br. s., 1H), 9.27 (s, 1H), 8.18 (d, J=2.4 Hz, 1H), 7.90-7.81 (m, 2H), 7.70 (d, J=2.9 Hz, 1H), 7.35 (d, J=8.3 Hz, 2H), 7.16-7.06 (m, 2H), 6.97-6.88 (m, 2H), 5.03 (br. s., 1H), 3.68 (dd, J=4.4, 12.2 Hz, 1H), 3.53 (dt, J=6.8, 10.3 Hz, 1H), 3.49-3.41 (m, 1H), 3.34-3.30 (m, 1H, under water peak), 2.22-2.02 (m, 2H), 1.36-1.22 (m, 4H)

Example 69, 70 and 71

4-(1-(5-chloro-2-(3-(3-fluorophenoxy)pyrrolidin-1-yl)nicotinamido)cyclopropyl)benzoic acid (racemic mixture) (E69)

4-(1-(5-chloro-2-(3-(3-fluorophenoxy)pyrrolidin-1-yl)nicotinamido)cyclopropyl)benzoic acid (enantiomer 1) (E70)

4-(1-(5-chloro-2-(3-(3-fluorophenoxy)pyrrolidin-1-yl)nicotinamido)cyclopropyl)benzoic acid (enantiomer 2) (E71)

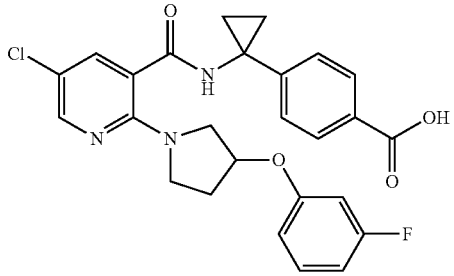 [SMILES: O=C(O)c1ccc(C2(NC(=O)c3cc(Cl)cnc3N3CCC(Oc4cccc(F)c4)C3)CC2)cc1]

The title compound (E69) (166 mg) was prepared according to the experimental procedure described in Example 7 starting from methyl 4-(1-(5-chloro-2-(3-(3-fluorophenoxy)pyrrolidin-1-yl)nicotinamido)cyclopropyl)benzoate (D197) (180 mg, 0.353 mmol).

MS: (ES/+) m/z: 496.2 [MH$^+$] C26H23ClFN3O4 requires 495.14
$^1$H NMR (400 MHz, DMSO-d$_6$) δ (ppm): 12.79 (br. s., 1H), 9.29 (s, 1H), 8.19 (d, J=2.4 Hz, 1H), 7.87 (d, J=8.6 Hz, 2H), 7.71 (d, J=2.4 Hz, 1H), 7.39-7.24 (m, 3H), 6.91-6.69 (m, 3H), 5.13 (br. s., 1H), 3.72 (dd, J=4.3, 12.1 Hz, 1H), 3.60-3.40 (m, 2H), 3.31-3.29 (m, 1H), 2.27-2.04 (m, 2H), 1.42-1.17 (m, 4H)

(E69) (25 mg) dissolved in and ethanol (3.7 ml) was separated by chiral HPLC [Daicel Chiralpack IC column (2×25 cm, 5 μm particle size). Mobile phase: isocratic premixed mixture of heptane 70%, ethanol 30% containing 0.1% of trifluoroacetic acid. Flow rate=10 ml/min. UV detection: 270 nm]. Collected fractions after solvent evaporation of the separated peaks, gave the title compounds (E70) (11 mg) and (E71) (11 mg) as single enantiomers.

(E70): (single enantiomer 1)
MS: (ES/+) m/z: 496.2 [MH$^+$] C26H23ClFN3O4 requires 495.14
$^1$H NMR (400 MHz, DMSO-d$_6$) δ (ppm): 9.27 (s, 1H), 8.19 (d, J=2.4 Hz, 1H), 7.87 (d, J=8.3 Hz, 2H), 7.70 (d, J=2.4 Hz, 1H), 7.39-7.27 (m, 3H), 6.91-6.72 (m, 3H), 5.13 (br. s., 1H), 3.71 (dd, J=4.4, 12.2 Hz, 1H), 3.58-3.39 (m, 2H), 3.32 (d, J=12.2 Hz, 1H), 2.26-2.14 (m, 1H), 2.12 (br. s., 1H), 1.37-1.22 (m, 4H)

(E71): (single enantiomer 2)
MS: (ES/+) m/z: 496.2 [MH$^+$] C26H23ClFN3O4 requires 495.14
$^1$H NMR (400 MHz, DMSO-d$_6$) δ (ppm): 9.27 (s, 1H), 8.19 (d, J=2.4 Hz, 1H), 7.87 (d, J=8.3 Hz, 2H), 7.70 (d, J=2.4 Hz, 1H), 7.39-7.25 (m, 3H), 6.88-6.71 (m, 3H), 5.13 (br. s., 1H), 3.72 (dd, J=4.6, 12.5 Hz, 1H), 3.60-3.42 (m, 2H), 3.32 (d, J=12.2 Hz, 1H), 2.25-2.14 (m, 1H), 2.11 (br. s., 1H), 1.38-1.23 (m, 4H)

Example 72

4-(1-(5-chloro-2-(3-(m-tolyloxy)pyrrolidin-1-yl)nicotinamido)cyclopropyl)benzoic acid (E72)

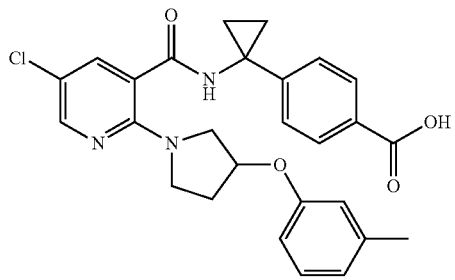 [SMILES: Cc1cccc(OC2CCN(c3ncc(Cl)cc3C(=O)NC3(c4ccc(C(=O)O)cc4)CC3)C2)c1]

The title compound (E72) (4 mg) was prepared according to the experimental procedure described in Example 7 starting from methyl 4-(1-(5-chloro-2-(3-(m-tolyloxy)pyrrolidin-1-yl)nicotinamido)cyclopropyl)benzoate (D198) (12 mg, 0.024 mmol)

MS: (ES/+) m/z: 492.2 [MH$^+$] C27H26ClN3O4 requires 491.16

$^1$H NMR (400 MHz, DMSO-d$_6$) δ (ppm): 9.28 (s, 1H), 8.19 (d, J=2.4 Hz, 1H), 7.87 (d, J=8.3 Hz, 2H), 7.70 (d, J=2.4 Hz, 1H), 7.35 (d, J=8.3 Hz, 2H), 7.16 (s, 1H), 6.83-6.63 (m, 3H), 5.07 (br. s., 1H), 3.70 (dd, J=4.2, 12.0 Hz, 1H), 3.61-3.41 (m, 2H), 3.30 (d, J=12.7 Hz, 1H), 2.28 (s, 3H), 2.23-2.04 (m, 2H), 1.42-1.14 (m, 4H)

Example 73, 74 and 75

4-(1-(5-chloro-2-(3-(4-(trifluoromethyl)phenoxy)
pyrrolidin-1-yl)nicotinamido)cyclopropyl)benzoic
acid (racemic mixture) (E73)

4-(1-(5-chloro-2-(3-(4-(trifluoromethyl)phenoxy)
pyrrolidin-1-yl)nicotinamido)cyclopropyl)benzoic
acid (Enantiomer 1) (E74)

4-(1-(5-chloro-2-(3-(4-(trifluoromethyl)phenoxy)
pyrrolidin-1-yl)nicotinamido)cyclopropyl)benzoic
acid (Enantiomer 2) (E75)

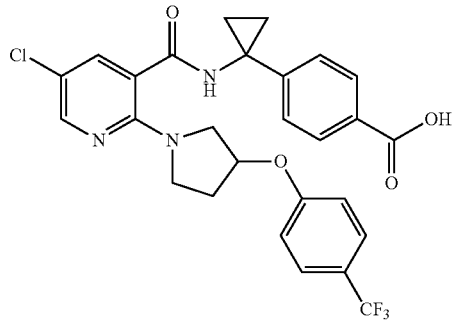 [SMILES: O=C(O)c1ccc(C2(NC(=O)c3cc(Cl)cnc3N3CCC(Oc4ccc(C(F)(F)F)cc4)C3)CC2)cc1]

To a solution of methyl 4-(1-(5-chloro-2-(3-(4-(trifluoromethyl)phenoxy)pyrrolidin-1-yl)nicotinamido)cyclopropyl)benzoate (D199) (24 mg, 0.428 mmol) in a mixture 1,4-dioxane and water (3 ml/1 ml) lithium hydroxide monohydrate (2.7 mg, 0.064 mmol) was added and the mixture was stirred 2 days at room temperature. After solvent evaporation the residue was diluted with water (5 ml) and HCl 1M (15 ml) and extracted with ethylacetate (3×20 ml). Collected organics after solvent evaporation gave the title compound (E73) (15 mg) as racemic mixture.

MS: (ES/+) m/z: 546.2 [MH$^+$] C27H23ClF3N3O4 requires 545.13

$^1$H NMR (400 MHz, METHANOL-d$_4$) δ (ppm): 8.17-8.09 (m, 1H), 8.01-7.94 (m, 2H), 7.64-7.55 (m, 3H), 7.50-7.44 (m, 2H), 7.06-6.98 (m, 2H), 5.13-5.06 (m, 1H), 3.79-3.60 (m, 2H), 3.55-3.47 (m, 1H), 3.40-3.40 (m, 1H), 2.28-2.10 (m, 2H), 1.44-1.28 (m, 4H)

(E73) (12 mg) dissolved in a mixture dimethylsulfoxide/ethanol/hexane (200 μl/300 μl/200 μl) was separated by chiral HPLC [Daicel Chiralpack IC column (2×25 cm, 5 μm particle size). Mobile phase: isocratic premixed mixture of hexane 80%, isopropanol 20% containing 0.2% of trifluoroacetic acid. Flow rate=10 ml/min. UV detection: 245 nm]. Collected fractions after solvent evaporation of the separated peaks, gave the title compounds (E74) (1 mg) and (E75) (1.3 mg) as single enantiomers.

(E74): (single enantiomer 1)
MS: (ES/+) m/z: 546.2 [MH$^+$] C27H23ClF3N3O4 requires 545.13

$^1$H NMR (400 MHz, DMSO-d$_6$) δ (ppm): 9.35-9.21 (m, 1H), 8.23-8.16 (m, 1H), 7.90-7.84 (m, 2H), 7.73-7.69 (m, 1H), 7.67-7.61 (m, 2H), 7.38-7.33 (m, 2H), 7.13-7.07 (m, 2H), 5.24-5.19 (m, 1H), 3.78-3.71 (m, 1H), 3.59-3.44 (m, 2H), 3.38-3.31 (m, 1H), 2.28-2.08 (m, 2H), 1.38-1.20 (m, 4H)

(E75): (single enantiomer 2)
MS: (ES/+) m/z: 546.2 [MH$^+$] C27H23ClF3N3O4 requires 545.13

$^1$H NMR (400 MHz, DMSO-d$_6$) δ (ppm): 9.32-9.24 (m, 1H), 8.23-8.12 (m, 1H), 7.92-7.83 (m, 2H), 7.75-7.68 (m, 1H), 7.67-7.59 (m, 2H), 7.40-7.30 (m, 2H), 7.14-7.06 (m, 2H), 5.27-5.17 (m, 1H), 3.79-3.70 (m, 1H), 3.60-3.44 (m, 2H), 3.39-3.34 (m, 1H), 2.26-2.11 (m, 2H), 1.35-1.24 (m, 4H)

Example 76

4-(1-(5-chloro-2-(3-((3-fluorophenoxy)methyl)pyrrolidin-1-yl)nicotinamido)cyclopropyl)benzoic acid (E76)

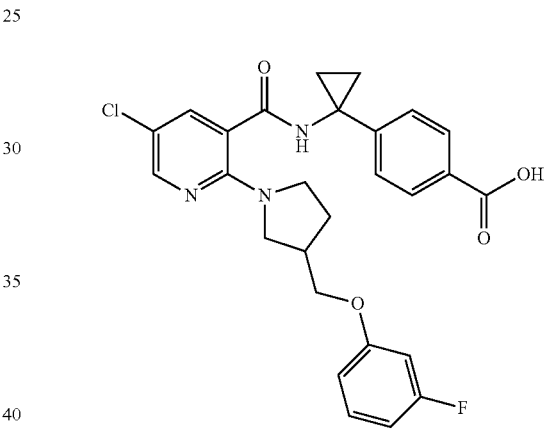

To a solution of methyl 4-(1-(5-chloro-2-(3-((3-fluorophenoxy)methyl)pyrrolidin-1-yl)nicotinamido)cyclopropyl) benzoate (D200) (37 mg, 0.070 mmol) in a mixture 1,4-dioxane and water (3:1) (2 ml) lithium hydroxide monohydrate (10 mg, 0.238 mmol) was added and the mixture was stirred 20 min (4 cycles of 5 min each) under microwaves irradiation. After solvent evaporation the residue was diluted with water (5 ml) and 1M HCl (5 ml) and extracted with ethylacetate (3×10 ml). Collected organics after solvent evaporation afforded a residue that was purified by ISOLUTE Spe-Si (1 g) eluting with a mixture dichloromethane/methanol 98:2. Collected fractions after solvent evaporation afforded the title compound (E76) (18.2 mg)

MS: (ES/+) m/z: 510.3 [MH$^+$] C27H25ClFN3O4 requires 509.15

$^1$H NMR (400 MHz, DMSO-d6) δ (ppm): 12.77 (br. s., 1H), 9.26 (s, 1H), 8.17 (d, J=2.4 Hz, 1H), 7.87 (d, J=8.3 Hz, 2H), 7.68 (d, J=2.4 Hz, 1H), 7.36 (d, J=8.3 Hz, 2H), 7.33-7.27 (m, 1H), 6.84-6.73 (m, 3H), 4.03 (dd, J=6.4, 9.8 Hz, 1H), 3.94-3.87 (m, 1H), 3.48-3.35 (m, 3H), 3.23 (dd, J=7.3, 10.8 Hz, 1H), 2.70-2.61 (m, 1H), 2.10-2.01 (m, 1H), 1.74 (dd, J=8.1, 12.0 Hz, 1H), 1.32 (d, J=5.4 Hz, 4H).

Example 77

4 (R)-4-(1-(5-chloro-2-(2-((3-fluorophenoxy)methyl)pyrrolidin-1-yl)nicotinamido)cyclopropyl)benzoic acid (E77)

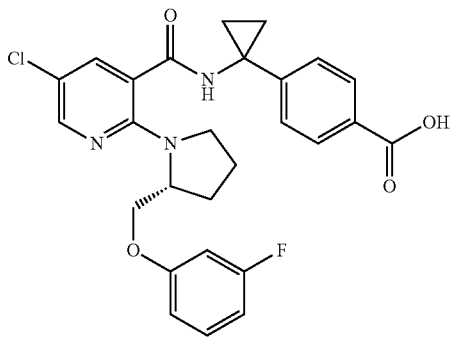 [SMILES: O=C(O)c1ccc(C2(NC(=O)c3cc(Cl)cnc3N3CCC[C@@H]3COc3cccc(F)c3)CC2)cc1]

The title compound (E77) (23.2 mg) was prepared according to the experimental procedure described in Example 76 starting from methyl (R)-4-(1-(5-chloro-2-(2-((3-fluorophenoxy)methyl)pyrrolidin-1-yl)nicotinamido)cyclopropyl)benzoate (D201) (78 mg, 0.149 mmol)

MS: (ES/+) m/z: 510.3 [MH$^+$] C27H25ClFN3O4 requires 509.15

$^1$H NMR (400 MHz, DMSO-d$_6$) δ (ppm): 12.80 (br. s., 1H), 9.27 (s, 1H), 8.21 (d, J=2.4 Hz, 1H), 7.91-7.85 (m, J=8.3 Hz, 2H), 7.71 (d, J=2.4 Hz, 1H), 7.40-7.35 (m, J=8.3 Hz, 2H), 7.30 (q, J=7.8 Hz, 1H), 6.91-6.80 (m, 2H), 6.78-6.71 (m, 1H), 4.60-4.52 (m, 1H), 4.21 (dd, J=3.2, 9.5 Hz, 1H), 3.83 (t, J=8.6 Hz, 1H), 3.36 (d, J=9.8 Hz, 1H), 3.09-3.01 (m, 1H), 2.10-1.85 (m, 3H), 1.78 (dd, J=5.6, 10.5 Hz, 1H), 1.35-1.28 (m, 4H).

Example 78

4 (S)-4-(1-(5-chloro-2-(2-((3-fluorophenoxy)methyl)pyrrolidin-1-yl)nicotinamido)cyclopropyl)benzoic acid (E78)

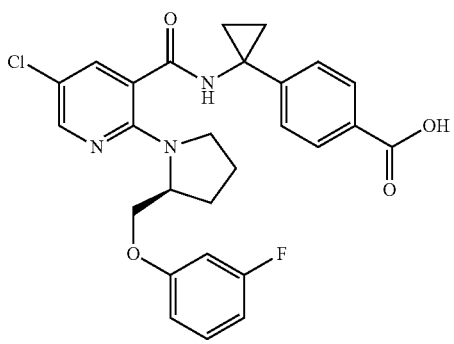 [SMILES: O=C(O)c1ccc(C2(NC(=O)c3cc(Cl)cnc3N3CCC[C@H]3COc3cccc(F)c3)CC2)cc1]

The title compound (E78) (28 mg) was prepared according to the experimental procedure described in Example 76 starting from methyl (S)-4-(1-(5-chloro-2-(2-((3-fluorophenoxy)methyl)pyrrolidin-1-yl)nicotinamido)cyclopropyl)benzoate (D202) (87 mg, 0.166 mmol)

MS: (ES/+) m/z: 510.3 [MH$^+$] C27H25ClFN3O4 requires 509.15

$^1$H NMR (400 MHz, DMSO-d$_6$) δ (ppm): 12.82 (br. s., 1H), 9.27 (s, 1H), 8.21 (d, J=2.9 Hz, 1H), 7.91-7.86 (m, J=8.3 Hz, 2H), 7.71 (d, J=2.4 Hz, 1H), 7.40-7.34 (m, J=8.3 Hz, 2H), 7.34-7.26 (m, 1H), 6.91-6.79 (m, 2H), 6.75 (dt, J=2.0, 8.3 Hz, 1H), 4.61-4.52 (m, 1H), 4.21 (dd, J=3.2, 9.5 Hz, 1H), 3.83 (t, J=8.6 Hz, 1H), 3.40-3.34 (m, 1H), 3.09-3.01 (m, 1H), 2.10-1.86 (m, 3H), 1.78 (dd, J=6.1, 10.5 Hz, 1H), 1.37-1.26 (m, 4H).

Example 79

4-(1-(5-chloro-2-(3-((3-fluorophenoxy)methyl)piperidin-1-yl)nicotinamido)cyclopropyl)benzoic acid (E79)

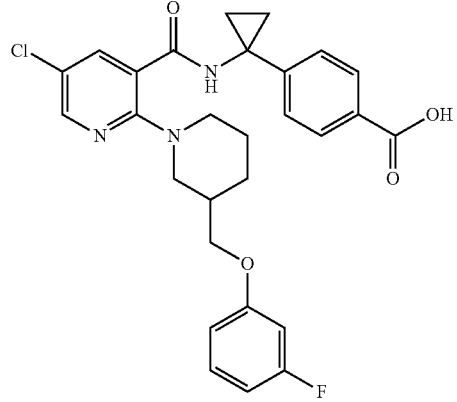 [SMILES: O=C(O)c1ccc(C2(NC(=O)c3cc(Cl)cnc3N3CCCC(COc4cccc(F)c4)C3)CC2)cc1]

The title compound (E79) (34.4 mg) was prepared according to the experimental procedure described in Example 76 starting from methyl 4-(1-(5-chloro-2-(3-((3-fluorophenoxy)methyl)piperidin-1-yl)nicotinamido)cyclopropyl)benzoate (D203) (95 mg, 0.176 mmol)

MS: (ES/+) m/z: 524.3 [MH$^+$] C28H27ClFN3O4 requires 523.17

$^1$H NMR (400 MHz, DMSO-d$_6$) δ (ppm): =9.28 (s, 1H), 8.25 (d, J=2.4 Hz, 1H), 7.85 (d, J=8.3 Hz, 2H), 7.76 (d, J=2.4 Hz, 1H), 7.35-7.26 (m, 3H), 6.81-6.71 (m, 3H), 3.92-3.73 (m, 3H), 3.59 (d, J=12.7 Hz, 1H), 3.18 (d, J=4.9 Hz, 1H), 2.88-2.73 (m, 2H), 2.02 (br. s., 1H), 1.83 (d, J=12.7 Hz, 1H), 1.63 (br. s., 1H), 1.49 (d, J=13.7 Hz, 1H), 1.37-1.31 (m, 4H).

Example 80

(S)-4-(1-(5-chloro-2-(3-(3-fluorophenoxy)pyrrolidin-1-yl)nicotinamido)cyclopropyl)benzoic acid (E80)

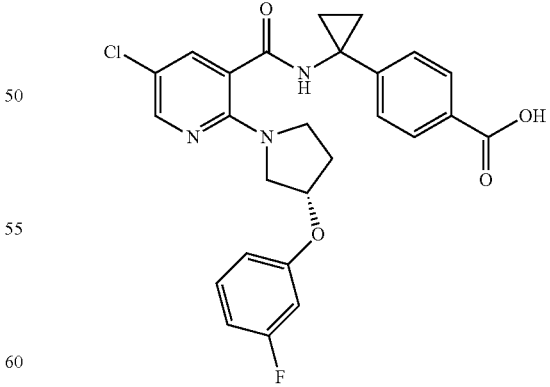

The title compound (E80) (54.8 mg) was prepared according to the experimental procedure described in Example 76 starting from methyl (S)-4-(1-(5-chloro-2-(3-(3-fluorophenoxy)pyrrolidin-1-yl)nicotinamido)cyclopropyl)benzoate (D204) (98 mg, 0.192 mmol)

MS: (ES/+) m/z: 496.2 [MH+] C26H23ClFN3O4 requires 495.14

$^1$H NMR (400 MHz, DMSO-d$_6$) δ (ppm): =12.77 (br. s., 1H), 9.27 (s, 1H), 8.19 (d, J=2.4 Hz, 1H), 7.87 (d, J=8.3 Hz, 2H), 7.70 (d, J=2.4 Hz, 1H), 7.35 (d, J=8.3 Hz, 2H), 7.33-7.27 (m, 1H), 6.85-6.73 (m, 3H), 5.13 (br. s., 1H), 3.71 (dd, J=4.4, 12.2 Hz, 1H), 3.58-3.42 (m, 2H), 3.34 (s, 1H), 2.24-2.06 (m, 2H), 1.35-1.23 (m, 4H).

Example 81

(R)-4-(1-(5-chloro-2-(3-(3-fluorophenoxy)pyrrolidin-1-yl)nicotinamido)cyclopropyl)benzoic acid (E81)

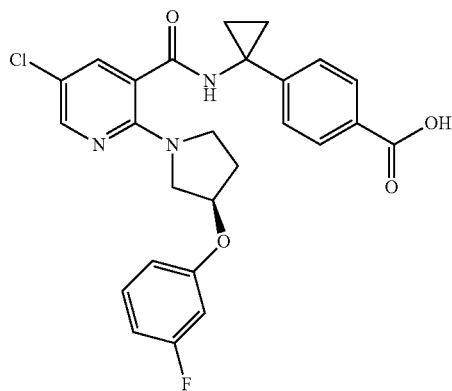 [SMILES: O=C(O)c1ccc(C2(NC(=O)c3cc(Cl)cnc3N3CC[C@@H](Oc4cccc(F)c4)C3)CC2)cc1]

The title compound (E81) (48.4 mg) was prepared according to the experimental procedure described in Example 76 starting from methyl (R)-4-(1-(5-chloro-2-(3-(3-fluorophenoxy)pyrrolidin-1-yl)nicotinamido)cyclopropyl)benzoate (D205) (94 mg, 0.184 mmol).

MS: (ES/+) m/z: 496.2 [MH+] C26H23ClFN3O4 requires 495.14

$^1$H NMR (400 MHz, DMSO-d$_6$) δ (ppm): =12.77 (br. s., 1H), 9.27 (s, 1H), 8.19 (d, J=2.4 Hz, 1H), 7.87 (d, J=8.3 Hz, 2H), 7.70 (d, J=2.4 Hz, 1H), 7.40-7.27 (m, 3H), 6.85-6.73 (m, 3H), 5.13 (br. s., 1H), 3.71 (dd, J=4.4, 12.2 Hz, 1H), 3.59-3.42 (m, 2H), 3.31 (br. s., 1H), 2.24-2.06 (m, 2H), 1.37-1.21 (m, 4H).

Example 82

N-(1-(4-(1H-tetrazol-5-yl)phenyl)cyclopropyl)-5-chloro-2-(3-(3-fluorophenoxy)azetidin-1-yl)nicotinamide (E82)

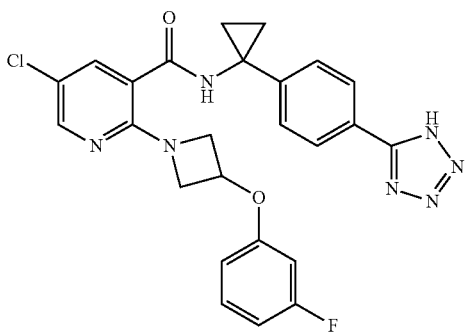 [SMILES: O=C(NC1(c2ccc(-c3nnn[nH]3)cc2)CC1)c1cc(Cl)cnc1N1CC(Oc2cccc(F)c2)C1]

To mixture of 5-chloro-2-(3-(3-fluorophenoxy)azetidin-1-yl)nicotinic acid (D77) (60 mg, 0.186 mmol) in dry dimethylformamide (1 ml), 1-Hydroxybenzotriazole hydrate (28.5 mg, 0.189 mmol), 1-Ethyl-3-[3-dimethylaminopropyl]carbodiimide Hydrochloride (53.5 mg, 0.279 mmol) were added followed by the addition of a solution of 1-(4-(1H-tetrazol-5-yl)phenyl)cyclopropanamine hydrochloride (D17) (44.2 mg, 0.186 mmol) and triethylamine (26 μl, 0.189 mmol) in dry dimethylformamide. The mixture was stirred for 1 h at room temperature. The solvent was evaporated in vacuo and the resulting residue was taken in NH$_4$Cl sat. sol (10 ml) and extracted with ethylacetate (2×10 ml). Collected organics after solvent evaporation afforded a residue that was washed with methanol (2 ml) to afford the title compound (E82) (30.8 mg)

MS: (ES/+) m/z: 506.2 [MH+] C25H21ClFN7O2 requires 505.14

1H NMR (400 MHz, DMSO-d6) δ=9.27 (s, 1H), 8.23 (d, J=2.4 Hz, 1H), 7.95-7.90 (m, J=8.8 Hz, 2H), 7.81 (d, J=2.4 Hz, 1H), 7.47-7.41 (m, J=8.8 Hz, 2H), 7.27 (d, J=7.3 Hz, 1H), 6.75-6.67 (m, 2H), 6.65 (d, J=8.3 Hz, 1H), 5.08 (d, J=2.9 Hz, 1H), 4.35 (dd, J=6.4, 9.8 Hz, 2H), 3.82 (dd, J=3.4, 10.3 Hz, 2H), 1.33 (s, 4H).

Example 83

Determination of In Vitro Effects of the Invention Compounds

Stable Expression of Human EP$_4$ Receptors in the Human Embryonic Kidney (HEK293) Cell Line The cDNA clone of human EP$_4$ receptor (NM_000958.2) was obtained from Invitrogen™: Ultimate™ ORF Clone Collection—Clone ID IOH46525. The coding sequence was subcloned in expression vector pcDNA™6.2/V5-DEST by Gateway technology (Invitrogen™).

Human embryonic kidney cells (HEK-293) were stably transfected with expression vector for human EP$_4$ receptor in according to the method described in FuGENE®6 Transfection Reagent's manual (Roche Applied Science®).

Preparation of Membrane Fraction:

The EP$_4$ transfected cells were grown in Dulbecco's modified Eagle's medium containing 10% fetal bovine serum and 10 μg/ml Blasticidin S HCl (selection medium) at 37° C. in a humidified atmosphere of 5% CO2 in air.

For the membrane preparation, cells in flask were harvested by hypotonical/mechanical lysis with chilled (4° C.) TE buffer (5 mM TRIS, 5 mM etylenediamine tetra-acetic acid (EDTA), pH 7.4).

Cells were detached and lysed with 10 ml of hypotonic lysis buffer and by scraping. The cell lysate was vortexed for 30 sec and centrifuged at 40000×g at 4° C. for 22 min.

a) Membrane Binding Assay[3H]-Prostaglandin E2

The membrane pellet was resuspended in the same buffer (5 mM TRIS, 5 mM ethylenediamine tetra-acetic acid (EDTA), pH 7.4), and protein concentration was determined by Bradford method (Bio-Bad® assay).

This membrane preparation was stored at −80° C. freezer until use for binding assay.

([$^3$H]-PGE$_2$) membranes binding assays toward hEP$_4$ receptors (human EP$_4$/HEK293 transfectant, see above) and hEP$_2$ receptors (human EP$_2$/HEK293 transfectant, purchased from PerkinElmer Inc) were performed in 10 mM MES-KOH buffer pH6, containing 10 mM MgCl$_2$ and 1 mM CaCl$_2$ for EP$_4$ binding assay or 50 mM Tris-Cl, BSA 0.5% for EP$_2$ binding assay (according to supplier indication).

Ten microgram of protein from membrane fractions were incubated in a total volume of 0.1 ml (EP$_4$) or 0.2 ml (EP$_2$) with 1 nM (EP$_4$) or 3 nM (EP$_2$) [$^3$H]-PGE$_2$ (PerkinElmer Inc, 171 Ci/mmol). In both assays to determine the total binding or non specific binding, 1% DMSO or 1 µM prostaglandin E$_2$ (EP$_4$) or 100 µM (EP$_2$) were added to reaction mixtures, respectively. Incubation was conducted in a polypropylene 96 multiwell for 90 min (EP$_4$) or 60 min (EP$_2$) at room temperature prior to separation of the bound and free radioligand by vacuum manifold rapid filtration on glass fiber filters (Unifilter GFB96, PerkinElmer Inc) pre-soaked in 0.3% polyethyleneimine. Filters were washed with ice cold buffer pH 7.4 (50 mM HEPES, NaCl 500 mM, BSA 0.1% for EP$_4$ binding assay or 50 mM Tris-Cl for EP$_2$ binding assays) and the residual [$^3$H]-PGE$_2$ binding determined by solid scintillation counter (TopCount, PerkinElmer Inc).

In standard competition experiments the compounds were tested in a concentration range from 1 nM to 1 µM, and IC$_{50}$ determined. The affinity (Ki) of each compound was calculated according to the Cheng-Prousoff equation: Ki=IC50/(1+([C]/Kd)). Results were expressed as pKi (−log 10 Ki (M))

Compounds of example 1 to 82 were tested according to method of example 83a in a final concentration range from 1 nM to 1 µM. All compounds showed good to excellent EP4 affinities having pKi values from 6 to 8.5 at EP4 receptor.

b) cAMP Assay on Human EP$_4$ Membrane of Transfected Cells.

The assay is based on the competition between endogenous cAMP and exogenously added biotinylated cAMP. The capture of cAMP is achieved by using a specific antibody conjugated to Donor beads.

Cell membranes prepared as described above, were resuspended in 1 ml stimulation buffer (HBSS 1×+BSA 0.1%+IBMX 0.5 mM+HEPES 5 mM+MgCl$_2$ 10 mM+GTP 1 nM+GDP 10 µM+ATP 100 µM–pH 7.4). Cell membranes were dispensed into white 384-well microplates at final concentration of 1 µg/well and used for the determination of cAMP with the alphascreen cAMP functional assay (EnVision—PerkinElmer). Cell membrane/anti-cAMP Acceptor beads mix (5 µl) and a mixture of analysed compounds (dissolved in 100% DMSO to a final maximal concentration of 0.01% DMSO)/PGE2 (5 µl) were incubated at room temperature (22-23° C.) for 30 min in the dark. The Biotinylated-cAMP and donor beads (15 µl) were dispensed into each well to start the competition reaction. After 1 h incubation RT (22-23° C.) in the dark the plate was read using EnVision platform to determine the cAMP level (excitation: 680 nm; emission: 520,620 nm).

In each experiment:
cAMP standard curve (concentration range from 1×10-6 to 1×10-11 M in. log intervals) with a negative control (no cAMP) a positive control:forskolin 10 µM Antagonism studies were performed stimulating HEK293 cell membrane with PGE2 3 nM. The AlphaScreen signal is plotted as a function of log concentration of cAMP and functional IC50 is determined. IC50 value is calculated by linear regression.

Some compounds were tested according to method of example 83b. All compounds showed good to excellent EP4 antagonism having functional IC50 values from 386 nM to 7.7 nM at EP4 receptor.

The results of membrane binding assay and cAMP assay on human EP$_4$ membrane of transfected cells selection of preferred compounds are summarised in table 1.

TABLE 1

| Example | Binding pKi | functional IC50 (nM) |
|---|---|---|
| E 1 | 6.4 | 235 |
| E 3 | 7.5 | 133 |
| E 4 | 6.7 | 102 |
| E 10 | 7.8 | 46 |
| E 11 | 7.0 | 386 |
| E 12 | 7.8 | 102 |
| E 13 | 7.6 | 187 |
| E 14 | 8.3 | 38 |
| E 15 | 7.9 | 70 |
| E 16 | 8.5 | 40 |
| E 17 | 7.7 | 82 |
| E 18 | 7.9 | 22 |
| E 19 | 7.3 | 87 |
| E 20 | 8.0 | 70 |
| E 21 | 7.2 | 191 |
| E 22 | 7.5 | 119 |
| E 24 | 7.5 | 92 |
| E 25 | 7.2 | 135 |
| E 28 | 7.1 | 197 |
| E 31 | 8.1 | 47 |
| E 32 | 7.6 | 76 |
| E 33 | 8.2 | 44.5 |
| E 34 | 8.5 | 43 |
| E 35 | 8.2 | 59 |
| E 36 | 8.4 | 30 |
| E 37 | 7.9 | 31 |
| E 38 | 7.9 | 19.3 |
| E 39 | 8.1 | 72 |
| E 40 | 8.3 | 10 |
| E 41 | 8.3 | 7.7 |
| E 42 | 8.5 | 35 |
| E 43 | 8.5 | 38 |
| E 44 | 8.0 | 17.5 |
| E 45 | 8.5 | 10 |
| E 47 | 7.2 | 228 |
| E 49 | 7.6 | 69 |
| E 50 | 7.9 | 23 |
| E 51 | 8.2 | 28 |
| E 52 | 7.7 | 74 |
| E 53 | 7.5 | 80 |
| E 54 | 7.6 | 75 |
| E 55 | 7.5 | 126 |
| E 56 | 8.0 | 46 |
| E 60 | 7.1 | 96.5 |
| E 62 | 7.6 | 46 |
| E 63 | 7.5 | 145 |
| E 64 | 7.5 | 99 |
| E 65 | 7.4 | 65 |
| E 66 | 7.4 | 43 |
| E 68 | 7.5 | 66 |
| E 69 | 7.3 | 308 |
| E 71 | 7.4 | 110 |
| E 76 | 7.5 | 24 |
| E 77 | 8.0 | 90 |
| E 80 | 7.4 | 99 |
| E 82 | 8.3 | 27 |

Example 84

Determination of PK of the Invention Compounds

The pharmacokinetics of compounds E10, E16, E34, E38, E51, were studied in male Han Wistar rats. The rats were treated intravenously and orally (n=3 for each dose route) with a compounds formulated as solutions. The rats were fitted with a jugular cannula for serial sampling. A full profile was acquired for each rat. Plasma extracts were quantitatively analyzed using a specific and sensitive LC-MS/MS bioanalytical method. Inter-individual variations between the three rats in each group were limited (CV for pharmacokinetic parameters was below 50%).

After intravenous injection all compounds showed moderate volume of distribution (Vss) ranging between 230 and 1100 ml, below ten fold the rat total body water, suggesting moderate compound distribution outside of the blood compartment. A range of clearance values were obtained for the different structure, ranging from low to high values (from 160 to 860 ml/h).

After oral administration, absorption was quite fast with a clear maximum concentration reached by 15 minutes for all compounds. The absolute oral bioavailability was good for all compounds with F higher than 40%, and reaching 90% for compound E16.

| Ex | Route | Dose (mg/kg) | CLp* (ml/h) | Vss* (ml) | t½* (h) | AUC 0-t (ng · h/ml) | AUC inf* (ng · h/ml) | F % | Cmax (ng/ml) | Tmax (h) | Tlast (h) |
|---|---|---|---|---|---|---|---|---|---|---|---|
| E10 | IV | 2.0 | 161 | 307 | 3.96 | 3090 | 3150 | | | | 24 |
| | PO | 2.0 | | | 4.85 | 1720 | 1820 | 56 | 923 | 0.25 | 24 |
| E16 | IV | 2.0 | 160 | 394 | 5.62 | 3290 | 3330 | | | | 24 |
| | PO | 2.0 | | | 3.12 | 2990 | 3000 | 91 | 1800 | 0.25 | 24 |
| E34 | IV | 1.0 | 863 | 227 | 0.34 | 300 | 302 | | | | 2 |
| | PO | 1.0 | | | 1.16 | 125 | 128 | 42 | 98.1 | 0.25 | 6 |
| E38 | IV | 1.0 | 341 | 1070 | 5.9 | 816 | 832 | | | | 24 |
| | PO | 1.0 | | | 2.59 | 551 | 598 | 59 | 374 | 0.25 | 6 |
| E51 | IV | 1.0 | 675 | 447 | 1.12 | 385 | 389 | | | | 6 |
| | PO | 1.0 | | | 1.14 | 225 | 231 | 58 | 151 | 0.25 | 6 |

*Clearance, volume, half-life and AUC inf expressions may automatically be taken from calculations extrapolated to infinity from unrevised regression, indicative only; clearance values and AUC will usually never be much affected by error, volumes of distribution and half-life may or may not be precisely assessable from the data collected.
In summary tables for preliminary communications volumes may be taken from data until tlast, in which case it will be approximated by default due to lack of terminal phase data.

What is claimed is:

1. A pyridine amide derivative of Formula (I):

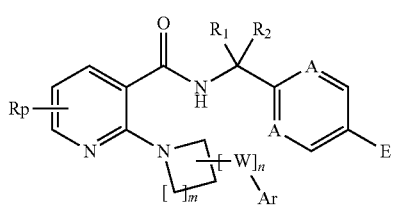

or a pharmaceutically acceptable salt thereof, wherein:

$R_1$ and $R_2$ are independently hydrogen, linear or branched (C1-C3)alkyl or joined together they form a cyclopropyl ring;

R is independently selected from the group consisting of halogens and trifluoromethyl and p is 1, 2 or 3;

A is C or N;

E is a group of formula (B) or (C), wherein

B is C(O)OH, C(O)O(C1-C3)alkyl, and

C is selected from the group consisting of:

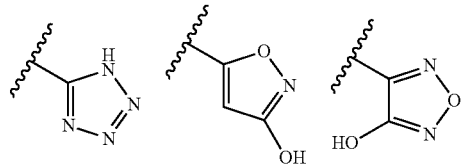

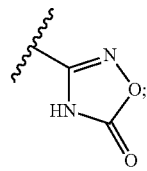

m is 1, 2 or 3, n is 0 or 1,

W is —O—, —O(C1-C3 alkyl)-; —(C1-C3 alkyl)O—; —C(O)—; —C(=N—O(C1-C3 alkyl))-; —NH— or —NH(C1-C3alkyl)-;

Ar is either (1) phenyl, optionally substituted with one or more substituents selected from the group consisting of: halogen, trifluoromethyl, trifluoromethoxy, methyl, —NH(C1-C3alkyl)-, —N(C1-C3alkyl)(C1-C3alkyl)-, a 5 to 7 membered heterocyclic ring containing one nitrogen atom which is covalently bonded to said phenyl and, optionally, containing one or two additional heteroatoms selected from N, O and S; or (2) a 5 or 6 membered heteroaromatic ring containing 1 to 3 heteroatoms selected from the group consisting of: S, O and N, such heteroaromatic ring being substituted with one or two substituents selected from the group consisting of: (C1-C3)alkyl, (C3-C5)cycloalkyloxy, and (C1-C3) alkylcarbonyl.

2. The pyridine amide derivative according to claim 1, wherein p is 1 and R is one selected from the group consisting of: halogen and trifluoromethyl.

3. The pyridine amide derivative according to claim 2, wherein p is 1 and R chlorine.

4. The pyridine amide derivative according to claim 1, wherein $R_1$ and $R_2$ are at least one selected from the group consisting of: hydrogen, methyl and a cyclopropane ring.

5. The pyridine amide derivative according to claim 4, wherein $R_1$ and $R_2$ form together a cyclopropane ring.

6. The pyridine amide derivative according to claim 1, wherein the pyridine amide derivative of Formula (I) is a compound of Formula (Ia), in which E is COOH and A is C:

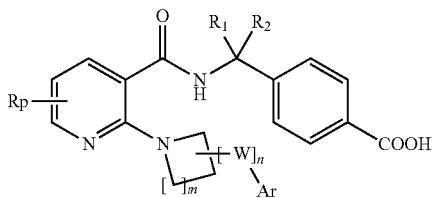

wherein Rp, $R_1$, $R_2$, W, Ar, m and have the same meaning as per Formula (I).

7. The pyridine amide derivative according to claim 6, wherein m is 1 or 2.

8. The pyridine amide derivative according to claim 6, wherein n is 0 and W is a bond.

9. The pyridine amide derivative according to claim 6, wherein W is at least one selected from the group consisting: of O, NH and N(C1-C3)alkyl.

10. The pyridine amide derivative according to claim 6, wherein Ar is phenyl, optionally substituted with one or more substituents selected from the group consisting of: halogen, trifluoromethyl, trifluoromethoxy, methyl, —NH(C1-C3alkyl)-, —N(C1-C3alkyl)(C1-C3alkyl)-, a from 5 to 7 membered heterocyclic ring containing one nitrogen atom, which is covalently bonded to said phenyl, and, optionally, containing one or two additional heteroatoms selected from the group consisting of: N, O and S.

11. The pyridine amide derivative according to claim 10, wherein Ar is phenyl substituted with fluorine.

12. The pyridine amide derivative according to claim 6, wherein Ar is a 5- or 6-membered heteroaromatic ring containing 1 to 3 heteroatoms selected from the group consisting of: S, O and N, such ring being substituted with one or two substituents selected from the group consisting of (C1-C3) alkyl, (C3-C5)cycloalkyloxy, and (C1-C3)alkylcarbonyl.

13. The pyridine amide derivative according to claim 12, wherein Ar is pyridine.

14. The pyridine amide derivative according to claim 1, wherein the pyridine amide derivative of Formula (I) is a compound of Formula (Ib), where E is B:

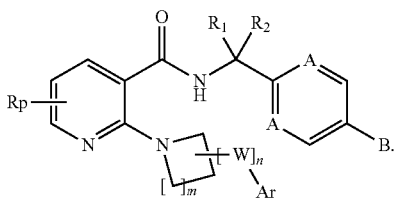

15. The pyridine amide derivative according to claim 14, wherein m is 1 or 2.

16. The pyridine amide derivative according to claim 14, wherein n is 0 and W is a bond.

17. The pyridine amide derivative according to claim 14, wherein W is selected from the group consisting of: O, NH and N(C1-C3)alkyl.

18. The pyridine amide derivative according to claim 14, wherein Ar is phenyl, optionally substituted with one or more halogen atoms, trifluoromethyl, trifluoromethoxy, methyl, —NH(C1-C3alkyl)-, —N(C1-C3alkyl)(C1-C3alkyl)-, a 5 to 7 membered heterocyclic ring containing one nitrogen atom, which is covalently bonded to said phenyl, and, optionally, containing one or two additional heteroatoms selected from the group consisting of: N, O and S.

19. The pyridine amide derivative according to claim 18, wherein Ar is phenyl substituted with said halogen atom.

20. The pyridine amide derivative according to claim 14, wherein Ar is a 5- or 6-membered heteroaromatic ring containing 1 to 3 heteroatoms selected from the group consisting of: S, O and N, such ring being substituted with one or two substituents selected from the group consisting of: (C1-C3) alkyl, (C3-C5)cycloalkyloxy, and (C1-C3)alkylcarbonyl.

21. The pyridine amide derivative according to claim 20, wherein Ar is pyridine.

22. The pyridine amide derivative according to claim 1, wherein the derivative of Formula (I) is selected from the group consisting of:
- 4-(1-(5-chloro-2-(2-phenylpyrrolidin-1-yl)nicotinamido) cyclopropyl)benzoic acid (racemic mixture)
- 4-(1-(5-chloro-2-(2-phenylpyrrolidin-1-yl)nicotinamido) cyclopropyl)benzoic acid (enantiomer 1)
- 4-(1-(5-chloro-2-(2-phenylpyrrolidin-1-yl)nicotinamido) cyclopropyl)benzoic acid (enantiomer 2)
- 4-(1-(5-chloro-2-(3-phenylpyrrolidin-1-yl)nicotinamido) cyclopropyl)benzoic acid
- 4-(1-(5-chloro-2-(3-phenylpyrrolidin-1-yl)nicotinamido) cyclopropyl)benzoic acid (enantiomer 1)
- 4-(1-(5-chloro-2-(3-phenylpyrrolidin-1-yl)nicotinamido) cyclopropyl)benzoic acid (enantiomer 2)
- 4-(1-(2-(2-benzylpyrrolidin-1-yl)-5-chloronicotinamido) cyclopropyl)benzoic acid (racemic mixture)
- 4-(1-(2-(2-benzylpyrrolidin-1-yl)-5-chloronicotinamido) cyclopropyl)benzoic acid (enantiomer 1)
- 4-(1-(2-(2-benzylpyrrolidin-1-yl)-5-chloronicotinamido) cyclopropyl)benzoic acid (enantiomer 2)
- 4-(1-(5-chloro-2-(3-phenoxyazetidin-1-yl)nicotinamido) cyclopropyl)benzoic acid
- (S)-4-(1-(5-chloro-2-(3-(4-fluorophenoxy)azetidin-1-yl) nicotinamido)ethyl)benzoic acid
- (S)-4-(1-(5-chloro-2-(3-(3-fluorophenoxy)azetidin-1-yl) nicotinamido)ethyl)benzoic acid
- 4-(1-(5-chloro-2-(3-(4-(trifluoromethyl)phenoxy)azetidin-1-yl)nicotinamido)cyclo-propyl)benzoic acid
- 4-(1-(5-chloro-2-(3-(3-(trifluoromethyl)phenoxy)azetidin-1-yl)nicotinamido)cyclo-propyl)benzoic acid
- 4-(1-(5-chloro-2-(3-(4-fluorophenoxy)azetidin-1-yl)nicotinamido)cyclopropyl)-benzoic acid
- 4-(1-(5-chloro-2-(3-(3-fluorophenoxy)azetidin-1-yl)nicotinamido)cyclopropyl)-benzoic acid
- 4-(1-(5-chloro-2-(3-(4-fluoro-3-(trifluoromethyl)phenoxy)azetidin-1-yl)nicotinamido)cyclopropyl)-benzoic acid
- 4-(1-(5-chloro-2-(3-(3-(trifluoromethoxy)phenoxy)azetidin-1-yl)nicotinamido)cyclopropyl)-benzoic acid
- 4-(1-(5-chloro-2-(3-(2,4-difluorophenoxy)azetidin-1-yl) nicotinamido)cyclopropyl)-benzoic acid
- 4-(1-(5-chloro-2-(3-(3,4-difluorophenoxy)azetidin-1-yl) nicotinamido)cyclopropyl)-benzoic acid
- 4-(1-(5-chloro-2-(3-(3-(piperazin-1-yl)phenoxy)azetidin-1-yl)nicotinamido)cyclo-propyl)benzoic acid
- 4-((5-chloro-2-(3-(3-fluorophenoxy)azetidin-1-yl)nicotinamido)methyl)benzoic acid
- 6-((5-chloro-2-(3-(3-fluorophenoxy)azetidin-1-yl)nicotinamido)methyl)nicotinic acid
- 6-((5-chloro-2-(3-(3-fluorophenoxy)azetidin-1-yl)nicotinamido)methyl)nicotinic acid
- 4-(1-(5-chloro-2-(3-(3-fluorobenzoyl)azetidin-1-yl)nicotinamido)cyclopropyl)benzoic acid 4-(1-(5-chloro-2-(3-((3-fluorophenyl)(methoxyimino)methyl)azetidin-1-yl)-nicotinamido)cyclopropyl)benzoic acid (isomeric mixture)
4-(1-(5-chloro-2-(3-(3-fluorophenyl)-3-hydroxyazetidin-1-yl)nicotinamido)cyclo-propyl)benzoic acid
4-(1-(5-chloro-2-(3-(4-fluorophenyl)-3-hydroxyazetidin-1-yl)nicotinamido)cyclo-propyl)benzoic acid
4-(1-(5-chloro-2-(3-((4-fluorophenoxy)methyl)azetidin-1-yl)nicotinamido)cyclo-propyl)benzoic acid
4-(1-(5-chloro-2-(3-((4-fluorophenoxy)methyl)azetidin-1-yl)nicotinamido)cyclo-propyl)benzoic acid
4-(1-(5-chloro-2-(3-((3-(trifluoromethyl)phenyl)amino)azetidin-1-yl)nicotinamido)-cyclopropyl)benzoic acid
4-(1-(5-chloro-2-(3-((3-fluorophenyl)amino)azetidin-1-yl)nicotinamido)-cyclopropyl)benzoic acid
4-(1-(5-chloro-2-(3-((4-fluorophenyl)amino)azetidin-1-yl)nicotinamido)cyclopropyl)-benzoic acid
4-(1-(5-chloro-2-(3-((4-fluoro-2-methylphenyl)amino)azetidin-1-yl)nicotinamido)-cyclopropyl)benzoic acid
4-(1-(5-chloro-2-(3-((2,4-difluorophenyl)amino)azetidin-1-yl)nicotinamido)-cyclopropyl)benzoic acid
4-(1-(5-chloro-2-(3-((2-methyl-4-(trifluoromethyl)phenyl)amino)azetidin-1-yl)-nicotinamido)cyclopropyl)benzoic acid
4-(1-(5-chloro-2-(3-((4-fluoro-2-methylphenyl)(methyl)amino)azetidin-1-yl)-nicotinamido)cyclopropyl)benzoic acid
4-(1-(2-(3-(3-fluorophenoxy)azetidin-1-yl)-5-(trifluoromethyl)nicotinamido)-cyclopropyl)benzoic acid
4-(1-(2-(3-(4-fluorophenoxy)azetidin-1-yl)-5-(trifluoromethyl)nicotinamido)-cyclopropyl)benzoic acid
4-(1-(2-(3-(4-chlorophenoxy)azetidin-1-yl)-5-(trifluoromethyl)nicotinamido)-cyclopropyl)benzoic acid
4-(1-(2-(3-(3-chlorophenoxy)azetidin-1-yl)-5-(trifluoromethyl)nicotinamido)-cyclopropyl)benzoic acid
4-(1-(2-(3-(4-fluoro-3-(trifluoromethyl)phenoxy)azetidin-1-yl)-5-(trifluoromethyl)-nicotinamido)cyclopropyl)benzoic acid
4-(1-(2-(3-(3-(trifluoromethoxy)phenoxy)azetidin-1-yl)-5-(trifluoromethyl)-nicotinamido)cyclopropyl)benzoic acid
4-(1-(2-(3-(2,4-difluorophenoxy)azetidin-1-yl)-5-(trifluoromethyl)nicotinamido)-cyclopropyl)benzoic acid
4-(1-(2-(3-(3,4-difluorophenoxy)azetidin-1-yl)-5-(trifluoromethyl)nicotinamido)-cyclopropyl)benzoic acid
4-(1-(2-(3-((5-methylisoxazol-3-yl)oxy)azetidin-1-yl)-5-(trifluoromethyl)-nicotinamido)cyclopropyl)benzoic acid
4-(1-(5-(trifluoromethyl)-2-(3-((6-(trifluoromethyl)pyridin-2-yl)oxy)azetidin-1-yl)nicotinamido)cyclopropyl)benzoic acid
4-(1-(2-(3-((5-fluoropyrimidin-2-yl)oxy)azetidin-1-yl)-5-(trifluoromethyl)-nicotinamido)cyclopropyl)benzoic acid
4-(1-(2-(3-((3-fluorophenyl)amino)azetidin-1-yl)-5-(trifluoromethyl)-nicotinamido)cyclopropyl)benzoic acid
4-(1-(2-(3-((4-fluorophenyl)amino)azetidin-1-yl)-5-(trifluoromethyl)nicotinamido)cyclopropyl)benzoic acid
4-(1-(2-(3-((4-fluoro-2-methylphenyl)amino)azetidin-1-yl)-5-(trifluoromethyl)-nicotinamido)cyclopropyl)benzoic acid
4-(1-(2-(3-((2,4-difluorophenyl)amino)azetidin-1-yl)-5-(trifluoromethyl)-nicotinamido)cyclopropyl)benzoic acid
4-(1-(5-fluoro-2-(3-(3-fluorophenoxy)azetidin-1-yl)nicotinamido)cyclopropyl)benzoic acid
4-(1-(5-fluoro-2-(3-(3-chlorophenoxy)azetidin-1-yl)nicotinamido)cyclopropyl)-benzoic acid
4-(1-(5-fluoro-2-(3-(3-(trifluoromethoxy)phenoxy)azetidin-1-yl)nicotinamido)-cyclopropyl)benzoic acid
4-(1-(5-fluoro-2-(3-((4-fluoro-2-methylphenyl)amino)azetidin-1-yl)nicotinamido)-cyclopropyl)benzoic acid
4-((1S)-1-(5-chloro-2-(3-(4-(trifluoromethyl)phenoxy)pyrrolidin-1-yl)nicotinamido)-ethyl)benzoic acid
4-((1S)-1-(5-chloro-2-(3-(3-(trifluoromethyl)phenoxy)pyrrolidin-1-yl)nicotinamido)-ethyl)benzoic acid
4-((1S)-1-(5-chloro-2-(3-(4-fluorophenoxy)pyrrolidin-1-yl)nicotinamido)-ethyl)benzoic acid
4-(1-(5-chloro-2-(3-phenoxy)pyrrolidin-1-yl)nicotinamido)cyclopropyl)benzoic acid (racemic mixture)
4-(1-(5-chloro-2-(3-phenoxy)pyrrolidin-1-yl)nicotinamido)cyclopropyl)benzoic acid (enantiomer 1)
4-(1-(5-chloro-2-(3-phenoxy)pyrrolidin-1-yl)nicotinamido)cyclopropyl)benzoic acid (enantiomer 2)
4-(1-(5-chloro-2-(3-(3-(trifluoromethyl)phenoxy)pyrrolidin-1-yl)nicotinamido)-cyclopropyl)benzoic acid (racemic mixture)
4-(1-(5-chloro-2-(3-(3-(trifluoromethyl)phenoxy)pyrrolidin-1-yl)nicotinamido)-cyclopropyl)benzoic acid (enantiomer 1)
4-(1-(5-chloro-2-(3-(3-(trifluoromethyl)phenoxy)pyrrolidin-1-yl)nicotinamido)-cyclopropyl)benzoic acid (enantiomer 2)
4-(1-(5-chloro-2-(3-(4-fluorophenoxy)pyrrolidin-1-yl)nicotinamido)cyclopropyl)-benzoic acid (racemic mixture)
4-(1-(5-chloro-2-(3-(4-fluorophenoxy)pyrrolidin-1-yl)nicotinamido)cyclopropyl)-benzoic acid (enantiomer 1)
4-(1-(5-chloro-2-(3-(4-fluorophenoxy)pyrrolidin-1-yl)nicotinamido)cyclopropyl)-benzoic acid (enantiomer 2)
4-(1-(5-chloro-2-(3-(3-fluorophenoxy)pyrrolidin-1-yl)nicotinamido)-cyclopropyl)benzoic acid (racemic mixture)
4-(1-(5-chloro-2-(3-(3-fluorophenoxy)pyrrolidin-1-yl)nicotinamido)cyclopropyl)-benzoic acid (enantiomer 1)
4-(1-(5-chloro-2-(3-(3-fluorophenoxy)pyrrolidin-1-yl)nicotinamido)cyclopropyl)-benzoic acid (enantiomer 2)
4-(1-(5-chloro-2-(3-(m-tolyloxy)pyrrolidin-1-yl)nicotinamido)cyclopropyl)benzoic acid
4-(1-(5-chloro-2-(3-(4-(trifluoromethyl)phenoxy)pyrrolidin-1-yl)nicotinamido)-cyclopropyl)benzoic acid (racemic mixture)
4-(1-(5-chloro-2-(3-(4-(trifluoromethyl)phenoxy)pyrrolidin-1-yl)nicotinamido)cyclo-propyl)benzoic acid (enantiomer 1)
4-(1-(5-chloro-2-(3-(4-(trifluoromethyl)phenoxy)pyrrolidin-1-yl)nicotinamido)cyclo-propyl)benzoic acid (enantiomer 2)
4-(1-(5-chloro-2-(3-((3-fluorophenoxy)methyl)pyrrolidin-1-yl)nicotinamido)cyclo-propyl)benzoic acid
4(R)-4-(1-(5-chloro-2-(2-((3-fluorophenoxy)methyl)pyrrolidin-1-yl)nicotinamido)cyclopropyl)benzoic acid
4(S)-4-(1-(5-chloro-2-(2-((3-fluorophenoxy)methyl)pyrrolidin-1-yl)nicotinamido)-cyclopropyl)benzoic acid
4-(1-(5-chloro-2-(3-((3-fluorophenoxy)methyl)piperidin-1-yl)nicotinamido)cyclo-propyl)benzoic acid
(R)-4-(1-(5-chloro-2-(3-(3-fluorophenoxy)pyrrolidin-1-yl)nicotinamido)cyclo-propyl)benzoic acid
(S)-4-(1-(5-chloro-2-(3-(3-fluorophenoxy)pyrrolidin-1-yl)nicotinamido)cyclo-propyl)benzoic acid, and
N-(1-(4-(1H-tetrazol-5-yl)phenyl)cyclopropyl)-5-chloro-2-(3-(3-fluorophenoxy)-azetidin-1-yl)nicotinamide.

23. The pyridine amide derivative according to claim 22, wherein the derivative of Formula (I) is selected from the group consisting of:

4-(1-(5-chloro-2-(2-phenylpyrrolidin-1-yl)nicotinamido) cyclopropyl)benzoic acid (racemic mixture)
4-(1-(5-chloro-2-(2-phenylpyrrolidin-1-yl)nicotinamido) cyclopropyl)benzoic acid (enantiomer 2)
4-(1-(5-chloro-2-(3-phenylpyrrolidin-1-yl)nicotinamido) cyclopropyl)benzoic acid
4-(1-(5-chloro-2-(3-phenoxyazetidin-1-yl)nicotinamido) cyclopropyl)benzoic acid
(S)-4-(1-(5-chloro-2-(3-(4-fluorophenoxy)azetidin-1-yl) nicotinamido)ethyl)benzoic acid
(S)-4-(1-(5-chloro-2-(3-(3-fluorophenoxy)azetidin-1-yl) nicotinamido)ethyl)benzoic acid
4-(1-(5-chloro-2-(3-(4-(trifluoromethyl)phenoxy)azetidin-1-yl)nicotinamido)cyclo-propyl)benzoic acid
4-(1-(5-chloro-2-(3-(3-(trifluoromethyl)phenoxy)azetidin-1-yl)nicotinamido)-cyclopropyl)benzoic acid
4-(1-(5-chloro-2-(3-(4-fluorophenoxy)azetidin-1-yl)nicotinamido)cyclopropyl)-benzoic acid
4-(1-(5-chloro-2-(3-(3-fluorophenoxy)azetidin-1-yl)nicotinamido)cyclopropyl)-benzoic acid
4-(1-(5-chloro-2-(3-(4-fluoro-3-(trifluoromethyl)phenoxy)azetidin-1-yl)nicotinamido)-cyclopropyl)benzoic acid
4-(1-(5-chloro-2-(3-(3-(trifluoromethoxy)phenoxy)azetidin-1-yl)nicotinamido)cyclo-propyl)benzoic acid
4-(1-(5-chloro-2-(3-(2,4-difluorophenoxy)azetidin-1-yl) nicotinamido)cyclopropyl)-benzoic acid
4-(1-(5-chloro-2-(3-(3,4-difluorophenoxy)azetidin-1-yl) nicotinamido)cyclopropyl)-benzoic acid
4-(1-(5-chloro-2-(3-(3-(piperazin-1-yl)phenoxy)azetidin-1-yl)nicotinamido)cyclo-propyl)benzoic acid
4-((5-chloro-2-(3-(3-fluorophenoxy)azetidin-1-yl)nicotinamido)methyl)benzoic acid
6-((5-chloro-2-(3-(3-fluorophenoxy)azetidin-1-yl)nicotinamido)methyl)nicotinic acid
4-(1-(5-chloro-2-(3-(3-fluorobenzoyl)azetidin-1-yl)nicotinamido)cyclopropyl)benzoic acid
4-(1-(5-chloro-2-(3-(4-fluorophenyl)-3-hydroxyazetidin-1-yl)nicotinamido)cyclo-propyl)benzoic acid
4-(1-(5-chloro-2-(3-((4-fluorophenoxy)methyl)azetidin-1-yl)nicotinamido)cyclo-propyl)benzoic acid
4-(1-(5-chloro-2-(3-((4-fluorophenoxy)methyl)azetidin-1-yl)nicotinamido)cyclo-propyl)benzoic acid
4-(1-(5-chloro-2-(3-((3-(trifluoromethyl)phenyl)amino) azetidin-1-yl)nicotinamido)-cyclopropyl)benzoic acid
4-(1-(5-chloro-2-(3-((3-fluorophenyl)amino)azetidin-1-yl)nicotinamido)cyclopropyl)-benzoic acid
4-(1-(5-chloro-2-(3-((4-fluorophenyl)amino)azetidin-1-yl)nicotinamido)cyclopropyl)-benzoic acid
4-(1-(5-chloro-2-(3-((4-fluoro-2-methylphenyl)amino) azetidin-1-yl)nicotinamido)-cyclopropyl)benzoic acid
4-(1-(5-chloro-2-(3-((2,4-difluorophenyl)amino)azetidin-1-yl)nicotinamido)-cyclopropyl)benzoic acid
4-(1-(5-chloro-2-(3-((2-methyl-4-(trifluoromethyl)phenyl)amino)azetidin-1-yl)-nicotinamido)cyclopropyl) benzoic acid
4-(1-(5-chloro-2-(3-((4-fluoro-2-methylphenyl)(methyl) amino)azetidin-1-yl)-nicotinamido)cyclopropyl)benzoic acid
4-(1-(2-(3-(3-fluorophenoxy)azetidin-1-yl)-5-(trifluoromethyl)nicotinamido)-cyclopropyl)benzoic acid
4-(1-(2-(3-(4-fluorophenoxy)azetidin-1-yl)-5-(trifluoromethyl)nicotinamido)-cyclopropyl)benzoic acid
4-(1-(2-(3-(4-chlorophenoxy)azetidin-1-yl)-5-(trifluoromethyl)nicotinamido)-cyclopropyl)benzoic acid
4-(1-(2-(3-(3-chlorophenoxy)azetidin-1-yl)-5-(trifluoromethyl)nicotinamido)-cyclopropyl)benzoic acid
4-(1-(2-(3-(4-fluoro-3-(trifluoromethyl)phenoxy)azetidin-1-yl)-5-(trifluoromethyl)-nicotinamido)cyclopropyl)benzoic acid
4-(1-(2-(3-(3-(trifluoromethoxy)phenoxy)azetidin-1-yl)-5-(trifluoromethyl)-nicotinamido)cyclopropyl)benzoic acid
4-(1-(2-(3-(2,4-difluorophenoxy)azetidin-1-yl)-5-(trifluoromethyl)-nicotinamido)cyclopropyl)benzoic acid
4-(1-(2-(3-(3,4-difluorophenoxy)azetidin-1-yl)-5-(trifluoromethyl)nicotinamido)-cyclopropyl)benzoic acid
4-(1-(5-(trifluoromethyl)-2-(3-((6-(trifluoromethyl)pyridin-2-yl)oxy)azetidin-1-yl)-nicotinamido)cyclopropyl) benzoic acid
4-(1-(2-(3-((3-fluorophenyl)amino)azetidin-1-yl)-5-(trifluoromethyl)nicotinamido)-cyclopropyl)benzoic acid
4-(1-(2-(3-((4-fluorophenyl)amino)azetidin-1-yl)-5-(trifluoromethyl)nicotinamido)-cyclopropyl)benzoic acid
4-(1-(2-(3-((4-fluoro-2-methylphenyl)amino)azetidin-1-yl)-5-(trifluoromethyl)-nicotinamido)cyclopropyl)benzoic acid
4-(1-(2-(3-((2,4-difluorophenyl)amino)azetidin-1-yl)-5-(trifluoromethyl)-nicotinamido)cyclopropyl)benzoic acid
4-(1-(5-fluoro-2-(3-(3-fluorophenoxy)azetidin-1-yl)nicotinamido)cyclopropyl)benzoic acid
4-(1-(5-fluoro-2-(3-(3-chlorophenoxy)azetidin-1-yl)nicotinamido)cyclopropyl)-benzoic acid
4-(1-(5-fluoro-2-(3-(3-(trifluoromethoxy)phenoxy)azetidin-1-yl)nicotinamido)cyclo-propyl)benzoic acid
4-(1-(5-fluoro-2-(3-((4-fluoro-2-methylphenyl)amino) azetidin-1-yl)nicotinamido)-cyclopropyl)benzoic acid
4-(1-(5-chloro-2-(3-phenoxy)pyrrolidin-1-yl)nicotinamido)cyclopropyl)benzoic acid (racemic mixture)
4-(1-(5-chloro-2-(3-phenoxy)pyrrolidin-1-yl)nicotinamido)cyclopropyl)benzoic acid (enantiomer 2)
4-(1-(5-chloro-2-(3-(3-(trifluoromethyl)phenoxy)pyrrolidin-1-yl)nicotinamido)cyclo-propyl)benzoic acid (racemic mixture)
4-(1-(5-chloro-2-(3-(3-(trifluoromethyl)phenoxy)pyrrolidin-1-yl)nicotinamido)-cyclopropyl)benzoic acid (enantiomer 1)
4-(1-(5-chloro-2-(3-(3-(trifluoromethyl)phenoxy)pyrrolidin-1-yl)nicotinamido)-cyclopropyl)benzoic acid (enantiomer 2)
4-(1-(5-chloro-2-(3-(4-fluorophenoxy)pyrrolidin-1-yl) nicotinamido)cyclopropyl)-benzoic acid (racemic mixture)
4-(1-(5-chloro-2-(3-(4-fluorophenoxy)pyrrolidin-1-yl) nicotinamido)cyclopropyl)-benzoic acid (enantiomer 2)
4-(1-(5-chloro-2-(3-(3-fluorophenoxy)pyrrolidin-1-yl) nicotinamido)cyclopropyl)-benzoic acid (racemic mixture)
4-(1-(5-chloro-2-(3-(3-fluorophenoxy)pyrrolidin-1-yl) nicotinamido)cyclopropyl)-benzoic acid (enantiomer 2)
4-(1-(5-chloro-2-(3-((3-fluorophenoxy)methyl)pyrrolidin-1-yl)nicotinamido)cyclo-propyl)benzoic acid
(R)-4-(1-(5-chloro-2-(2-((3-fluorophenoxy)methyl)pyrrolidin-1-yl)nicotinamido) cyclopropyl)benzoic acid
(S)-4-(1-(5-chloro-2-(3-(3-fluorophenoxy)pyrrolidin-1-yl)nicotinamido) cyclopropyl)benzoic acid, and
N-(1-(4-(1H-tetrazol-5-yl)phenyl)cyclopropyl)-5-chloro-2-(3-(3-fluorophenoxy)-azetidin-1-yl)nicotinamide.

24. The pyridine amide derivative according to claim 23, wherein the derivative of Formula (I) is selected from the group consisting of:
- 4-(1-(5-chloro-2-(3-phenoxyazetidin-1-yl)nicotinamido) cyclopropyl)benzoic acid
- 4-(1-(5-chloro-2-(3-(3-fluorophenoxy)azetidin-1-yl)nicotinamido)cyclopropyl)-benzoic acid
- 6-((5-chloro-2-(3-(3-fluorophenoxy)azetidin-1-yl)nicotinamido)methyl)nicotinic acid
- 4-(1-(5-chloro-2-(3-((4-fluoro-2-methylphenyl)amino) azetidin-1-yl)nicotinamido)-cyclopropyl)benzoic acid
- 4-(1-(2-(3-(3-fluorophenoxy)azetidin-1-yl)-5-(trifluoromethyl)nicotinamido)cyclo-propyl)benzoic acid, and
- 4-(1-(2-(3-((4-fluoro-2-methylphenyl)amino)azetidin-1-yl)-5-(trifluoromethyl)-nicotinamido)cyclopropyl)benzoic acid.

25. A pharmaceutical composition comprising a derivative of Formula (I) according to claim 1 and a pharmaceutically acceptable carrier.

26. A method for antagonizing the EP4 receptor in a patient having an EP4 mediated disease comprising the step of administering a pyridine amide derivative according to claim 1 to said patient.

27. The method according to claim 26, wherein said disease is selected from the group consisting of: acute and chronic pain, inflammatory pain, arthritis, cancer, endometriosis and migraine.

* * * * *